United States Patent
Ratcliffe et al.

(10) Patent No.: US 10,385,065 B2
(45) Date of Patent: Aug. 20, 2019

(54) ANTIBACTERIAL COMPOUNDS

(71) Applicant: Redx Pharma PLC, Macclesfield (GB)

(72) Inventors: Andrew Ratcliffe, Cheshire (GB); Anthony Huxley, Cheshire (GB); David Lyth, Cheshire (GB); Gary Noonan, Cheshire (GB); Ralph Kirk, Cheshire (GB); Mario Uosis-Martin, Cheshire (GB); Neil Stokes, Cheshire (GB)

(73) Assignee: Redx Pharma PLC, Cheshire (GB)

( * ) Notice: Subject to any disclaimer, the term of this patent is extended or adjusted under 35 U.S.C. 154(b) by 0 days.

(21) Appl. No.: 15/302,539

(22) PCT Filed: Apr. 10, 2015

(86) PCT No.: PCT/GB2015/051107
§ 371 (c)(1),
(2) Date: Oct. 7, 2016

(87) PCT Pub. No.: WO2015/155549
PCT Pub. Date: Oct. 15, 2015

(65) Prior Publication Data
US 2017/0158708 A1 Jun. 8, 2017

(30) Foreign Application Priority Data
Apr. 10, 2014 (GB) .................. 1406486.9

(51) Int. Cl.
| | |
|---|---|
| *C07D 498/02* | (2006.01) |
| *C07D 498/14* | (2006.01) |
| *C07D 498/16* | (2006.01) |
| *A61K 31/4375* | (2006.01) |
| *C07D 519/00* | (2006.01) |
| *A61K 31/4745* | (2006.01) |
| *A61K 31/5383* | (2006.01) |
| *C07D 498/04* | (2006.01) |
| *C07D 513/04* | (2006.01) |

(52) U.S. Cl.
CPC ........ *C07D 498/02* (2013.01); *A61K 31/4375* (2013.01); *A61K 31/4745* (2013.01); *A61K 31/5383* (2013.01); *C07D 498/04* (2013.01); *C07D 498/14* (2013.01); *C07D 498/16* (2013.01); *C07D 513/04* (2013.01); *C07D 519/00* (2013.01); *Y02A 50/478* (2018.01); *Y02A 50/483* (2018.01)

(58) Field of Classification Search
None
See application file for complete search history.

(56) References Cited

U.S. PATENT DOCUMENTS

| | | |
|---|---|---|
| 2010/0256112 A1 | 10/2010 | Bradbury et al. |
| 2013/0079337 A1 | 3/2013 | Benazet et al. |
| 2013/0143907 A1 | 6/2013 | Norimine et al. |

FOREIGN PATENT DOCUMENTS

| | | |
|---|---|---|
| EP | 2573073 A1 | 3/2013 |
| WO | WO-2005/118583 A1 | 12/2005 |
| WO | WO-2007/041076 A2 | 4/2007 |
| WO | WO-2008131134 A1 | 10/2008 |
| WO | WO-2011073378 A1 | 6/2011 |
| WO | WO-2014/163146 A1 | 10/2014 |

OTHER PUBLICATIONS

Chemical Abstract Registry No. 1280293-19-7, indexed in the Registry File on STN CAS Online Apr. 14, 2011.*
Search Report issued by Intellectual Property Office in corresponding Application No. GB1406486.9, dated Nov. 14, 2014.
Amin, et al., "Synthesis, Analgesic and Anti-Inflammatory Activities Evaluation of Some Bi-, Tri- and Tetracyclic Condensed Pyrimidines," Eur J Med Chem, 44(11): 4572-4584 (2009).
International Search Report for International Patent Application No. PCT/GB2015/051107, dated Jun. 11, 2015, 5 pages.

* cited by examiner

*Primary Examiner* — Po-Chih Chen
(74) *Attorney, Agent, or Firm* — Foley Hoag LLP

(57) ABSTRACT

The invention relates to antibacterial and anti-mycobacterial drug compounds of formula I. It also relates to pharmaceutical formulations of antibacterial drug compounds. It also relates to uses of the derivatives in treating bacterial infections, and methods of treating bacterial infections. The invention is also directed to antibacterial drug compounds capable of treating bacterial infections that are currently hard to treat with existing drug compounds, e.g., those caused by resistant bacterial or mycobacterial strains.

24 Claims, No Drawings

ANTIBACTERIAL COMPOUNDS

RELATED APPLICATIONS

This application is a § 371 national stage application based on Patent Cooperation Treaty Application serial number PCT/GB2015/051107, filed Apr. 10, 2015; which claims the benefit of priority to GB 1406486.9, filed Apr. 10, 2014.

This invention relates to antibacterial and anti-mycobacterial drug compounds containing a tricyclic ring system. It also relates to pharmaceutical formulations of antibacterial drug compounds. It also relates to uses of the derivatives in treating bacterial infections and to methods of treating bacterial infections. The invention is also directed to antibacterial drug compounds which are capable of treating bacterial infections which are currently hard to treat with existing drug compounds, e.g. those caused by resistant bacterial or mycobacterial strains.

The increasing occurrence of bacterial resistance to antibiotics is viewed by many as being one of the most serious threats to the future health and happiness of mankind. Multidrug resistance has become common among some pathogens, e.g. *Staphylococcus aureus, Streptococcus pneumoniae, Clostridium difficile* and *Pseudomonas aeruginosa*. Of these, *Staphylococcus aureus*, a Gram positive bacterium, is the most concerning due to its potency and its capacity to adapt to environmental conditions. MRSA (methicillin resistant *Staphylococcus aureus*) is probably the most well known resistant strain and has reached pandemic proportions. Of particular concern is the increasing incidence of 'community acquired' infections, i.e. those occurring in subjects with no prior hospital exposure. Many strains of MRSA are also resistant to fluoroquinolone antibiotics, in addition to β-lactam antibiotics such as methicillin.

While less wide-spread, antibiotic resistant Gram negative strains, such as either *Escherichia coli* NDM-1 (New Delhi metallo-β-lactamase) mutation or *Klebsiella pneumoniae* with the same mutation, are also very difficult to treat. Frequently only expensive antibiotics such as vancomycin and colistin are effective against these strains.

One specific area were antibacterial resistance is posing a problem is in the treatment of gonorrhoea. Gonorrhoea is a human sexually-transmitted infection (STI) caused by the Gram-negative bacterium *Neisseria gonorrhoeae*, a species of the genus *Neisseria* that also includes the pathogen *N. meningitidis*, which is one of the aetiological agents of meningitis. Gonorrhoea is a significant global public health problem. In 2008 there were a total of 106 million estimated new cases of *N. gonorrhoeae* infection (Global Incidence and Prevalence of Selected Curable Sexually Transmitted Infections-2008, World Health Organization). It is the second most commonly reported infectious disease in the United States. According to the Centers for Disease Control and Prevention (CDC) there are an estimated 820,000 gonococcal infections per year in the United States (Antibiotic Resistance Threats in the United States, 2013, Centers for Disease Control and Prevention. Throughout the twentieth and twenty-first centuries gonorrhoea has been treated with a range of antibiotics. The sulphonamides were the first antibiotics used for the treatment of gonorrhoea, followed by penicillin, tetracycline and spectinomycin. In each case the development of resistance to these drugs by *N. gonorrhoeae* led to their use being discontinued. The fluoroquinolone antibiotics ciprofloxacin and ofloxacin were also historically recommended for the treatment of gonorrhoea. However, by 2007, fluoroquinolone resistance rates had reached 15% of gonococcal isolates and their use was abandoned. Current treatment recommendations comprise the cephalosporin antibiotics cefixime or ceftriaxone in combination with azithromycin or doxycycline. Resistance to cefixime and ceftriaxone has emerged in recent years. The CDC estimates that approximately 246,000 of the 820,000 gonococcal infections per year in the United States are drug-resistant (Antibiotic Resistance Threats in the United States, 2013, Centers for Disease Control and Prevention). *N. gonorrhoeae* has evolved diverse molecular resistance mechanisms to overcome the inhibitory effects of antibiotics. Examples include: i) alterations in the folP gene that encodes the dihydropteroate synthase enzymes that are the target of the sulphonamides; ii) plasmids bearing the bla$_{TEM-1}$ gene, encoding a TEM-1-type β-lactamase; iii) single nucleotide polymorphisms in the tetracycline- and spectinomycin-binding regions of the ribosomal target; and iv) mutations in the gyrA and parC genes that code for subunits of DNA gyrase and topoisomerase IV that are targeted by the fluoroquinolones.

A further disease in which the development of resistance and multidrug resistance is of particular concern is TB. From the 17$^{th}$ century to the early-20$^{th}$ century TB was one of the most common causes of death, particularly amongst the urban poor. The development of effective treatments and vaccinations through the middle part of the 20$^{th}$ century led to a sharp reduction in the number of deaths arising from the disease. TB is usually caused by *Mycobacterium tuberculosis*. Mycobacteria are aerobic bacteria and, as a result, tuberculosis infections most often develop in the lungs (pulmonary tuberculosis), although this is not always the case. Mycobacteria lack an outer cell membrane and as such they are often classified as Gram-positive bacteria, although they are in many ways atypical. They have a unique cell wall which provides protection against harsh conditions (e.g. acidic, oxidative) but also provides natural protection against many antibiotics. Other antibiotics, such as beta-lactams, are inactive against TB due to the intrinsic activity of the compounds in the mycobacteria. Thus, a drug molecule may have excellent activity against other bacterial strains but no activity against wild-type TB. A number of TB-specific antibiotics have been developed, such as isoniazid, rifampicin, pyrazinamide and ethambutol and these are typically used in combination. Unfortunately, there is now increasing incidence of multidrug-resistant TB (MDR-TB). MDR-TB often arises when a treatment for TB has been interrupted. MDR-TB is the term typically used to refer to TB which has developed a resistance to isoniazid and rifampicin. MDR-TB can also be resistant to fluoroquinolones and also to the so-called 'second line' injectable anti-TB drugs: kanamycin, capreomycin and amikacin, with such resistances again commonly developing due to interruptions in treatment regimes. Where a strain of TB is resistant to isoniazid and rifampicin as well as one fluoroquinolone and one of the injectable anti-TB drugs, it is known as extensively drug resistant (XDR-TB). MDR-TB and XDR-TB are often found in those who have been previously treated for TB, but these forms of TB are just as infectious as wild-type TB and the incidence of MDR-TB and XDR-TB around the world is increasing. According to a 2013 World Health Organisation report, infections arising from XDR-TB had at that time been identified in 84 different countries. There have even been some reports of strains of TB which were resistant to all drugs tested against them (so-called 'totally drug resistant tuberculosis', TDR-TB).

The 'second line' anti-TB drugs and other antibiotics typically used to treat resistant infections can have unfavourable side effects.

The fluoroquinolone antibacterial family are synthetic broad-spectrum antibiotics. They were originally introduced to treat Gram negative bacterial infections, but are also used for the treatment of Gram positive strains. One problem with existing fluoroquinolones can be the negative side effects that may sometimes occur as a result of fluoroquinolone use. In general, the common side-effects are mild to moderate but, on occasion, more serious adverse effects occur. Some of the serious side effects that occur, and which occur more commonly with fluoroquinolones than with other antibiotic drug classes, include central nervous system (CNS) toxicity and cardiotoxicity. In cases of acute overdose there may be renal failure and seizure.

In spite of the numerous different antibiotics known in the art for a variety of different infections, there continues to be a need to provide antibiotics that can provide an effective treatment in a reliable manner. In addition, there remains a need for antibiotic drugs which can avoid or reduce the side-effects associated with known antibiotics.

It is an aim of certain embodiments of this invention to provide new antibiotics. In particular, it is an aim of certain embodiments of this invention to provide antibiotics which are active against resistant strains of Gram positive and/or Gram negative bacteria. It is an aim of certain embodiments of this invention to provide compounds which have activity which is comparable to those of existing antibiotics, and ideally which is better. It is an aim of certain embodiments of this invention to provide such activity against wild-type strains at the same time as providing activity against one or more resistant strains.

It is an aim of certain embodiments of this invention to provide antibiotics which exhibit reduced cytotoxicity relative to prior art compounds and existing therapies.

It is an aim of certain embodiments of this invention to provide treatment of bacterial infections which is effective in a selective manner at a chosen site of interest. Another aim of certain embodiments of this invention is to provide antibiotics having a convenient pharmacokinetic profile and a suitable duration of action following dosing. A further aim of certain embodiments of this invention is to provide antibiotics in which the metabolised fragment or fragments of the drug after absorption are GRAS (Generally Regarded As Safe).

Certain embodiments of the present invention satisfy some or all of the above aims.

COMPOUNDS OF THE INVENTION

In a first aspect, the invention provides a compound of formula (I), or a pharmaceutically acceptable salt or N-oxide thereof:

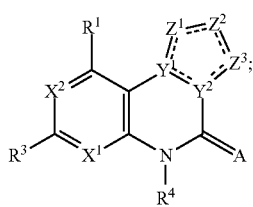

(I)

wherein $X^1$ is independently selected from: N and $CR^5$;
$X^2$ is independently selected from: N and $CR^2$;
$=A$ is independently selected from: $=O$, $=S$, $=NR^6$ and $=NOR^6$;
$Y^1$ and $Y^2$ are each independently selected from C and N; $Z^1$, $Z^2$ and $Z^3$ are each independently selected from O, S, $S(O)_2$, $S(O)$, $NR^{11}$, $CR^{12}$ and $C=W$; wherein W is selected from O, S or $NR^6$; with the proviso that if none of $Z^1$, $Z^2$ and $Z^3$ is $C=W$, then the ring formed by $Z^1$, $Z^2$, $Z^3$, $Y^1$ and $Y^2$ contains two endocyclic double bonds and, if one of $Z^1$, $Z^2$ and $Z^3$ is $C=W$, then the ring formed by $Z^1$, $Z^2$, $Z^3$, $Y^1$ and $Y^2$ contains a single endocyclic double bond; and with the further proviso that at least one of $Z^1$, $Z^2$, $Z^3$, $Y^1$ and $Y^2$ is O, S, N or $NR^{11}$;

$R^1$ is independently selected from: H, F, $NR^6R^7$, $NR^6NR^6R^7$ and $C_1$-$C_4$-alkyl;

$R^2$ is independently selected from: H, $C_1$-$C_4$ alkyl and halo;

$R^3$ is independently selected from: $-(CR^8R^8)_{n\text{-}3\text{-}10}$ heterocycloalkyl, $-(CR^8R^8)_n$-aryl, $-(CR^8R^8)_n$-heteroaryl, and $-(CR^8R^8)_n$-$C_3$-$C_{10}$ cycloalkyl; wherein the aryl, heteroaryl, heterocycloalkyl or cycloalkyl group is optionally substituted with 1, 2 or 3 $R^{15}$ groups; wherein $R^{15}$ is independently at each occurrence selected from: oxo, $=NR^6$, $=NOR^6$, $_{3\text{-}5}$-heterocycloalkyl, halo, nitro, cyano, $NR^6R^7$, $NR^6S(O)_2R^6$, $NR^6CONR^6R^6$, $NR^6CO_2R^6$, $OR^6$; $SR^6$, $SOR^6$, $SO_3R^6$, $SO_2R^6$, $SO_2NR^6R^6$, $CO_2R^6$, $C(O)R^6$, $CONR^6R^6$, $C(O)NR^6CR^6R^6C(O)OR^6$, $C_1$-$C_4$-alkyl, $C_2$-$C_4$-alkenyl, $C_2$-$C_4$-alkynyl, $C_1$-$C_4$ haloalkyl, $CR^6R^6OR^6$, $CR^6R^6NR^7R^6$, and $=CR^6CR^6R^6NR^7R^6$;

$R^4$ is independently selected from: $C_1$-$C_8$ alkyl, $C_2$-$C_8$ alkenyl, $C_2$-$C_8$ alkynyl, $C_1$-$C_8$ haloalkyl, $-(CR^8R^8)_n$-$C_3$-$C_6$ cycloalkyl, $-(CR^8R^8)_n$-$C_3$-$C_6$ heterocycloalkyl, $-(CR^8R^8)_n$-$C_3$-$C_6$ halocycloalkyl, $-(CR^8R^8)_n$-phenyl, and $-(CR^8R^8)_n$-heteroaryl;

$R^5$ is independently selected from: H, O—$C_1$-$C_8$ alkyl, halo, $C_1$-$C_8$ alkyl, $C_2$-$C_8$ alkenyl, $C_2$-$C_8$ alkynyl, $C_1$-$C_8$ haloalkyl, O—$C_1$-$C_8$ haloalkyl, $C_3$-$C_6$ cycloalkyl, $C_3$-$C_6$ heterocycloalkyl, $C_3$-$C_6$ halocycloalkyl; or $R^4$ and $R^5$ together form an alkylene or heteroalkylene chain of the form $-(CR^8R^8)_r$—$W^1$—$(CR^8R^8)_s$—$W^2$—$(CR^8R^8)_t$— and which is attached at its respective ends to the substitution point for $R^4$ and $R^5$ respectively; wherein $W^1$ and $W^2$ are each independently selected from: a bond, O, S and $NR^9$; wherein r, s, and t are each independently an integer selected from 0, 1 and 2 and wherein definitions of r, s, t, $W^1$ and $W^2$ are chosen such that the total length of the alkylene or heteroalkylene chain is 2, 3 or 4 atoms;

$R^6$, $R^9$, and $R^{13}$ are independently at each occurrence selected from: H, $C_1$-$C_4$ alkyl, and $C_1$-$C_4$ haloalkyl;

$R^7$ and $R^{14}$ are each independently at each occurrence selected from: H, $C_1$-$C_4$ alkyl, $C_1$-$C_4$ haloalkyl, $S(O)_2$—$C_1$-$C_4$alkyl, $C(O)$—$C_1$-$C_4$ alkyl, $C(O)$—O—$C_1$-$C_4$ alkyl and $CH_2$-phenyl;

$R^8$ is independently at each occurrence selected from: H, Me, $CF_3$ and F;

where the nitrogen to which $R^{11}$ is attached has a formal double bond to one of its neighbouring atoms in the ring formed by $Z^1$, $Z^2$, $Z^3$, $Y^1$ and $Y^2$, $R^{11}$ is absent; or, where the nitrogen to which $R^{11}$ is attached is attached via formal single bonds to both of its neighbouring atoms in the in the ring formed by $Z^1$, $Z^2$, $Z^3$, $Y^1$ and $Y^2$, $R^{11}$ is independently selected from: H, $C_1$-$C_4$ alkyl, and $C_1$-$C_4$ haloalkyl;

$R^{12}$ may be independently at each occurrence selected from: H, halo, nitro, cyano, $NR^{13}R^{14}$, $NR^{13}S(O)_2R^{13}$, $NR^{13}CONR^{13}R^{13}$, $NR^{13}CO_2R^{13}$, $OR^{13}$; $SR^{13}$, $SOR^{13}$, $SO_3R^{13}$, $SO_2R^{13}$, $SO_2NR^{13}R^{13}$, $CO_2R^{13}C(O)R^{13}$, CONR$^{13}$R$^{13}$, C$_1$-C$_4$-alkyl, C$_2$-C$_4$-alkenyl, C$_2$-C$_4$-alkynyl, C$_1$-C$_4$ haloalkyl, CR$^{13}$R$^{13}$OR$^{13}$, CR$^{13}$R$^{13}$OC(O)R$^{13}$ and CR$^{13}$R$^{13}$NR$^{13}$R$^{14}$;

and n is an integer independently selected at each occurrence from 0, 1, 2 and 3; and wherein each of the aforementioned aryl, heteroaryl, C$_3$-C$_{10}$ heterocycloalkyl or C$_3$-C$_{10}$ cycloalkyl groups is monocyclic or bicyclic; and where the groups R$^1$, R$^2$, R$^4$, R$^6$, R$^7$, R$^9$, and R$^{15}$ groups is an alkyl, alkenyl, alkynyl, haloalkyl, cycloalkyl, halocycloalkyl, heterocycloalkyl, aryl (e.g. phenyl) or heteroaryl groups, that group is optionally substituted, where chemically possible, by 1 to 5 substituents which are each independently at each occurrence selected from: oxo, =NR$^a$, =NOR$^a$, halo, nitro, cyano, NR$^a$R$^a$, NR$^a$S(O)$_2$R$^a$, NR$^a$-CONR$^a$R$^a$, NR$^a$CO$_2$R$^a$, OR$^a$; SR$^a$, S(O)R$^a$, S(O)$_2$OR$^a$, S(O)$_2$R$^a$, S(O)$_2$NR$^a$R$^a$, CO$_2$R$^a$C(O)R$^a$, CONR$^a$R$^a$, C$_1$-C$_4$-alkyl, C$_2$-C$_4$-alkenyl, C$_2$-C$_4$-alkynyl, C$_1$-C$_4$ haloalkyl, CR$^b$R$^b$OR$^a$, CR$^b$R$^b$NR$^a$R$^a$, and =CR$^b$CR$^b$R$^b$NR$^a$R$^a$; wherein R$^a$ is independently at each occurrence selected from: H, C$_1$-C$_4$ alkyl and C$_1$-C$_4$ haloalkyl; and R$^b$ is independently at each occurrence selected from: H, halogen, C$_1$-C$_4$ alkyl and C$_1$-C$_4$ haloalkyl.

In an embodiment, the compound of formula (I) is a compound of formula (II):

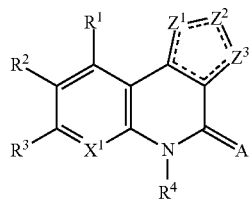

(II)

wherein R$^1$, R$^2$, R$^3$, R$^4$, X$^1$, A are as defined above for formula (I) and Z$^1$, Z$^2$ and Z$^3$, together with the carbon atoms to which Z$^1$ and Z$^3$ are attached form a 5-membered heteroaromatic ring as described above. Thus, Z$^1$ and Z$^3$ may each be independently selected from O, S, S(O), NR$^{11}$ and CR$^{12}$; Z$^2$ is independently selected from O, S, S(O), NR$^{11}$, CR$^{12}$ and C=W; wherein W is selected from O, S or NR$^6$; with the proviso that if Z$^2$ is not C=W, then the ring formed by Z$^1$, Z$^2$, Z$^3$ together with the carbon atoms to which Z$^1$ and Z$^3$ are attached contains two endocyclic double bonds and if Z$^2$ is C=W, the bond between the two carbon atoms to which Z$^1$ and Z$^3$ are attached is a double bond; and with the further proviso that at least one of Z$^1$, Z$^2$ and Z$^3$ is O, S or NR$^{11}$.

In an embodiment, the compound of formula (I) is a compound of formula (III):

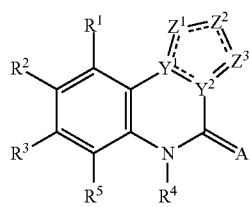

(III)

wherein R$^1$, R$^2$, R$^3$, R$^4$, R$^5$, A, Z$^1$, Z$^2$, Z$^3$, Y$^1$ and Y$^2$ are as defined above for formula (I).

In an embodiment, the compound of formula (I) is a compound of formula (IV):

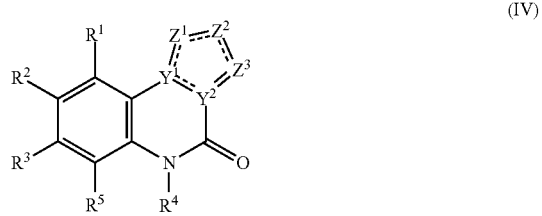

(IV)

wherein R$^1$, R$^2$, R$^3$, R$^4$, R$^5$, Z$^1$, Z$^2$, Z$^3$, Y$^1$ and Y$^2$ are as defined above for formula (I).

In an embodiment, the compound of formula (I) is a compound of formula (V):

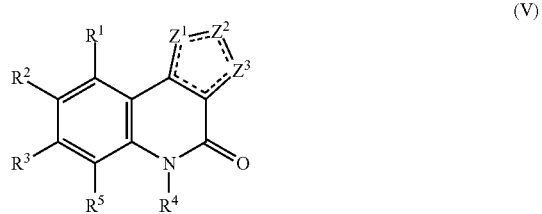

(V)

wherein R$^1$, R$^2$, R$^3$, R$^4$ and R$^5$ and are as defined above for formula (I) and Z$^1$, Z$^2$ and Z$^3$ are as defined above for formula (II). It may be that Z$^1$, Z$^2$ and Z$^3$ are selected such that the 5-membered ring which comprises Z$^1$, Z$^2$ and Z$^3$ is an oxazole, thiazole, isoxazole or thioxazole ring. Thus it may be that Z$^1$, Z$^2$ and Z$^3$ are selected from CR$^{12}$, O, S and N, wherein a single one of Z$^1$, Z$^2$ and Z$^3$ is N and that N must form part of a C=N endocyclic double bond; and wherein a single one of Z$^1$, Z$^2$ and Z$^3$ is CR$^{12}$. For the absence of doubt, the remaining Z$^1$, Z$^2$ or Z$^3$ is selected from O and S.

In an embodiment, the compound of formula (I) is a compound of formula (VI):

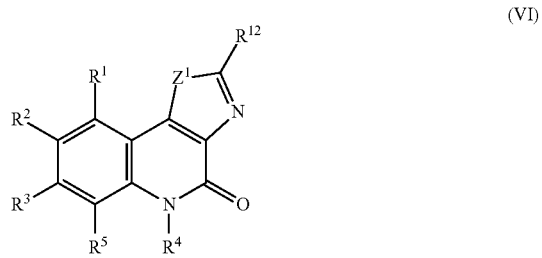

(VI)

wherein R$^1$, R$^2$, R$^3$, R$^4$, R$^5$ and R$^{12}$ are as defined above for formula (I) and wherein Z$^1$ is selected from S and O. It may be that Z$^1$ is O.

In an embodiment, the compound of formula (I) is a compound of formula (VII):

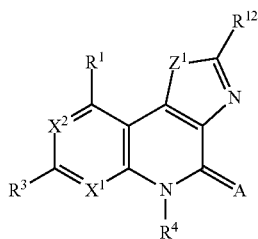
(VII)

wherein R$^1$, R$^2$, R$^3$, R$^4$, R$^{12}$, X$^1$, X$^2$ and A are as defined above for formula (I). Thus the compound may be a compound of formula (VIIa):

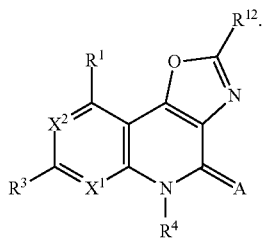
(VIIa)

In an embodiment, the compound of formula (I) is a compound of formula (VIII):

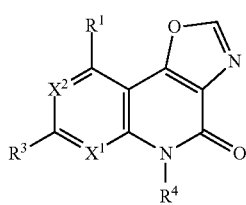
(VIII)

wherein R$^1$, R$^2$, R$^3$, R$^4$, X$^1$ and X$^2$ are as defined above for formula (I).

In an embodiment, the compound of formula (I) has a structure according to any one or more of formulae (IX) to (XXXXXVI):

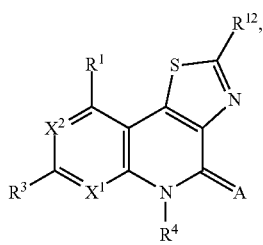
(IX)

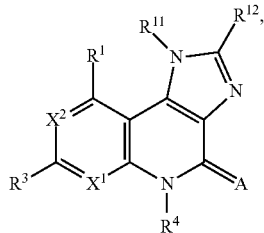
(X)

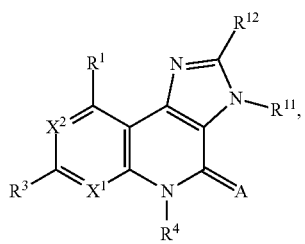
(XI)

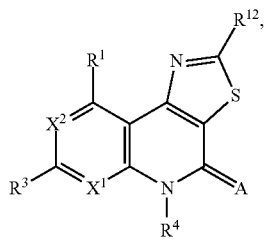
(XII)

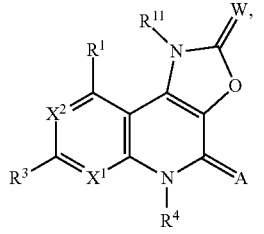
(XIII)

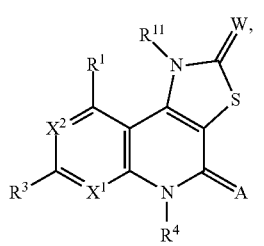
(XIV)

(XV)

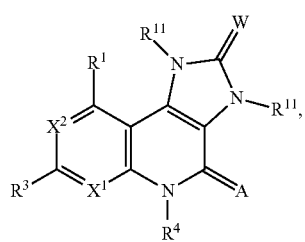
(XVI)
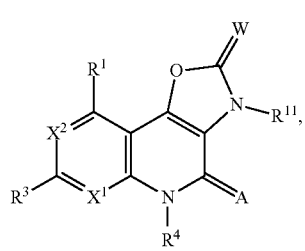
(XVII)
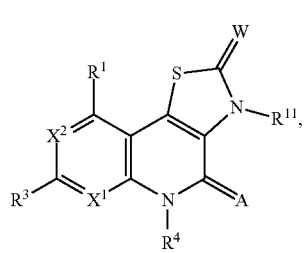
(XVIII)
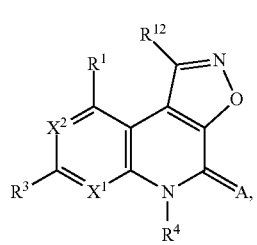
(XIX)
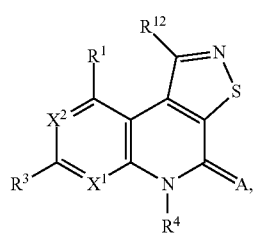
(XX)
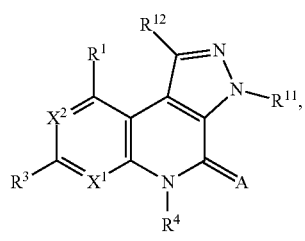
(XXI)
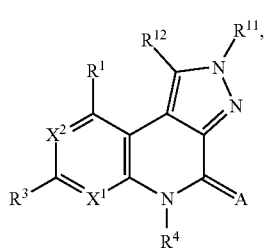
(XXII)
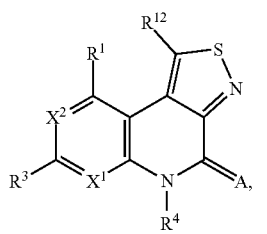
(XXIII)
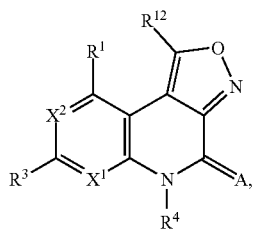
(XXIV)
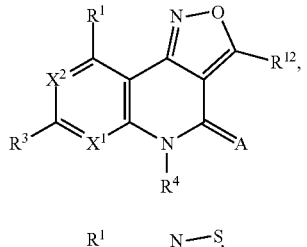
(XXV)
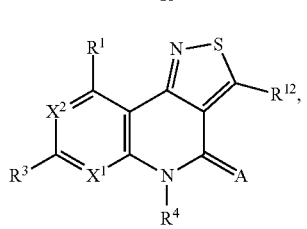
(XXVI)
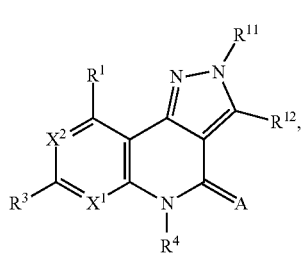
(XXVII)
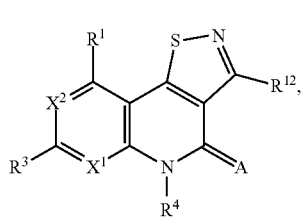
(XXVIII)

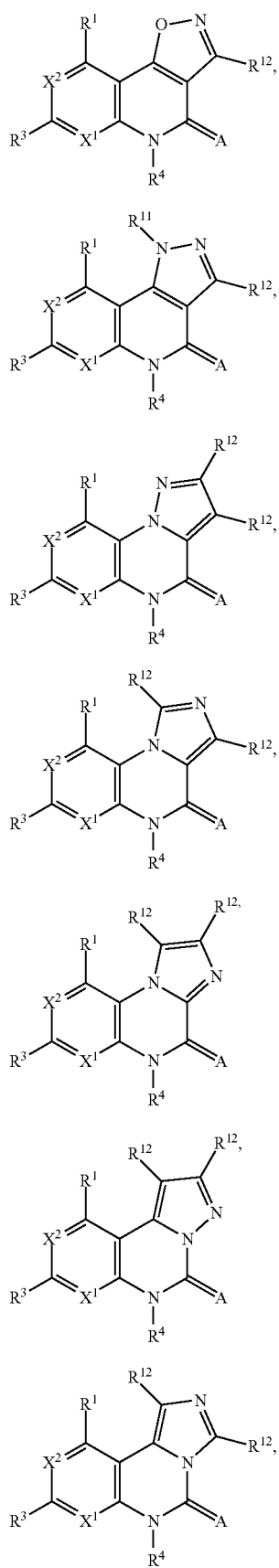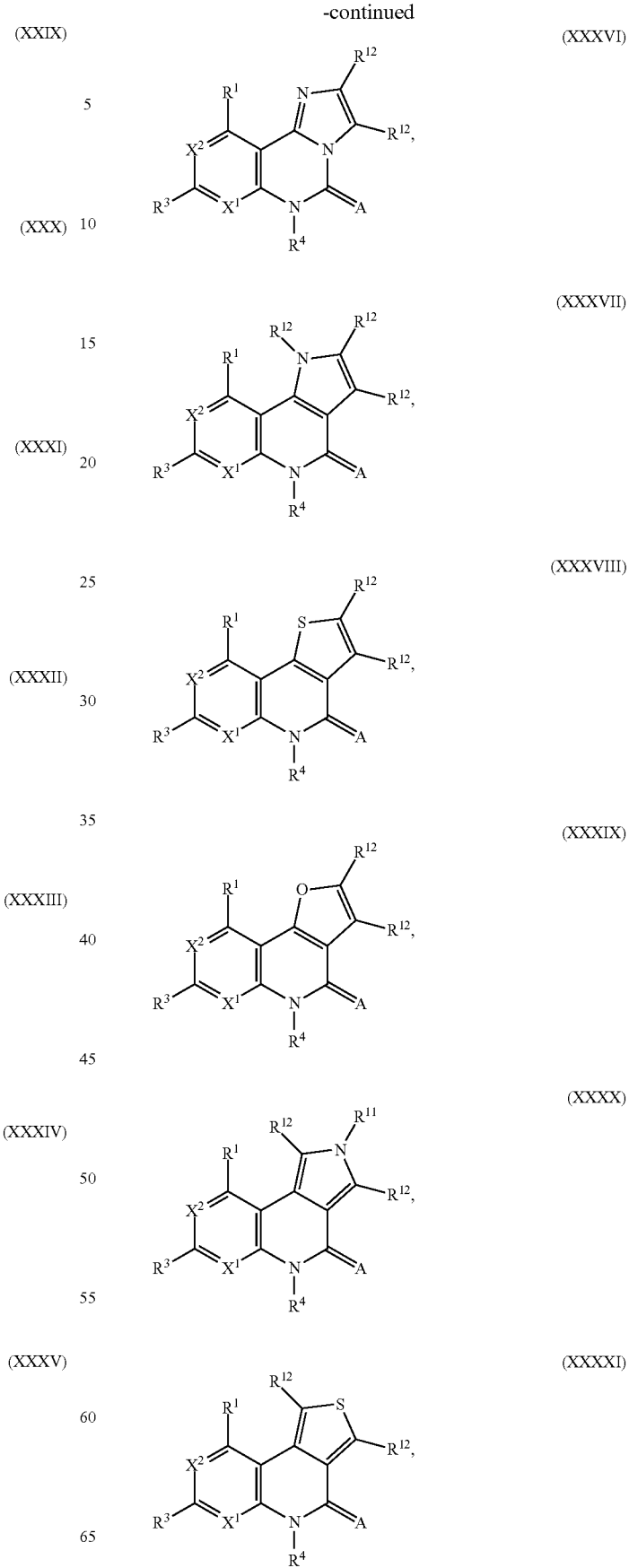

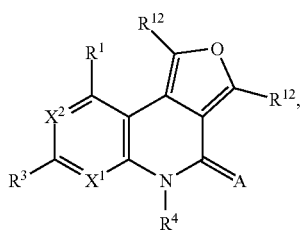
(XXXXII)
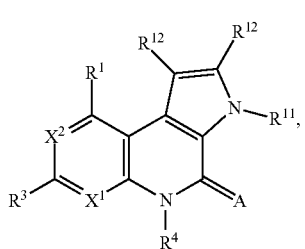
(XXXXIII)
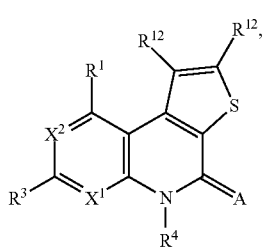
(XXXXIV)
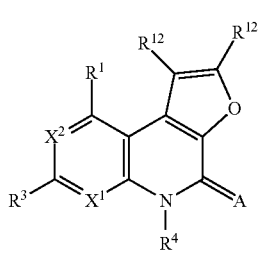
(XXXXV)
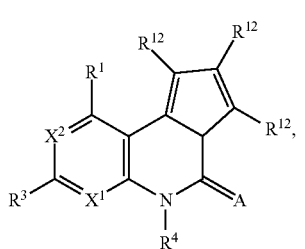
(XXXXVI)
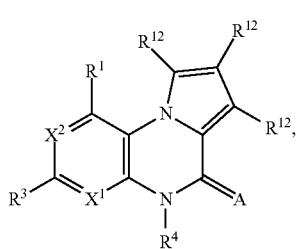
(XXXXVII)
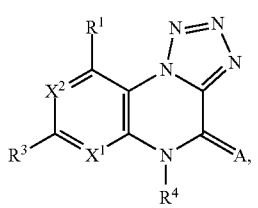
(XXXXVIII)
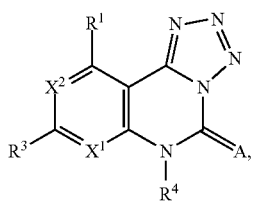
(XXXXIX)
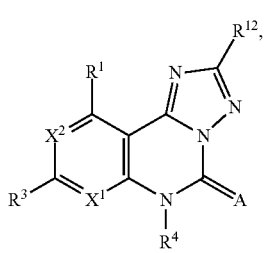
(XXXXX)
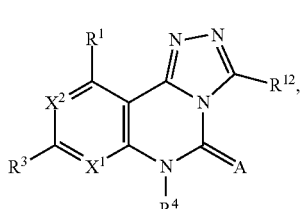
(XXXXXI)
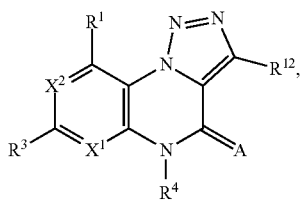
(XXXXXII)
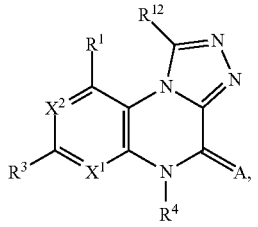
(XXXXXIII)
(XXXXXIV)

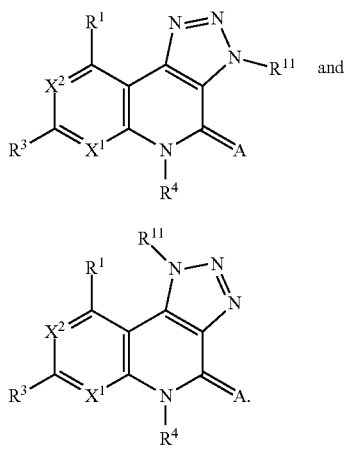

(XXXXXV) and (XXXXXVI)

wherein $R^1$, $R^2$, $R^3$, $R^4$, $R^{11}$, $R^{12}$, W, $X^1$, $X^2$ and A are as defined above for formula (I).

The following statements apply to compounds of any of formulae (I) to (XXXXXVI). These statements are independent and interchangeable. In other words, any of the features described in any one of the following statements may (where chemically allowable) be combined with the features described in one or more other statements below. In particular, where a compound is exemplified or illustrated in this specification, any two or more of the statements below which describe a feature of that compound, expressed at any level of generality, may be combined so as to represent subject matter which is contemplated as forming part of the disclosure of this invention in this specification.

$X^1$ may be N. Alternatively, $X^1$ may be $CR^5$.

$X^2$ may be N. Preferably, $X^2$ is $CR^2$.

A may be selected from O or S. Preferably, A is O.

Preferably, $R^1$ is independently selected from: H, $NR^7R^7$, and $C_1$-$C_4$-alkyl. Thus, $R^1$ may be H. $R^1$ may be $NR^7R^7$, e.g. $NHR^7$. $R^1$ may be $C_1$-$C_4$-alkyl, e.g. methyl.

$R^2$ may be independently selected from: H and F. $R^2$ may be H. $R^2$ may be halo, e.g. F.

$R^3$ is independently selected from: $_3$-10 heterocycloalkyl, phenyl, and 5, 6- or 9 membered heteroaryl comprising 1 or 2 nitrogen atoms within the ring system; wherein the aryl, heteroaryl or heterocycloalkyl group is optionally substituted with 1, 2 or 3 $R^{15}$ groups; wherein $R^{15}$ is independently at each occurrence selected from: oxo, =$NR^6$, =$NOR^6$, $_{3-5}$-heterocycloalkyl, halo, nitro, cyano, $NR^6R^7$, $NR^6CONR^6R^6$, $OR^6$; $SR^6$, $SOR^6$, $S(O)_2OR^6$, $S(O)_2R^6$, $S(O)_2NR^6R^6$, $CO_2R^6$, $C(O)R^6$, $CONR^6R^6$, $C_1$-$C_4$-alkyl, $C_2$-$C_4$-alkenyl, $C_2$-$C_4$-alkynyl, $C_1$-$C_4$ haloalkyl, $CR^6R^6OR^6$, $CR^6R^6NR^7R^6$, and =$CR^6CR^6R^6NR^7R^7$.

$R^3$ may be —$(CR^8R^9)_{n\text{-}3\text{-}10}$ heterocycloalkyl, e.g. $_{3-10}$ heterocycloalkyl. Typically, $R^3$ will be an N-heterocycloalkyl group. N-heterocycloalkyl groups may be monocyclic or bicyclic and comprise 1 to 3 nitrogen atoms in the heterocyclic ring system and $R^3$ may be attached to the rest of the molecule via a carbon or a nitrogen in the ring system. It may be that the N-heterocycloalkyl group is attached to the rest of the molecule via the or each nitrogen in the ring system. Any nitrogen in the ring system which is not at a bridgehead or is not the point of attachment of $R^3$ to the rest of the molecule will be $NR^{17}$; wherein $R^{17}$ is independently selected from: H, $C_1$-$C_4$ alkyl. Unless otherwise stated, any N-heterocycloalkyl group mentioned as a possibility for $R^3$ may be unsubstituted or may be substituted with 1 to 3 $R^{15}$ groups selected from oxo, =$NOR^6$, $NR^6R^7$, $OR^6$, $C_1$-$C_4$-alkyl, $C_2$-$C_4$-alkenyl, $C_2$-$C_4$-alkynyl, $CR^6R^6NR^6R^7$ and =$CR^6CR^6R^6NR^6R^7$.

$R^3$ may be a monocyclic $C_3$-$C_7$N-heterocycloalkyl group. Thus, $R^3$ may be a piperazine ring. $R^3$ may thus be a piperazine ring substituted with a methyl group, e.g. an N-methyl piperazine ring, a 3-methyl piperazine ring, or a 2-methyl piperazine ring. Alternatively, $R^3$ may be an unsubstituted piperizine group. Any piperazine group will typically be attached to the rest of the molecule via one of the nitrogens in the ring system. Possibly, $R^3$ is an azetidine, pyrrolidine or piperidine ring, optionally wherein the ring nitrogen attaches the aziridine, pyrrolidine or piperidine ring to the rest of the compound. $R^3$ may be an azetidine, pyrrolidine or piperidine ring wherein the ring nitrogen attaches the azetidine, pyrrolidine or piperidine ring to the rest of the compound and which is substituted with a single hydroxyl group. $R^3$ may be a piperidine ring substituted with a single hydroxyl group, e.g. a 4-hydroxy-piperidine ring. $R^3$ may be a pyrrolidine substituted with a single hydroxyl group, e.g. a 3-hydroxypyrrolidine. $R^3$ is a 3-hydroxy aziridine group. $R^3$ may be a bicylic $C^7$-$C^{10}$N-heterocycloalkyl group. Specific examples of $R^3$ groups include:

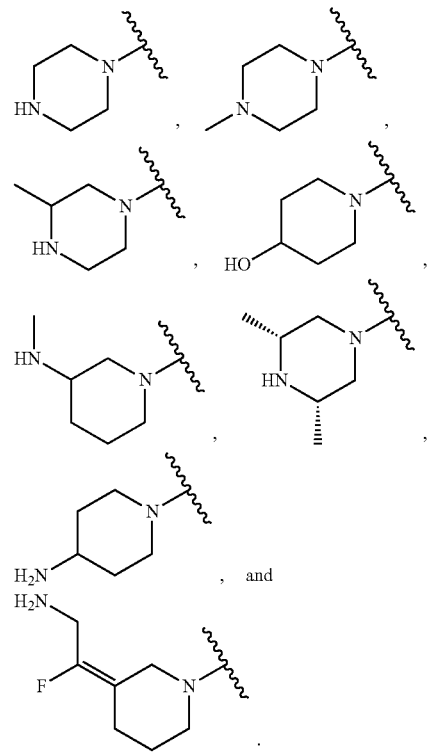

Further examples include:

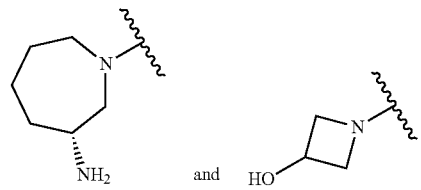

$R^3$ may be a bicyclic $C_7$-$C_{10}$N-heterocycloalkyl group. The bicyclic N-heterocycloalkyl group may be attached to the rest of the molecule via either a carbon or a nitrogen in the ring system.

Preferably, $R^3$ is

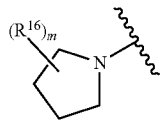

wherein $R^{16}$ is $R^{15}$; or wherein two $R^{16}$ groups together with the carbon or carbons to which they are attached form a 3-6 membered cycloalkyl, a 3-6 membered heterocycloalkyl ring or a 6-membered aryl or 5- or 6-membered heteroaryl ring. Where two $R^{16}$ groups form a heterocycloalkyl ring, that ring will comprise 1 or 2 heteroatoms selected from N, O and S in the ring system. Where two $R^{16}$ groups form a cycloalkyl, heterocycloalkyl ring, that ring may be substituted with one or two $R^{15}$ groups; wherein $R^{15}$ is independently selected from oxo, =NOR$^6$, NR$^6$R$^7$, OR$^6$, $C_1$-$C_4$-alkyl, $C_2$-$C_4$-alkenyl, $C_2$-$C_4$-alkynyl, CR$^6$R$^6$NR$^6$R$^7$ and =CR$^6$CR$^6$R$^6$NR$^6$R$^7$. m is an integer independently selected from 0, 1, 2, 3 and 4.

It may be that two $R^{16}$ groups do not form a cycloalkyl or heterocycloalkyl ring. In other words $R^3$ may be

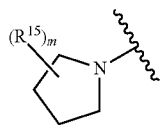

m may be 1. Thus, $R^3$ may be

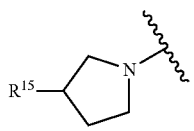

$R^{15}$ may be NR$^6$R$^7$. Each $R^6$ and $R^7$ in $R^{15}$ may be H (e.g. $R^{15}$ may be NH$_2$). Each $R^6$ and $R^7$ in $R^{15}$ may independently be $C_1$-$C_4$ alkyl, e.g. each $R^6$ and $R^7$ in $R^{15}$ may independently be methyl (e.g. $R^{15}$ may be NMe$_2$). $R^{15}$ may be OR$^6$. $R^6$ may be H and thus, $R^{15}$ may be OH. $R^{15}$ may be CR$^6$R$^6$NR$^6$R$^7$. $R^{15}$ may be CMe$_2$NR$^6$R$^7$ ... $R^{15}$ may be CR$^6$R$^6$NH$_2$. $R^{15}$ may be CMe$_2$NH$_2$.

m may be 2. In one particular example where m is 2, $R^{15}$ may at one instance be =NOR$^6$ (e.g. =NOMe), and at the other instance be CR$^6$R$^6$NR$^6$R$^7$ (e.g. CH$_2$NR$^6$R$^7$ or CH$_2$NH$_2$).

Two $R^{16}$ groups may form a 3-6 membered heterocycloalkyl ring, e.g. a 6-membered heterocycloalkyl ring, e.g. a vicinally fused 6 membered heterocycloalkyl ring. A specific example of a 6-membered heterocycloalkyl ring would be a morpholine ring. The two $R^{16}$ groups may also form a 3-6 membered cycloalkyl ring, e.g. a 3-membered ring. Thus, two $R^{16}$ groups may form a vicinally fused 3-membered ring or a spiro fused 3-membered ring. That 3-membered ring (e.g. that vicinally fused 3-membered ring) may be substituted with one or two $R^{15}$ groups independently selected from oxo, =NOR$^6$, NR$^6$R$^7$, OR$^6$, $C_1$-$C_4$-alkyl, $C_2$-$C_4$-alkenyl, $C_2$-$C_4$-alkynyl, CR$^6$R$^6$NR$^6$R$^7$ and =CR$^6$CR$^6$R$^6$NR$^6$R$^7$. Thus, the 3-membered ring (e.g. that vicinally fused 3-membered ring) may be substituted with an NR$^6$R$^7$ group, e.g. a NH$_2$ group.

In cases in which two $R^{16}$ groups form a 3 to 6-membered cycloalkyl or 3 to 6-membered heterocycloalkyl ring, there may be one or more other $R^{16}$ groups, e.g. m may be 4. Such additional $R^{16}$ groups will generally not form a 3 to 6-membered cycloalkyl or a 3 to 6-membered heterocycloalkyl ring and will thus be $R^{15}$ groups. $R^{15}$ may be $C_1$-$C_4$ alkyl, e.g. methyl. $R^{15}$ may be NR$^6$R$^7$, e.g. NH$_2$.

Specific examples of $R^3$ groups include:

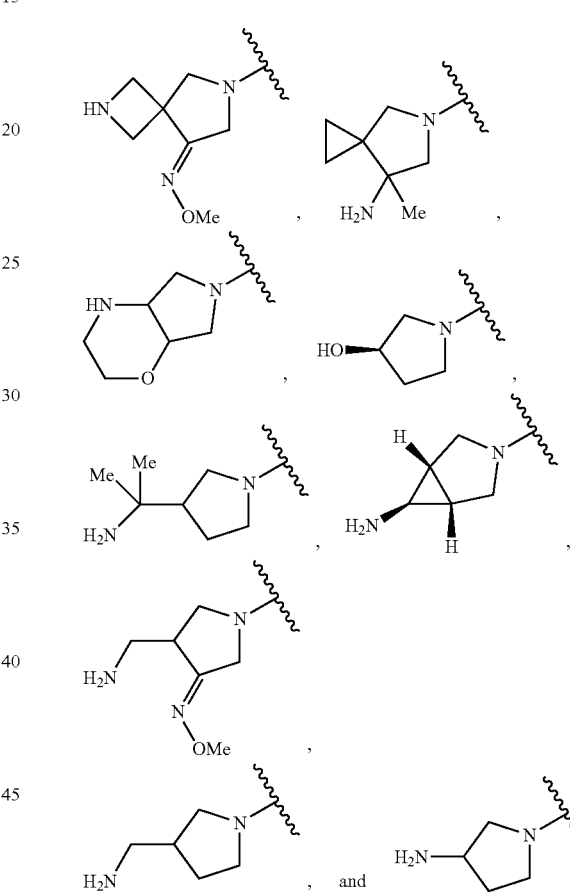

$R^3$ may be $C_3$-$C_8$ cycloalkyl group. Typically, where $R^3$ is a $C_3$-$C_8$ cycloalkyl group, it is substituted with at least one group selected from NR$^6$R$^7$, OR$^6$, $C_1$-$C_4$-alkyl, $C_2$-$C_4$-alkenyl, $C_2$-$C_4$-alkynyl, CR$^8$R$^8$NR$^6$R$^7$ and =CR$^6$CR$^8$R$^8$NR$^6$R$^7$. Specifically, $R^3$ may be a cyclopropyl group substituted with a NH$_2$ group.

A specific example of an $R^3$ group is

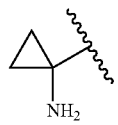

$R^3$ may be an aryl group, e.g. a phenyl group. $R^3$ may be a phenyl group with at least one NR$^6$R$^7$, CONR$^6$R$^6$, CR⁶R⁶OR⁶ or CR⁶R⁶NR⁶R⁷ group and optionally further substituted with from 1 to 3 groups independently selected from halo, C₁-C₄ haloalkyl and C₁-C₄ alkyl, e.g. a phenyl group with at least one NR⁶R⁷, CONR⁶R⁶, or CR⁶R⁶NR⁶R⁷ group and optionally further substituted with from 1 to 3 halo groups (e.g. fluoro groups). Thus, R³ may be a phenyl group with at least one NR⁶R⁷ or CR⁶R⁶NR⁶R⁷ group and optionally further substituted with from 1-3 groups independently selected from halo, C₁-C₄ haloalkyl and C₁-C₄ alkyl, e.g. a phenyl group with at least one NR⁶R⁷ or CR⁶R⁶NR⁶R⁷ group and optionally further substituted with from 1-3 halo groups (e.g. fluoro groups). In particular embodiments, R³ may be a group selected from:

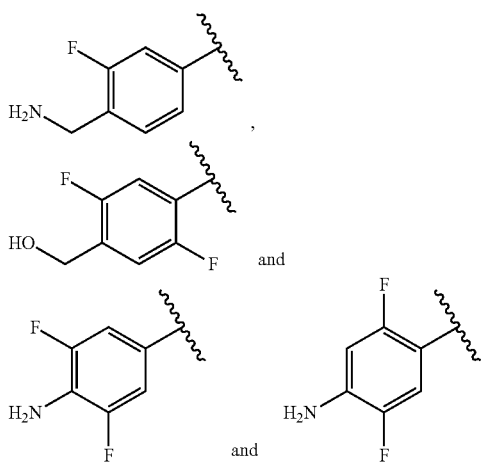

R³ may also be a heteroaryl group. R³ may be a heteroaryl group comprising at least one nitrogen atom in the ring structure. R³ may be a heteroaryl group comprising at least one nitrogen atom in the ring system and substituted with at least one NR⁶R⁷, CONR⁶R⁶, or CR⁶R⁶NR⁶R⁷ group and optionally further substituted with from 1 to 3 groups independently selected from halo, C₁-C₄ haloalkyl and C₁-C₄ alkyl. R³ may be a heteroaryl group comprising at least one nitrogen atom in the ring system and substituted with at least one NR⁶R⁷ group.

Exemplary R³ groups include:

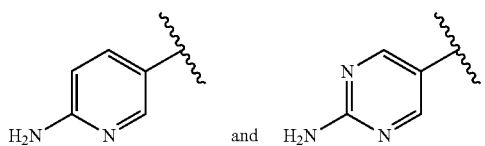

R³ may be a 9-membered bicyclic heteroaryl group. R³ may be a 9-membered heteroaryl group comprising 1, 2 or 3 (e.g. 1 or 2) nitrogen atoms in the ring system. R³ may be an indazole group, e.g. R³ may be

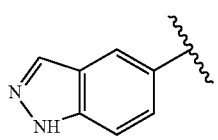

R³ may be a benzimiazole, e.g. R³ may be

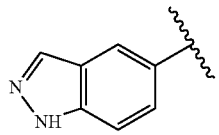

R³ may be a benzoxadiazole, e.g. R³ may be

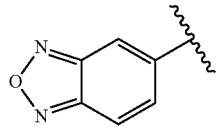

R³ may be indole, e.g. R³ may be

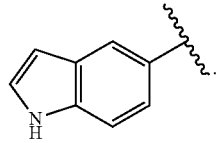 [SMILES: *c1ccc2[nH]ccc2c1]

It may be that R³ is not a benztriazole. R³ may comprise a pyridine ring fused to a 5 membered heteroaryl ring, e.g. a 5-membered heteroaryl ring comprising 1 or 2 nitrogen atoms in the ring. Thus, further exemplary R³ groups include

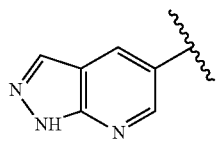 [SMILES: *c1cnc2[nH]ncc2c1]

and

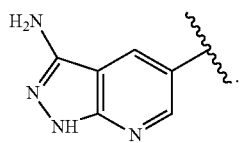

R³ may be a 6-membered monocyclic heteroaryl group comprising from 1 to 2 nitrogen atoms in the ring system. Thus R³ may be a group selected from pyridinyl, pyrimidine, pyrazine. Where R³ is a 6-membered monocyclic heteroaryl group, it may be substituted with at least one NR⁶R⁷, CONR⁶R⁶, or CR⁶R⁶NR⁶R⁷ group and optionally further substituted with from 1 to 3 groups independently selected from halo, C₁-C₄ haloalkyl and C₁-C₄ alkyl. Where R³ is a 6-membered monocyclic heteroaryl group, it may be substituted with at least one NR⁶R⁷ group. Thus, R³ may be an amino-pyridinyl group (e.g. a 6-amino-pyridin-3-yl group) or an amino pyrimidine (e.g. 2-amino-pyrimidin-5-yl group).

R³ may be a 5-membered monocyclic heteroaryl group comprising from 1 to 2 nitrogen atoms in the ring system, e.g. a thiazole or pyrazole.

In certain preferred embodiments, $R^3$ is selected from phenyl, pyridinyl, pyrimidine, pyrazine and 9-membered heteroaryl group comprising 1 or 2 nitrogen atoms in the ring system.

In certain preferred embodiments, $R^3$ is selected from phenyl or 6-membered heteroaryl (e.g. pyridine or pyrimidine) and has an $NR^6R^7$ (e.g. an $NH_2$) group situated para to the position at which the $R^3$ group is attached to the rest of the molecule.

$R^4$ may independently be selected from: $C_1$-$C_6$ alkyl, $C_1$-$C_6$ haloalkyl, $-(CR^8R^8)_n$-$C_3$-$C_6$ cycloalkyl, $-(CR^8R^8)_n$-$C_3$-$C_6$ halocycloalkyl; $-(CR^8R^8)_n$-phenyl and $-(CR^8R^8)_n$-pyridyl. Preferably, $R^4$ may independently selected from $C_1$-$C_6$ alkyl, $C_1$-$C_6$ haloalkyl, $-(CR^8R^8)_n$-$C_3$-$C_6$ cycloalkyl and $-(CR^8R^8)_n$-$C_3$-$C_6$ halocycloalkyl. Preferably, n is 0. $R^4$ may be selected from $C_1$-$C_6$ alkyl and $-(CH_2)_n$-$C_3$-$C_6$ cycloalkyl, wherein n is an integer selected from 0, 1, 2 and 3. Alternatively, $R^4$ may be selected from $C_1$-$C_6$ haloalkyl and $-(CR^8R^8)_n$-$C_3$-$C_6$ halocycloalkyl, wherein n is an integer selected from 0, 1, 2 and 3. Thus, $R^4$ may be selected from $C_1$-$C_6$ alkyl (e.g. $C_2$-$C_4$ alkyl) and $C_3$-$C_6$ cycloalkyl (e.g. $C_3$-$C_4$ cycloalkyl). $R^4$ may be selected from $C_3$-$C_6$ cycloalkyl and $C_3$-$C_6$ halocycloalkyl. $R^4$ may be $C_3$-$C_6$ cycloalkyl. In a particular embodiment, $R^4$ is ethyl. In another particular embodiment, $R^4$ is cyclopropyl.

$R^5$ may be independently selected from: H, O—$C_1$-$C_4$ alkyl, halo, $C_1$-$C_4$ alkyl, $C_1$-$C_4$ haloalkyl and O—$C_1$-$C_4$ haloalkyl. Preferably, $R^5$ is independently selected from: O—$C_1$-$C_4$ alkyl, $C_1$-$C_4$ alkyl, $C_1$-$C_4$ haloalkyl and O—$C_1$-$C_4$ haloalkyl. $R^5$ may be H. $R^5$ may be $C_1$ or F. $R^5$ may be methyl. $R^5$ may be OMe.

It may be that $R^2$ is F and $R^5$ is H. It may be that $R^2$ is H and $R^5$ is $C_1$-$C_4$ alkyl, (e.g. Me). It may be that $R^2$ is F and $R^5$ is Cl.

In a preferred alternative, $R^4$ and $R^5$ together form an alkylene or heteroalkylene chain of the form $-(CR^8R^8)_r-W^1-(CR^8R^8)_s-W^2-(CR^8R^8)_t-$ and which is attached at its respective ends to the substitution point for $R^4$ and $R^5$ respectively; wherein $W^1$ and $W^2$ are each independently selected from: a bond, O, S and $NR^9$; wherein r, s, and t are each independently an integer selected from 0, 1 and 2 and wherein definitions of r, s, t, $W^1$ and $W^2$ are chosen such that the total length of the alkylene or heteroalkylene chain is 2, 3 or 4 atoms. It may be that r, s, t, $W^1$ and $W^2$ are chosen such that the total length of the alkylene or heteroalkylene chain is 3 atoms. It may be that r is 0 and $W^1$ is O. Preferably, $R^4$ and $R^5$ may together form an alkylene or heteroalkylene chain of the form $-W^1-(CR^8R^8)_s-$. For the absence of doubt, $W^1$ is attached to the rest of the molecule at the substitution point for $R^5$ and the $CR^8R^8$ at the opposite end of the chain to $W^1$ is attached to the rest of the molecule at the substitution point for $R^4$. Preferably, s is 2. Preferably, $W^1$ is O.

Thus, preferably, $R^5$ is independently selected from: Cl, O—$C_1$-$C_4$ alkyl, $C_1$-$C_4$ alkyl, $C_1$-$C_4$ haloalkyl and O—$C_1$-$C_4$ haloalkyl; or $R^4$ and $R^5$ may together form an alkylene or heteroalkylene chain of the form —O—$(CR^8R^8)_2$— and which is attached at its respective ends to the substitution point for $R^4$ and $R^5$ respectively.

In certain preferred embodiments, $R^5$ is Me and $R^4$ is cyclopropyl.

It may be that n is always 0.

It may be that A is O; $R^1$ is independently selected from: H, $NR^6R^7$, and $C_1$-$C_4$-alkyl; $X^1$ is $CR^5$; $X^2$ is $CR^2$; $R^4$ is independently selected from $C_1$-$C_6$ alkyl, $C_1$-$C_6$ haloalkyl, $-(CR^8R^8)_n$-$C_3$-$C_6$ cycloalkyl and $-(CR^8R^8)_n$-$C_3$-$C_6$ halocycloalkyl and $R^5$ is independently selected from: Cl, O—$C_1$-$C_4$ alkyl, $C_1$-$C_4$ alkyl, $C_1$-$C_4$ haloalkyl and O—$C_1$-$C_4$ haloalkyl; or $R^4$ and $R^5$ may together form an alkylene or heteroalkylene chain of the form —O—$(CR^8R^8)_2$— and which is attached at its respective ends to the substitution point for $R^4$ and $R^5$ respectively.

Furthermore, it may be that $R^1$ is H. It may also be that $R^5$ is $C_1$-$C_4$ alkyl. $R^3$ may be selected from phenyl and 6- or 9-membered heteroaryl comprising at least one nitrogen.

It may be that $Y^1$ and $Y^2$ are both C. Preferably, $Y^1$ and $Y^2$ are not both N.

It may be that no more than one of $Z^1$, $Z^2$ and $Z^3$ is selected from N or $NR^{11}$. Thus, $Z^1$ and $Z^3$ may each be independently selected from O, S, S(O), $NR^{11}$ and $CR^{12}$; $Z^2$ is independently selected from O, S, S(O), $NR^{11}$, $CR^{12}$ and C=W; wherein W is selected from O, S or $NR^6$; with the proviso that if $Z^2$ is not C=W, then the ring formed by $Y^1$, $Y^2$, $Z^1$, $Z^2$, $Z^3$ contains two endocyclic double bonds and if $Z^2$ is C=W, the bond between $Y^1$ and $Y^2$ (which may both be C) is a double bond; and with the further proviso that at least one of $Z^1$, $Z^2$ and $Z^3$ is O, S or $NR^{11}$. It may be that $Z^2$ is C=W, e.g. C=O.

It may be that $Z^1$, $Z^2$ and $Z^3$ are each independently selected from O, S, $NR^{11}$ and $CR^{12}$. Thus, it may be that $Y^1$ and $Y^2$ are each independently selected from C and N; $Z^1$, $Z^2$ and $Z^3$ are each independently selected from O, S, $NR^{11}$ and $CR^{12}$; with the proviso that the ring formed by $Z^1$, $Z^2$, $Z^3$, $Y^1$ and $Y^2$ contains two endocyclic double bonds; and with the further proviso that at least one of $Z^1$, $Z^2$, $Z^3$, $Y^1$ and $Y^2$ is O, S, N or $NR^{11}$.

It may be that $Z^1$, $Z^2$, $Z^3$, $Y^1$ and $Y^2$ together form an imidazole, tetrazole, pyrazole or pyrole ring. It may be that one of $Y^1$ and $Y^2$ is N and the other is C. Thus, it may be that $Z^1$, $Z^2$, $Z^3$, $Y^1$ and $Y^2$ together form an imidazole, tetrazole, pyrazole or pyrole ring in which one of $Y^1$ and $Y^2$ is N. It may be that $Y^1$ is N. It may be that $Y^2$ is N.

It may be that $Z^1$, $Z^2$, $Z^3$, $Y^1$ and $Y^2$ together form a thiophene, furan, or pyrrole ring. Thus, it may be that a single one of $Z^1$, $Z^2$ and $Z^3$ is independently selected from O, S and $NR^{11}$ and the remaining two of $Z^1$, $Z^2$ and $Z^3$ are each $CR^{12}$.

It may be that $Z^1$, $Z^2$, $Z^3$, $Y^1$ and $Y^2$ together form a pyrazole, oxazole, imidazole, thiazole, isoxazole or isothiazole ring. Thus, it may be that a single one of $Z^1$, $Z^2$ and $Z^3$ is independently $CR^{12}$ and the remaining two of $Z^1$, $Z^2$ and $Z^3$ are selected from O, S and $NR^{11}$.

It may be that $Z^1$, $Z^2$, $Z^3$, $Y^1$ and $Y^2$ together form a oxazole, thiazole, isoxazole or isothiazole ring. Thus, it may be that both $Y^1$ and $Y^2$ are C and $Z^1$, $Z^2$ and $Z^3$ are selected from $CR^{12}$, O, S and N; wherein a single one of $Z^1$, $Z^2$ and $Z^3$ is N and that N must form part of a C=N endocyclic double bond; and wherein a single one of $Z^1$, $Z^2$ and $Z^3$ is $CR^{12}$. For the absence of doubt, the remaining $Z^1$, $Z^2$ or $Z^3$ is selected from O and S.

$R^{12}$ may be independently at each occurrence selected from: H, halo, nitro, cyano, $S(O)R^{13}$, $S(O)_2OR^{13}$, $S(O)_2R^{13}$, $S(O)_2NR^{13}R^{14}$, $CO_2R^{13}C(O)R^{13}$, $CONR^{13}R^{13}$, $C_1$-$C_4$-alkyl, $C_2$-$C_4$-alkynyl, $C_2$-$C_4$-alkenyl, $C_1$-$C_4$ haloalkyl, $CR^{13}R^{13}OR^{13}$ and $CR^{13}R^{13}NR^{13}R^{14}$. $R^{12}$ may be independently at each occurrence selected from: halo, nitro, cyano, $S(O)R^{13}$, $S(O)_2OR^{13}$, $S(O)_2R^{13}$, $S(O)_2NR^{13}R^{13}$, $CO_2R^{13}$, $C(O)R^{13}$, $CONR^{13}R^{13}$, $C_1$-$C_4$-alkyl, $C_2$-$C_4$-alkynyl, $C_2$-$C_4$-alkenyl, $C_1$-$C_4$ haloalkyl, $CR^{13}R^{13}OR^{13}$ and $CR^{13}R^{13}NR^{13}R^{14}$. $R^{12}$ may be independently at each occurrence selected from: H, halo, nitro, $C_1$-$C_4$-alkyl, $C_2$-$C_4$-alkenyl, $C_2$-$C_4$-alkynyl, $C_1$-$C_4$ haloalkyl. $R^{12}$ may be independently at each occurrence selected from: halo, nitro, $C_1$-$C_4$-alkyl, $C_2$-$C_4$-alkenyl, $C_2$-$C_4$-alkynyl, $C_1$-$C_4$ haloalkyl $CR^{13}R^{13}OR^{13}$ and $CR^{13}R^{13}NR^{13}R^{14}$, $R^{12}$ may be independently at each occurrence selected from: $C_1$-$C_4$-alkyl, $C_2$-$C_4$-alkenyl, $C_2$-$C_4$-alkynyl, $C_1$-$C_4$ haloalkyl $CR^{13}R^{13}OR^{13}$ and $CR^{13}R^{13}NR^{13}R^{14}$. $R^{12}$ may be independently at each occurrence selected from: H, $C_1$-$C_4$-alkyl, $C_2$-$C_4$-alkenyl, $C_2$-$C_4$-alkynyl, $C_1$-$C_4$ haloalkyl $CR^{13}R^{13}OR^{13}$ and $CR^{13}R^{13}NR^{13}R^{14}$, $R^{12}$ may be independently at each occurrence selected from: H, $C_1$-$C_4$-alkyl, $CR^{13}R^{13}OR^{13}$ and $CR^{13}R^{13}NR^{13}R^{14}$. $R^{12}$ may be independently selected from $CR^{13}R^{13}OR^{13}$ and $CR^{13}R^{13}NR^{13}R^{14}$. $R^{12}$ may be $CR^{13}R^{13}NR^{13}R^{14}$.

Where present, W is preferably O.

It may be that A is O; $R^1$ is H; $X^1$ is $CR^5$; $X^2$ is $CR^2$; $R^3$ is selected from phenyl and 6- or 9-membered heteroaryl comprising at least one nitrogen; $R^4$ is independently selected from $C_1$-$C_4$ alkyl, $C_1$-$C_4$ haloalkyl, cyclopropyl and halocyclopropyl and $R^5$ is independently selected from: O—$C_1$-$C_4$ alkyl, $C_1$-$C_4$ alkyl; or $R^4$ and $R^5$ may together form an alkylene or heteroalkylene chain of the form —O—$(CR^8R^9)_2$— and which is attached at its respective ends to the substitution point for $R^4$ and $R^5$ respectively; both $Y^1$ and $Y^2$ are C and $Z^1$, $Z^2$ and $Z^3$ are selected from $CR^{12}$, O, S and N; wherein a single one of $Z^1$, $Z^2$ and $Z^3$ is N and that N must form part of a C=N endocyclic double bond; wherein a single one of $Z^1$, $Z^2$ and $Z^3$ is $CR^{12}$ and wherein $R^{12}$ is independently at each occurrence selected from: H, $C_1$-$C_4$-alkyl, $CR^{13}R^{13}OR^{13}$ and $CR^{13}R^{13}NR^{13}R^{14}$.

The compound of formula (I) may be any one of Examples 1 to 110 below, either in the form of a free base or of a pharmaceutically acceptable salt.

The compound of formula (I) may be:

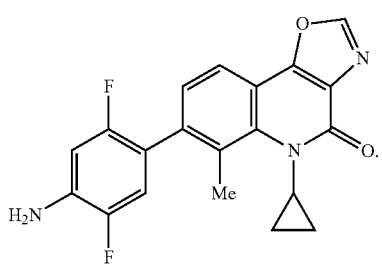 [SMILES: Cc1c(-c2cc(F)c(N)cc2F)ccc2c3ocnc3c(=O)n(C3CC3)c12]

The compound of formula (I) may be selected from:

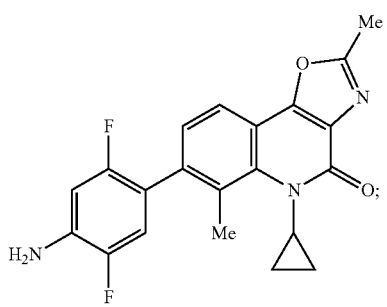

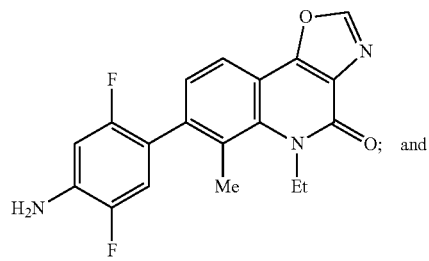

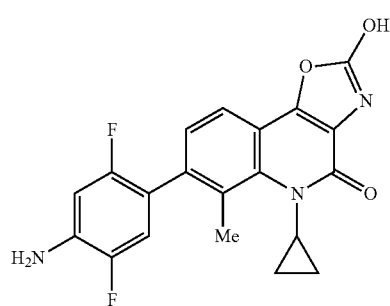

(which may be present in the form

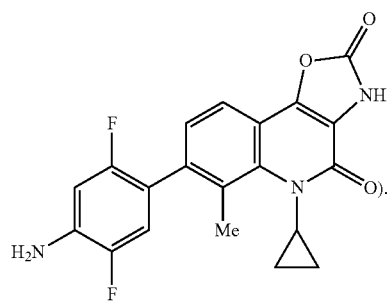

The compound of formula (I) may be selected from:

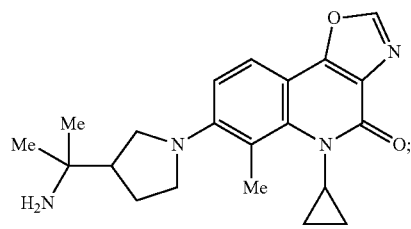

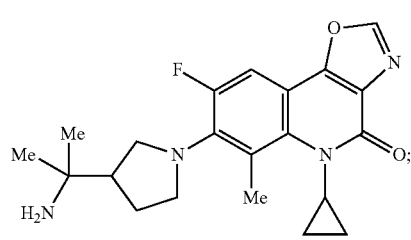

-continued
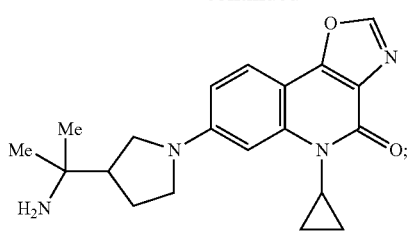
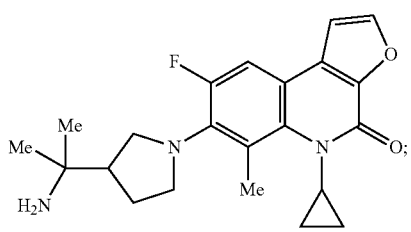
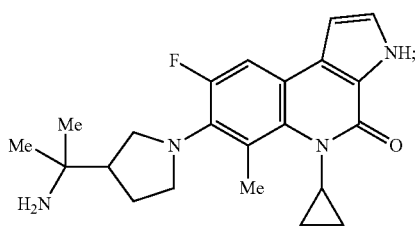
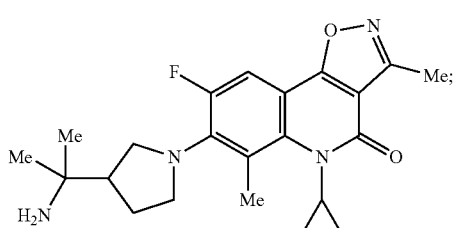
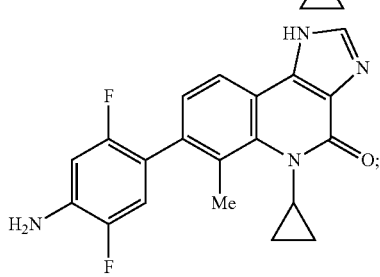
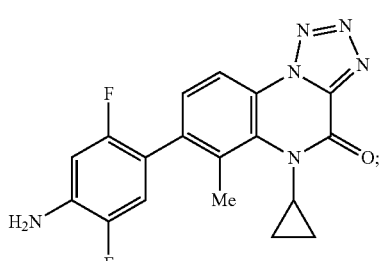
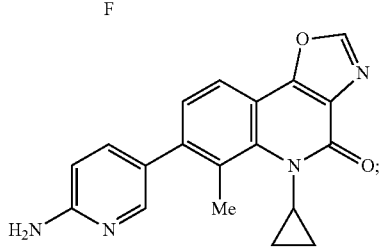
-continued
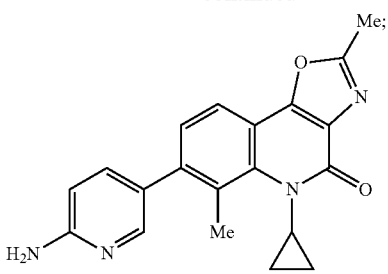
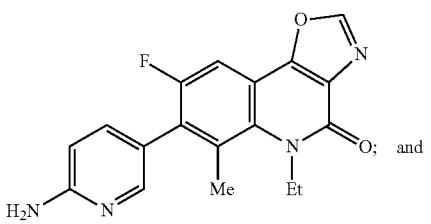
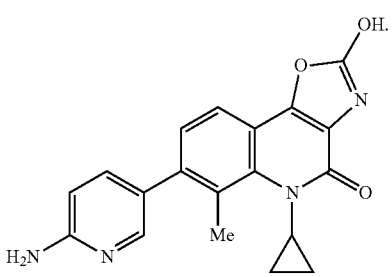
The compound may be selected from:
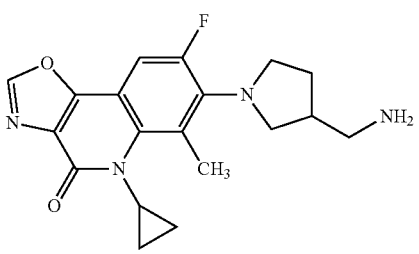
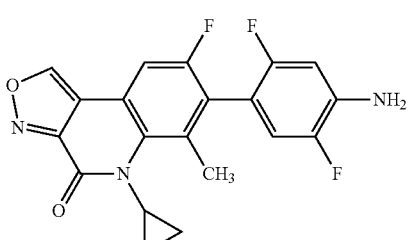
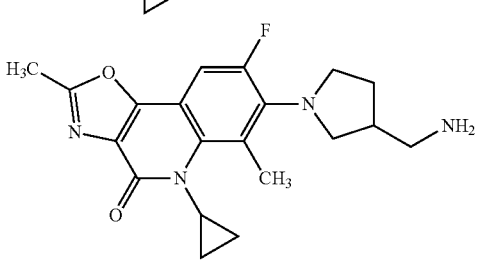

-continued
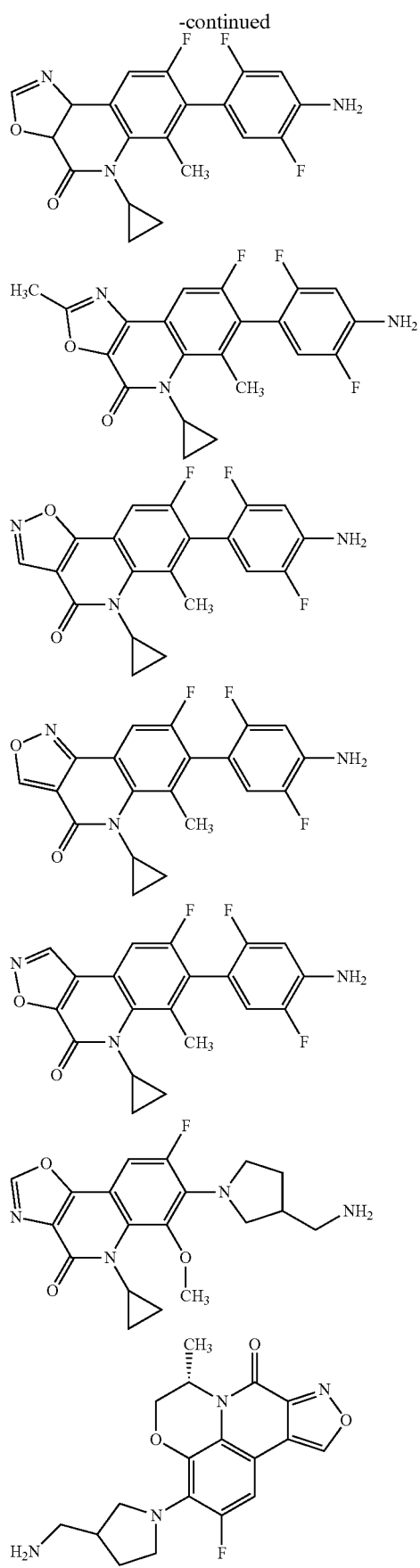
-continued
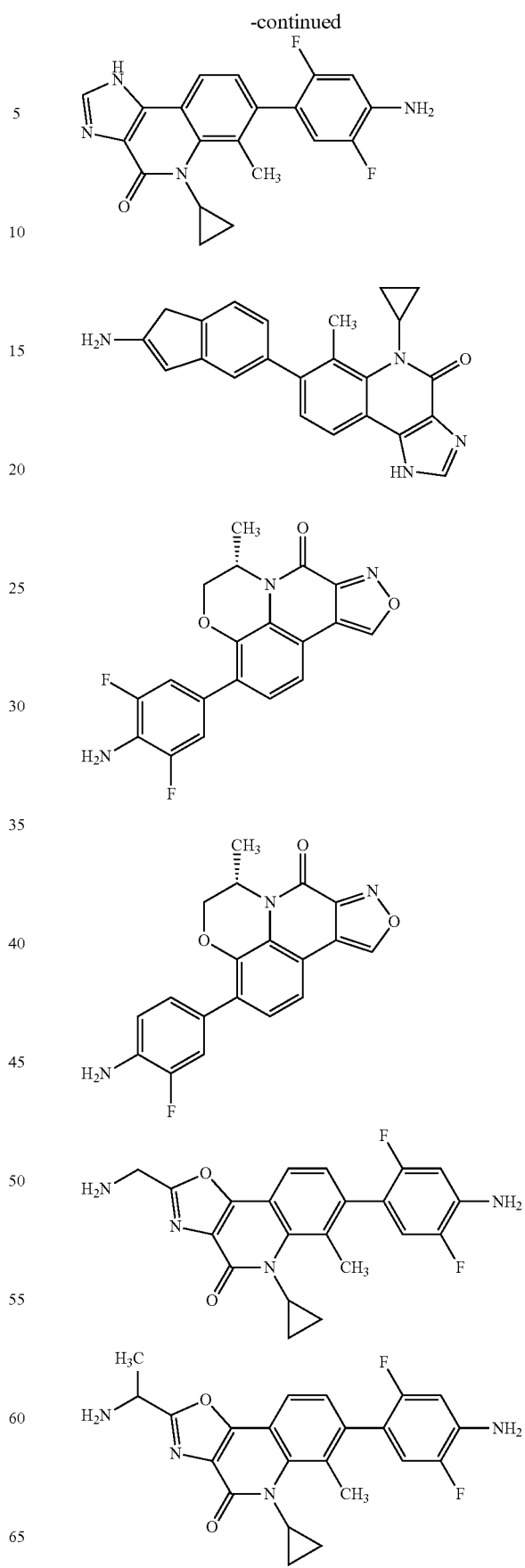

29
-continued

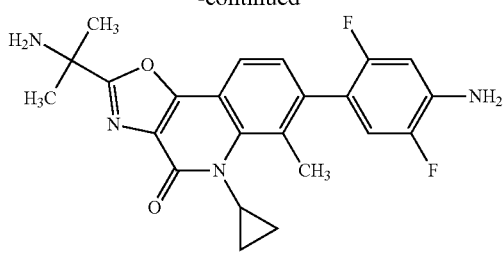
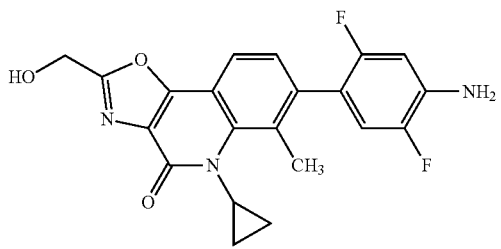
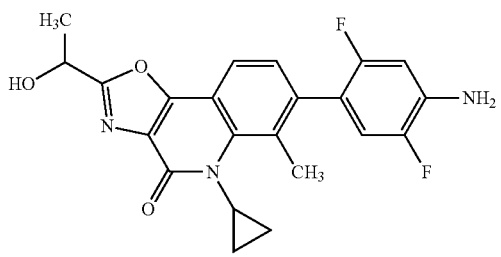
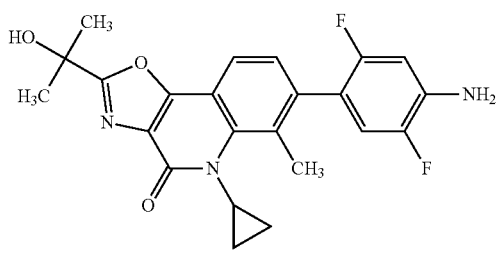
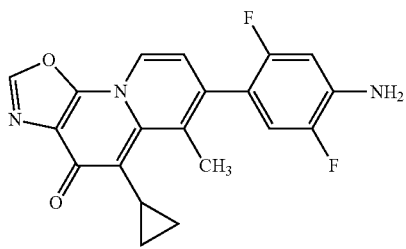
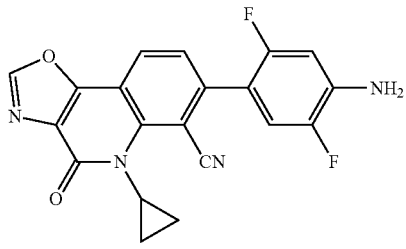
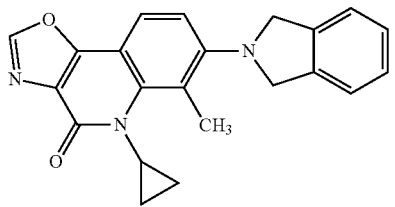

30
-continued

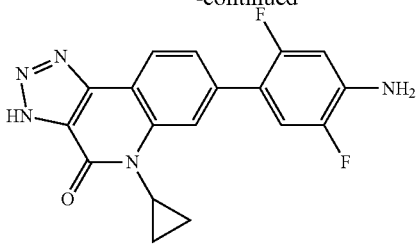
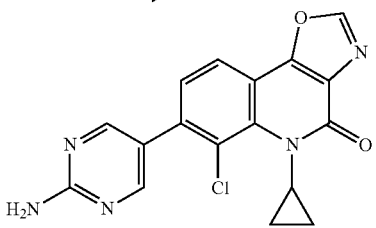
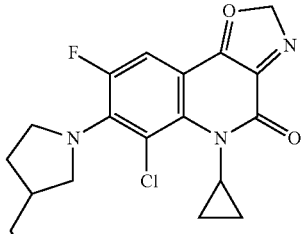
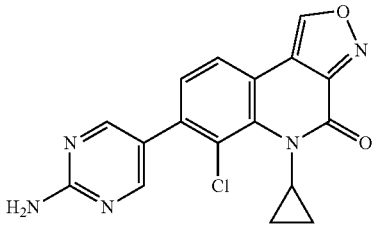

The invention includes compounds as described in the following numbered paragraphs:

1. A compound of formula (Ia), or a pharmaceutically acceptable salt thereof:

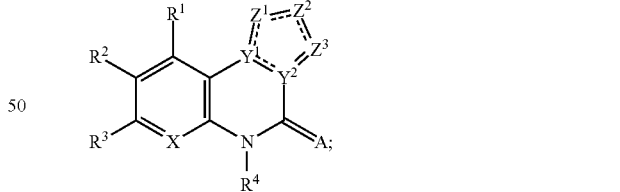

wherein X is independently selected from: N and $CR^5$;
=A is independently selected from: =O, =S, =$NR^6$ and =$NOR^6$;
$Z^1$, $Z^2$, $Z^3$, $Y^1$ and $Y^2$ together form a substituted or unsubstituted 5-membered heteroaromatic ring; with the proviso that when the 5-membered heteroaromatic ring comprises the group —C(WH)=N— in which the C and N atoms are each represented by a label selected from $Z^1$, $Z^2$ and $Z^3$ and W is selected from O, S or $NR^6$, that group may be present in a non-heteroaromatic form having the structure: —C(=W)—$NR^{10}$—;

$R^1$ is independently selected from the group consisting: H, F, $NR^7R^7$, $NR^7NR^7R^7$ and $C_1$-$C_4$-alkyl;

$R^2$ is independently selected from the group: H or F;

$R^3$ is independently selected from the group consisting of: —$(CR^8R^8)_n$—$C_3$-$C_{10}$ heterocycloalkyl, —$(CR^8R^8)_n$-aryl, —$(CR^8R^8)_n$-heteroaryl, and —$(CR^8R^8)_n$—$C_3$-$C_{10}$ cycloalkyl;

$R^4$ is independently selected from the group consisting of: $C_1$-$C_8$ alkyl, $C_2$-$C_8$ alkenyl, $C_2$-$C_8$ alkynyl, $C_1$-$C_8$ haloalkyl, —$(CR^8R^8)_n$—$C_3$-$C_6$ cycloalkyl, —$(CR^8R^8)_n$—$C_3$-$C_6$ heterocycloalkyl, —$(CR^8R^8)_n$—$C_3$-$C_6$ halocycloalkyl, —$(CR^8R^8)_n$-phenyl, and —$(CR^8R^8)_n$-heteroaryl;

$R^5$ is independently selected from the group consisting of: H, O—$C_1$-$C_8$ alkyl, halo, $C_1$-$C_8$ alkyl, $C_2$-$C_8$ alkenyl, $C_2$-$C_8$ alkynyl, $C_1$-$C_8$ haloalkyl, O—$C_1$-$C_8$ haloalkyl, $C_3$-$C_6$ cycloalkyl, $C_3$-$C_6$ heterocycloalkyl, $C_3$-$C_6$ halocycloalkyl; or $R^4$ and $R^5$ together form an alkylene or heteroalkylene chain of the form —$(CR^8R^8)_r$—$W^1$—$(CR^8R^8)_s$—$W^2$—$(CR^8R^8)_t$—and which is attached at its respective ends to the substitution point for $R^4$ and $R^5$ respectively; wherein $W^1$ and $W^2$ are each independently selected from: a bond, O, S and $NR^9$; wherein r, s, and t are each independently an integer selected from 0, 1 and 2 and wherein definitions of r, s, t, $W^1$ and $W^2$ are chosen such that the total length of the alkylene or heteroalkylene chain is 2, 3 or 4 atoms;

$R^6$, $R^9$ and $R^{10}$ are independently at each occurrence selected from: H, $C_1$-$C_4$ alkyl, and $C_1$-$C_4$ haloalkyl;

$R^7$ is independently at each occurrence selected from: H, $C_1$-$C_4$ alkyl, $C_1$-$C_4$ haloalkyl, $S(O)_2$—$C_1$-$C_4$alkyl and $C(O)$—$C_1$-$C_4$ alkyl;

$R^8$ is independently at each occurrence selected from: H, Me, $CF_3$ and F; and n is an integer independently selected at each occurrence from 0, 1, 2 and 3; and wherein each of the aforementioned aryl, heteroaryl, $C_3$-$C_{10}$ heterocycloalkyl or $C_3$-$C_{10}$ cycloalkyl groups is monocyclic or bicyclic; and each of the aforementioned alkyl, alkenyl, alkynyl, haloalkyl, cycloalkyl, halocycloalkyl, heterocycloalkyl, aryl (e.g. phenyl) and heteroaryl groups (including the 5-membered ring formed by $Z^1$, $Z^2$, $Z^3$, $Y^1$ and $Y^2$) is optionally substituted, where chemically possible, by 1 to 5 substituents which are each independently at each occurrence selected from the group consisting of: oxo, =$NR^a$, =$NOR^a$, halo, nitro, cyano, $NR^aR^a$, $NR^aS(O)_2R^a$, $NR^a$-$CONR^aR^a$, $NR^aCO_2R^a$, $OR^a$; $SR^a$, $SOR^a$, $SO_3R^a$, $SO_2R^a$, $SO_2NR^aR^a$, $CO_2R^aC(O)R^a$, $CONR^aR^a$, $C_1$-$C_4$-alkyl, $C_2$-$C_4$-alkenyl, $C_2$-$C_4$-alkynyl, $C_1$-$C_4$ haloalkyl, $CR^bR^bNR^aR^a$, and =$CR^bCR^bR^bNR^aR^a$; wherein $R^a$ is independently at each occurrence selected from H, $C_1$-$C_4$ alkyl and $C_1$-$C_4$ haloalkyl; and $R^b$ is independently at each occurrence selected from H, halogen, $C_1$-$C_4$ alkyl and $C_1$-$C_4$ haloalkyl.

2. A compound of paragraph 1, wherein the compound of formula (I) is a compound of formula (VIIb):

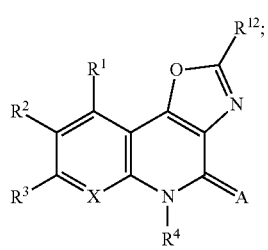

(VIIb)

wherein $R^{12}$ may be independently at each occurrence selected from: H, halo, nitro, cyano, $NR^aR^a$, $NR^aS(O)_2R^a$, $NR^aCONR^aR^a$, $NR^aCO_2R^a$, $OR^a$; $SR^a$, $SOR^a$, $SO_3R^a$, $SO_2R^a$, $SO_2NR^aR^a$, $CO_2R^aC(O)R^a$, $CONR^aR^a$, $C_1$-$C_4$-alkyl, $C_2$-$C_4$-alkenyl, $C_2$-$C_4$-alkynyl, $C_1$-$C_4$ haloalkyl, and $CR^bR^bNR^aR^a$.

3. A compound of paragraph 1 or paragraph 2, wherein A is O.

4. A compound of any preceding paragraph, wherein X is N.

5. A compound of any one of paragraphs 1 to 3, wherein X is $CR^5$.

6. A compound of any preceding paragraph, wherein $R^3$ is a monocyclic or bicyclic N-heterocycloalkyl group which comprises 1 to 3 nitrogen atoms in the heterocyclic ring system and wherein $R^3$ may be attached to the rest of the molecule via a carbon or a nitrogen in the ring system; and wherein any nitrogen in the ring system which is not at a bridgehead or is not the point of attachment of $R^3$ to the rest of the molecule is an $NR^7$ group and wherein the N-heterocycloalkyl group may be unsubstituted or may be substituted with 1 to 3 groups selected from oxo, =$NOR^a$, $NR^aR^a$, $OR^a$, $C_1$-$C_4$-alkyl, $C_2$-$C_4$-alkenyl, $C_2$-$C_4$-alkynyl, $CR^bR^bN$-$R^aR^a$ and =$CR^bCR^bR^bNR^aR^a$; wherein $R^a$ is independently at each occurrence selected from H, $C_1$-$C_4$ alkyl and $C_1$-$C_4$ haloalkyl; and $R^b$ is independently at each occurrence selected from H, halogen, $C_1$-$C_4$ alkyl and $C_1$-$C_4$ haloalkyl.

7. A compound of any one of paragraphs 1 to 5, wherein $R^3$ is a phenyl group with at least one $NR^aR^a$, $CONR^aR^a$ or $CR^bR^bNR^aR^a$ group and optionally further substituted with from 1-3 groups independently selected from halo, $C_1$-$C_4$ haloalkyl and $C_1$-$C_4$ alkyl.

8. A compound of any preceding paragraph, wherein $R^4$ is independently selected from $C_1$-$C_6$ alkyl, $C_1$-$C_6$ haloalkyl, —$(CR^8R^8)_n$—$C_3$-$C_6$ cycloalkyl and —$(CR^8R^8)_n$—$C_3$-$C_6$ halocycloalkyl.

9. A compound of paragraph 8, wherein $R^4$ is $C_3$-$C_6$ cycloalkyl.

10. A compound of paragraph 9, wherein $R^4$ is cyclopropyl.

For formula (Ia) above, $Z^1$, $Z^2$, $Z^3$, $Y^1$ and $Y^2$ together form a 5-membered ring fused to the rest of the molecule at the positions indicated with the label $Y^1$ and $Y^2$. The fused ring will be orientated such that any oxygen or sulphur in the ring occupies one of the positions indicated with the label $Z^1$, $Z^2$ or $Z^3$. Where the ring comprises one or more nitrogen atoms, the or each nitrogen may occupy one of the positions indicated with the label $Z^1$, $Z^2$, $Z^3$, $Y^1$ or $Y^2$. Exemplary heteroaromatic rings include thiophene (or thiophene sulfoxide), furan, pyrrole, pyrazole, oxazole, imidazole, thiazole (or thioazole sulfoxide), isoxazole, isothiazole (or isothiazole sulfoxide), triazole (1,2,3-triazole or 1,2,4-triazole) or tetrazole. The heteroaromatic rings may be substituted. When the 5-membered heteroaromatic ring comprises the group —C(WH)=N— in which the C and N atoms are both represented by labels selected from $Z^1$, $Z^2$ and $Z^3$ and W is selected from O, S or $NR^6$, that group may be present in a non-heteroaromatic form having the structure: —C(=W)—$NR^6$—. Where $R^6$ is H and $R^{10}$ is H, the group —C(WH)=N— and the group —C(=W)—$NR^{10}$— are tautomeric form of each other. The compounds may be present entirely in one tautomeric form or entirely in the other or as a mixture of the two.

Included within the scope of the present invention are all stereoisomers, geometric isomers and tautomeric forms of the compounds of the invention, including compounds exhibiting more than one type of isomerism, and mixtures of one or more thereof. Also included are acid addition or base salts wherein the counter ion is optically active, for example, d-lactate or l-lysine, or racemic, for example, dl-tartrate or dl-arginine.

Compounds of the invention containing one or more asymmetric carbon atoms can exist as two or more stereoisomers. Where a compound of the invention contains a double bond such as a C=C or C=N group, geometric cis/trans (or Z/E) isomers are possible. Specifically, the oxime groups present in certain compounds of the invention may be present as the E-oxime, as the Z-oxime or as a mixture of both in any proportion. Cis/trans isomers may be separated by conventional techniques well known to those skilled in the art, for example, chromatography and fractional crystallisation.

Where structurally isomeric forms of a compound are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety.

Conventional techniques for the preparation/isolation of individual enantiomers when necessary include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of the invention contains an acidic or basic moiety, a base or acid such as 1-phenylethylamine or tartaric acid.

The resulting diastereomeric mixture may be separated by chromatography and/or fractional crystallization and one or both of the diastereoisomers converted into the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, "Stereochemistry of Organic Compounds" by E. L. Eliel and S. H. Wilen (Wiley, 1994).

It follows that a single compound may exhibit more than one type of isomerism.

The term $C_m$-$C_n$ refers to a group with m to n carbon atoms.

The term "alkyl" refers to a linear or branched hydrocarbon chain. For example, $C_1$-$C_6$ alkyl may refer to methyl, ethyl, n-propyl, iso-propyl, n-butyl, sec-butyl, tert-butyl, n-pentyl and n-hexyl. The alkyl groups may be unsubstituted or substituted by one or more substituents. Specific substituents for each alkyl group independently may be fluorine, $OR^a$ or $NR^aR^a$.

The term "haloalkyl" refers to a hydrocarbon chain substituted with at least one halogen atom independently chosen at each occurrence from: fluorine, chlorine, bromine and iodine. The halogen atom may be present at any position on the hydrocarbon chain. For example, $C_1$-$C_6$ haloalkyl may refer to chloromethyl, flouromethyl, trifluoromethyl, chloroethyl e.g. 1-chloroethyl and 2-chloroethyl, trichloroethyl e.g. 1,2,2-trichloroethyl, 2,2,2-trichloroethyl, fluoroethyl e.g. 1-fluoroethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl. A haloalkyl group may be a fluoroalkyl group, i.e. a hydrocarbon chain substituted with at least one fluorine atom.

The term "alkenyl" refers to a branched or linear hydrocarbon chain containing at least one double bond. The double bond(s) may be present as the E or Z isomer (e.g. cis or trans). The double bond may be at any chemically possible position of the hydrocarbon chain. For example, "$C_2$-$C_6$ alkenyl" may refer to ethenyl, propenyl, butenyl, butadienyl, pentenyl, pentadienyl, hexenyl and hexadienyl. The alkenyl groups may be unsubstituted or substituted by one or more substituents. Specific substituents for any saturated carbon in each alkenyl group independently may be fluorine, $OR^a$ or $NR^aR^a$.

The term "alkynyl" refers to a branched or linear hydrocarbon chain containing at least one triple bond. The triple bond may be at any possible position of the hydrocarbon chain. For example, "$C_2$-$C_6$ alkynyl" may refer to ethynyl, propynyl, butynyl, pentynyl and hexynyl. The alkynyl groups may be unsubstituted or substituted by one or more substituents. Specific substituents for any saturated carbon in each alkynyl group independently may be fluorine, $OR^a$ or $NR^aR^a$.

The term "cycloalkyl" refers to a saturated hydrocarbon ring system containing 3, 4, 5 or 6 carbon atoms. For example, "$C_3$-$C_6$ cycloalkyl" may refer to cyclopropyl, cyclobutyl, cyclopentyl and cyclohexyl. The cycloalkyl groups may be unsubstituted or substituted by one or more substituents. Specific substituents for each cycloalkyl group independently may be fluorine, $OR^a$ or $NHR^a$.

The term "$_{m-n}$heterocycloalkyl" may refer to a m to n membered monocyclic or bicyclic saturated or partially saturated group comprising 1 or 2 heteroatoms independently selected from O, S and N in the ring system (in other words 1 or 2 of the atoms forming the ring system are selected from O, S and N). By partially saturated it is meant that the ring may comprise one or two double bonds. This applies particularly to monocyclic rings with from 5 to 8 members. The double bond will typically be between two carbon atoms but may be between a carbon atom and a nitrogen atom. Examples of heterocycloalkyl groups include; piperidine, piperazine, morpholine, thiomorpholine, pyrrolidine, tetrahydrofuran, tetrahydrothiophene, dihydrofuran, tetrahydropyran, dihydropyran, dioxane, azepine. An N-heterocycloalkyl group is a heterocycloalkyl group comprises at least one nitrogen atom in the ring system. Bicyclic systems may be spiro-fused, i.e. where the rings are linked to each other through a single carbon atom; vicinally fused, i.e. where the rings are linked to each other through two adjacent carbon or nitrogen atoms; or they may be share a bridgehead, i.e. the rings are linked to each other through two non-adjacent carbon or nitrogen atoms. The heterocycloalkyl groups may be unsubstituted or substituted by one or more substituents. Specific substituents for each heterocycloalkyl group may independently be fluorine, $OR^a$ or $NHR^a$.

Aryl groups have from 6 to 20 carbon atoms as appropriate to satisfy valency requirements. Aryl groups satisfy the Huckel rule. Aryl groups may be optionally substituted phenyl groups, optionally substituted biphenyl groups, optionally substituted naphthalenyl groups or optionally substituted anthracenyl groups. Equally, aryl groups may include non-aromatic carbocyclic portions.

A 5-membered heteroaromatic ring may be an aromatic ring with 1-4 (e.g. 1-3)heteroatoms selected from O, S and N in the ring system, e.g. pyrrole, furan, thiophene, pyrazole, imidazole, oxazole, isoxazole, triazole, oxadiazole, thiodiazole, triazole or tetrazole. Where the ring contains a nitrogen in the ring system, that nitrogen may be attached via a double bond to one of the neighbouring atoms, in which case the nitrogen will be unsubstituted or it may be attached via a single bond to both of the neighbouring atoms, in which case the nitrogen will be substituted with an $R^{11}$ group.

Heteroaryl groups may be 5- or 6-membered heteroaryl groups. Heteroaryl groups may be selected from: 5-membered heteroaryl groups in which the heteroaromatic ring is substituted with 1-3 heteroatoms selected from O, S and N; and 6-membered heteroaryl groups in which the heteroaromatic ring is substituted with 1-2 nitrogen atoms; 9-membered bicyclic heteroaryl groups in which the heteroaromatic system is substituted with 1-4 heteroatoms selected from O, S and N; 10-membered bicyclic heteroaryl groups in which the heteroaromatic system is substituted with 1-4 nitrogen atoms. Specifically, heteroaryl groups may be selected from: pyrrole, furan, thiophene, pyrazole, imidazole, oxazole, isoxazole, triazole, oxadiazole, thiodiazole, pyridine, pyridazine, pyrimidine, pyrazine, indole, isoindole, benzofuran, isobenzofuran, benzothiophene, indazole, benzimidazole, benzoxazole, benzthiazole, benzisoxazole, purine, quinoline, isoquinoline, cinnoline, quinazoline, quinoxaline, pteridine, phthalazine, naphthyridine.

The aryl and heteroaryl groups are optionally substituted with 1 to 5 substituents which are each independently at each occurrence selected from the group consisting of: halo, nitro, cyano, $NR^aR^a$, $NR^aS(O)_2R^a$, $NR^aCONR^aR^a$, $NR^aCO_2R^a$, $OR^a$; $SR^a$, $SOR^a$, $SO_3R^a$, $SO_2R^a$, $SO_2NR^aR^a$, $CO_2R^aC(O)R^a$, $CONR^aR^a$, $C_1$-$C_4$-alkyl, $C_2$-$C_4$-alkenyl, $C_2$-$C_4$-alkynyl, $C_1$-$C_4$ haloalkyl and $CR^bR^bNR^aR^a$; wherein $R^a$ is independently at each occurrence selected from H, $C_1$-$C_4$ alkyl and $C_1$-$C_4$ haloalkyl; and $R^b$ is independently at each occurrence selected from H, halogen, $C_1$-$C_4$ alkyl and $C_1$-$C_4$ haloalkyl.

An endocyclic double bond is formed between two atoms which both form part of a ring.

An exocyclic double bond is formed between one atom which forms part of a ring and one atom which does not form part of the ring.

Where the compound of formula (I) is an N-oxide, it will typically be a pyridine N-oxide, i.e. the nitrogen of the pyridine may be $N^+$—$O^-$. Alternatively, it may be that the compound of the invention is not an N-oxide.

The present invention also includes all pharmaceutically acceptable isotopically-labelled compounds of formulae (I) to (XXXXXVI) wherein one or more atoms are replaced by atoms having the same atomic number, but an atomic mass or mass number different from the atomic mass or mass number most commonly found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labelled compounds can generally be prepared by conventional techniques known to those skilled in the art or by processes analogous to those described using an appropriate isotopically-labelled reagent in place of the non-labelled reagent previously employed.

Medical Uses, Methods of Treatment and Pharmaceutical Formulations

Each of the compounds of the present invention may be used as a medicament. Thus, in another aspect of the invention, there is provided compound as defined above for the treatment of bacterial infections.

The compounds and formulations of the present invention may be used in the treatment of a wide range of bacterial infections. In some embodiments, the compounds can be used to treat bacterial infections caused by one or more resistant strains of bacteria. In a further embodiment, the compounds can be used to treat bacterial infections caused by one or more resistant strains of Gram positive bacteria. In a further embodiment, the compounds can be used to treat bacterial infections caused by one or more resistant strains of Gram negative bacteria.

The compounds and formulations of the present invention can be used to treat both Gram positive and Gram negative bacterial infections such as infections of the genitourinary system, the respiratory tract, the gastrointestinal tract, the ear, the skin, the throat, soft tissue, bone and joints (including infections caused by *Staphylococcus aureus*). The compounds can be used to treat pneumonia, sinusitis, acute bacterial sinusitis, bronchitis, acute bacterial exacerbation of chronic bronchitis, anthrax, chronic bacterial prostatitis, acute pyelonephritis, pharyngitis, tonsillitis, *Escherichia coli*, prophylaxis before dental surgery, cellulitis, acnes, cystitis, infectious diarrhoea, typhoid fever, infections caused by anaerobic bacteria, peritonitis, bacterial vaginosis, pelvic inflammatory disease, pseudomembranous colitis, *Helicobacter pylori*, acute gingivitis, Crohn's disease, rosacea, fungating tumours, impetigo. In one embodiment, the compounds of the invention can be used to treat infections caused by a resistant strain of bacteria. In a further embodiment, the compounds can be used to treat infections caused by a resistant strain of Gram positive bacteria and/or resistant strains of Gram negative bacteria.

The compounds and formulations of the invention may be used to treat infections caused by bacteria which are in the form of a biofilm.

The term 'resistant' is intended to refer to strains of bacteria that have shown non-susceptibility to one or more known antibacterial drug. A non-susceptible strain is one in which the MIC of a given compound or class of compounds for that strain has shifted to a higher number than for corresponding susceptible strains. For example, it may refer to strains that are non-susceptible to β-lactam antibiotics, strains that are non-susceptible to one or more fluoroquinolones and/or strains that are non-susceptible to one or more other antibiotics (i.e. antibiotics other than β-lactams and fluoroquinolones).

In certain embodiments, the term 'resistant' may refer to one in which the MIC of a given compound or class of compounds for that strain has shifted to a significantly higher number than for corresponding susceptible strains. A bacterial strain might be said to be resistant to a given antibiotic when it is inhibited in vitro by a concentration of this drug that is associated with a high likelihood of therapeutic failure.

The bacterial strain may (e.g. the MRSA strain) be resistant to one or more fluoroquinolone antibiotics, e.g. one or more antibiotics selected from levofloxacin, enoxacin, fleroxacin, lomefloxacin, nadifloxacin, norfloxacin, rufloxacin, balofloxacin, grepafloxacin, pazufloxacin, sparfloxacin, temafloxacin, tosufloxacin, besifloxacin, clinafloxacin, garenoxacin, gemifloxacin, gatifloxacin, sitafloxacin, trovafloxacin, prulifloxacin, ciprofloxacin, pefloxacin, moxifloxacin, ofloxacin, delafloxacin, zabofloxacin, avarofloxacin, finafloxacin.

The compounds of the invention may be particularly effective at treating infections caused by Gram positive bacteria. The compounds of the invention may be particularly effective at treating infections caused by Gram positive bacteria which are resistant to one or more fluoroquinolone antibiotics. The compounds of the invention may be particularly effective at treating infections caused by MRSA and/or methicillin-resistant *S. epidermidis*. The compounds of the invention may be particularly effective at treating infections caused by strains of *Staphylococcus aureus* and/or *S. epidermidis* which are resistant to one or more fluoroquinolone antibiotics. The compounds of the invention may be particularly effective at treating infections caused by MRSA and/or methicillin-resistant *S. epidermidis* that is also resistant to one or more fluoroquinolone antibiotics. The compounds of the invention may be particularly effective at treating infections caused by Gram negative bacteria. The compounds of the invention may be particularly effective at treating infections caused by Gram negative bacteria which are resistant to one or more fluoroquinolone antibiotics.

The compounds of the invention may be particularly effective at treating infections caused by *Neisseria* spp., *Haemophilus* spp., *Legionella* spp., *Pasteurella* spp., *Bordetella* spp., *Brucella* spp., *Francisella* spp. and *Moraxella* spp. These pathogens are all fastidious Gram-negative organisms. A fastidious bacterium is one having a complex nutritional requirement, i.e. one which will only grow when specific nutrients are included in the culture medium. As an example *Neisseria gonorrhoeae* requires, amongst other supplements, iron, several amino acids, cofactors and vitamins in order to grow. Members of the fastidious Gram-negative bacteria group often share common antibiotic susceptibility profiles.

Pathogenic *Neisseria* species include *Neisseria gonorrhoeae* (the pathogen responsible for gonorrhoea) and *Neisseria meningitidis* (one of the pathogens responsible for bacterial meningitis). Infections which can be treated include secondary infections which can arise from lack of treatment of a primary *Neisseria gonorrhoeae* infection. Exemplary secondary infections include urethritis, dysuria, epididymitis, pelvic inflammatory disease, cervicitis and endometritis and also systemic gonococcal infections (e.g. those manifesting as arthritis, endocarditis or meningitis). The gonorrhoea infection may be one caused by a strain of *Neisseria gonorrhoeae* which is resistant to at least one known antibacterial drug, e.g. at least one β-lactam drug.

The compounds of the invention can be used to treat or prevent mycobacterial infections, e.g. mycobacterial infections caused by resistant strains of mycobacteria. Thus, they can be used to treat TB or leprosy. The compounds may be used to treat resistant strains of TB, e.g. MDR-TB (i.e. TB infections caused by strains which are resistant to isoniazid and rifampicin), XDR-TB (i.e. TB infections caused by strains which are resistant to isoniazid, rifampicin, at least one fluoroquinolone and at least one of kanamycin, capreomycin and amikacin) and/or TDR-TB (i.e. TB infections caused by strains which have proved resistant to every drug tested against it with the exception of a compound of the invention).

The compounds and formulations of the present invention can be used to treat or to prevent infections caused by bacterial strains associated with biowarfare. These may be strains which are category A pathogens as identified by the US government (e.g. those which cause anthrax, plague etc.) and/or they may be strains which are category B pathogens as identified by the US government (e.g. those which cause Glanders disease, mellioidosis etc). In a specific embodiment, the compounds and formulations of the present invention can be used to treat or to prevent infections caused by Gram positive bacterial strains associated with biowarfare (e.g. anthrax). More particularly, the compounds and formulations may be used to treat category A and/or category B pathogens as defined by the US government on 1 Jan. 2014.

The compounds of the present invention may also be used in treating other conditions treatable by eliminating or reducing a bacterial infection. In this case they will act in a secondary manner alongside for example a chemotherapeutic agent used in the treatment of cancer.

The compounds of the invention may also be useful in treating other forms of infectious disease, e.g. fungal infections, parasitic infections and/or viral infections.

The compounds of the present invention can be used in the treatment of the human body.

They may be used in the treatment of the animal body. In particular, the compounds of the present invention can be used to treat commercial animals such as livestock. Alternatively, the compounds of the present invention can be used to treat companion animals such as cats, dogs, etc.

The compounds of the invention may be obtained, stored and/or administered in the form of a pharmaceutically acceptable salt. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids. Also included are acid addition or base salts wherein the counter ion is optically active, for example, d-lactate or l-lysine, or racemic, for example, dl-tartrate or dl-arginine.

Compounds of the invention may exist in a single crystal form or in a mixture of crystal forms or they may be amorphous. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

For the above-mentioned compounds of the invention the dosage administered will, of course, vary with the compound employed, the mode of administration, the treatment desired and the disorder indicated. For example, if the compound of the invention is administered orally, then the daily dosage of the compound of the invention may be in the range from 0.01 micrograms per kilogram body weight (µg/kg) to 100 milligrams per kilogram body weight (mg/kg).

A compound of the invention, or pharmaceutically acceptable salt thereof, may be used on their own but will generally be administered in the form of a pharmaceutical composition in which the compounds of the invention, or pharmaceutically acceptable salt thereof, is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

The compounds of the invention may be administered in combination with other active compounds (e.g. antifungal compounds, oncology compounds) and, in particular, with other antibacterial compounds. The compound of the invention and the other active (e.g. the other antibacterial compound) may be administered in different pharmaceutical formulations either simultaneously or sequentially with the other active. Alternatively, the compound of the invention and the other active (e.g. the other antibacterial compound) may form part of the same pharmaceutical formulation.

Examples of other bacterial compounds which could be administered with the compounds of the invention are penems, carbapenems, fluoroquinolones, β-lactams, vancomycin, erythromycin or any other known antibiotic drug molecule.

In particular, the compounds of the invention can be administered with fluoroquinolone antibiotics, e.g. one or more antibiotics selected from: levofloxacin, enoxacin, fleroxacin, lomefloxacin, nadifloxacin, norfloxacin, rufloxacin, balofloxacin, grepafloxacin, pazufloxacin, sparfloxacin, temafloxacin, tosufloxacin, besifloxacin, clinafloxacin, garenoxacin, gemifloxacin, gatifloxacin, sitafloxacin, trovafloxacin, prulifloxacin, ciprofloxacin, pefloxacin, moxifloxacin, ofloxacin, delafloxacin, zabofloxacin, avarofloxacin, finafloxacin.

Depending on the mode of administration of the compounds of the invention, the pharmaceutical composition which is used to administer the compounds of the invention will preferably comprise from 0.05 to 99% w (percent by weight) compounds of the invention, more preferably from 0.05 to 80% w compounds of the invention, still more preferably from 0.10 to 70% w compounds of the invention, and even more preferably from 0.10 to 50% w compounds of the invention, all percentages by weight being based on total composition.

The pharmaceutical compositions may be administered topically (e.g. to the skin) in the form, e.g., of creams, gels, lotions, solutions, suspensions, or systemically, e.g. by oral administration in the form of tablets, capsules, syrups, powders, suspensions, solutions or granules; or by parenteral administration in the form of a sterile solution, suspension or emulsion for injection (including intravenous, subcutaneous, intramuscular, intravascular or infusion); or by rectal administration in the form of suppositories; or by inhalation (i.e. in the form of an aerosol or by nebulisation).

If administered topically, high-dosages of the compounds of the invention can be administered. Thus, a compound with an in vitro MIC of, for example, 16-64 µg/mL may still provide an effective treatment against certain bacterial infections.

For oral administration the compounds of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compounds of the invention may be admixed with, for example, a vegetable oil or polyethylene glycol. Hard gelatine capsules may contain granules of the compound using either the above-mentioned excipients for tablets. Also liquid or semisolid formulations of the compound of the invention may be filled into hard gelatine capsules. Liquid preparations for oral application may be in the form of syrups or suspensions, for example, solutions containing the compound of the invention, the balance being sugar and a mixture of ethanol, water, glycerol and propylene glycol.

Optionally such liquid preparations may contain colouring agents, flavouring agents, sweetening agents (such as saccharine), preservative agents and/or carboxymethylcellulose as a thickening agent or other excipients known to those skilled in art.

For intravenous (parenteral) administration the compounds of the invention may be administered as a sterile aqueous or oily solution.

The size of the dose for therapeutic purposes of compounds of the invention will naturally vary according to the nature and severity of the conditions, the age and sex of the animal or patient and the route of administration, according to well known principles of medicine Dosage levels, dose frequency, and treatment durations of compounds of the invention are expected to differ depending on the formulation and clinical indication, age, and co-morbid medical conditions of the patient. The standard duration of treatment with compounds of the invention is expected to vary between one and seven days for most clinical indications.

It may be necessary to extend the duration of treatment beyond seven days in instances of recurrent infections or infections associated with tissues or implanted materials to which there is poor blood supply including bones/joints, respiratory tract, endocardium, and dental tissues.

In another aspect the present invention provides a pharmaceutical formulation comprising a compound of the invention and a pharmaceutically acceptable excipient. The formulation may further comprise one or more other antibiotics, e.g. one or more fluoroquinolone antibiotics. Illustrative fluoroquinolone antibiotics include levofloxacin, enoxacin, fleroxacin, lomefloxacin, nadifloxacin, norfloxacin, rufloxacin, balofloxacin, grepafloxacin, pazufloxacin, sparfloxacin, temafloxacin, tosufloxacin, besifloxacin, clinafloxacin, garenoxacin, gemifloxacin, gatifloxacin, sitafloxacin, trovafloxacin, prulifloxacin, ciprofloxacin, pefloxacin, moxifloxacin, ofloxacin, delafloxacin, zabofloxacin, avarofloxacin, finafloxacin.

In another aspect of the invention is provided a method of treating a bacterial infection, the method comprising treating a subject in need thereof with a therapeutically effective amount of a compound of the invention.

In an aspect of the invention is provided a compound of the invention for medical use. The compound may be used in the treatment of any of the diseases, infections and indications mentioned in this specification.

In yet another aspect of the invention is provided a compound for use in the preparation of a medicament. The medicament may be for use in the treatment of any of the diseases, infections and indications mentioned in this specification.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Synthesis

The skilled man will appreciate that adaptation of methods known in the art could be applied in the manufacture of the compounds of the present invention.

For example, the skilled person will be immediately familiar with standard textbooks such as "Comprehensive Organic Transformations—A Guide to Functional Group Transformations", RC Larock, Wiley-VCH (1999 or later editions), "March's Advanced Organic Chemistry—Reactions, Mechanisms and Structure", MB Smith, J. March, Wiley, (5th edition or later) "Advanced Organic Chemistry, Part B, Reactions and Synthesis", F A Carey, R J Sundberg, Kluwer Academic/Plenum Publications, (2001 or later editions), "Organic Synthesis—The Disconnection Approach", S Warren (Wiley), (1982 or later editions), "Designing Organic Syntheses" S Warren (Wiley) (1983 or later editions), "Guidebook To Organic Synthesis" RK Mackie and DM Smith (Longman) (1982 or later editions), etc., and the references therein as a guide.

The skilled chemist will exercise his judgement and skill as to the most efficient sequence of reactions for synthesis of a given target compound and will employ protecting groups as necessary. This will depend inter alia on factors such as the nature of other functional groups present in a particular substrate. Clearly, the type of chemistry involved will influence the choice of reagent that is used in the said synthetic steps, the need, and type, of protecting groups that are employed, and the sequence for accomplishing the protection/deprotection steps. These and other reaction parameters will be evident to the skilled person by reference to standard textbooks and to the examples provided herein.

Sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc (1999), and references therein.

Throughout this specification these abbreviations have the following meanings:

ACN = Acetonitrile
DCM = Dichloromethane
DMSO = dimethyl sulfoxide
FBS = Foetal Bovine Serum
HEPES = 4-(2-Hydroxyethyl)-1-piperazineethanesulponic acid
IPA = Isopropanol
THF = tetrahydrofuran
aq. = Aqueous
DMF = N,N-dimethylformamide
dppf = 1,1'-Bis(diphenylphosphino)ferrocene
TFA = trifluoroacetic acid Exemplary compounds of the invention may be made according to the synthetic Schemes A-X. Throughout Schemes A-X, W represents a halogen.

Certain compounds of formula (XXXXVIII) can be made via Schemes A and B:

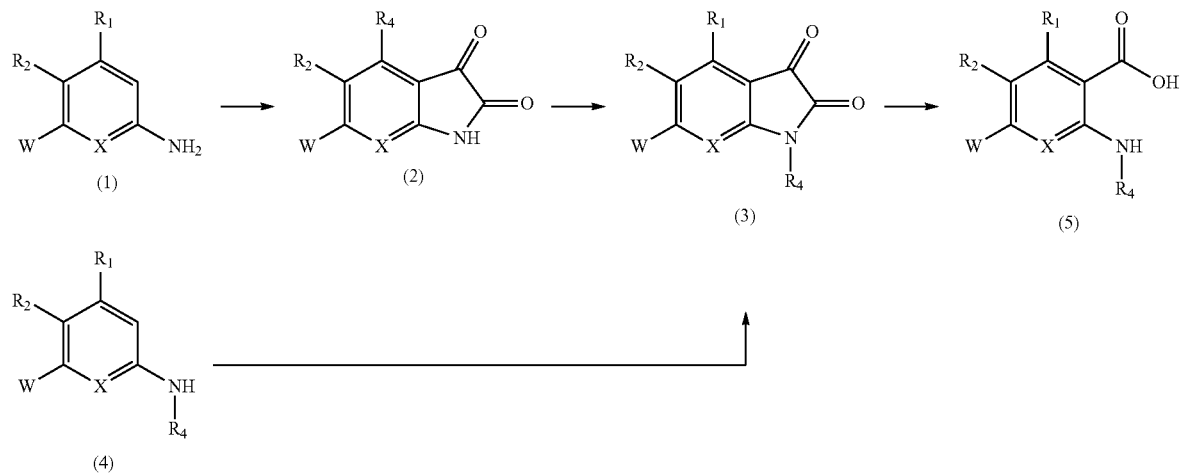

Scheme A

Amine (1) can be converted into α-keto-amide (2) using chloral hydrate (e.g. in the presence of HCl and $Na_2SO_4$ in water followed by $NH_2OH.HCl$). α-Keto-amide can subsequently alkylated with $R^4W$ in the presence of a base (e.g. $K_2CO_3$ optionally with heating) to form amide (3). Amide (3) can alternatively be made from amine (4) via a reaction with oxalyl chloride (e.g. in DCM optionally with heating) followed by a ring closing Friedel-Crafts reaction (e.g. with $AlCl_3$ optionally at 0° C.). Key intermediate (5) can be obtained from amide (3) by reaction with $H_2O_2$ and aq NaOH (e.g. at room temperature).

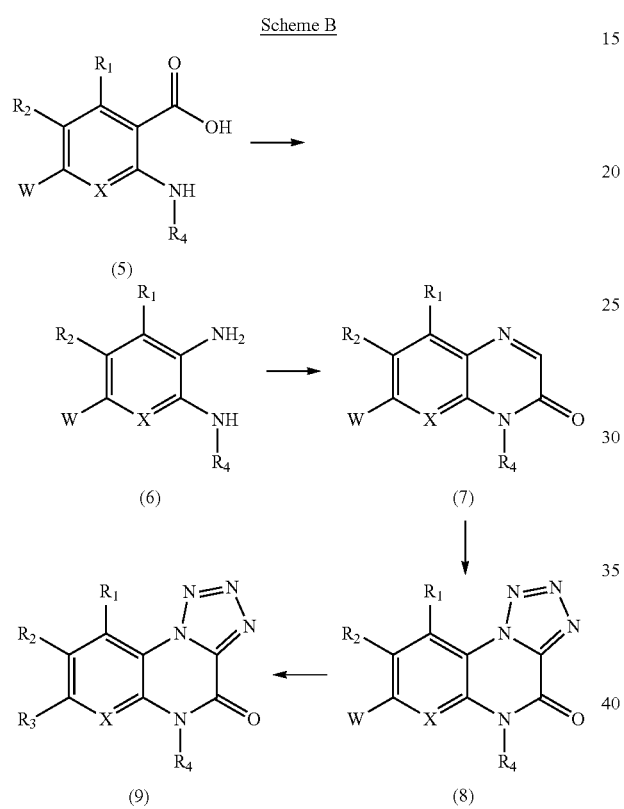

Scheme B

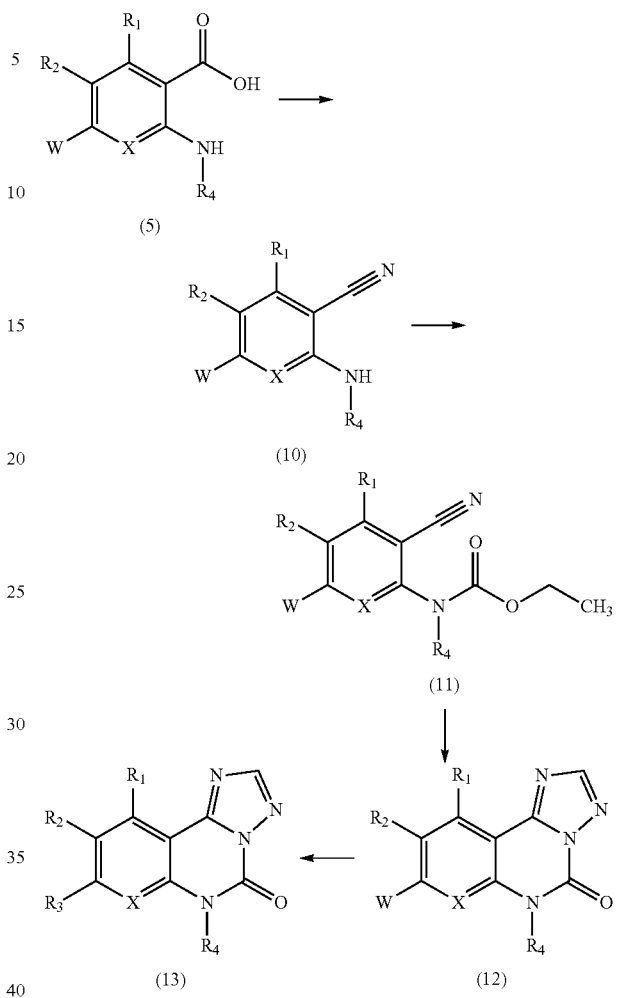

Scheme C

Acid amine (5) can be converted into diamine (6) via a Curtius rearrangement (e.g. using diphenylphosphorylazide in dioxane and heat followed by ′BuOH and treating the product with TFA). A condensation reaction (e.g. using ethanol as a solvent optionally with heating) with an appropriate α-ester-aldehyde (e.g. $EtO_2CCHO$) can provide bicycle (7). Tetrazole formation can be effected by reaction with $H_2O_2$ and aq NaOH and then by $POCl_3$ in DCM (optionally at a temperature of from 0° C. to 45° C.) followed by azide displacement of the resultant halide (e.g. with $NaN_3$ in acetonitrile optionally at room temperature). Finally, tetrazole (8) can be converted into tetrazole (9) (a subset of compounds of formula (XXXXVIII)). Where $R^3$=aryl or heteroaryl, this can be achieved by cross coupling with $arylB(OH)_2$ or $heteroarylB(OH)_2$ using standard Suzuki coupling conditions. Where $R^3$=$C_3$-$C_{10}$ heterocycloalkyl, this can be achieved by nucleophilic displacement of W using standard conditions or by standard Buchwald coupling conditions.

Certain compounds of formula (XXXXX) can be made via Scheme C:

The synthesis again starts with acid amine (5) which is initially converted into the nitrile via dehydration of the corresponding unsubstituted amide. The amide can be made for example by treatment with thionyl chloride and DMF in THF (optionally with heating) to form the acid chloride and subsequent reaction with ammonia gas (e.g. in THF at 0° C.) and the dehydration can be achieved by treating the amide with $P_2O_5$ (optionally at room temperature initially and then heating to 75° C.). Carbamate formation (e.g. using ClC(O)OEt with $NaHCO_3$ in 2-butanone) provides carbamate (11). Cyclisation with formic hydrazide (e.g. in DMF with heating) provides 1,2,4-triazole (12) which can finally be converted into triazole (13) (a subset of compounds of formula (XXXXX)). Where $R^3$=aryl or heteroaryl, this can be achieved by cross coupling with $arylB(OH)_2$ or heteroarylB $(OH)_2$ using standard Suzuki coupling conditions. Where $R^3$=$C_3$-$C_{10}$ heterocycloalkyl, this can be achieved by nucleophilic displacement of W using standard conditions or by standard Buchwald coupling conditions.

Certain compounds of formula (XXXXXIII) can be made via Scheme D:

Scheme D

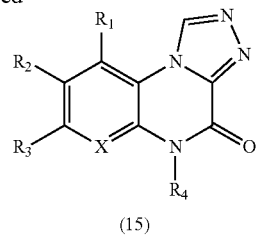

Triazole (14) can be prepared from intermediate (7) by reaction with $H_2O_2$ and aq NaOH and then with $POCl_3$ in DCM (optionally at a temperature of from 0° C. to 45° C.) followed by hydrazine displacement of the resultant halide (e.g. in ethanol). The resultant hydrazide product can be converted into triazole (14) by reaction with triethylorthoformate. Triazole (14) can then be converted into 1,2,4-triazole (15) (a subset of compounds of formula (XXXXXIII)). Where $R^3$=aryl or heteroaryl, this can be achieved by cross coupling with arylB(OH)$_2$ or heteroarylB(OH)$_2$ using standard Suzuki coupling conditions. Where $R^3$=$C_3$-$C_{10}$ heterocycloalkyl, this can be achieved by nucleophilic displacement of W using standard conditions or by standard Buchwald coupling conditions.

Certain compounds of formula (XXXXXIV) can be made via Scheme E:

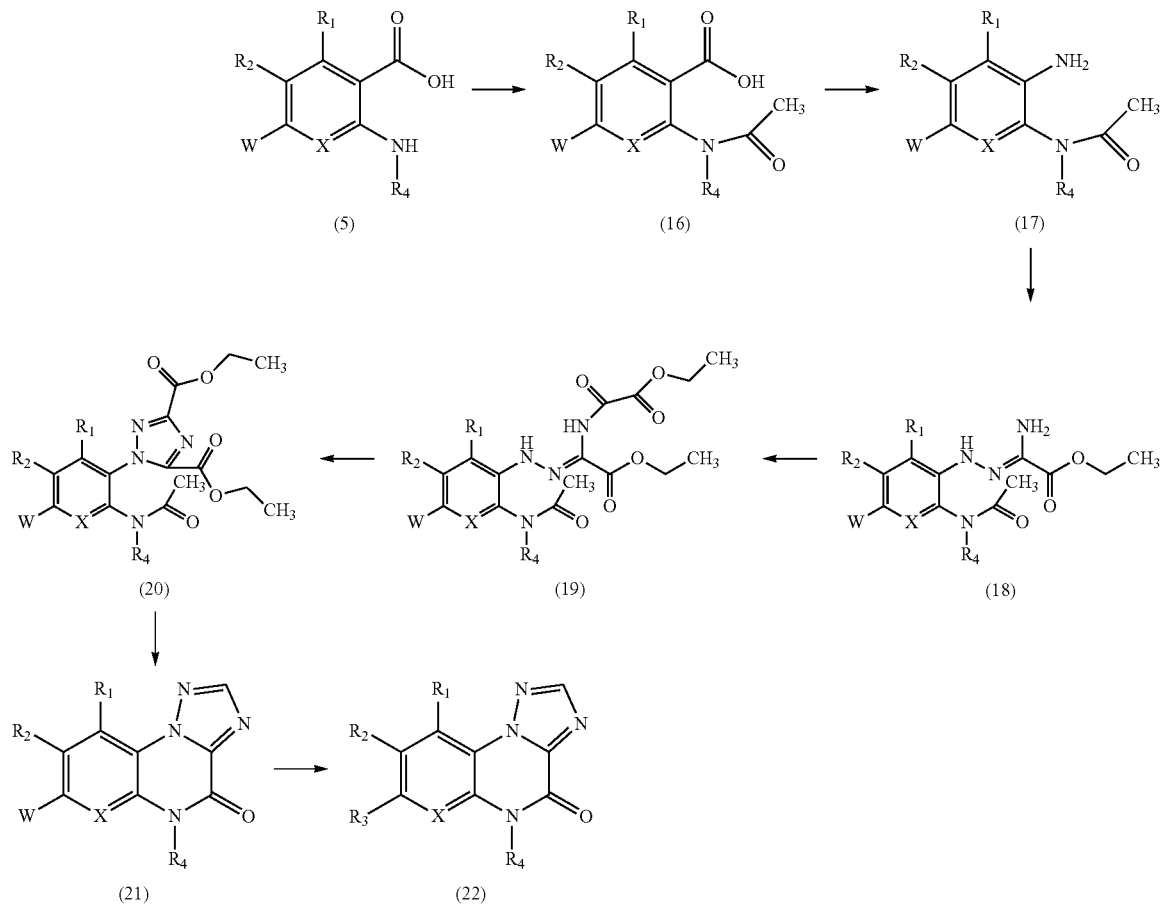

Intermediate (5) can be acetylated (e.g. with AcCl, Et₃N optionally in dioxane at room temperature). Acid (16) can be converted into amine (17) via a Curtius rearrangement (e.g. using diphenylphosphorylazide in dioxane and heat followed by ᵗBuOH and treating the product with TFA). Diazotisation reaction (e.g. with HCl and NaNO₂ optionally in ethanol at 0-5° C.) followed by reaction with ethyl-2-chloroacetoacetate (e.g. in the presence of NaOAc) and treatment of the product with NH₃ (g) (e.g. in THF) can provide compound (18). ClC(O)CO₂Et (e.g. in Et₂O at room temperature) can then be used to generate compound (19) which upon heating can cyclise to form triazole (20). Decarboxylation and deacetylation (e.g. by heating with NaOH in ethanol) can produce triazole (21). Triazole (21) can then be converted into 1,2,4-triazole (22) (a subset of compounds of formula (XXXXXIV)). Where R³=aryl or heteroaryl, this can be achieved by cross coupling with arylB(OH)₂ or heteroarylB(OH)₂ using standard Suzuki coupling conditions. Where R³=C₃-C₁₀ heterocycloalkyl, this can be achieved by nucleophilic displacement of W using standard conditions or by standard Buchwald coupling conditions.

Certain compounds of formula (XXXXXV) can be made via Scheme F:

Addition of ethyldiazoacetate (e.g. with Et₂NH and ethanol) to intermediate (3) can provide alcohol (23) which, upon treatment with a Lewis acid and t-BuOH (e.g. BF₃.OEt₂ in acetonitrile and t-BuOH optionally at room temperature) can ring open to form alkyne (24). 1,3-dipolar cycloaddition with benzyl azide (e.g. with heating in toluene) can provide triazole (25). Upon carbamate removal (e.g. with TFA) and heating triazole (25) can cyclise to form tricycle (26). Tricycle (26) can then finally be converted into 1,2,3-triazole (27) (a subset of compounds of formula (XXXXXV)). Where R³=aryl or heteroaryl, this can be achieved by cross coupling with arylB(OH)₂ or heteroarylB(OH)₂ using standard Suzuki coupling conditions. Where R³=C₃-C₁₀ heterocycloalkyl, this can be achieved by nucleophilic displacement of W using standard conditions or by standard Buchwald coupling conditions. After introduction of the R³ group, the triazole can be deprotected by removing the benzyl group (e.g. with Pd/C and H₂ optionally in ethanol) to provide triazole (27).

Certain compounds of formula (XXXXXI) can be made via Scheme G:

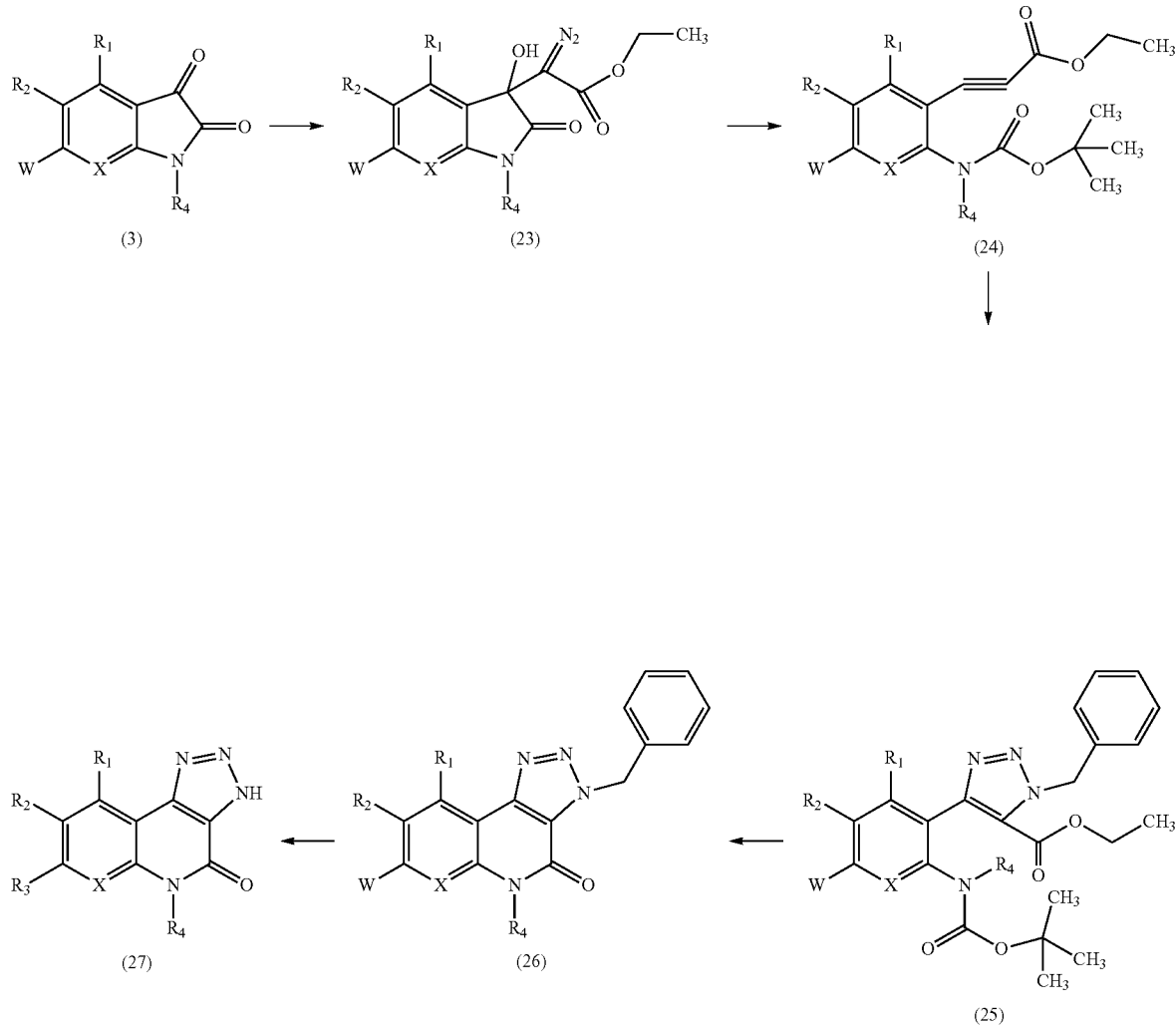

Scheme G

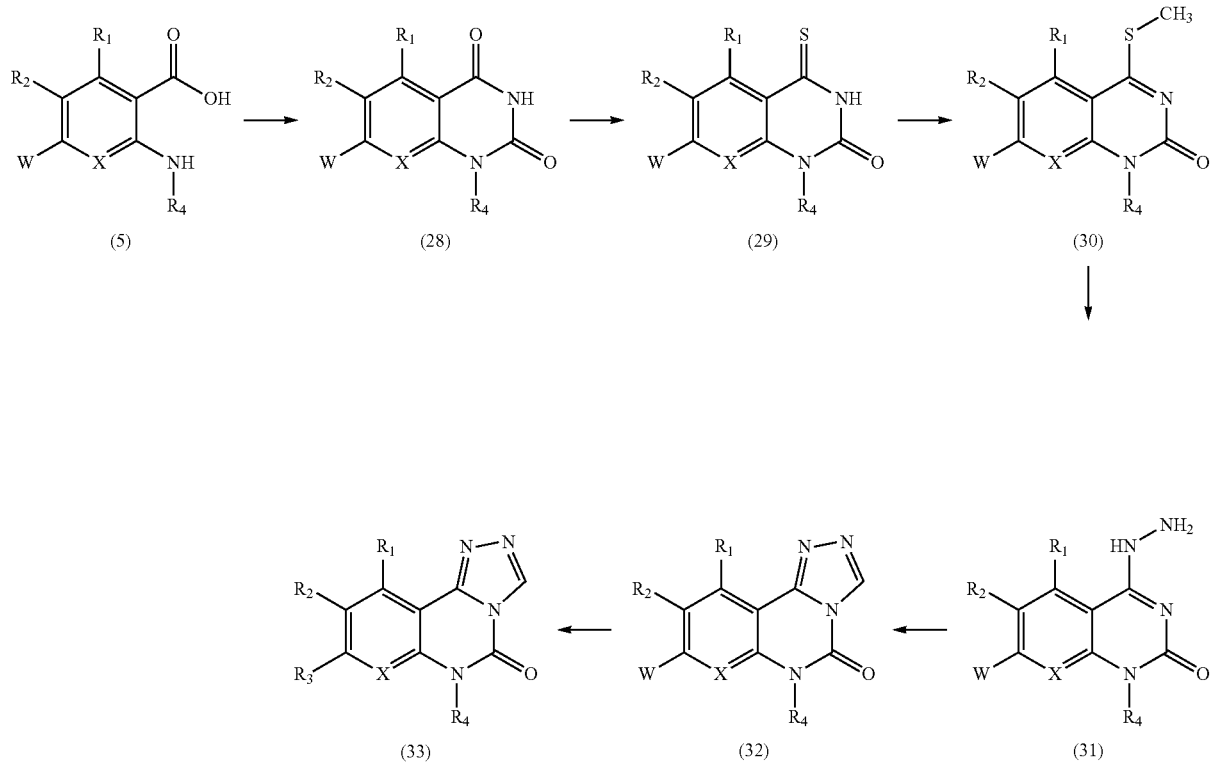

Reaction of urea with intermediate (5) (e.g. by heating in a high-boiling solvent such as DMSO) can provide bicycle (28). Treatment with Lawesson's reagent (e.g. in dioxane) and subsequent methylation (e.g. by heating with MeI in acetone) can provide thiane (30). Displacement of the SMe group with hydrazide (e.g. by heating in ethanol) can produce hydrazide (31) which, upon reaction with triethylorthoformate (e.g. with TFA) can give triazole (32). Triazole (32) can then be converted into 1,2,4-triazole (33) (a subset of compounds of formula (XXXXXI)). Where $R^3$=aryl or heteroaryl, this can be achieved by cross coupling with arylB(OH)$_2$ or heteroarylB(OH)$_2$ using standard Suzuki coupling conditions. Where $R^3$=C$_3$-C$_{10}$ heterocycloalkyl, this can be achieved by nucleophilic displacement of W using standard conditions or by standard Buchwald coupling conditions.

Certain compounds of formula (XXXXIX) can be made via Scheme H:

Scheme H

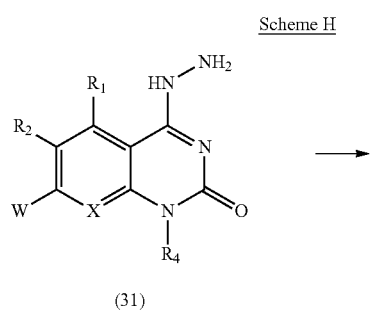

Intermediate (31) can be converted into tetrazole (34) (e.g. using NaNO$_2$ and HCl optionally in ethanol at 0-5° C.). Tetrazole (34) can then be converted into tetrazole (35) (a subset of compounds of formula (XXXXIX)). Where $R^3$=aryl or heteroaryl, this can be achieved by cross coupling with arylB(OH)$_2$ or heteroarylB(OH)$_2$ using standard Suzuki coupling conditions. Where $R^3$=C$_3$-C$_{10}$ heterocycloalkyl, this can be achieved by nucleophilic displacement of W using standard conditions or by standard Buchwald coupling conditions.

Certain compounds of formula (XXXII) can be made via Scheme I:

Scheme I

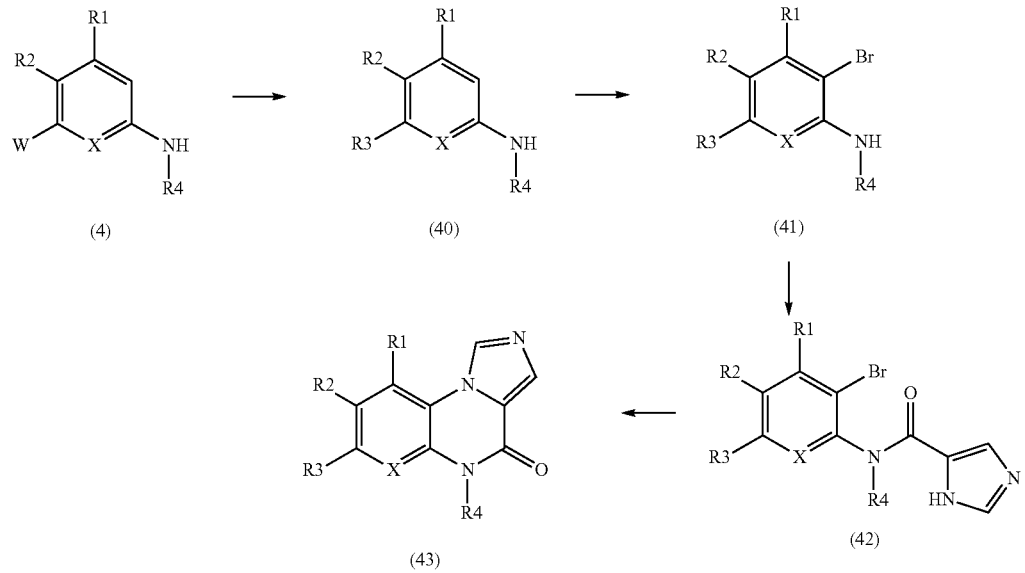

Amine (40) can be obtained from intermediate (4). Where R³=aryl or heteroaryl, this can be achieved by cross coupling with arylB(OH)₂ or heteroarylB(OH)₂ using standard Suzuki coupling conditions. Where R³=C₃-C₁₀ heterocycloalkyl, this can be achieved by nucleophilic displacement of W using standard conditions or by standard Buchwald coupling conditions. Bromination (e.g. using Br₂ in acetic acid and sodium acetate optionally at room temperature) can provide bromide (41). Subsequent acylation with an appropriate acylating agent (e.g. the acid chloride, exemplary conditions being with NEt₃ optionally in THF with heating) can provide amide (42). Finally a intramolecular cross-coupling reaction (e.g. using Cu₂O, 4,7-dimethoxy-1,10-phenanthroline, Cs₂CO₃, PEG, n-PrCN, A) can provide imidazole (43) (a subset of compounds of formula (XXXII)).

Certain compounds of formula (XXXIII) can be made via Scheme J

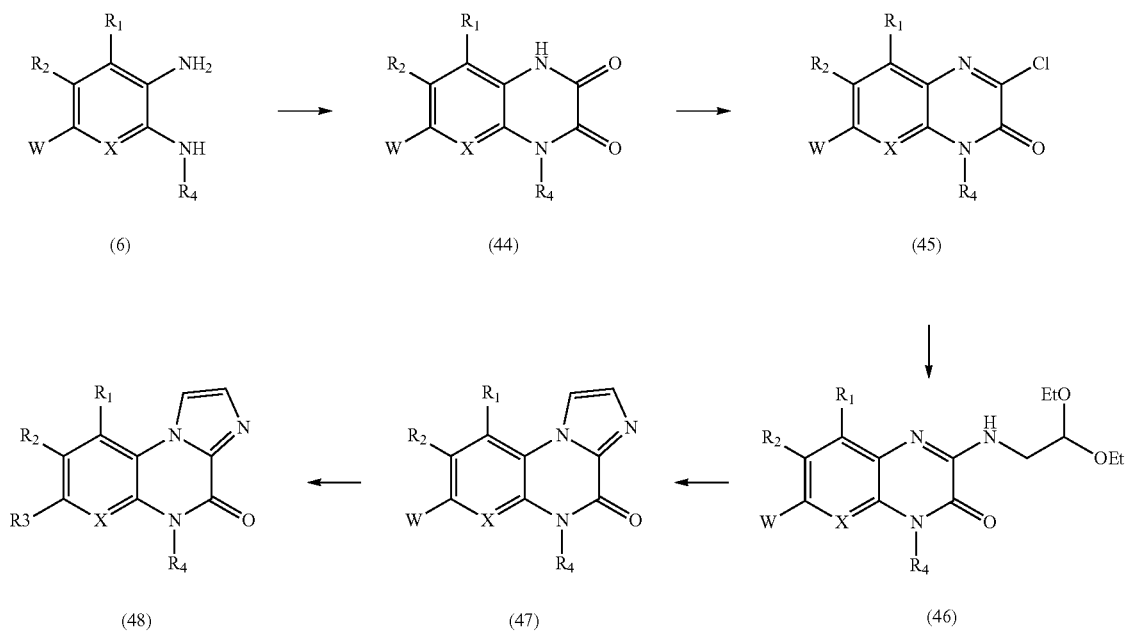

Intermediate (6) can be converted into chloride (45) by treatment with oxalyl chloride (e.g. in DCM at room temperature) followed by treatment with POCl₃ (optionally with heat). Chloride displacement with aminoacetaldehyde diethyl acetal can provide acetal (46) which in the presence of acid (e.g. tosic acid in isopropyl alcohol) can cyclise to form imidazole (47). Imidazole (47) can then be converted into imidazole (48) (a subset of compounds of formula (XXXIII)). Where $R^3$=aryl or heteroaryl, this can be achieved by cross coupling with arylB(OH)$_2$ or heteroarylB(OH)$_2$ using standard Suzuki coupling conditions. Where $R^3$=$C_3$-$C_{10}$ heterocycloalkyl, this can be achieved by nucleophilic displacement of W using standard conditions or by standard Buchwald coupling conditions.

Certain compounds of formula (XI) can be made via Scheme K:

optionally in DMF at room temperature) and then deprotecting the amine (in the case of 4-methoxybenzylamine this can be achieved using TFA, e.g. in DCM at room temperature). Reduction of the nitro group (e.g. by heating with sodium hydrosulfite in ethanol and water) can provide the diamine (52) which can be converted into the imidazole (53) by reaction with triethylorthoformate (e.g. by heating with triethylorthoformate). Imidazole (53) can be converted into imidazole (54) (a subset of compounds of formula (XI)). Where $R^3$=aryl or heteroaryl, this can be achieved by cross coupling with arylB(OH)$_2$ or heteroarylB(OH)$_2$ using standard Suzuki coupling conditions. Where $R^3$=$C_3$-$C_{10}$ heterocycloalkyl, this can be achieved by nucleophilic displacement of W using standard conditions or by standard Buchwald coupling conditions.

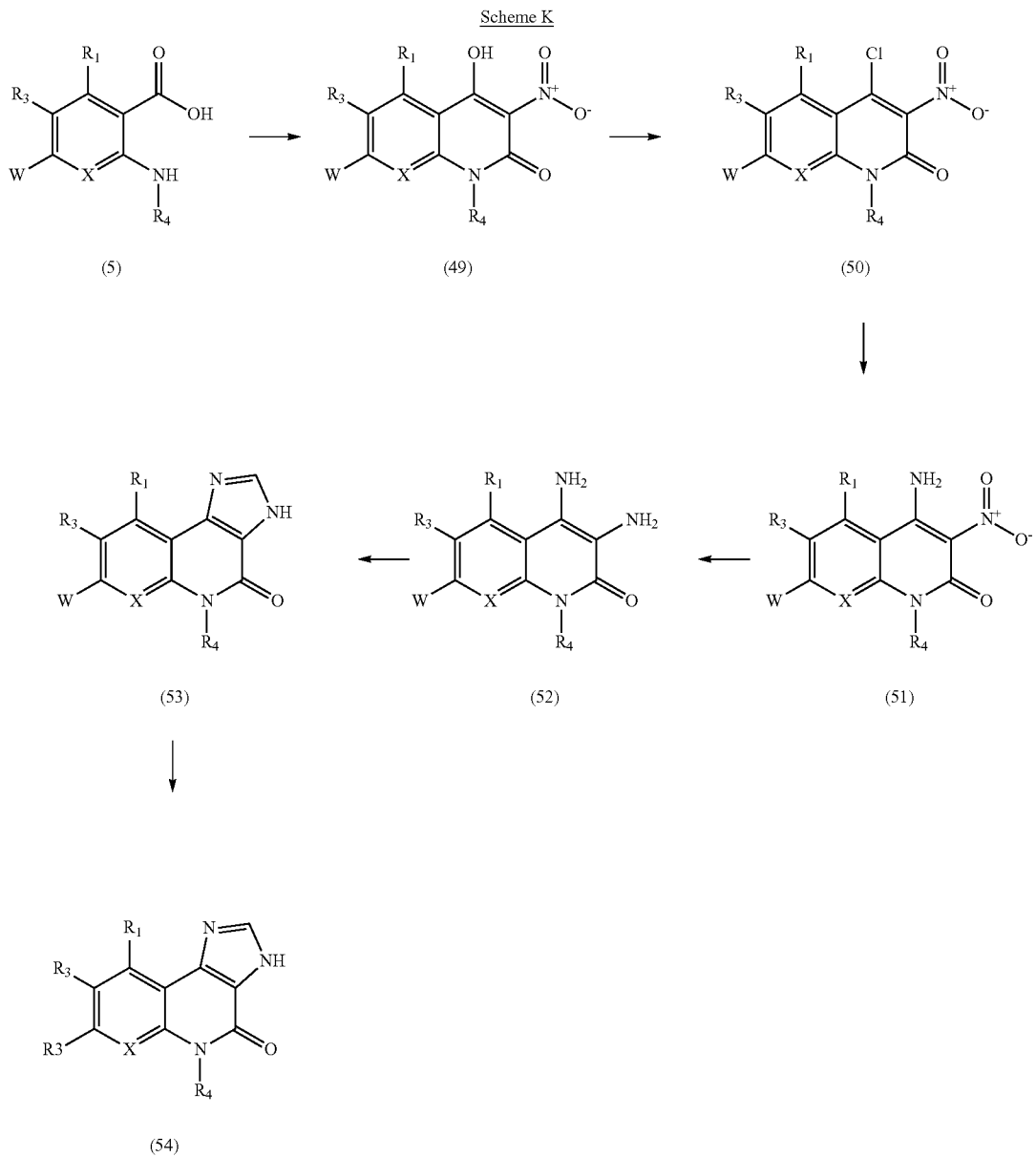

Scheme K

Intermediate (5) can be converted to enol (49) by reaction with phosgene (e.g. in THF at room temperature) followed by ethyl nitroacetate (e.g. heating with NEt$_3$ in THF). Enol (49) can be converted into enamine (51) by chlorination (e.g. by heating with POCl$_3$), displacement of the resultant chlorine with a protected amine (e.g. 4-methoxybenzylamine Certain compounds of formula (XII) can be made via Scheme L:

Scheme L

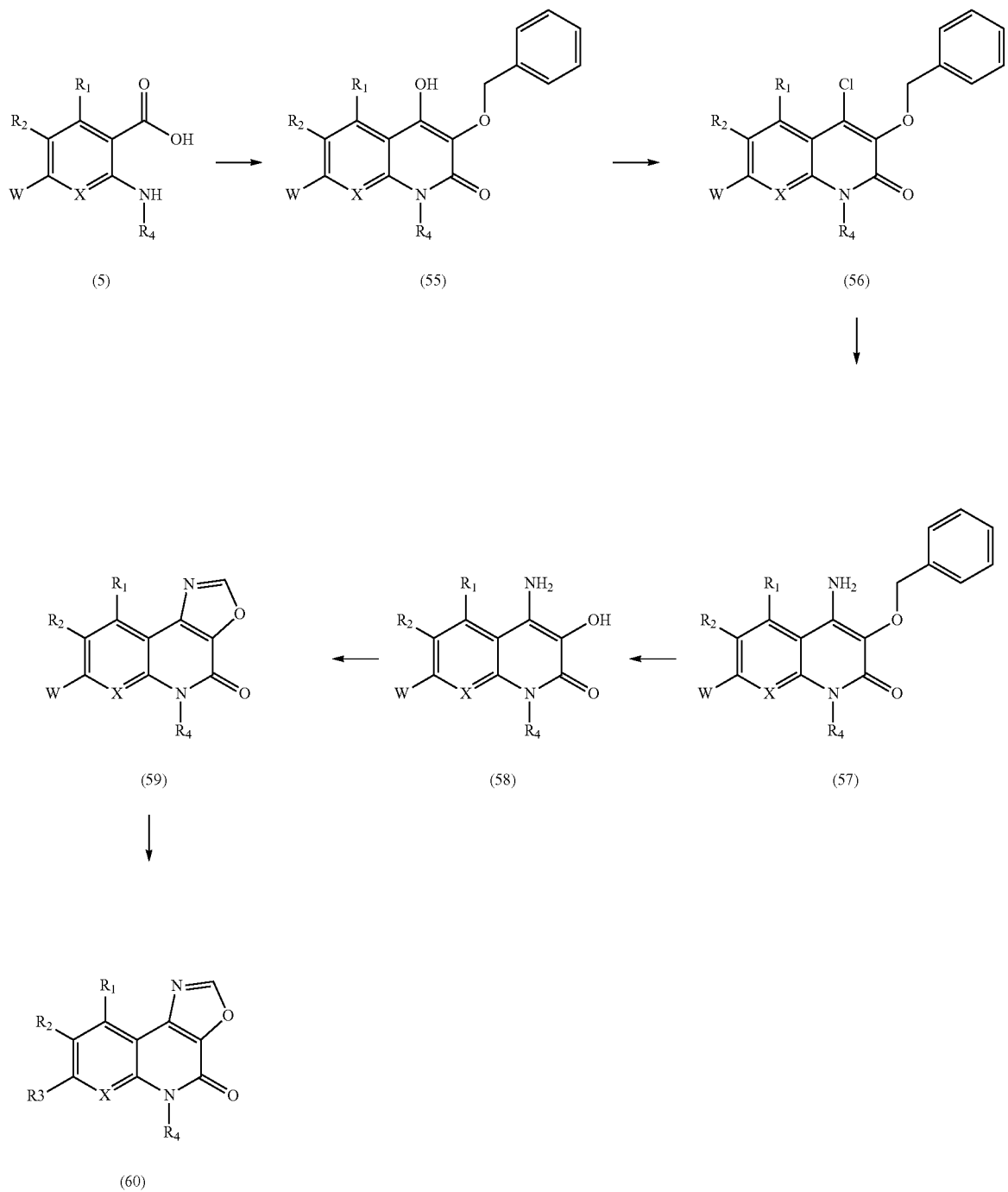

Intermediate (5) can be converted into bicycle (55) by reaction with phosgene (e.g. in THF at room temperature) followed by ethyl 2-(benzyloxy)acetate (e.g. by heating with NEt$_3$ in THF). A similar chlorination, amination, deprotection sequence to that used in Scheme K above can generate amine (57). The benzyl protecting group of amine (57) can be removed (e.g. using Pd/C and H$_2$ in methanol at room temperature) to provide aminoenol (58) which can be converted into the oxazole (59) by reaction with triethylorthoformate (e.g. by heating with triethylorthoformate). Oxazole (59) can be converted into oxazole (60) (a subset of compounds of formula (XII)). Where R$^3$=aryl or heteroaryl, this can be achieved by cross coupling with arylB(OH)$_2$ or heteroarylB(OH)$_2$ using standard Suzuki coupling conditions. Where R$^3$=C$_3$-C$_{10}$ heterocycloalkyl, this can be achieved by nucleophilic displacement of W using standard conditions or by standard Buchwald coupling conditions.

Certain compounds of formula (XXXIV) can be made via Scheme M:

Scheme M

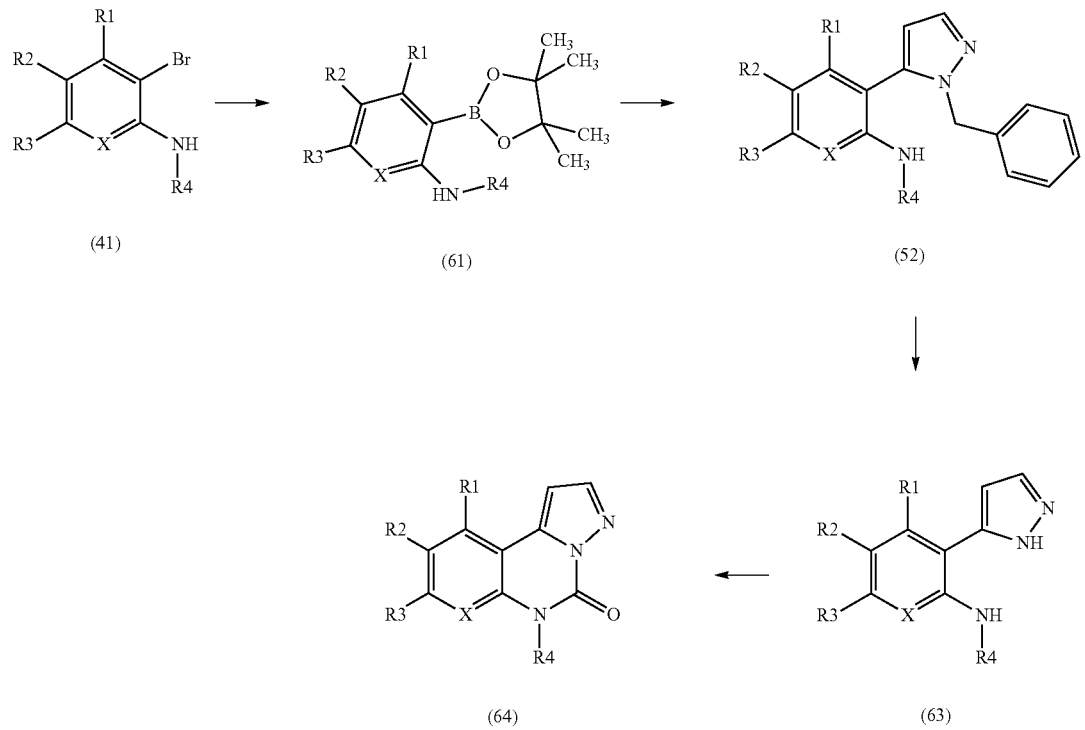

A sequential palladium coupling of intermediate (41) to bis(pinacolato)diboron (e.g. using Pd(dppf)Cl₂ and KOAc in 1,4 dioxane at 80° C.) and then to 1-benzyl-5-bromopyrazole (e.g. using Pd(dppf)Cl₂ and Cs₂CO₃ in a 10:1 dioxane:water mixture at 70° C.) provides pyrazole (52). Removal of the benzyl protecting group (e.g. using Pd/C and H₂ in methanol at room temperature) and subsequent reaction with phosgene (e.g. in THF at room temperature) or an equivalent reagent can provide pyrazole (64) (a subset of compounds of formula (XXXIV))

Certain compounds of formula (XXXI) can be made via Scheme N:

Scheme N

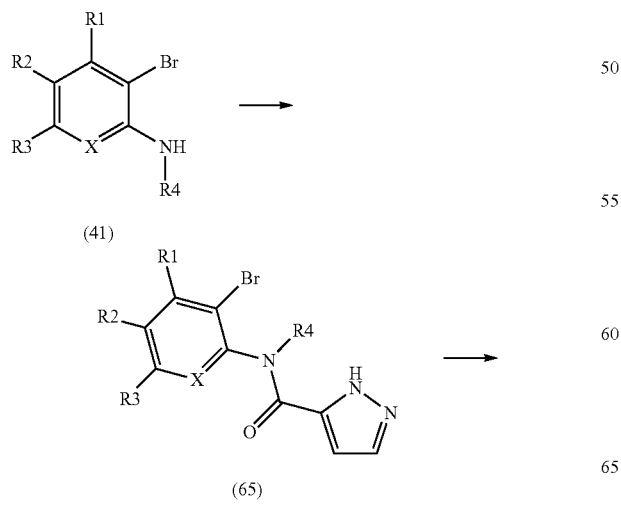

-continued

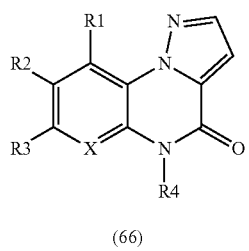

Reaction of intermediate (41) with an appropriate acylating agent (e.g. 2H-pyrazole-3-carboxylic acid, exemplary conditions being to do so by heating with propylphosphonic anhydride and diisopropylamine in THF) can provide amide (65) which can undergo an intramolecular cross-coupling reaction (e.g., using Cu₂O, 4,7-dimethoxy-1,10-phenanthroline, Cs₂CO₃, PEG, n-PrCN, A) to provide pyrazole (66) (a subset of compounds of formula (XXXI))

Certain compounds of formula (XXI) can be made via Scheme O:

Scheme O

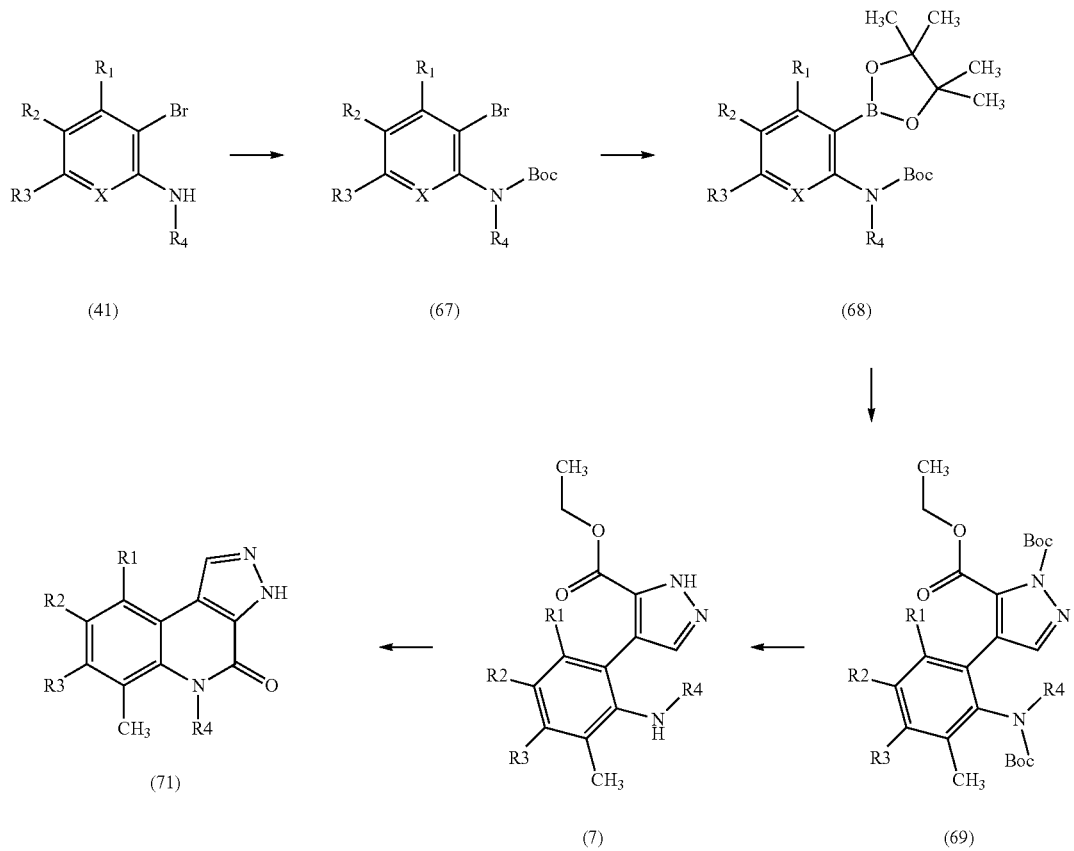

Boc protection of amine (41) can provide carbamate (67). A sequential palladium coupling of intermediate (41) to bis(pinacolato)diboron (e.g. using Pd(dppf)Cl$_2$ and KOAc in 1,4 dioxane at 80° C.) and then to Boc-protected 4-bromo-1H-pyrazole-5-carboxylic acid methyl ester (e.g. using Pd(dppf)Cl$_2$ and Cs$_2$CO$_3$ in a 10:1 dioxane:water mixture at 70° C.) provides pyrazole (69). Boc deprotection (e.g. using TFA in DCM at room temperature) followed by ester hydrolysis (e.g. using aq. NaOH in ethanol) and lactam formation (e.g. by heating with propylphosphonic anhydride and diisopropylamine in THF) can provide pyrazole (71) (a subset of compounds of formula (XXI)).

Certain compounds of formula (XXX) can be made via Scheme P:

Scheme P

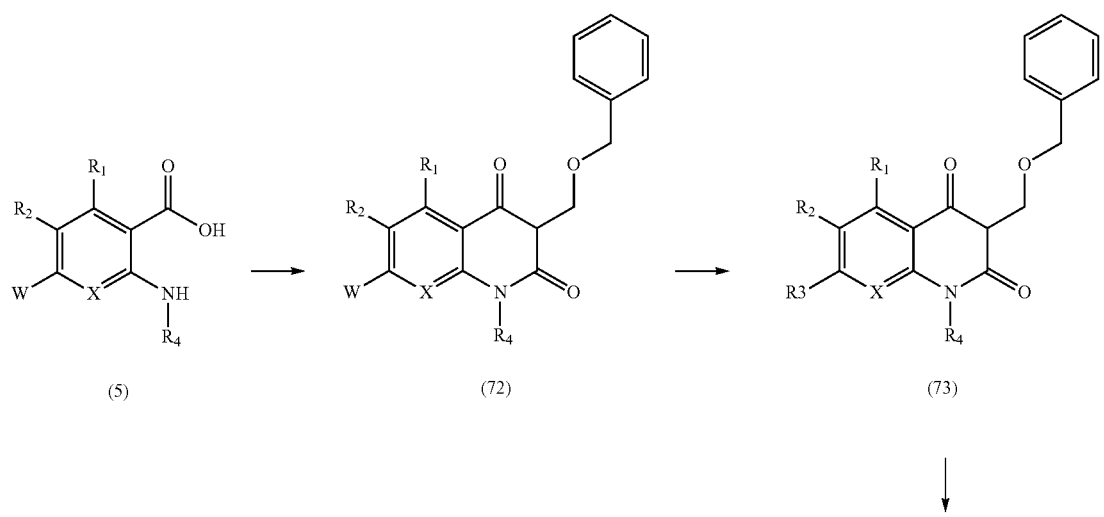

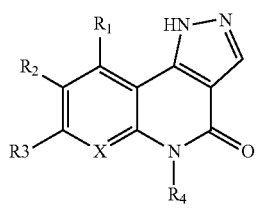

(75)

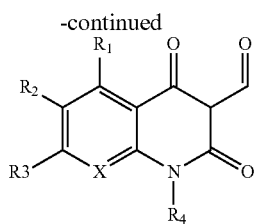

(74)

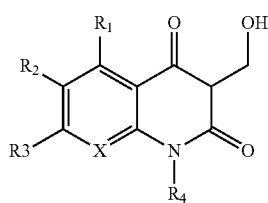

(79)

Intermediate (5) can be converted into β-ketoamide (72) by reaction with phosgene (e.g. in THF at room temperature) followed by ethyl 3-(benzyloxy)propanoate (e.g with heating in DMF following deprotonation of ethyl 3-(benzyloxy)propanoate with NaH). R-Ketoamide (72) can be converted into β-ketoamide (73). Where $R^3$=aryl or heteroaryl, this can be achieved by cross coupling with arylB(OH)$_2$ or heteroarylB(OH)$_2$ using standard Suzuki coupling conditions. Where $R^3$=$C_3$-$C_{10}$ heterocycloalkyl, this can be achieved by nucleophilic displacement of W using standard conditions or by standard Buchwald coupling conditions. Removal of the benzyl protecting group (e.g. using Pd/C and H$_2$ optionally in MeOH at room temperature) followed by oxidation (e.g. using Dess-Martin Periodinane optionally in DCM at room temperature) can provide aldehyde (75). Treatment of aldehyde (75) with hydrazine (e.g. as hydrazine hydrate in THF in the presence of acetic acid) can provide pyrazole (76) (a subset of compounds of formula (XXX)).

Certain compounds of formulae (VI), (VII) and (VIII) can be made via Scheme Q:

Intermediate (5) can be converted into oxazole (77) by treating with triphosgene (e.g. in THF at room temperature) and reacting the product with ethyl isocyanate (e.g. by heating in the presence of NEt$_3$ in THF). Cyclisation (e.g. by heating with NaH in DMF) can provide oxazole (78) which can be converted into oxazole (79) (a subset of compounds of each of formulae (VI), (VII) and (VIII)). Where $R^3$=aryl or heteroaryl, this can be achieved by cross coupling with arylB(OH)$_2$ or heteroarylB(OH)$_2$ using standard Suzuki coupling conditions. Where $R^3$=$C_3$-$C_{10}$ heterocycloalkyl, this can be achieved by nucleophilic displacement of W using standard conditions or by standard Buchwald coupling conditions.

Certain compounds of formula (IX) can be made via Scheme R:

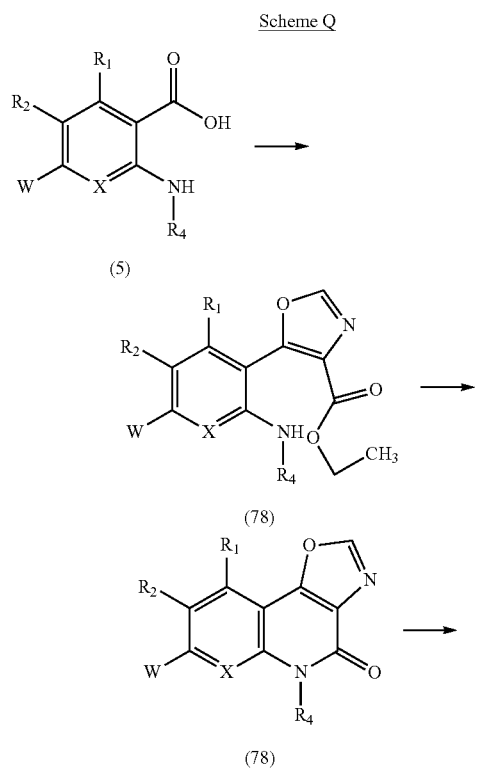

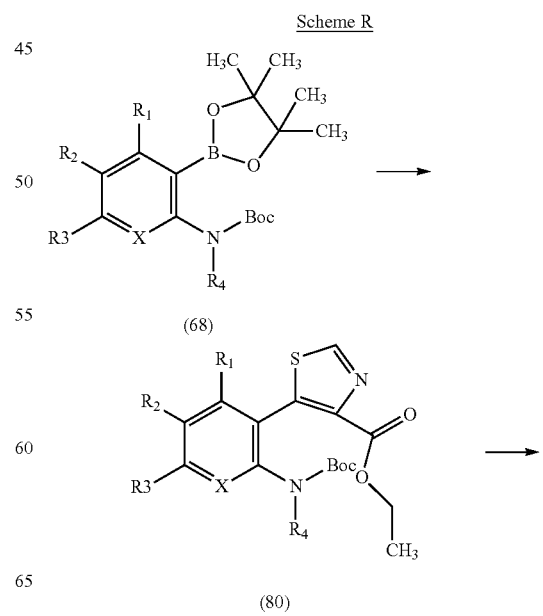

-continued

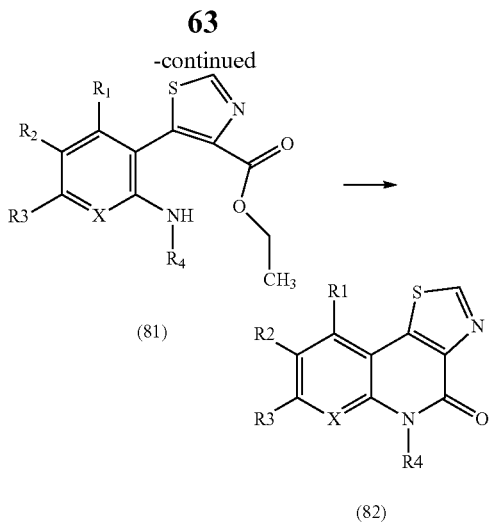

Coupling of intermediate (68) with 5-ethyl-5-iodothiazole-4-carboxylate (e.g. using Pd(dppf)Cl$_2$ and Cs$_2$CO$_3$ in a 10:1 dioxane:water mixture at 70° C. provides thiazole (80). Boc deprotection (e.g. using TFA in DCM at room temperature) followed cyclisation (e.g. by heating with NaH in DMF) can provide thiazole (82) (a subset of compounds of formula (IX)).

Certain compounds of the following formulae (XIX), (XXIV), (XXV), (XXIX), (XXXVII), (XXXVIII), (XXXIX), (XXXX), (XXXXI), (XXXXII), (XXXXIII), (XXXXIV) and (XXXXV) can be made via Scheme S:

Intermediate (4) can be converted into iodide (83) (e.g. by treating with iodine and NaHCO$_3$ optionally in EtOAc at room temperature). Acylation with an acid chloride (84) (e.g. using Et$_3$N in THF at room temperature) can provide amide (85) which, following an intramolecular Heck reaction (e.g. by heating amide (85) with Pd(PPh$_3$)$_4$ and NEt$_3$ in acetonitrile) can give tricycle (86). Tricycle (86) can be converted into tricycle (87) (e.g. compounds of formulae (XIX), (XXIV), (XXV), (XXIX), (XXXVII), (XXXVIII), (XXXIX), (XXXX), (XXXXI), (XXXXII), (XXXXIII), (XXXXIV) and (XXXXV)). Where R$^3$=aryl or heteroaryl, this can be achieved by cross coupling with arylB(OH)$_2$ or heteroarylB(OH)$_2$ using standard Suzuki coupling conditions. Where R$^3$=C$_3$-C$_{10}$ heterocycloalkyl, this can be achieved by nucleophilic displacement of W using standard conditions or by standard Buchwald coupling conditions.

Certain compounds of formula (XXXXVI) can be made via Scheme T:

Scheme S

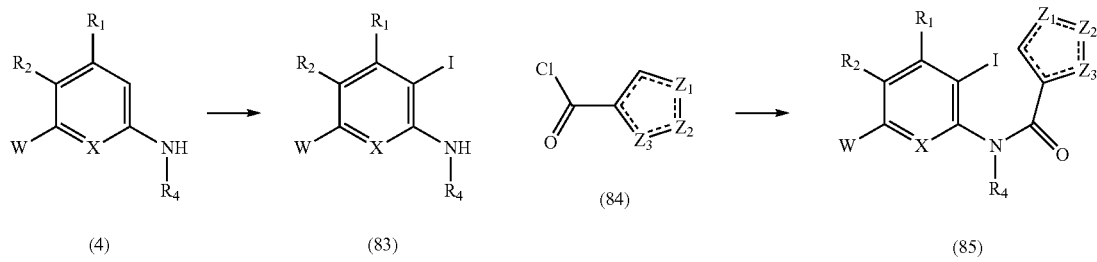

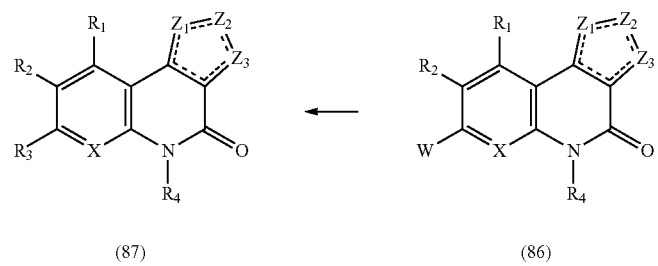

Scheme T

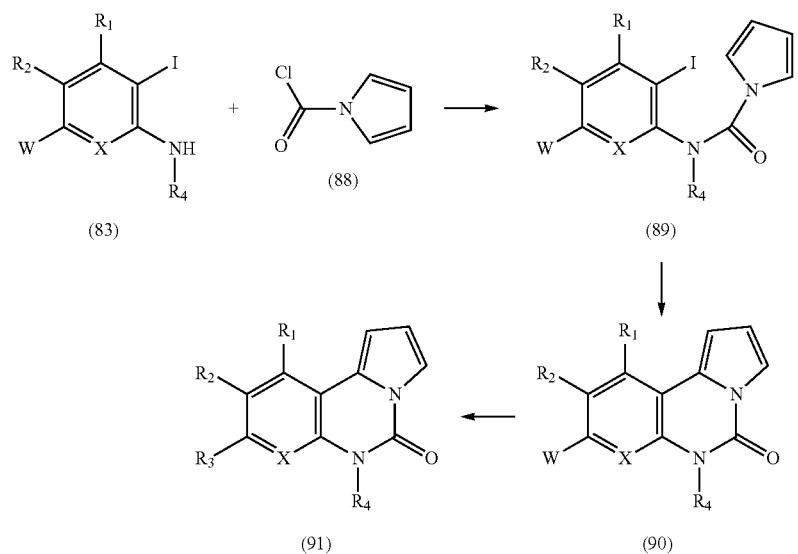

Acylation of iodide (83) with acyl chloride (88) (e.g. using Et$_3$N in THF at room temperature) can provide amide (89) which, following an intramolecular Heck reaction (e.g. by heating amide (89) with Pd(PPh$_3$)$_4$ and NEt$_3$ in acetonitrile) can give tricycle (90). Tricycle (90) can be converted into tricycle (91) (a subset of compounds of formula (XXXXVI)). Where R$^3$=aryl or heteroaryl, this can be achieved by cross coupling with arylB(OH)$_2$ or heteroarylB(OH)$_2$ using standard Suzuki coupling conditions. Where R$^3$=C$_3$-C$_{10}$ heterocycloalkyl, this can be achieved by nucleophilic displacement of W using standard conditions or by standard Buchwald coupling conditions.

Certain compounds of formula (XXXXVII) can be made via Scheme U:

Scheme U

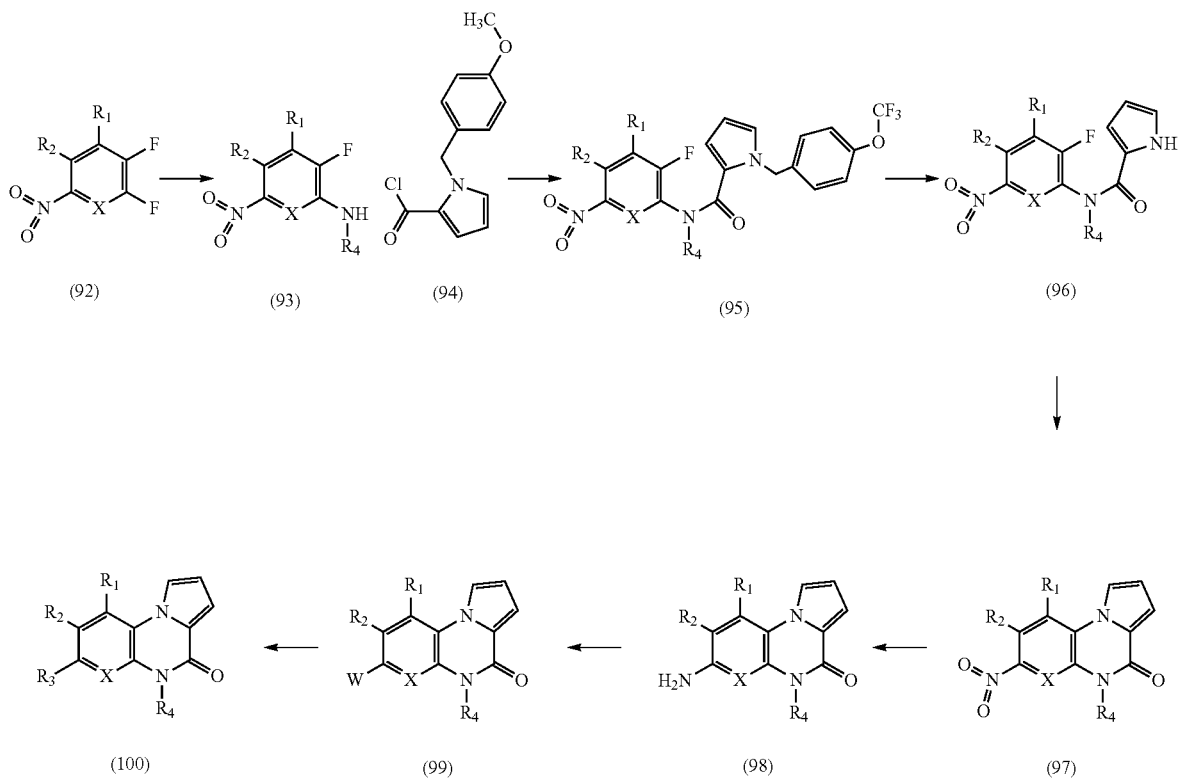

Reaction of fluoride (92) with NHR⁴ can provide amine (93) (e.g by heating in DMSO). Acylation of amine (93) with acyl chloride (94) (e.g. using Et₃N in THF at room temperature) can provide amide (95) which upon deprotection (e.g. using TFA in DCM at room temperature) can give pyrrole (96). An addition-elimination cyclisation reaction (e.g. by heating pyrrole (96) with K₂CO₃ in DMSO) can furnish tricycle (97). Tricycle (97) can be converted into tricycle (98) by reduction of the nitro group (e.g. using Pd/C and H₂ optionally in methanol at room temperature) followed by halogen replacement of the amine. Where W is F this can be achieved using NaNO₂, HCl, HBF₄ at −5° C. to 0° C.; where W is Br this can be achieved by heating amine (98) with HBr in water and then reacting with CuBr and NaNO₂, again heated in water; and where W is C₁ this can be achieved by heating amine (98) with HCl in water and then reacting with CuCl and NaNO₂, again heated in water. Tricycle (99) can be converted into tricycle (100) (a subset of compounds of formula (XXXXVII)). Where R³=aryl or heteroaryl, this can be achieved by cross coupling with arylB(OH)₂ or heteroarylB(OH)₂ using standard Suzuki coupling conditions. Where R³=C₃-C₁₀ heterocycloalkyl, this can be achieved by nucleophilic displacement of W using standard conditions or by standard Buchwald coupling conditions.

All of the above Schemes A-U provide compounds of the invention in which A is O. Such compounds (i.e. compounds of formula (36)) can be converted into compounds in which A is S, =NR⁶ and =NOR⁶ according to Schemes V, W and X.

Scheme V

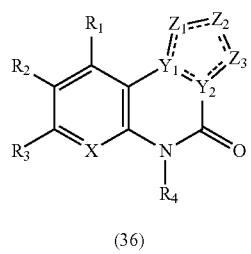

(36)

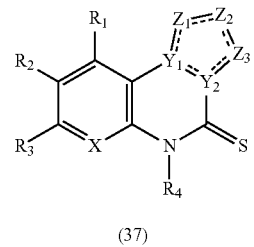

(37)

Amide (36) can, for example, be converted to thioamide (37) by heating with P₂S₅ in pyridine.

Scheme W

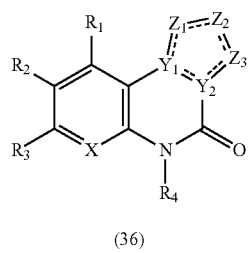

(36)

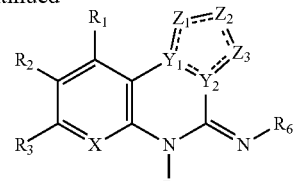

(38)

Amide (36) can, for example, be converted to amidine (38) by heating with POCl₃ and heating the product with the primary amine NH₂R⁶.

Scheme X

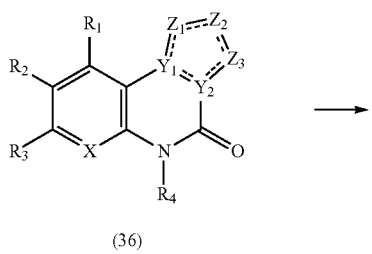

(36)

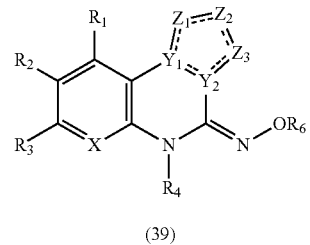

(39)

Amide (36) can, for example, be converted to oxime (39) by heating with POCl₃ and heating the product with the O-substituted hydroxylamine NH₂OR⁶.

EXPERIMENTAL

Analytical Methods

NMR spectra were obtained on a LC Bruker AV400 using a 5 mm QNP probe (Method A) or Bruker AVIII 400 Nanobay using a 5 mm BBFQ with z-gradients (Method B).

MS was carried out on a Waters ZQ MS (Method A and B) or ACQ-SQD2#LCA081 (Method C) using H₂O and ACN (0.1-0.05% formic acid—high pH; 0.05% ammonia—low pH). Wavelengths were 254 and 210 nM.

Method A

Column: Gemini NX C18, 5 μm, 50×2 mm. Column flow rate was 1 mL/min. Injection volume 10 μL

| Time (min) | H₂O % | ACN % |
|---|---|---|
| 0 | 95 | 5 |
| 4 | 5 | 95 |
| 4.45 | 5 | 95 |
| 4.5 | 95 | 5 |
| 5 | | STOP |

Method B

Column: Waters XBridge C18, 5 μm, 50×2.1 mm. Flow rate: 0.8 mL/min. Injection volume 10 μL

| Time (min) | H$_2$O % | ACN % |
|---|---|---|
| 0 | 95 | 5 |
| 4 | 5 | 95 |
| 4.45 | 5 | 95 |
| 4.5 | 95 | 5 |
| 5 | STOP | |

Method C

Column: ACQUITY UPLC® BEH C18 1.7 µm, 50×2.1 mm. Flow rate: 0.6 mL/min. Injection volume 2 µL.

| Time (min) | H$_2$O % | ACN % |
|---|---|---|
| 0 | 95 | 5 |
| 0.30 | 95 | 5 |
| 2.00 | 5 | 95 |
| 2.60 | 95 | 5 |
| 3.00 | STOP | |

Method D

Column: YMC-Triart C18 50×2 mm, 5 uM. Flow rate: 0.8 mL/min. Injection volume 5 µL.

| Time (min) | H$_2$O % | ACN % | % H$_2$O:ACN 50 v/v + 1% formic acid |
|---|---|---|---|
| 0 | 95 | 0 | 5 |
| 4 | 0 | 95 | 5 |
| 4.4 | 0 | 95 | 5 |
| 4.5 | 95 | 5 | 0 |
| 4.5 | STOP | | |

Method E

Column YMC Triart-C18 50×2 mm, 5 uM Flow rate: 0.8 mL/min. Injection volume 5 µL Mobile Phase A H2O, B MeCN C 1% formic in 50% H2O/50% MeCN

| Time (min) | A | B | C |
|---|---|---|---|
| 0 | 95 | 0 | 5 |
| 2.0 | 95 | 0 | 5 |
| 12.0 | 0 | 95 | 5 |
| 14.0 | 0 | 95 | 5 |
| 14.1 | 95 | 0 | 5 |

Preparative HPLC was performed using a Waters 3100 Mass detector (Method A) or Waters 2767 Sample Manager (Method B) using H$_2$O and ACN (0.1-0.05% formic acid—high pH; 0.05% ammonia—low pH).

Method A

Column: XBridge™ prep C18 5 µM OBD 19×100 mm. Flow rate: 20 mL/min.

Method B

Column: XBridge™ prep C18 5 µM OBD 19×100 mm. Flow rate: 20 mL/min.

Example 1—7-(4-amino-2,5-difluoro-phenyl)-5-cyclopropyl-6-methyl-oxazolo[4,5-c]quinolin-4-one A (a) 3-bromo-N-(1-methoxycyclopropyl)-2-methyl-aniline

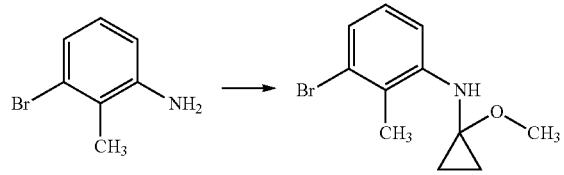

To a stirring solution of 3-bromo-2-methyl-aniline (14.6 mL, 118.25 mmol) in MeOH (200 mL) was added acetic acid (27.1 mL, 472.99 mmol). To the solution was added (1-ethoxycyclopropoxy)-trimethyl-silane (28.5 mL, 141.9 mmol) dropwise at room temperature and the resulting reaction mixture was heated to reflux overnight. After consumption of all starting material (monitored by LCMS) the mixture was concentrated in vacuo to obtain the title product as colourless oil in quantitative yield, which was used without further purification.

LC-MS (Method A) 256.3/258.3 [M+H]$^+$; RT 2.85 min (b) 3-bromo-N-cyclopropyl-2-methyl-aniline

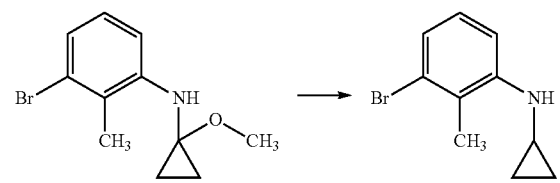

To a solution of 3-bromo-N-(1-methoxycyclopropyl)-2-methyl-aniline (31.0 g, 121.03 mmol) in THF (50 mL) was added borane THF complex (242.1 mL, 242.06 mmol) dropwise at 0° C. over 20 min. The resulting mixture was allowed to warm to room temperature, stirred for 3 h and then refluxed for 18 h. After consumption of starting material (followed by LCMS), the reaction mixture was cooled to room temperature and carefully quenched with MeOH until bubbling stopped. Organic solvents were removed under reduced pressure. The residue was then poured into H$_2$O (200 mL) and extracted with Et$_2$O (3×50 mL). The combined organic layers were washed with brine (50 mL), dried over MgSO$_4$, filtered and concentrated in vacuo to give 3-bromo-N-cyclopropyl-2-methyl-aniline in quantitative yield. The product was used in the next step without further purification.

LC-MS (Method A) 226.3/228.3 [M+H]$^+$; RT 3.07 min

(c) 6-bromo-1-cyclopropyl-7-methyl-indoline-2,3-dione

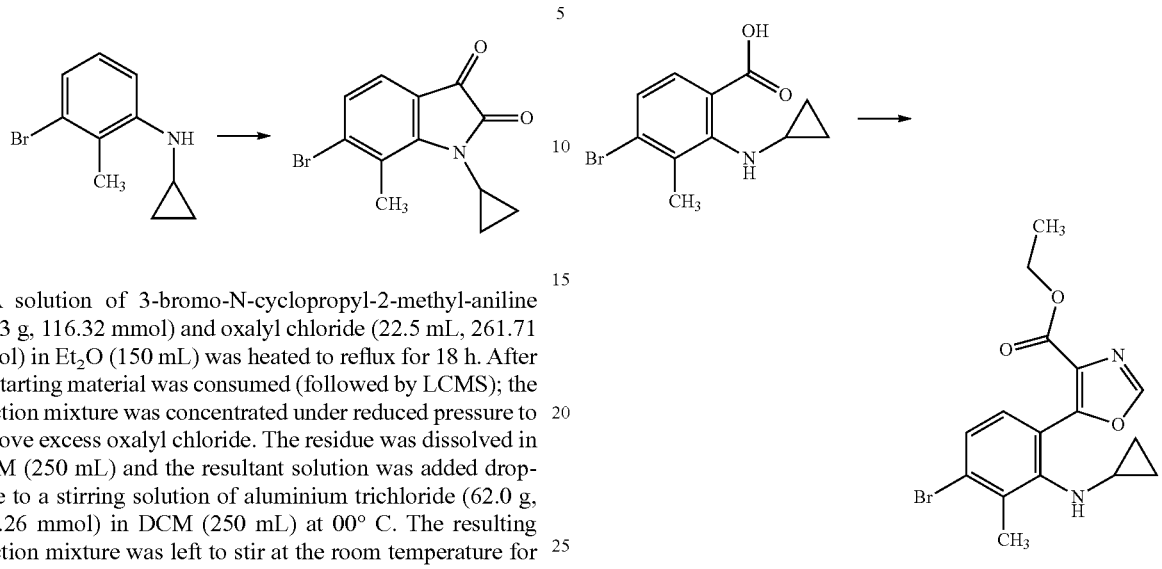

A solution of 3-bromo-N-cyclopropyl-2-methyl-aniline (26.3 g, 116.32 mmol) and oxalyl chloride (22.5 mL, 261.71 mmol) in Et$_2$O (150 mL) was heated to reflux for 18 h. After all starting material was consumed (followed by LCMS); the reaction mixture was concentrated under reduced pressure to remove excess oxalyl chloride. The residue was dissolved in DCM (250 mL) and the resultant solution was added dropwise to a stirring solution of aluminium trichloride (62.0 g, 465.26 mmol) in DCM (250 mL) at 00° C. The resulting reaction mixture was left to stir at the room temperature for 18 h before concentrating under reduced pressure. The residue was diluted with EtOAc, and carefully quenched with aqueous NaHCO$_3$. Multiple extractions and washes of organic layers were combined, washed with brine and dried over MgSO$_4$. The filtrate was concentrated in vacuo to give the crude product, which was purified by flash chromatography eluting with DCM to give 6-bromo-1-cyclopropyl-7-methyl-indoline-2,3-dione (6.87 g, 21%) as a bright orange solid.

LC-MS (Method A) 280.3/282.3 [M+H]$^+$; RT 2.34 min

(d) 4-bromo-2-(cyclopropylamino)-3-methyl-benzoic acid

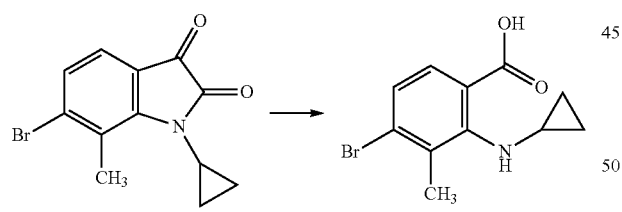

To a solution of 6-bromo-1-cyclopropyl-7-methyl-indoline-2,3-dione (790 mg, 2.82 mmol) in 2M aqueous NaOH (15 mL, 798.81 mmol) at 0° C., was added H$_2$O$_2$ (1.2 mL, 39.07 mmol) dropwise and the resulting reaction mixture was left to stir at room temperature for 2 h. After completion of the reaction, (monitored by LCMS), the reaction mixture was acidified to pH=4-5 with 2M aqueous HCl and then extracted with EtOAc (2×300 mL). The combined organic layers were washed with brine (300 mL), dried over Na$_2$SO$_4$, filtered and concentrated in vacuo to give 4-bromo-2-(cyclopropylamino)-3-methyl-benzoic acid (760 mg, 99%) as a pale yellow-beige colour solid.

LC-MS (Method A) 270.3/272.3 [M+H]$^+$; RT 2.29 min

(e) ethyl 5-[4-bromo-2-(cyclopropylamino)-3-methyl-phenyl]oxazole-4-carboxylate To a solution of 4-bromo-2-(cyclopropylamino)-3-methyl-benzoic acid (530 mg, 1.96 mmol) in dry THF (15 mL) at room temperature under N$_2$ was added triphosgene (348 mg, 1.17 mmol) in one portion. After stirring at room temperature for 3 h the solvent was carefully removed in vacuo. To the resulting residue under N$_2$ was added dry THF (10 mL), followed by Et$_3$N (2.18 mL, 15.7 mmol) dropwise. To the resulting mixture was added ethyl isocyanoacetate (0.32 mL, 2.94 mmol) in one portion and the reaction heated to 60° C. overnight. The reaction was cooled to room temperature and the solvent was removed under reduced pressure. The residue was then partitioned between EtOAc (20 mL) and brine (20 mL). 2M aqueous HCl was then added to adjust the aq. pH to around 3. The EtOAc layer was then separated, washed 4 times with H$_2$O, dried over MgSO$_4$, filtered and concentrated in vacuo. The crude product was purified by flash chromatography eluting with 50% Petroleum ether (40-60)/EtOAc to afford ethyl 5-[4-bromo-2-(cyclopropylamino)-3-methyl-phenyl]oxazole-4-carboxylate (370 mg, 52%) as an off white solid.

LC-MS (Method A) 365.3/367.3 [M+H]$^+$; RT 2.72 min

(f) 7-bromo-5-cyclopropyl-6-methyl-oxazolo[4,5-c]quinolin-4-one

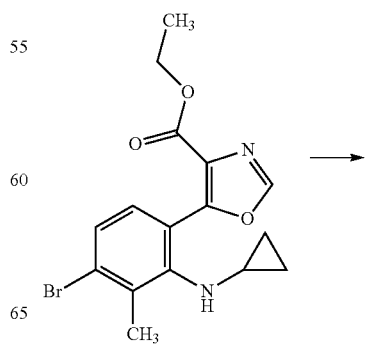

-continued

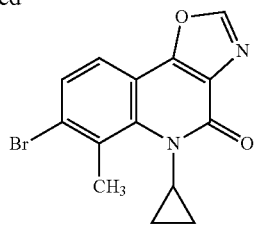

To a solution of ethyl 5-[4-bromo-2-(cyclopropylamino)-3-methyl-phenyl]oxazole-4-carboxylate (370 mg, 1.01 mmol) in dry DMF (5 mL) was added NaH (60% dispersed in mineral oil) (61 mg, 1.52 mmol) in one portion. This was then heated to 100° C. for 1 h, after which time the reaction mixture was cooled to room temperature. EtOAc and H$_2$O were added and the layers separated. The aq. layer was washed once with EtOAc and the combined organic extracts were washed a further 4 times with H$_2$O to remove DMF. The combined organic extracts were dried over MgSO$_4$, filtered, concentrated in vacuo and purified by flash chromatography using 50% Petroleum ether (40-60)/EtOAc as the eluent system to afford 7-bromo-5-cyclopropyl-6-methyl-oxazolo[4,5-c]quinolin-4-one (112 mg, 35%) as an off white solid.

LC-MS (Method A) 319.3/321.3 [M+H]$^+$; RT 2.13 min (g) 7-(4-amino-2,5-difluoro-phenyl)-5-cyclopropyl-6-methyl-oxazolo[4,5-c]quinolin-4-one A

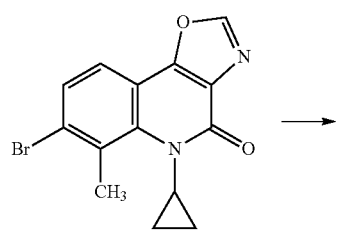

A mixture of 7-bromo-5-cyclopropyl-6-methyl-oxazolo[4,5-c]quinolin-4-one (213 mg, 0.67 mmol), 2,5-difluoro-4-(4,4,5,5-tetramethyl-1,3,2-dioxaborolan-2-yl)aniline (204 mg, 0.80 mmol), Cs$_2$CO$_3$ (326 mg, 1 mmol) and 1,1'-bis(diphenylphosphino)ferrocene-palladium(II) dichloride dichloromethane complex (65 mg, 0.08 mmol) in toluene (3 mL), IPA (1 mL) and H$_2$O (1 mL) was heated to 70° C. for 1.5 h. The reaction mixture was filtered through Celite and concentrated to dryness. The mixture was then redissolved in MeOH and purified by flash chromatography using a gradient eluent system of 100% Petroleum ether (40-60) to 100% EtOAc. The fractions containing the desired product were concentrated in vacuo and triturated with ice cold Et$_2$O to give 7-(4-amino-2,5-difluoro-phenyl)-5-cyclopropyl-6-methyl-oxazolo[4,5-c]quinolin-4-one A as a yellow solid (41 mg, 17%).

$^1$H NMR (Method A) (CDCl$_3$): δ ppm 8.07 (s, 1H), 7.76 (d, J=7.8 Hz 1H), 7.21 (d, J=7.2 Hz, 1H), 6.97-6.93 (m, 1H), 6.63-6.59 (m, 1H), 4.00 (s, 2H), 3.66-3.60 (m, 1H), 2.53 (s, 3H), 1.27-1.19 (m, 2H), 0.67-0.65 (m, 2H); LC-MS (Method A) 368.4 [M+H]$^+$; RT 2.10 min Example 2—7-(4-amino-2,5-difluoro-phenyl)-5-ethyl-6-methyl-oxazolo[4,5-c]quinolin-4-one B (a) 6-bromo-7-methyl-indoline-2,3-dione

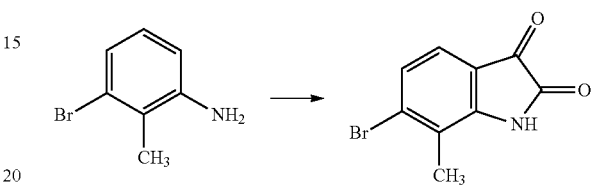

A mixture of 3-bromo-2-methylaniline (10 mL, 60.52 mmol), chloral hydrate (14.86 g, 89.86 mmol) and anhydrous Na$_2$SO$_4$ (94.56 g, 665.74 mmol) in hydrochloric acid (6.4 mL, 211.24 mmol) and H$_2$O (700 mL) was stirred vigorously at room temperature overnight. To the resulting mixture, hydroxylamine hydrochloride (5.86 g, 84.26 mmol) was added and the mixture was heated to reflux overnight. The reaction mixture was ice cooled, and the resulting precipitate was collected by vacuum filtration and washed copiously with H$_2$O and dried under suction. The precipitate was re-dissolved in EtOAc (~500 mL) and washed with H$_2$O (300 mL) and brine (300 mL) then dried over MgSO$_4$. The resulting filtrate was removed in vacuo to give 6-bromo-7-methyl-indoline-2,3-dione as a dark brown solid in quantitative yield, which was used directly in the next step without further purification.

LC-MS 238.5/240.5 [M+H]$^+$; RT 1.84 min (b) 6-bromo-1-ethyl-7-methyl-indoline-2,3-dione

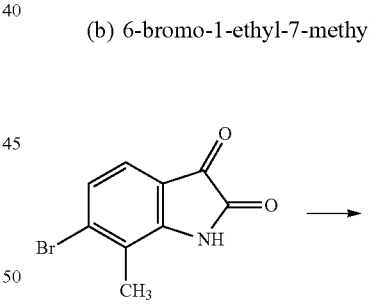

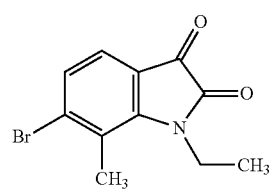

Iodoethane (7.61 mL, 94.65 mmol) was added dropwise to a solution of 6-bromo-7-methyl-indoline-2,3-dione (11.36 g, 47.32 mmol) and anhydrous K$_2$CO$_3$ (7.85 g, 56.79 mmol) in dry DMF (20 mL) and the reaction mixture was heated to 100° C. After 1 h the reaction mixture was then diluted with EtOAc (100 mL) and H$_2$O (100 mL) and the phases separated. The aqueous phase was extracted with EtOAc (2×70 mL) and the combined organic phases were washed with brine (200 mL) and dried over MgSO$_4$. The resulting filtrate was removed in vacuo to give 6-bromo-1-ethyl-7-methyl-indoline-2,3-dione (11.2 g, 88% yield) as a brown crystalline solid which was used directly in the next step without further purification.

LC-MS (Method A) 268.3/270.3 [M+H]$^+$; RT 2.32 min (c) 4-bromo-2-(ethylamino)-3-methyl-benzoic acid

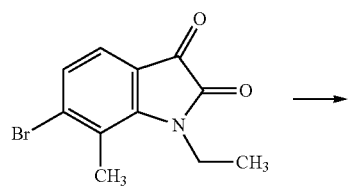

Dropwise to a solution of 6-bromo-1-ethyl-7-methyl-indoline-2,3-dione (10.0 g, 37.3 mmol) in 2M aq. NaOH (100 mL) was added H$_2$O$_2$ (53.3 mL, 522.17 mmol) and the resulting reaction mixture was left to stir at room temperature for 2 h. The reaction mixture was diluted with DCM (150 mL) and the phases were separated. The aq. phase was acidified to pH 3 with 2M aqueous HCl and the resulting precipitate was filtered, collected and dried overnight in a heated desiccator at 40° C. to give 4-bromo-2-(ethylamino)-3-methyl-benzoic acid (5.2 g, 54% yield) as a pale yellow crystalline solid.

LC-MS (Method A) 258.3/260.3 [M]$^+$; RT 1.25 min (d) 7-bromo-1-ethyl-4-hydroxy-8-methyl-3-nitro-quinolin-2-one

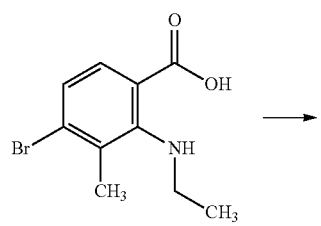

To a solution of 4-bromo-2-(ethylamino)-3-methyl-benzoic acid (1.74 g, 6.74 mmol) in dry THF (20 mL) at room temperature under N$_2$ atmosphere was added triphosgene (1.2 g, 4.03 mmol) in one portion. This was allowed to stir at room temperature for 3 h, after which time the solvent was carefully removed in vacuo (rotary evaporator was prohibited from reaching>40° C. vacuum was set at 1 mbar, and reached between 1-10 mbar) to give a thick red oil which was diluted with dry THF (10 mL) under a N$_2$ atmosphere. To the resulting solution Et$_3$N (7.5 mL, 53.93 mmol) was added dropwise, followed by the addition of ethyl nitroacetate (1.12 mL, 10.11 mmol) in one portion. The reaction mixture was heated to 60° C. overnight, after which time the solvent was removed in vacuo (maintaining bath temperature<40° C.). The residue was then partitioned between EtOAc (20 mL) and brine (20 mL). 2M aqueous HCl was then added to adjust the pH to around 3. The organic phase was separated, dried over Na$_2$SO$_4$, filtered and the solvent removed in vacuo to give 7-bromo-1-ethyl-4-hydroxy-8-methyl-3-nitro-quinolin-2-one as an orange solid in quantitative yield, which was used in the next step without further purification.

LC-MS (Method A) 327.3/329.3 [M]$^+$; RT 2.08 min (e) 3-amino-7-bromo-1-ethyl-4-hydroxy-8-methyl-quinolin-2-one

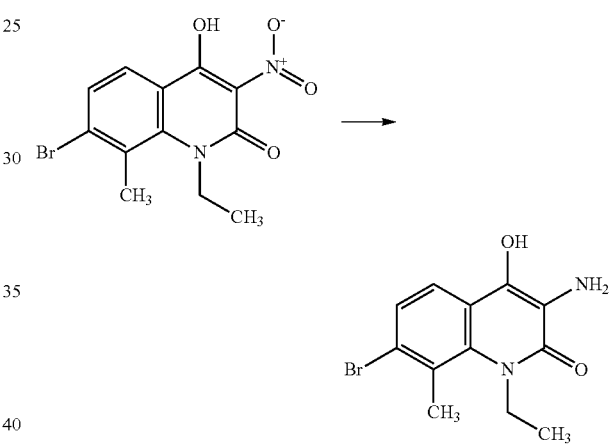

Sodium hydrosulfite (3.5 g, 20.1 mmol) was added to a stirred solution of 7-bromo-1-ethyl-4-hydroxy-8-methyl-3-nitro-quinolin-2-one (2.63 g, 8.04 mmol) in EtOH (20 mL) and H$_2$O (4 mL) and heated to reflux for 1 h. The reaction mixture was filtered through filter paper and the solvent removed in vacuo. Purification by flash column chromatography eluting with 0-10% MeOH in DCM gave 3-amino-7-bromo-1-ethyl-4-hydroxy-8-methyl-quinolin-2-one (652 mg, 27%) as a yellow crystalline solid.

LC-MS (Method A) 297.3/299.3 [M]$^+$; RT 1.77 min (f) 7-bromo-5-ethyl-6-methyl-oxazolo[4,5-c]quinolin-4-one

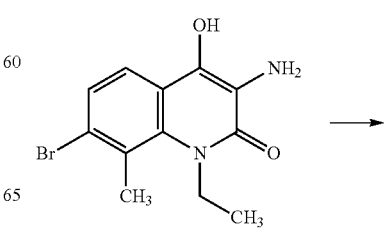

-continued

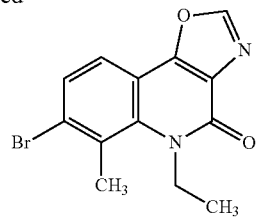

To 3-amino-7-bromo-1-ethyl-4-hydroxy-8-methyl-quinolin-2-one (101 mg, 0.34 mmol) was added to triethyl orthoformate (5. mL, 0.34 mmol). The reaction mixture was heated to 105° C. for 2 h, then excess triethyl orthoformate was removed in vacuo. Column chromatography eluting with 30-70% EtOAc in Petroleum ether (40-60) gave 7-bromo-5-ethyl-6-methyl-oxazolo[4,5-c]quinolin-4-one in quantitative yield, which was used in the next step without further purification.

LC-MS (Method A) 307.3/309.3 [M]$^+$; RT 2.15 min (g) 7-(4-amino-2,5-difluoro-phenyl)-5-ethyl-6-methyl-oxazolo[4,5-c]quinolin-4-one B

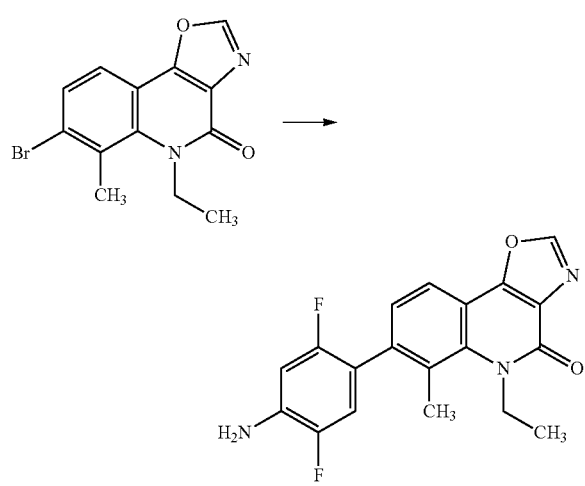

A mixture of 7-bromo-5-ethyl-6-methyl-oxazolo[4,5-c]quinolin-4-one (82 mg, 0.27 mmol), 2,5-difluoro-4-(4,4,5,5-tetramethyl-1,3,2-dioxaborolan-2-yl)aniline (81 mg, 0.32 mmol), Cs$_2$CO$_3$ (130 mg, 0.40 mmol) and 1,1'-bis(diphenylphosphino)ferrocene-palladium(II) dichloride dichloromethane complex (43 mg, 0.05 mmol) in toluene (3 mL), IPA (1 mL) and H$_2$O (1 mL) was heated to 70° C. for 1 h. The reaction mixture was then filtered through Celite and the solvent removed in vacuo. Purification by flash column chromatography eluting with 30-70% EtOAc in Petroleum ether (40-60) gave 7-(4-amino-2,5-difluoro-phenyl)-5-ethyl-6-methyl-oxazolo[4,5-c]quinolin-4-one B (13 mg, 13%) as a light purple crystalline solid.

$^1$H NMR (Method A) (CDCl$_3$): δ ppm 8.09 (s, 1H), 7.83 (d, J=8.0 Hz, 1H), 7.24 (d, J=8.0 Hz, 1H), 6.95 (1H, dd, J=11.0 Hz, 7.0 Hz, 1H), 6.61 (dd, J=11.0 Hz, 7.0 Hz, 1H), 4.55 (m, 2H), 3.99 (m, 2H), 2.45 (d, J=1.5 Hz, 3H), 1.32 (t, J=7.0 Hz, 3H); LC-MS (Method A) 356.4 [M+H]$^+$; RT 2.11 min Example 3—7-(4-amino-2,5-difluoro-phenyl)-5-cyclopropyl-6-methyl-3H-oxazolo[4,5-c]quinoline-2,4-dione C (a) 7-bromo-1-cyclopropyl-4-hydroxy-8-methyl-3-nitro-quinolin-2-one

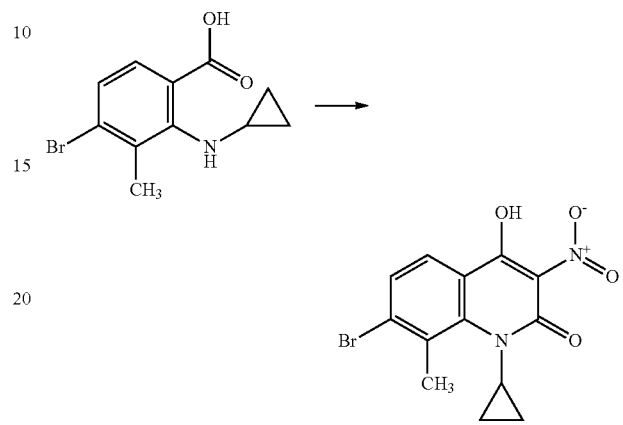

To a solution of 4-bromo-2-(cyclopropylamino)-3-methyl-benzoic acid (18 g, 66.64 mmol) (prepared as described in Example 1 step (d)) in dry THF (360 mL) at room temperature under N$_2$ atmosphere was added triphosgene (11.83 g, 39.85 mmol) in one portion. This was allowed to stir at room temperature for 3 h, after which time the solvent was carefully removed in vacuo (rotary evaporator was prohibited from reaching>40° C. Vacuum was set at 1 mbar, and reached between 1-10 mbar) to give a thick red oil which was diluted with dry THF (450 mL) under a N$_2$ atmosphere. To the resulting solution Et$_3$N (74.3 mL, 533.1 mmol) was added dropwise, followed by the addition of ethyl nitroacetate (11.1 mL, 99.96 mmol) in one portion. The reaction mixture was heated to 60° C. overnight, after which time the solvent was removed in vacuo. The residue was then partitioned between EtOAc (100 mL) and brine (100 mL). 2M aqueous HCl was then added to adjust the pH to around 3.

The organic phase was separated, dried over Na$_2$SO$_4$, filtered and the solvent removed in vacuo to give an orange oil. Purification by flash column chromatography eluting initially with 50-100% EtOAc in Petroleum ether (40-60) switching to 5-10% MeOH in DCM gave 7-bromo-1-cyclopropyl-4-hydroxy-8-methyl-3-nitro-quinolin-2-one (6 g, 27%) as a yellow solid.

LC-MS (Method B) 339.3.2/341.2 [M]$^+$; RT 1.60 min (b) 7-(4-amino-2,5-difluoro-phenyl)-1-cyclopropyl-4-hydroxy-8-methyl-3-nitro-quinolin-2-one

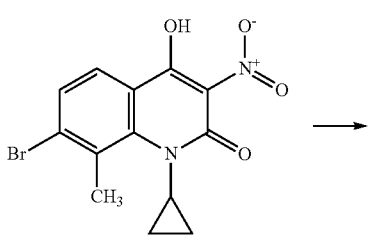

(d) 7-(4-amino-2,5-difluoro-phenyl)-5-cyclopropyl-6-methyl-3H-oxazolo[4,5-c]quinoline-2,4-dione C

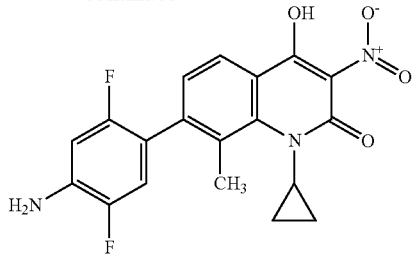

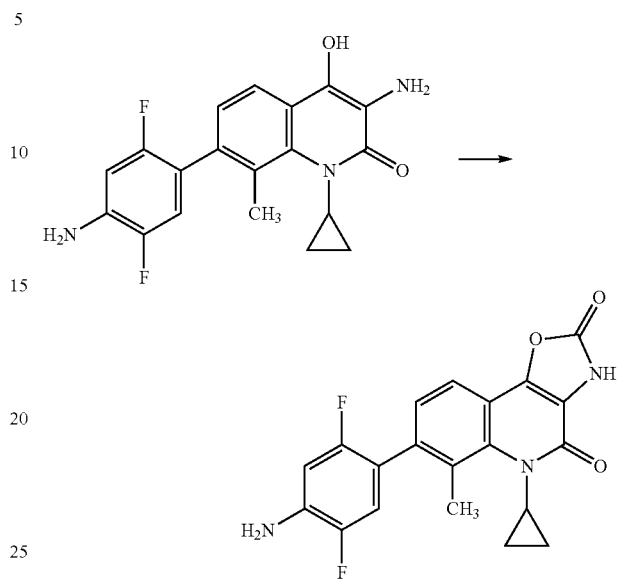

A mixture of 7-bromo-1-cyclopropyl-4-hydroxy-8-methyl-3-nitro-quinolin-2-one (2.4 g, 7.08 mmol), 4-amino-2,5-difluorobenzeneboronic acid pinacol ester (1.99 g, 7.78 mmol), [1,1'-bis(diphenylphosphino)ferrocene]palladium (II) chloride dichloromethane complex (578 mg, 0.71 mmol), Cs$_2$CO$_3$ (6.92 g, 21.23 mmol) in 1,4-dioxane (40 mL) and H$_2$O (4 mL). This was then heated to 70° C. for 2 h. The reaction mixture was then filtered through Celite and the solvent removed in vacuo. Purification by flash column chromatography eluting with 20-80% MeOH in DCM gave 7-(4-amino-2,5-difluoro-phenyl)-5-ethyl-6-methyl-oxazolo[4,5-c]quinolin-4-one (1.5 g, 55%) as a yellow crystalline solid.

LC-MS (Method B) 388.4 [M+H]$^+$; RT 1.90 min (c) 3-amino-7-(4-amino-2,5-difluoro-phenyl)-1-cyclopropyl-4-hydroxy-8-methyl-quinolin-2-one

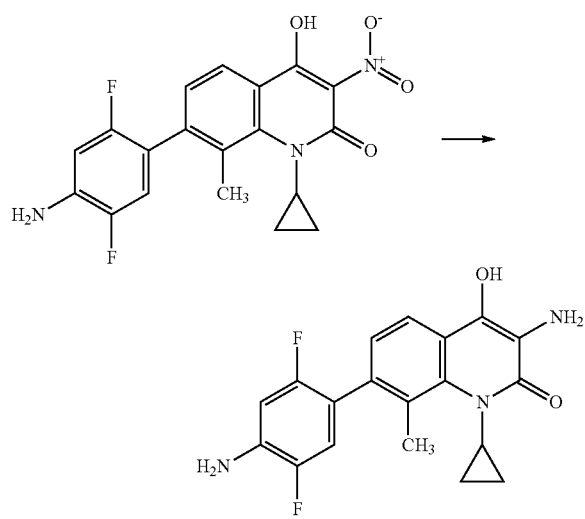

Sodium hydrosulfite (0.56 g, 3.23 mmol) was added to a stirred solution of 7-(4-amino-2,5-difluoro-phenyl)-1-cyclopropyl-4-hydroxy-8-methyl-3-nitro-quinolin-2-one (0.5 g, 1.29 mmol) in EtOH (5 mL) and H$_2$O (1 mL) and stirred for 2 h at room temperature. A precipitate formed which was filtered off and washed with H$_2$O (20 ml), followed by Et$_2$O (20 mL). The grey solid was then kept under vacuum overnight to give the desired product as a grey solid, which was used in the next step without further purification.

LC-MS (Method B) 358.4 [M+H]$^+$; RT 1.62 min

To a solution of 3-amino-7-(4-amino-2,5-difluoro-phenyl)-1-cyclopropyl-4-hydroxy-8-methyl-quinolin-2-one (100 mg, 0.28 mmol) in THF (10 mL) was added triphosgene (33 mg, 0.11 mmol) and allowed to stir at room temp for 4 h. To the reaction mixture was added H$_2$O and the solvents were removed in vacuo. Purification by flash column chromatography eluting with 5-10% MeOH in DCM gave 7-(4-amino-2,5-difluoro-phenyl)-5-cyclopropyl-6-methyl-3H-oxazolo[4,5-c]quinoline-2,4-dione C as an olive solid (103 mg, 96% yield).

$^1$H NMR (Method B) (DMSO-d$_6$): δ ppm 8.09 (s, 1H), 7.64 (d, J=8.0 Hz, 1H), 7.22 (d, J=8.0 Hz, 1H), 6.95 (1H, dd, J=12.0 Hz, 8.0 Hz, 1H), 6.60 (dd, J=12.0 Hz, 8.0 Hz, 1H), 3.96 (bs, 2H), 3.58 (m, 1H), 2.52 (d, J=1.5 Hz, 3H), 1.29 (m, 2H), 0.68 (m, 2H); LC-MS (Method B) 384.4 [M+H]$^+$; RT 2.90 min Example 4—7-(4-amino-2,5-difluoro-phenyl)-5-cyclopropyl-2,6-dimethyl-oxazolo[4,5-c]quinolin-4-one D (a) 3-amino-7-bromo-1-cyclopropyl-4-hydroxy-8-methyl-quinolin-2-one

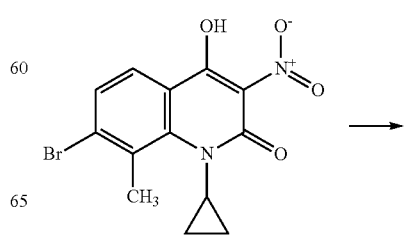

81

-continued

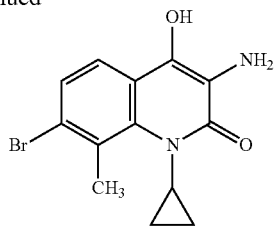

Using the method described in Example 2 step (e) and using 7-bromo-1-cyclopropyl-4-hydroxy-8-methyl-3-nitro-quinolin-2-one (prepared as described in Example 3 step (a)) 3-amino-7-bromo-1-cyclopropyl-4-hydroxy-8-methyl-quinolin-2-one was prepared as a pale brown solid and used in the next step without further purification.

LC-MS (Method C) 308.9/310.8 [M+H]+, RT 1.38 min (b) N-(7-bromo-1-cyclopropyl-4-hydroxy-8-methyl-2-oxo-3-quinolyl)acetamide

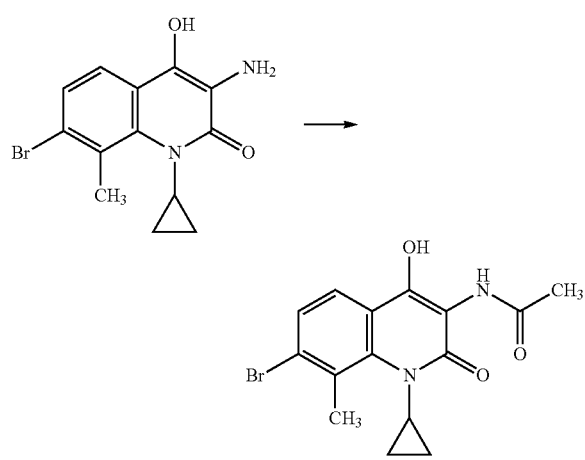

Anhydrous Et₃N (0.23 mL, 1.66 mmol) and acetyl chloride (0.07 mL, 0.99 mmol) were added dropwise to a solution of 3-amino-7-bromo-1-cyclopropyl-4-hydroxy-8-methyl-quinolin-2-one (205 mg, 0.66 mmol) in THF (5 mL). The mixture, sheltered from light, was refluxed for 5 h, cooled to room temperature and allowed to stir at room temperature overnight. It was then diluted with H₂O (10 mL) and acidified with 6M aqueous HCl. The aqueous layer was extracted with EtOAc (2×20 mL). The combined organic layers were washed with aq. NaHCO₃ (10 mL) and brine (10 mL), dried over Na₂SO₄, filtered and the solvent removed under vacuo to give N-(7-bromo-1-cyclopropyl-4-hydroxy-8-methyl-2-oxo-3-quinolyl)acetamide (101 mg, 43%) as a brown oil. The product used in the next step without further purification.

LC-MS (Method C) 350.9/352.8 [M+H]+, RT 1.81 min

82

(c) 7-bromo-5-cyclopropyl-2,6-dimethyl-oxazolo[4,5-c]quinolin-4-one

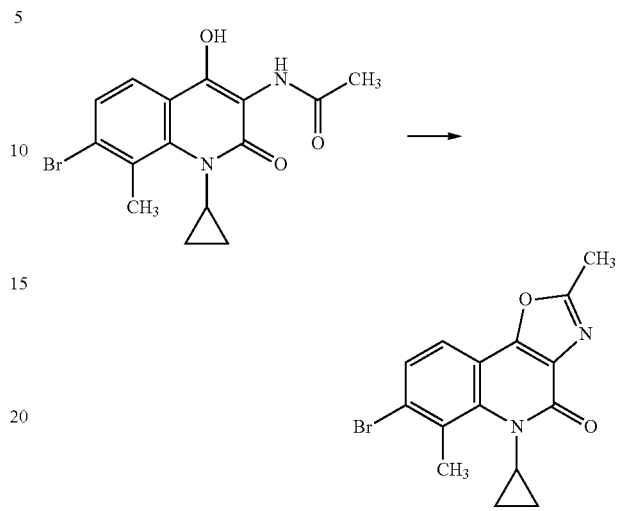

Glacial acetic acid (1.0 mL, 17.47 mmol) and trifluoroacetic acid (1.0 mL, 13.07 mmol) were added to N-(7-bromo-1-cyclopropyl-4-hydroxy-8-methyl-2-oxo-3-quinolyl)acetamide (101 mg, 0.29 mmol) in a microwave vial. The solution was then irradiated with microwaves at 200° C. for 20 min, allowed to cool and solvent removed under vacuo. To the residue was added EtOAc (20 mL) and the solution washed with aq. NaHCO₃ (5 mL) followed by brine (5 mL). The organic layer was then dried over Na₂SO₄, filtered and the solvent removed under vacuo. The resulting residue was purified by flash chromatography eluting with 6% MeOH/DCM to give 7-bromo-5-cyclopropyl-2,6-dimethyl-oxazolo[4,5-c]quinolin-4-one (36 mg, 38%) as a pale yellow solid.

LC-MS (Method C) 332.9/334.8 [M+H]+, RT 1.68 min (d) 7-(4-amino-2,5-difluoro-phenyl)-5-cyclopropyl-2,6-dimethyl-oxazolo[4,5-c]quinolin-4-one D

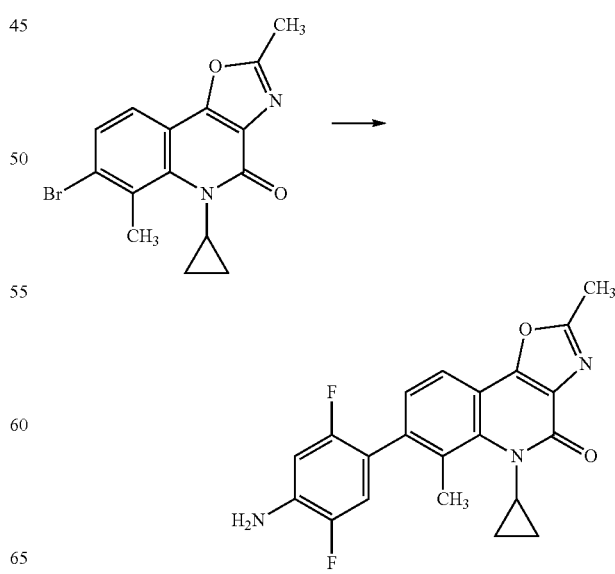

A mixture of 7-bromo-5-cyclopropyl-2,6-dimethyl-oxazolo[4,5-c]quinolin-4-one (107 mg, 0.32 mmol), 4-amino-2,5-difluorobenzeneboronic acid pinacol ester (122 mg, 0.48 mmol), [1,1'-bis(diphenylphosphino)ferrocene]Palladium (II) chloride dichloromethane complex (26 mg, 0.03 mmol) and Cs$_2$CO$_3$ (313 mg, 0.96 mmol) were dissolved in 1,2-dimethoxyethane (1.5 mL) and H$_2$O (0.5 mL). The solution was then irradiated with microwaves at 120° C. for 20 min, allowed to cool and then diluted with EtOAc (50 mL). The resulting organics were washed with saturated aq. Na$_2$CO$_3$ (2×20 mL) followed by brine (20 mL). The organic layer was then separated, dried over Na$_2$SO$_4$, filtered and solvent removed under vacuo. The resulting residue was then purified by reverse phase mass directed auto-preparative HPLC (Method A) to give 7-(4-amino-2,5-difluoro-phenyl)-5-cyclopropyl-2,6-dimethyl-oxazolo[4,5-c]quinolin-4-one D (23 mg 19% yield) as a white solid.

$^1$H NMR (Method B) (CD$_3$OD): δ ppm 7.78-7.81 (d, J=8.0 Hz, 1H), 7.28-7.30 (d, J=8.0, 1H), 6.95-6.99 (dd, J=11.3 Hz, 6.9 Hz, 1H), 6.66-6.71 (dd, J=11.3 Hz, 7.4 Hz, 1H), 3.63-3.66 (m, 1H), 2.70 (s, 3H), 2.57 (s, 3H), 1.27 (d, 2H), 0.61 (s, 2H); LC-MS (Method C) 382.2 [M+H]$^+$, RT 1.60 min Example 5—7-(4-amino-2-fluoro-phenyl)-5-cyclopropyl-6-methyl-oxazolo[4,5-c]quinolin-4-one E

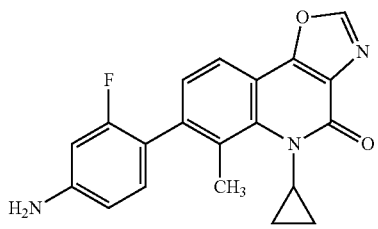 [SMILES: Cc1c(-c2ccc(N)cc2F)ccc2c3ocnc3c(=O)n(C3CC3)c12]

Prepared using 3-fluoro-4-(4,4,5,5-tetramethyl-1,3,2-dioxaborolan-2-yl)aniline and 7-bromo-5-cyclopropyl-6-methyl-oxazolo[4,5-c]quinolin-4-one (prepared as described in Example 1 step (f)) and a similar procedure to that described in Example 1 step (g)

$^1$H NMR (Method A) (CDCl$_3$): δ ppm 8.07 (s, 1H), 7.75 (d, J=8.0 Hz, 1H), 7.24 (d, J=8.0 Hz, 1H), 7.09 (m, 1H), 6.56 (m, 1H), 6.50 (m, 1H), 3.92 (s, 2H), 3.63 (m, 1H), 2.52 (m, 3H), 1.30-1.23 (m, 2H), 0.67 (s, 2H); LC-MS (Method D) 350.5 [M+H]$^+$; RT 1.97 min.

Example 6—7-(5-aminopyrazin-2-yl)-5-cyclopropyl-6-methyl-oxazolo[4,5-c]quinolin-4-one F (a) 5-cyclopropyl-6-methyl-7-(4,4,5,5-tetramethyl-1,3,2-dioxaborolan-2-yl)-oxazolo[4,5-c]quinolin-4-one

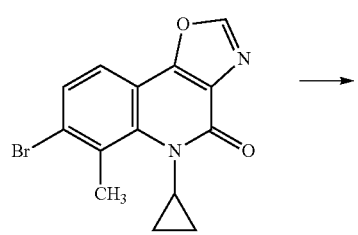

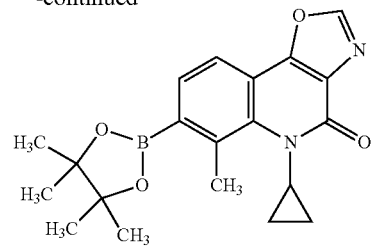

To a solution of 7-bromo-5-cyclopropyl-6-dimethyl-oxazolo[4,5-c]quinolin-4-one (prepared as described in Example 1 step (f)) (1.64 g, 5.14 mmol) in 1,2-dimethoxyethane (30 mL) under N$_2$ was added potassium acetate (1.51 g, 15.42 mmol), bis(pinacolato)diboron (1.70 g, 6.68 mmol) and [1,1'-bis(diphenylphosphino)ferrocene]palladium(II) chloride dichloromethane complex (210 mg, 0.26 mmol). The resulting reaction mixture was heated to 75° C. for 72 h. On cooling the reaction mixture was partitioned between EtOAc (50 mL) and H$_2$O (50 ml). The organic phase was separated and dried (MgSO$_4$), filtered and evaporated in vacuo. The resulting residue was purified by flash chromatography using a gradient of 0-100% EtOAc in DCM to give 5-cyclopropyl-6-dimethyl-7-(4,4,5,5-tetramethyl-1,3,2-dioxaborolan-2-yl)oxazolo[4,5-c]quinolin-4-one (1.6 g, 85% yield) as a brown foam.

LC-MS (Method D) 367.5 [M+H]$^+$; RT 2.83 min (b) 7-(5-aminopyrazin-2-yl)-5-cyclopropyl-6-methyl-oxazolo[4,5-c]quinolin-4-one F

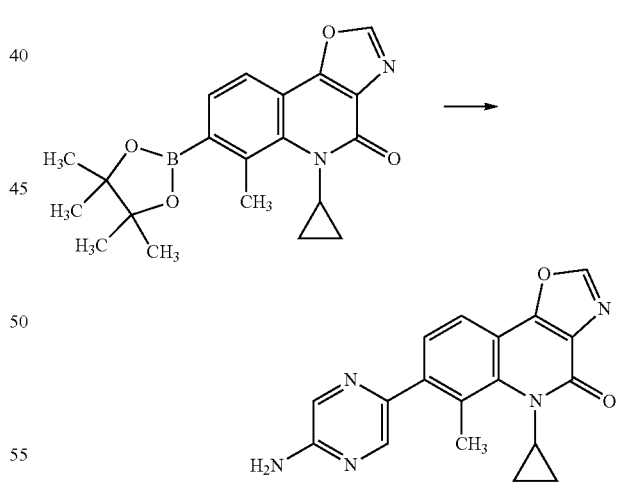

Prepared using 5-cyclopropyl-6-dimethyl-7-(4,4,5,5-tetramethyl-1,3,2-dioxaborolan-2-yl)oxazolo[4,5-c]quinolin-4-one and 5-bromo-2-pyrazinamin and a similar procedure to that described in Example 1 step (g)

$^1$H NMR (Method A) (CDCl$_3$): b ppm 8.22 (d, J=1.5 Hz, 1H), 8.14 (d, J=1.5 Hz, 1H), 8.08 (s, 1H), 7.81 (d, J=8.0 Hz, 1H), 7.44 (d, J=8.0 Hz, 1H), 4.71 (s, 2H), 3.65 (m, 1H), 2.64 (s, 3H), 1.34-1.21 (m, 2H), 0.70 (m, 2H); LC-MS (Method D) 334.4 [M+H]$^+$; RT 4.73 min.

Example 7—5-cyclopropyl-6-methyl-7-phenyl-oxazolo[4,5-c]quinolin-4-one G

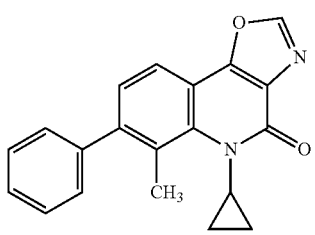 [SMILES: Cc1c(-c2ccccc2)ccc2c3ocnc3c(=O)n(C3CC3)c12]

Prepared using 4,4,5,5-tetramethyl-2-phenyl-1,3,2-dioxaborolane and 7-bromo-5-cyclopropyl-6-methyl-oxazolo[4,5-c]quinolin-4-one (prepared as described in Example 1 step (f)) and a similar procedure to that described in Example 1 step (g)

$^1$H NMR (Method A) (CDCl$_3$): δ ppm 8.07 (s, 1H), 7.78 (d, J=8.0 Hz, 1H), 7.53-7.36 (m, 5H), 7.28 (d, J=8.0 Hz, 1H), 3.70-3.59 (m, 1H), 2.54 (s, 3H), 1.35-1.21 (m, 2H), 0.75-0.66 (m, 2H); LC-MS (Method D) 317.5 [M+H]$^+$; RT 7.04 min.

Example 8—4-(5-cyclopropyl-2,6-dimethyl-4-oxo-oxazolo[4,5-c]quinolin-7-yl)benzoic acid H

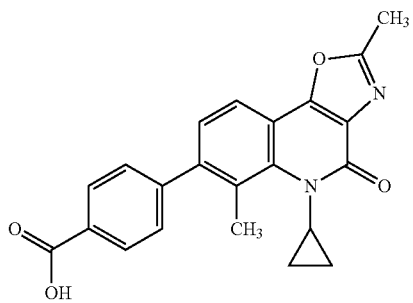 [SMILES: Cc1nc2c(=O)n(C3CC3)c3c(C)c(-c4ccc(C(=O)O)cc4)ccc3c2o1]

Prepared using 4-(4,4,5,5-tetramethyl-1,3,2-dioxaborolan-2-yl)benzoic acid and 7-bromo-5-cyclopropyl-2,6-dimethyl-oxazolo[4,5-c]quinolin-4-one (prepared as described in Example 4 step (c)) and a similar procedure to that described in Example 4 step (d)

$^1$H NMR (Method B) (CD$_3$OD): δ ppm 8.26-8.08 (m, 2H), 7.87 (d, J=8.0 Hz, 1H), 7.65-7.51 (m, 2H), 7.38 (d, J=8.0 Hz, 1H), 3.67 (m, 1H), 2.71 (s, 3H), 2.60 (s, 3H), 1.34 (m, 2H), 0.75-0.60 (m, 2H); LC-MS (Method C) 375.1 [M$^+$ H$^+$], RT 1.47 min

Example 9—7-[4-{aminomethyl)phenyl]-5-cyclopropyl-2,6-dimethyl-oxazolo[4,5-c]quinolin-4-one I

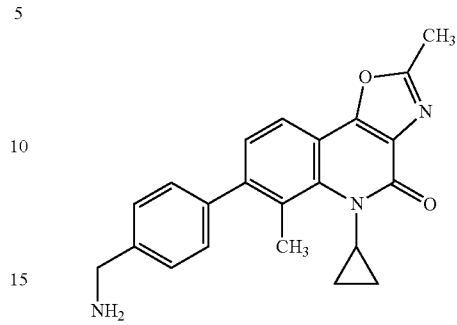

Prepared using 1-[4-(4,4,5,5-tetramethyl-1,3,2-dioxaborolan-2-yl)phenyl]methanamine hydrochloride and 7-bromo-5-cyclopropyl-2,6-dimethyl-oxazolo[4,5-c]quinolin-4-one (prepared as described in Example 4 step (c)) and a similar procedure to that described in Example 4 step (d)

$^1$H NMR (Method B) (CD$_3$OD): δ ppm 8.50 (br s, 1H), 7.85 (d, J=8.0 Hz, 1H), 7.71-7.47 (m, 4H), 7.33 (d, J=8.0 Hz, 1H), 4.21 (s, 2H), 3.65 (m, 1H), 2.70 (s, 3H), 2.57 (s, 3H), 1.37-1.28 (m, 2H), 0.66 (m, 2H); LC-MS (Method C) 360.4 [M$^+$ H$^+$], RT 1.15 min

Example 10—5-cyclopropyl-7-(1H-indazol-5-yl)-2,6-dimethyl-oxazolo{4,5-c]quinolin-4-one J

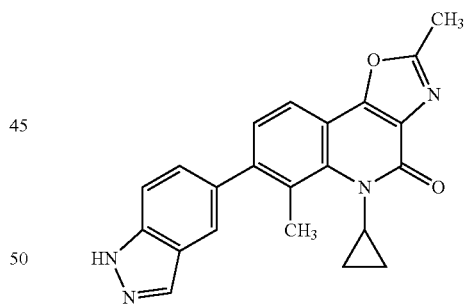

Prepared using 5-[4-(4,4,5,5-tetramethyl-1,3,2-dioxaborolan-2-yl)-1H-indazole and 7-bromo-5-cyclopropyl-2,6-dimethyl-oxazolo[4,5-c]quinolin-4-one (prepared as described in Example 4 step (c)) and a similar procedure to that described in Example 4 step (d)

$^1$H NMR (Method B) (DMSO-d$_6$): δ ppm 13.20 (s, 1H), 8.20-8.14 (m, 1H), 7.83 (s, 1H), 7.76 (d, J=7.9 Hz, 1H), 7.67 (d, J=8.6 Hz, 1H), 7.44 (dd, J=8.6, 1.6 Hz, 1H), 7.35 (d, J=8.0 Hz, 1H), 3.58 (m, 1H), 2.65 (s, 3H), 2.50 (s, 3H), 1.35-1.18 (m, 2H), 0.65-0.47 (m, 2H); LC-MS (Method C) 371.1 [M$^+$ H$^+$], RT 1.71 min Example 11—tert-butyl 3-[4-(5-cyclopropyl-2,6-dimethyl-4-oxo-oxazolo[4,5-c]quinolin-7-yl)pyrazol-1-yl]azetidine-1-carboxylate K

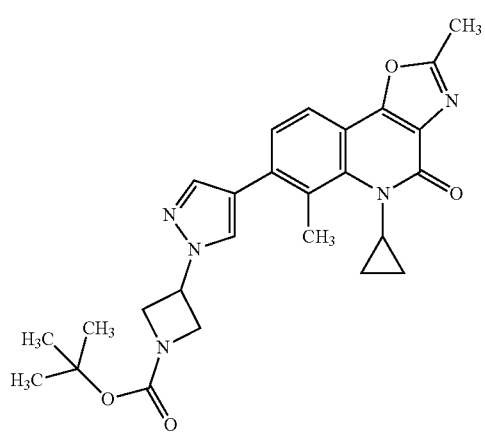 [SMILES: Cc1nc2c(=O)n(C3CC3)c3c(C)c(-c4cnn(C5CN(C(=O)OC(C)(C)C)C5)c4)ccc3c2o1]

Prepared using tert butyl 3-[4-(4,4,5,5-tetramethyl-1,3,2-dioxaborolan-2-yl)pyrazol-1-yl]azetine-1-carboxylate and 7-bromo-5-cyclopropyl-2,6-dimethyl-oxazolo[4,5-c]quinolin-4-one (prepared as described in Example 4 step (c)) and a similar procedure to that described in Example 4 step (d)

¹H NMR (Method B) (CDCl₃): δ ppm 7.77 (s, 1H), 7.70 (s, 1H), 7.68 (d, J=8.1 Hz, 1H), 7.30 (d, J=8.1 Hz, 1H), 5.20-5.07 (m, 1H), 4.54-4.30 (m, 4H), 3.71-3.58 (m, 1H), 2.69 (s, 3H), 2.67 (s, 3H), 1.48 (s, 9H), 1.35-1.19 (m, 2H), 0.70-0.54 (m, 2H); LC-MS (Method C) 476.5 [M⁺ H⁺], RT 1.68 min Example 12—7-[1-(azetidin-3-yl)pyrazol-4-yl]-5-cyclopropyl-2,6-dimethyl-oxazolo[4,5-c]quinolin-4-one L

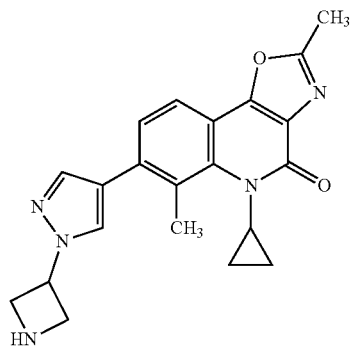 [SMILES: Cc1nc2c(=O)n(C3CC3)c3c(C)c(-c4cnn(C5CNC5)c4)ccc3c2o1]

Prepared from Example 11 by deprotection of the BOC group using the method described in Example 49 step (j)

¹H NMR (Method B) (CD₃OD): δ ppm 8.56 (br s, 1H), 8.07 (s, 1H), 7.98 (s, 1H), 7.79 (d, J=8.1 Hz, 1H), 7.46 (d, J=8.1 Hz, 1H), 4.68-4.48 (m, 4H), 3.75-3.60 (m, 1H), 3.37 (m, 1H), 2.76 (s, 3H), 2.69 (s, 3H), 1.51-1.14 (m, 2H), 0.75-0.40 (m, 2H); LC-MS (Method C) 376.3 [M⁺ H⁺], RT 1.09 min Example 13—7-(4-amino-3-fluoro-phenyl)-5-cyclopropyl-2,6-dimethyl-oxazolo[4,5-c]quinolin-4-one M

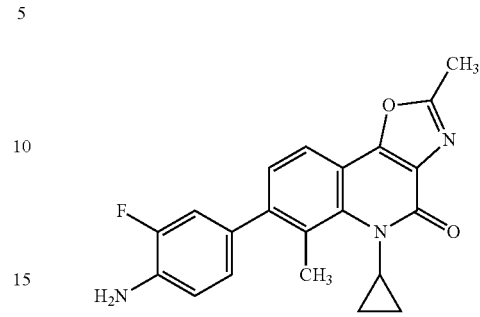

Prepared using 2-fluoro-4-(4,4,5,5-tetramethyl-1,3,2-dioxaborolan-2-yl)aniline and 7-bromo-5-cyclopropyl-2,6-dimethyl-oxazolo[4,5-c]quinolin-4-one (prepared as described in Example 4 step (c)) and a similar procedure to that described in Example 4 step (d)

¹H NMR (Method B) (CD₃OD): δ ppm 7.73 (d, J=8.1 Hz, 1H), 7.28 (d, J=7.9 Hz, 1H), 7.07-6.91 (m, 3H), 3.61 (m, 1H), 2.67 (s, 3H), 2.57 (s, 3H), 1.30 (m, 2H), 0.61 (m, 2H); LC-MS (Method C) 364.2 [M+H]⁺; RT 1.92 min Example 14—7-(2-aminopyrimidin-5-yl)-5-cyclopropyl-6-methyl-oxazolo[4,5-c]quinolin-4-one N

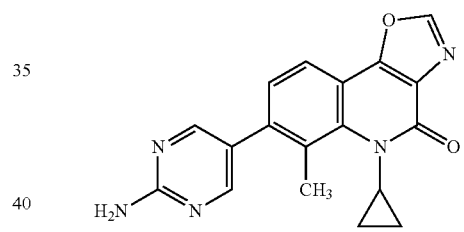

Prepared using 5-(4,4,5,5-tetramethyl-1,3,2-dioxaborolan-2-yl)-2-pyrimidinamine and 7-bromo-5-cyclopropyl-6-methyl-oxazolo[4,5-c]quinolin-4-one (prepared as described in Example 1 step (f)) and a similar procedure to that described in Example 1 step (g)

¹H NMR (Method B) (CDCl₃): δ ppm 8.44 (s, 2H), 8.11 (s, 1H), 7.83 (d, J=7.9 Hz, 1H), 7.23 (d, J=7.5 Hz, 1H), 5.66 (br s, 2H), 3.66 (br s, 1H), 2.61 (s, 3H), 1.32 (m, 2H), 0.69 (m, 2H); LC-MS (Method C) 334.1 [M+H]⁺; RT 1.14 min Example 15—7-(1H-benzimidazol-5-yl)-5-cyclopropyl-6-methyl-oxazolo[4,5-c]quinolin-4-one O

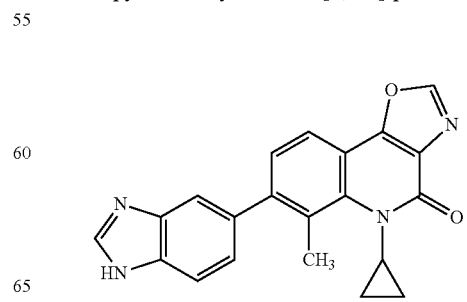

Prepared using 5-cyclopropyl-6-dimethyl-7-(4,4,5,5-tetramethyl-1,3,2-dioxaborolan-2-yl)oxazolo[4,5-c]quinolin-4-one (prepared as described in Example 6 step (a)) and tert butyl 5-bromobenzimidazole-1-carboxylate and a similar procedure to that described in Example 1 step (g), followed by deprotection of the BOC group using the method described in Example 49 step (j)

$^1$H NMR (Method A) (DMSO-d$_6$): δ ppm 12.59 (s, 0.5H), 12.55 (s, 0.5H), 8.80 (s, 1H), 8.31 (d, J=2.3 Hz, 1H), 7.82 (d, J=8.1 Hz, 1H), 7.77 (d, J=8.4 Hz, 0.5H), 7.71 (m, 1H), 7.65 (d, J=8.9 Hz, 0.5H), 7.56 (s, 0.5H), 7.37 (d, J=8.1 Hz, 1H), 7.30 (d, J=8.4 Hz, 0.5H), 7.27 (d, J=8.4 Hz, 0.5H), 3.59 (m, 1H), 1.26 m, 2H), 0.58 (m, 2H); LC-MS (Method D) 357.4 [M+H]$^+$; RT 1.54 min Example 16—7-(2-aminopyrimidin-5-yl)-5-cyclopropyl-2,6-dimethyl-oxazolo[4,5-c]quinolin-4-one P

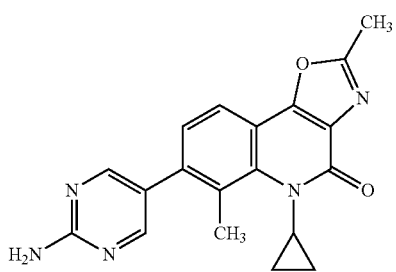

Prepared using 5-(4,4,5,5-tetramethyl-1,3,2-dioxaborolan-2-yl)-2-pyrimidinamine and 7-bromo-5-cyclopropyl-,2,6-dimethyl-oxazolo[4,5-c]quinolin-4-one (prepared as described in Example 4 step (c)) and a similar procedure to that described in Example 4 step (d)

$^1$H NMR (Method B) (CD$_3$OD): δ ppm 8.41 (s, 2H), 7.85 (d, J=8.1 Hz, 1H), 7.35 (d, J=7.9 Hz, 1H), 3.66 (m, 1H), 2.70 (s, 3H), 2.65 (s, 3H), 1.33 (m, 2H), 0.84 (m, 2H); LC-MS (Method C) 348.1 [M+H]$^+$; RT 1.21 min Example 17—4-(5-cyclopropyl)-2,6-dimethyl-4-oxo-oxazolo[4,5-c]quinolin-7-yl)benzenesulphonamide Q

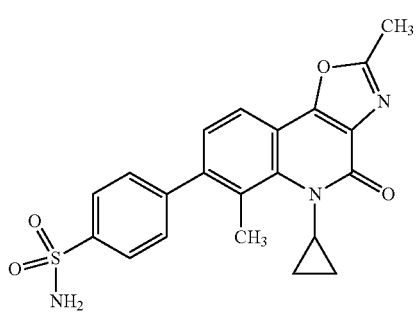 [SMILES: Cc1nc2c(=O)n(C3CC3)c3c(C)c(-c4ccc(S(N)(=O)=O)cc4)ccc3c2o1]

Prepared using 4-(4,4,5,5-tetramethyl-1,3,2-dioxaborolan-2-yl)benzenesulphonamide and 7-bromo-5-cyclopropyl-2,6-dimethyl-oxazolo[4,5-c]quinolin-4-one (prepared as described in Example 4 step (c)) and a similar procedure to that described in Example 4 step (d)

$^1$H NMR (Method A) (DMSO-d$_6$): δ ppm 8.04-7.98 (m, 2H), 7.83 (d, J=8.0 Hz, 1H), 7.76-7.68 (m, 2H), 7.51 (s, 2H), 7.35 (d, J=8.0 Hz, 1H), 3.62 (dq, J=7.1, 4.0, 3.6 Hz, 1H), 2.71 (s, 3H), 2.54 (s, 3H), 1.33-1.26 (m, 2H), 0.64-0.53 (m, 2H); LC-MS (Method E) 410.4 [M+H]$^+$; RT 6.18 min Example 18—5-cyclopropyl-7-(1H-indol-5-yl)-2,6-dimethyl-oxazolo[4,5-c]quinolin-4-one R

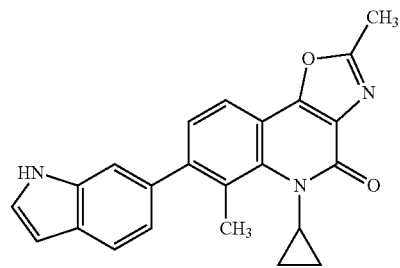 [SMILES: Cc1nc2c(=O)n(C3CC3)c3c(C)c(-c4ccc5cc[nH]c5c4)ccc3c2o1]

Prepared using indole-6-boronic acid pinacol ester and 7-bromo-5-cyclopropyl-2,6-dimethyl-oxazolo[4,5-c]quinolin-4-one (prepared as described in Example 4 step (c)) and a similar procedure to that described in Example 4 step (d)

$^1$H NMR (Method A) (DMSO-d$_6$): δ ppm 11.15 (s, 1H), 7.65 (d, J=8.0 Hz, 1H), 7.53 (s, 1H), 7.45 (d, J=8.3 Hz, 1H), 7.39-7.32 (m, 1H), 7.26 (d, J=8.0 Hz, 1H), 7.10 (dd, J=8.4, 1.7 Hz, 1H), 6.47-6.43 (m, 1H), 3.50 (tt, J=6.8, 3.9 Hz, 1H), 2.58 (s, 3H), 1.22-1.15 (m, 2H), 0.52-0.45 (m, 2H); LC-MS (Method E) 370.4 [M+H]$^+$; RT 7.61 min.

Example 19—7-(4-amino-3,5-difluoro-phenyl)-5-methyl-oxazolo[4,5-c]quinolin-4-one S

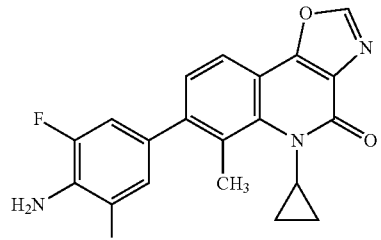

Prepared using 5-cyclopropyl-6-dimethyl-7-(4,4,5,5-tetramethyl-1,3,2-dioxaborolan-2-yl)oxazolo[4,5-c]quinolin-4-one (prepared as described in Example 6 step (a)) and 4-bromo-2,6-difluoroaniline and a similar procedure to that described in Example 1 step (g)

$^1$H NMR (Method A) (CDCl$_3$): δ ppm 8.07 (s, 1H), 7.75 (d, J=8.0 Hz, 1H), 7.22 (d, J=8.0 Hz, 1H), 6.95-6.84 (m, 1H), 3.88 (br s, 2H), 3.67-3.60 (m, 1H), 2.56 (s, 3H), 1.34-1.25 (m, 2H), 0.71-0.64 (m, 2H); LC-MS (Method A) 368.5 [M+H]$^+$; RT 2.48 min

Example 20—5-cyclopropyl-6-methyl-7-(1H-pyrazolo[3,4-b]pyridine-5-yl)oxazolo[4,5-c]quinolin-4-one T

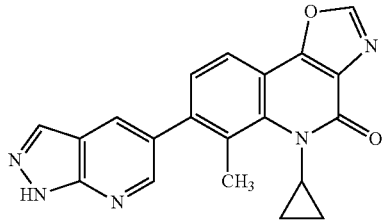 [SMILES: Cc1c(-c2cnc3[nH]ncc3c2)ccc2c3ocnc3c(=O)n(C3CC3)c12]

Prepared using tert butyl 5-(4,4,5,5-tetramethyl-1,3,2-dioxaborolan-2-yl)pyrazolo[3,4-b]pyridine-1-carboxylate and 7-bromo-5-cyclopropyl-, 6-methyl-oxazolo[4,5-c]quinolin-4-one (prepared as described in Example 1 step (f)) and a similar procedure to that described in Example 1, step (g), followed by deprotection of the BOC group using the method described in Example 49 step (j)

$^1$H NMR (Method A) (CDCl$_3$): b ppm 8.67 (d, J=2.0 Hz, 1H), 8.21 (s, 1H), 8.16 (d, J=2.0 Hz, 1H), 8.11 (s, 1H), 7.85 (d, J=8.0 Hz, 1H), 7.32 (d, J=8.0 Hz, 1H), 3.71-3.63 (m, 1H), 2.59 (s, 3H), 1.39-1.31 (m, 2H), 0.78-0.70 (m, 2H); LC-MS (Method A) 358.5 [M+H]$^+$; RT 1.77 min

Example 21—7-(3-amino-1H-pyrazolo[3,4-b]pyridine-5-yl)-5-cyclopropyl-6-methyl-oxazolo[4,5-c]quinolin-4-one U

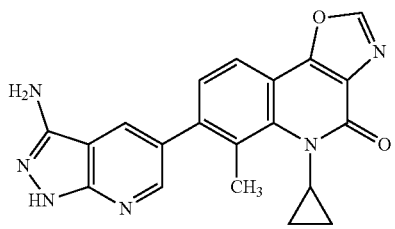 [SMILES: Cc1c(-c2cnc3[nH]nc(N)c3c2)ccc2c3ocnc3c(=O)n(C3CC3)c12]

Prepared using tert butyl 3-[bis(tert-butoxycarbonyl)amino]-5-(4,4,5,5-tetramethyl-1,3,2-dioxaborolan-2-yl)pyrazolo[3,4-b]pyridine-1-carboxylate and 7-bromo-5-cyclopropyl-6-methyl-oxazolo[4,5-c]quinolin-4-one (prepared as described in Example 1 step (f)) and a similar procedure to that described in Example 1 step (g), followed by deprotection of the BOC groups using the method described in Example 49 step (j)

$^1$H NMR (Method A) (CDCl$_3$): δ ppm 10.15 (br s, 1H), 8.57 (d, J=2.0 Hz, 1H), 8.10 (s, 1H), 7.97 (d, J=2.0 Hz, 1H), 7.83 (d, J=8.0 Hz, 1H), 7.30 (d, J=8.0 Hz, 1H), 4.29 (br s, 2H), 3.70-3.62 (m, 1H), 2.58 (s, 3H), 1.37-1.29 (m, 2H), 0.76-0.68 (m, 2H); LC-MS (Method A) 373.4 [M+H]$^+$; RT 1.58 min

Example 22—5-cyclopropyl-7-[2,5-difluoro-4-(1-hydroxyethyl)phenyl]-6-methyl-oxazolo[4,5-c]quinolin-4-one V

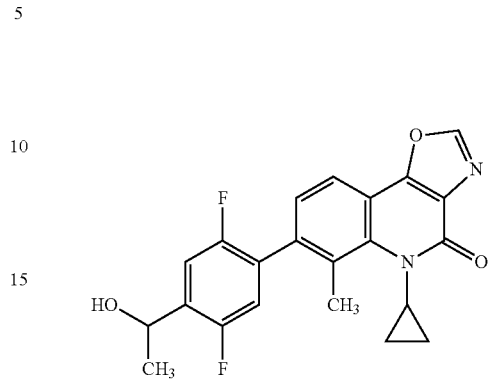

Prepared using 1-[2,5-difluoro-4-(4,4,5,5-tetramethyl-1,3,2-dioxaborolan-2-yl)phenyl]ethanol and 7-bromo-5-cyclopropyl-, 6-methyl-oxazolo[4,5-c]quinolin-4-one (prepared as described in Example 1 step (f)) and a similar procedure to that described in Example 1 step (g)

$^1$H NMR (Method B) (CDCl$_3$): δ ppm 8.09 (s, 1H), 7.79 (d, J=7.9 Hz, 1H), 7.37 (dd, J=9.9, 6.0 Hz, 1H), 7.22 (d, J=7.9 Hz, 1H), 7.00 (dd, J=9.9, 5.8 Hz, 1H), 5.27 (m, 1H), 3.63 (m, 1H), 2.52 (d, J=1.4 Hz, 3H), 1.58 (d, J=6.4 Hz, 3H), 1.24 (m, 2H), 0.66 (m, 2H); LC-MS (Method C) 397.1 [M+H]$^+$; RT 1.54 min

Example 23—7-(6-amino-3-pyridyl)-5-cyclopropyl-2,6-dimethyl-oxazolo[4,5-c]quinolin-4-one W

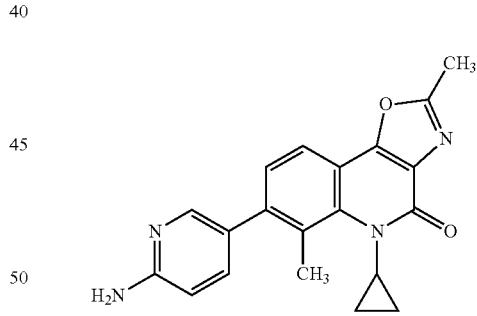

Prepared using 2-aminopyridine-5-boronic acid pinacol ester and 7-bromo-5-cyclopropyl-2,6-dimethyl-oxazolo[4,5-c]quinolin-4-one (prepared as described in Example 4 step (c)) and a similar procedure to that described in Example 4 step (d)

$^1$H NMR (Method B) (CD$_3$OD): δ ppm 7.98 (dd, J=2.5, 0.8 Hz, 1H), 7.84-7.80 (m, 1H), 7.67 (dd, J=8.7, 2.4 Hz, 1H), 7.33 (d, J=8.0 Hz, 1H), 6.78 (dd, J=8.7, 0.8 Hz, 1H), 3.65 (m, 1H), 2.69 (s, 3H), 2.62 (s, 3H), 1.31 (d, J=6.0 Hz, 2H), 0.65-0.60 (m, 2H); LC-MS (Method C) 347.2 [M+H]$^+$; RT 1.06 min Example 24—4-(5-cyclopropyl)-2,6-dimethyl-4-oxo-oxazolo[4,5-c]quinolin-7-yl)-2,5-difluoro-benzonitrile X

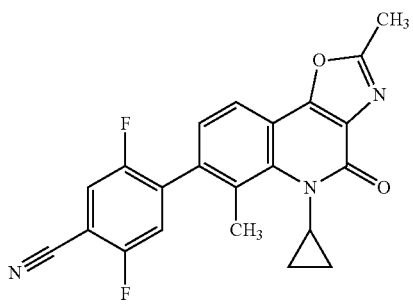 [SMILES: Cc1nc2c(=O)n(C3CC3)c3c(C)c(-c4cc(F)c(C#N)cc4F)ccc3c2o1]

Prepared using 2,5-difluoro-4-(4,4,5,5-tetramethyl-1,3,2-dioxaborolan-2-yl)benzonitrile and 7-bromo-5-cyclopropyl-2,6-dimethyl-oxazolo[4,5-c]quinolin-4-one (prepared as described in Example 4 step (c)) and a similar procedure to that described in Example 4 step (d)

¹H NMR (Method B) (CDCl₃): δ ppm 7.77 (d, J=7.9 Hz, 1H), 7.47 (dd, J=8.1, 5.1 Hz, 1H), 7.25-7.22 (m, 1H), 7.17 (d, J=8.0 Hz, 1H), 3.62 (m, 1H), 2.69 (s, 3H), 2.51 (d, J=1.5 Hz, 3H), 1.26 (m, 2H), 0.65 (m, 2H); LC-MS (Method C) 392.1 [M+H]⁺; RT 2.09 min Example 25—5-cyclopropyl-7-[2,5-difluoro-4-(hydroxymethyl)phenyl]-6-methyl-oxazolo[4,5-c]quinolin-4-one Y

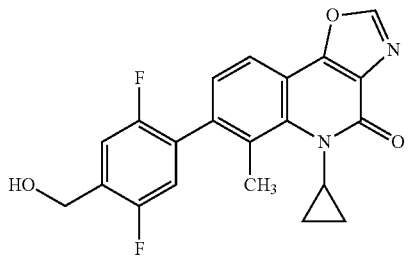 [SMILES: Cc1c(-c2cc(F)c(CO)cc2F)ccc2c3ocnc3c(=O)n(C3CC3)c12]

Prepared using [2,5-difluoro-4-(4,4,5,5-tetramethyl-1,3,2-dioxaborolan-2-yl)phenyl]methanol and 7-bromo-5-cyclopropyl-6-methyl-oxazolo[4,5-c]quinolin-4-one (prepared as described in Example 1 step (f)) and a similar procedure to that described in Example 1 step (g)

¹H NMR (Method B) (CDCl₃): δ ppm 8.10 (s, 1H), 7.80 (dd, J=8.0, 0.7 Hz, 1H), 7.33 (dd, J=9.5, 5.9 Hz, 1H), 7.23 (d, J=8.0 Hz, 1H), 7.04 (dd, J=9.6, 5.8 Hz, 1H), 4.85 (s, 2H), 3.70-3.57 (m, 1H), 1.57 (s, 3H), 1.27 (m, 2H), 0.67 (m, 2H); LC-MS (Method C) 383.1 [M+H]⁺; RT 1.47 min Example 26—4-(5-cyclopropyl)-2,6-dimethyl-4-oxo-oxazolo[4,5-c]quinolin-7-yl)benzamide Z

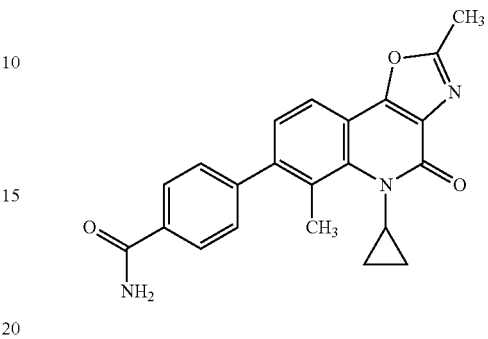

Prepared using 4-(4,4,5,5-tetramethyl-1,3,2-dioxaborolan-2-yl)benzamide and 7-bromo-5-cyclopropyl-2,6-dimethyl-oxazolo[4,5-c]quinolin-4-one (prepared as described in Example 4 step (c)) and a similar procedure to that described in Example 4 step (d)

¹H NMR (Method B) (CDCl₃): δ ppm 7.93 (d, J=8.2 Hz, 2H), 7.74 (d, J=8.0 Hz, 1H), 7.50 (d, J=8.1 Hz, 2H), 7.24 (d, J=8.2 Hz, 1H), 3.63 (m, 1H), 2.69 (s, 3H), 2.52 (s, 3H), 1.33-1.26 (m, 2H), 0.73-0.65 (m, 2H); LC-MS (Method C) 374.1 [M+H]⁺; RT 1.44 min Example 27—5-cyclopropyl-7-(1H-indazol-6-yl)-2,6-dimethyl-oxazolo[4,5-c]quinolin-4-one A1

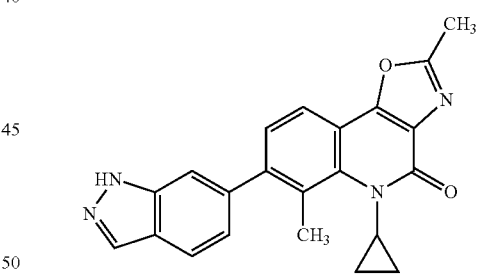

Prepared using 6-[4-(4,4,5,5-tetramethyl-1,3,2-dioxaborolan-2-yl)-1H-indazole and 7-bromo-5-cyclopropyl-2,6-dimethyl-oxazolo[4,5-c]quinolin-4-one (prepared as described in Example 4 step (c)) and a similar procedure to that described in Example 4 step (d)

¹H NMR (Method B) (CDCl₃): δ ppm 8.16 (d, J=1.0 Hz, 1H), 7.84 (dd, J=8.3, 0.9 Hz, 1H), 7.73 (d, J=8.0 Hz, 1H), 7.53 (q, J=1.1 Hz, 1H), 7.30 (d, J=7.9 Hz, 1H), 7.22 (dd, J=8.3, 1.3 Hz, 1H), 3.71-3.57 (m, 1H), 2.68 (s, 3H), 2.54 (s, 3H), 1.24 (m, 2H), 0.71 (m, 2H); LC-MS (Method C) 371.3 [M+H]⁺; RT 1.50 min

Example 28—7-[4-(2-aminopropan-2-yl)phenyl]-5-cyclopropyl-2,6-dimethyloxazolo[4,5-c]quinolin-4-one B1

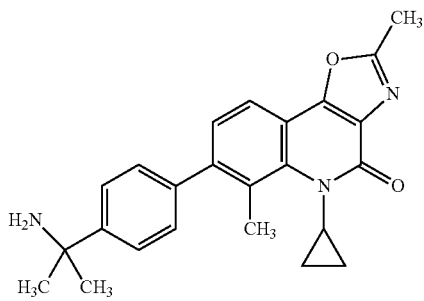 [SMILES: Cc1nc2c(=O)n(C3CC3)c3c(C)c(-c4ccc(C(C)(C)N)cc4)ccc3c2o1]

Prepared using 2-[4-(4,4,5,5-tetramethyl-1,3,2-dioxaborolan-2-yl)phenyl]propan-2-amine and 7-bromo-5-cyclopropyl-2,6-dimethyl-oxazolo[4,5-c]quinolin-4-one (prepared as described in Example 4 step (c)) and a similar procedure to that described in Example 4 step (d)

$^1$H NMR (Method B) (D$_2$O): δ ppm 7.77 (d, J=8.0 Hz, 1H), 7.70-7.55 (m, 4H), 7.35 (d, J=8.0 Hz, 1H), 3.76 (s, 3H), 3.62 (s, 1H), 2.69 (s, 3H), 2.51 (s, 3H), 1.82 (s, 3H), 1.30 (m 2H), 0.64 (m, 2H); LC-MS (Method C) 371.1 [M+H]$^+$; RT 1.26 min

Example 29—5-cyclopropyl-2,6-dimethyl-7-(1H-pyrazol-4-yl)oxazolo[4,5-c]quinolin-4-one C1

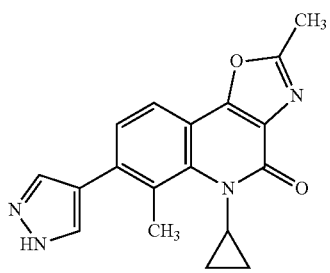 [SMILES: Cc1nc2c(=O)n(C3CC3)c3c(C)c(-c4cn[nH]c4)ccc3c2o1]

Prepared using tert butyl 4-(4,4,5,5-tetramethyl-1,3,2-dioxaborolan-2-yl)-1H-pyrazole-1-carboxylate and 7-bromo-5-cyclopropyl-, 6-methyl-oxazolo[4,5-c]quinolin-4-one (prepared as described in Example 1 step (f)) and a similar procedure to that described in Example 1 step (g), followed by deprotection of the BOC group using the method described in Example 49 step (j)

$^1$H NMR (Method B) (CDCl$_3$): δ ppm 7.82 (s, 2H), 7.68 (d, J=8.1 Hz, 1H), 7.33 (d, J=8.0 Hz, 1H), 3.66 (m, 1H), 2.69 (d, J=7.3 Hz, 6H), 1.27 (m, 2H), 0.64 (m, 2H); LC-MS (Method C) 321.1 [M+H]$^+$; RT 1.26 min

Example 30—ethyl-2-[{4-(5-cyclopropyl-6-methyl-4-oxo-oxazolo[4,5-c]quinolin-7-yl)benzoyl}amino]acetate D1

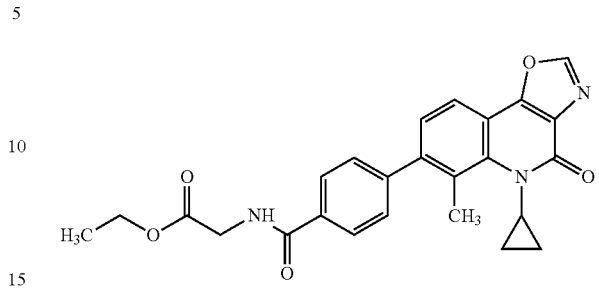

Prepared using ethyl N-[4-(dihydroxyboryl)benzoyl] glycinate and 7-bromo-5-cyclopropyl-6-methyl-oxazolo[4,5-c]quinolin-4-one (prepared as described in Example 1 step (f)) and a similar procedure to that described in Example 1 step (g)

$^1$H NMR (Method A) (CDCl$_3$): δ ppm 8.09 (s, 1H), 7.97-7.90 (m, 2H), 7.80 (d, J=8.0 Hz, 1H), 7.52-7.44 (m, 2H), 6.72 (t, 1H), 4.34-4.25 (m, 4H), 3.64 (m, 1H), 2.53 (s, 3H), 1.57 (s, 3H), 1.31-1.28 (m, 2H), 0.70 (m, 2H); LC-MS (Method D) 446.4 [M+H]$^+$; RT 2.36 min

Example 31—2-[{4-(5-cyclopropyl-6-methyl-4-oxo-oxazolo[4,5-c]quinolin-7-yl)benzoyl}amino]acetic acid E1

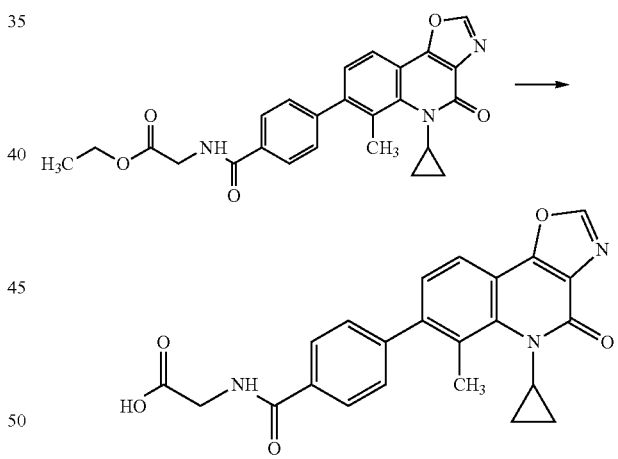

To a solution of ethyl-2-[{4-(5-cyclopropyl-6-methyl-4-oxo-oxazolo[4,5-c]quinolin-7-yl)benzoyl}amino]acetate (prepared as described in Example 30) (47.2 mg, 0.10 mmol) in H$_2$O (4.71 mL) was added Et$_3$N (1.18 mL, 8.45 mmol) and the solution left to stir rapidly overnight. When the reaction had gone to completion the solvent was removed in vacuo to give 2-[{4-(5-cyclopropyl-6-methyl-4-oxo-oxazolo[4,5-c]quinolin-7-yl)benzoyl}amino]acetic acid E1 (29 mg, 65% yield) as the Et$_3$N salt.

$^1$H NMR (Method A) (CDCl$_3$): δ ppm 7.98-7.91 (m, 2H), 7.70 (d, J=8.0 Hz, 1H), 7.45-7.39 (m, 2H), 7.22 (d, J=8.0 Hz, 1H), 4.06 (d, J=4.2 Hz, 2H), 3.63-3.56 (m, 1H), 2.66 (s, 3H), 2.49 (s, 3H), 1.24 (m, 2H), 0.66 (m, 2H); LC-MS (Method D) 432.4 [M+H]$^+$; RT 2.03 min

Example 32—5-cyclopropyl-7-(2,5-difluoro-4-hydroxy-phenyl)-2,6-dimethyl-oxazolo[4,5-c]quinolin-4-one F1

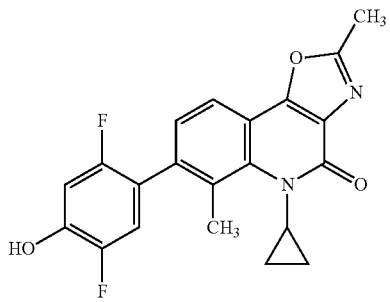 [SMILES: Cc1nc2c(=O)n(C3CC3)c3c(C)c(-c4cc(F)c(O)cc4F)ccc3c2o1]

Prepared using 2,5-difluoro-4-(4,4,5,5-tetramethyl-1,3,2-dioxaborolan-2-yl)phenol and 7-bromo-5-cyclopropyl-2,6-dimethyl-oxazolo[4,5-c]quinolin-4-one (prepared as described in Example 4 step (c)) and a similar procedure to that described in Example 4 step (d)

$^1$H NMR (Method B) (CD$_3$OD): δ ppm 7.83 (d, J=8.0 Hz, 1H), 7.33-7.28 (m, 1H), 7.11 (dd, J=11.1, 6.9 Hz, 1H), 6.86-6.76 (m, 1H), 3.65 (m, 1H), 2.70 (s, 3H), 2.61-2.51 (m, 3H), 0.91 (m, 2H), 0.61 (m, 2H); LC-MS (Method C) 383.1 [M+H]$^+$; RT 1.53 min

Example 33—4-(5-cyclopropyl-2,6-dimethyl-4-oxo-oxazolo[4,5-c]quinolin-7-yl)-3-fluoro-benzonitrile G1

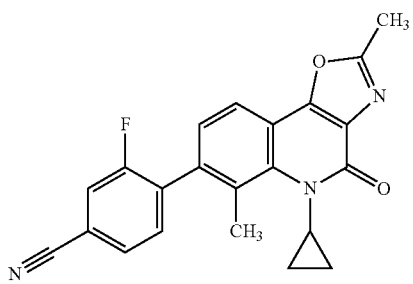 [SMILES: Cc1nc2c(=O)n(C3CC3)c3c(C)c(-c4ccc(C#N)cc4F)ccc3c2o1]

Prepared using 3-fluoro-4-(4,4,5,5-tetramethyl-1,3,2-dioxaborolan-2-yl)benzonitrile and 7-bromo-5-cyclopropyl-2,6-dimethyl-oxazolo[4,5-c]quinolin-4-one (prepared as described in Example 4 step (c)) and a similar procedure to that described in Example 4 step (d)

$^1$H NMR (Method B) (CDCl$_3$): δ 7.76 (d, J=7.9 Hz, 1H), 7.60 (dd, J=7.9, 1.5 Hz, 1H), 7.55-7.43 (m, 2H), 7.17 (d, J=8.0 Hz, 1H), 3.60 (m, 1H), 2.68 (s, 3H), 2.49 (d, J=1.5 Hz, 3H), 1.26 (m, 2H), 0.64 (m, 2H); LC-MS (Method C) 374.2 [M+H]$^+$; RT 1.68 min

Example 34—5-cyclopropyl-7-[2,5-difluoro-4-(hydroxymethyl)phenyl]-2,6-dimethyl-oxazolo[4,5-c]quinolin-4-one H1

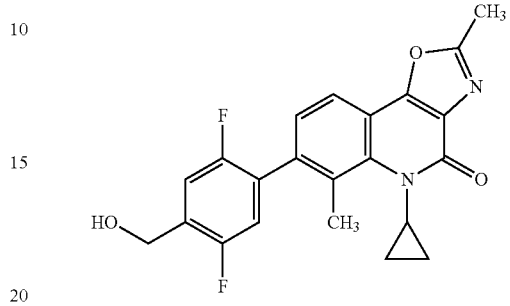

Prepared using [2,5-difluoro-4-(4,4,5,5-tetramethyl-1,3,2-dioxaborolan-2-yl)phenyl]methanol and 7-bromo-5-cyclopropyl-2,6-dimethyl-oxazolo[4,5-c]quinolin-4-one (prepared as described in Example 4 step (c)) and a similar procedure to that described in Example 4 step (d)

$^1$H NMR (Method B) (CDCl$_3$): δ ppm 7.73 (d, J=8.0 Hz, 1H), 7.32 (dd, J=9.5, 6.0 Hz, 1H), 7.20 (d, J=8.0 Hz, 1H), 7.03 (dd, J=9.6, 5.8 Hz, 1H), 4.85 (s, 2H), 3.67-3.57 (m, 1H), 2.68 (s, 3H), 2.52 (d, J=1.4 Hz, 3H), 1.27 (m, 2H), 0.66 (m, 2H); LC-MS (Method C) 397.1 [M+H]$^+$; RT 1.59 min

Example 35—4-(5-cyclopropyl-2,6-dimethyl-4-oxo-oxazolo[4,5-c]quinolin-7-yl)-2,5-difluoro-benzamide I1 (redx05694)

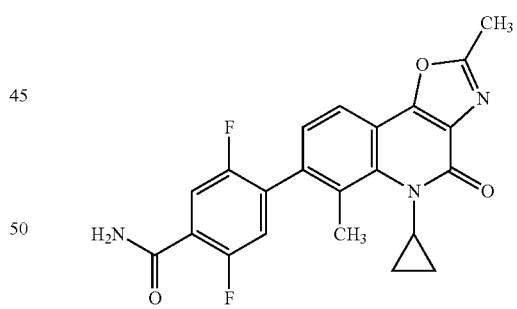

Prepared using 2,5-difluoro-4-(4,4,5,5-tetramethyl-1,3,2-dioxaborolan-2-yl)benzamide and 7-bromo-5-cyclopropyl-2,6-dimethyl-oxazolo[4,5-c]quinolin-4-one (prepared as described in Example 4 step (c)) and a similar procedure to that described in Example 4 step (d)

$^1$H NMR (Method B) (CDCl$_3$): δ ppm 7.96 (dd, J=9.6, 6.3 Hz, 1H), 7.76 (dd, J=8.1, 0.7 Hz, 1H), 7.23-7.12 (m, 2H), 6.74 (m, 1H), 5.90 (m, 1H), 3.62 (m, 1H), 2.69 (s, 3H), 2.52 (d, J=1.5 Hz, 3H), 1.25 (m, 2H), 0.66 (m, 2H); LC-MS (Method C) 410.1 [M+H]*; RT 1.59 min Example 36—7-[4-(aminomethyl)-3-fluoro-phenyl]-5-cyclopropyl-2,6-dimethyl-oxazolo[4,5-c]quinolin-4-one J1

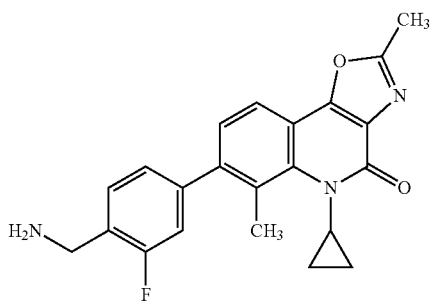 [SMILES: Cc1nc2c(=O)n(C3CC3)c3c(C)c(-c4ccc(CN)c(F)c4)ccc3c2o1]

Prepared using 4-(aminomethyl)-3-fluorophenylboronic acid and 7-bromo-5-cyclopropyl-2,6-dimethyl-oxazolo[4,5-c]quinolin-4-one (prepared as described in Example 4 step (c)) and a similar procedure to that described in Example 4 step (d)

$^1$H NMR (Method B) (CDCl$_3$): δ ppm 7.70 (d, J=8.0 Hz, 1H), 7.47 (t, 1H), 7.24-7.03 (m, 3H), 4.03 (s, 2H), 3.67-3.56 (m, 1H), 2.68 (s, 3H), 2.52 (s, 3H), 1.31-1.24 (m, 2H), 0.67 (m, 2H); LC-MS (Method C) 378.1 [M+H]$^+$; RT 1.11 min Example 37—5-cyclopropyl-7-[2-(2-hydroxypropan-2-yl)pyrimidin-5-yl]-2,6-dimethyl-oxazolo[4,5-c]quinolin-4-one K1

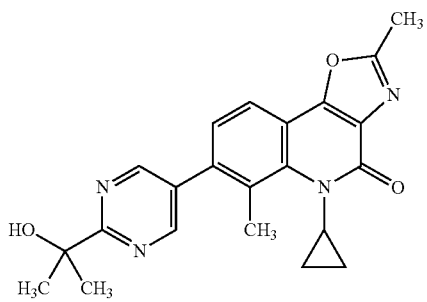 [SMILES: Cc1nc2c(=O)n(C3CC3)c3c(C)c(-c4cnc(C(C)(C)O)nc4)ccc3c2o1]

Prepared using 2-[5-(4,4,5,5-tetramethyl-1,3,2-dioxaborolan-2-yl)pyrimidin-2-yl]propan-2-ol and 7-bromo-5-cyclopropyl-2,6-dimethyl-oxazolo[4,5-c]quinolin-4-one (prepared as described in Example 4 step (c)) and a similar procedure to that described in Example 4 step (d)

$^1$H NMR (Method B) (CDCl$_3$): δ ppm 8.81 (s, 2H), 7.80 (dd, J=7.9, 0.7 Hz, 1H), 7.23 (d, J=8.0 Hz, 1H), 4.61 (s, 1H), 3.64 (m, 1H), 2.70 (s, 2H), 2.59 (s, 3H), 1.69 (s, 6H), 1.31 (m, 2H), 0.68 (m, 2H); LC-MS (Method C) 391.1 [M+H]$^+$; RT 2.92 min Example 38—7-(4-amino-3-fluorophenyl)-5-cyclopropyl-6-methyl-oxazolo[4,5-c]quinolin-4-one L1

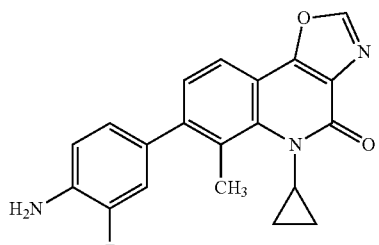

Prepared using 2-fluoro-4-(4,4,5,5-tetramethyl-1,3,2-dioxaborolan-2-yl)aniline and 7-bromo-5-cyclopropyl-6-methyl-oxazolo[4,5-c]quinolin-4-one (prepared as described in Example 1 step (f)) and a similar procedure to that described in Example 1 step (g)

$^1$H NMR (Method A) (CDCl$_3$): δ ppm 8.06 (s, 1H), 7.74 (d, J=8.0 Hz, 1H), 7.24 (d, J=8.0 Hz, 1H), 7.06 (dd, J=11.8, 1.9 Hz, 1H), 6.99 (ddd, J=8.1, 1.9, 0.7 Hz, 1H), 6.87 (dd, J=9.0, 8.2 Hz, 1H), 3.87 (s, 2H), 3.67-3.60 (m, 1H), 2.56 (s, 3H), 1.33-1.28 (m, 2H), 0.70-0.66 (m, 2H); LC-MS (Method B) 350.5 [M$^+$ H$^+$], RT 2.08 min Example 39—5-cyclopropyl-7-(1H-indazol-5-yl)-6-methyl-oxazolo[4,5-c]quinolin-4-one M1

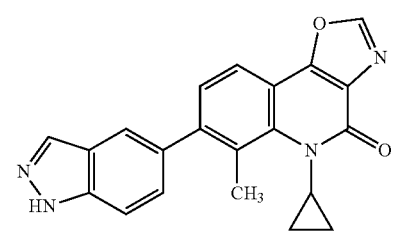 [SMILES: Cc1c(-c2ccc3[nH]ncc3c2)ccc2c3ocnc3c(=O)n(C3CC3)c12]

Prepared using 6-[4-(4,4,5,5-tetramethyl-1,3,2-dioxaborolan-2-yl)-1H-indazole and 7-bromo-5-cyclopropyl-6-methyl-oxazolo[4,5-c]quinolin-4-one (prepared as described in Example 1 step (f)) and a similar procedure to that described in Example 1 step (g)

$^1$H NMR (Method A) (CDCl$_3$): δ ppm 10.62 (s, 1H), 8.17 (s, 1H), 8.10 (s, 1H), 7.80 (d, J=8.0 Hz, 1H), 7.78 (dd, J=1.6, 0.8 Hz, 1H), 7.65 (d, J=8.6 Hz, 1H), 7.44 (dd, J=8.6, 1.5 Hz, 1H), 7.34 (d, J=8.0 Hz, 1H), 3.71-3.61 (m, 1H), 2.56 (s, 3H), 1.36-1.31 (m, 2H), 0.76-0.71 (m, 2H); LC-MS (Method B) 357.4 [M$^+$ H$^+$], RT 1.84 min

Example 40—7-(4-aminophenyl)-5-cyclopropyl-6-methyl-oxazolo[4,5-c]quinolin-4-one N1

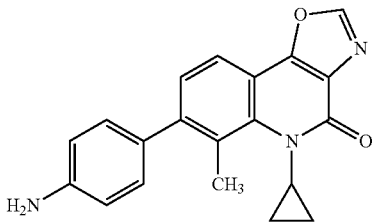 [SMILES: Cc1c(-c2ccc(N)cc2)ccc2c3ocnc3c(=O)n(C3CC3)c12]

Prepared using 4-aminophenyl boronic acid pinacol ester and 7-bromo-5-cyclopropyl-6-methyl-oxazolo[4,5-c]quinolin-4-one (prepared as described in Example 1 step (f)) and a similar procedure to that described in Example 1 step (g)

$^1$H NMR (Method A) (CDCl$_3$): δ ppm 8.05 (s, 1H), 7.74 (d, J=8.0 Hz, 1H), 7.26 (d, J=8.0 Hz, 2H), 7.21 (d, J=8.5 Hz, 2H), 6.78 (d, J=8.5 Hz, 2H), 3.82 (s, 2H), 3.66-3.62 (m, 1H), 2.56 (s, 3H), 1.32-1.27 (m, 2H), 0.71-0.66 (m, 2H); LC-MS (Method B) 332.2 [M$^+$ H$^+$], RT 4.64 min

Example 41—5-cyclopropyl-7-[2-(dimethylamino)pyrimidin-5-yl]-6-methyl-oxazolo[4,5-c]quinolin-4-one O1

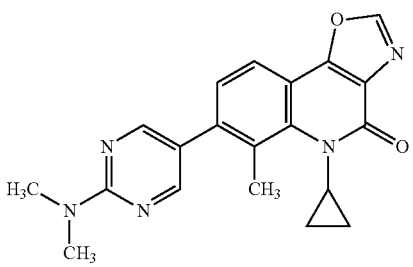 [SMILES: Cc1c(-c2cnc(N(C)C)nc2)ccc2c3ocnc3c(=O)n(C3CC3)c12]

Prepared using 5-cyclopropyl-6-dimethyl-7-(4,4,5,5-tetramethyl-1,3,2-dioxaborolan-2-yl)oxazolo[4,5-c]quinolin-4-one (prepared as described in Example 6 step (a)) and 5-bromo-2-N,N-dimethylaminopyrimidine and a similar procedure to that described in Example 1 step (g)

$^1$H NMR (Method A) (CDCl$_3$): δ ppm 8.41 (s, 2H), 8.07 (s, 1H), 7.78 (d, J=7.9 Hz, 1H), 7.21 (d, J=8.0 Hz, 1H), 3.66-3.61 (m, 1H), 3.27 (s, 6H), 2.60 (s, 3H), 1.31-1.26 (m, 2H), 0.72-0.63 (m, 2H); LC-MS (Method D) 362.5 [M$^+$ H$^+$], RT 2.19 min

Example 42—7-(5-acetylpyridin-2-yl)-5-cyclopropyl-6-methyl-oxazolo[4,5-c]quinolin-4-one P1

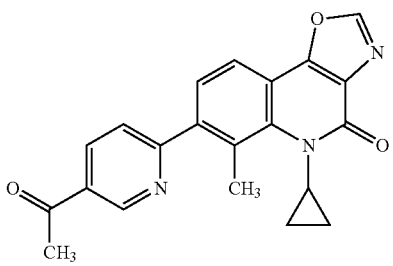 [SMILES: CC(=O)c1ccc(-c2ccc3c4ocnc4c(=O)n(C4CC4)c3c2C)nc1]

Prepared using 5-cyclopropyl-6-dimethyl-7-(4,4,5,5-tetramethyl-1,3,2-dioxaborolan-2-yl)oxazolo[4,5-c]quinolin-4-one (prepared as described in Example 6 step (a)) and 1-(6-bromo-3-pyridyl)ethanone and a similar procedure to that described in Example 1 step (g)

$^1$H NMR (Method A) (CDCl$_3$) δ ppm 9.30 (dd, J=2.3, 0.9 Hz, 1H), 8.35 (dd, J=8.2, 2.3 Hz, 1H), 8.10 (s, 1H), 7.83 (d, J=8.0 Hz, 1H), 7.62 (dd, J=8.1, 1.0 Hz, 1H), 7.45 (d, J=8.0 Hz, 1H), 3.67-3.62 (m, 1H), 2.71 (s, 3H), 2.60 (s, 3H), 1.35-1.28 (m, 2H), 0.76-0.64 (m, 2H); LC-MS (Method D) 360.5 [M$^+$ H$^+$], RT 1.96 min

Example 43—5-cyclopropyl-6-methyl-7-(1,2-oxazol-4-yl)-oxazolo[4,5-c]quinolin-4-one

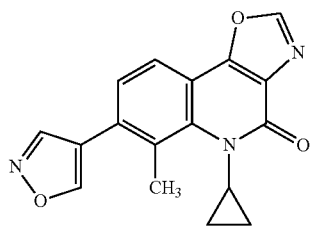 [SMILES: Cc1c(-c2cnoc2)ccc2c3ocnc3c(=O)n(C3CC3)c12]

Prepared using 5-cyclopropyl-6-dimethyl-7-(4,4,5,5-tetramethyl-1,3,2-dioxaborolan-2-yl)oxazolo[4,5-c]quinolin-4-one (prepared as described in Example 6 step (a)) and 4-bromo-1,2-oxazole and a similar procedure to that described in Example 1 step (g)

$^1$H NMR (Method A) (CDCl$_3$): δ ppm 8.63 (s, 1H), 8.50 (s, 1H), 8.09 (s, 1H), 7.79 (d, J=8.0 Hz, 1H), 7.30 (d, J=8.0 Hz, 1H), 3.69-3.64 (m, 1H), 2.60 (s, 3H), 1.31-1.27 (m, 2H), 0.66-0.62 (m, 2H); LC-MS (Method D) 308.4 [M$^+$ H$^+$], RT 2.18 min.

Example 44—7-(1H-1,2,3-benzotriazol-5-yl)-5-cyclopropyl-6-methyl-oxazolo[4,5-c]quinolin-4-one R1

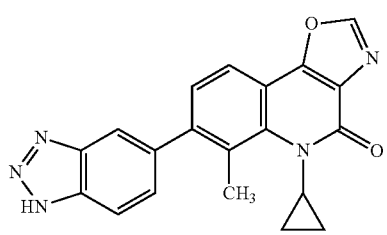 [SMILES: Cc1c(-c2ccc3[nH]nnc3c2)ccc2c3ocnc3c(=O)n(C3CC3)c12]

Prepared using 5-cyclopropyl-6-dimethyl-7-(4,4,5,5-tetramethyl-1,3,2-dioxaborolan-2-yl)oxazolo[4,5-c]quinolin-4-one (prepared as described in Example 6 step (a)) and 5-bromo-1H-benzotriazole and a similar procedure to that described in Example 1 step (g)

$^1$H NMR (Method A) (DMSO-d$_6$): δ ppm 8.73 (s, 1H), 8.16 (d, J=8.5 Hz, 1H), 8.05 (d, J=8.7 Hz, 1H), 7.96 (d, J=7.6 Hz, 1H), 7.49 (d, J=7.3 Hz, 1H), 7.34 (t, J=7.4 Hz, 1H), 3.60-3.54 (m, 2H), 1.23-1.18 (m, 2H), 0.54-0.50 (m, 2H); LC-MS (Method D) 358.4 [M$^+$ H$^+$], RT 1.84 min.

Example 45—5-cyclopropyl-7-(5-hydroxypyridin-2-yl)-6-methyl-oxazolo[4,5-c]quinolin-4-one S1

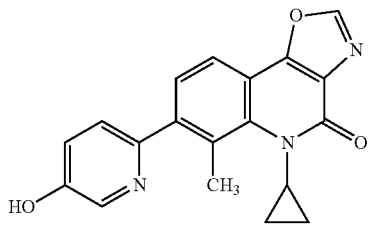 [SMILES: Cc1c(-c2ccc(O)cn2)ccc2c3ocnc3c(=O)n(C3CC3)c12]

Prepared using 5-cyclopropyl-6-dimethyl-7-(4,4,5,5-tetramethyl-1,3,2-dioxaborolan-2-yl)oxazolo[4,5-c]quinolin-4-one (prepared as described in Example 6 step (a)) and 6-bromopyridin-3-ol and a similar procedure to that described in Example 1 step (g)

$^1$H NMR (Method A) (CDCl$_3$): δ ppm 8.43-8.39 (m, 1H), 8.08 (s, 1H), 7.80 (d, J=8.0 Hz, 1H), 7.43 (d, J=8.0 Hz, 1H), 7.41-7.36 (m, 1H), 7.35-7.27 (m, 2H), 3.71-3.59 (m, 1H), 2.59 (s, 3H), 1.29-1.26 (m, 2H), 0.72-0.68 (m, 2H); LC-MS (Method D) 334.4 [M$^+$ H$^+$], RT 1.44 min.

Example 46—7-(2,1,3-benzoxadiazol-5-yl)-5-cyclopropyl-6-methyl-oxazolo[4,5-c]quinolin-4-one T1

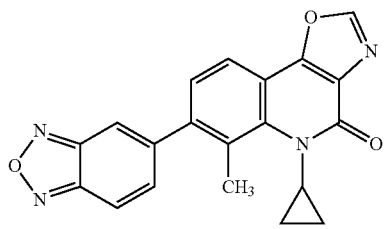 [SMILES: Cc1c(-c2ccc3nonc3c2)ccc2c3ocnc3c(=O)n(C3CC3)c12]

Prepared using 5-cyclopropyl-6-dimethyl-7-(4,4,5,5-tetramethyl-1,3,2-dioxaborolan-2-yl)oxazolo[4,5-c]quinolin-4-one (prepared as described in Example 6 step (a)) and 5-bromo-2,1-3-benzoxadiazole and a similar procedure to that described in Example 1 step (g)

$^1$H NMR (Method A) (CDCl$_3$): δ ppm 8.11 (s, 1H), 7.95 (dd, J=9.2, 1.1 Hz, 1H), 7.85 (d, J=5.5 Hz, 1H), 7.84 (d, J=1.1 Hz, 1H), 7.48 (dd, J=9.2, 1.4 Hz, 1H), 7.31 (d, J=8.0 Hz, 1H), 3.67-3.62 (m, 1H), 2.59 (s, 4H), 1.35-1.30 (m, 2H), 0.72-0.68 (m, 2H); LC-MS (Method E) 359.4 [M$^+$ H$^+$], RT 7.22 min

Example 47—4-{5-cyclopropyl-6-methyl-4-oxo-oxazolo[4,5-c]quinolin-7-yl}-2,5-difluorobenzoic acid U1

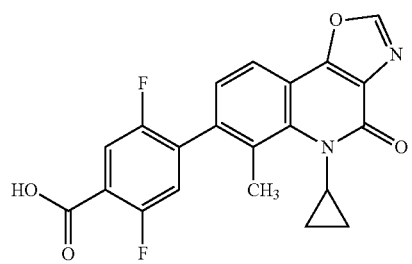 [SMILES: Cc1c(-c2cc(F)c(C(=O)O)cc2F)ccc2c3ocnc3c(=O)n(C3CC3)c12]

Prepared using 5-cyclopropyl-6-dimethyl-7-(4,4,5,5-tetramethyl-1,3,2-dioxaborolan-2-yl)oxazolo[4,5-c]quinolin-4-one (prepared as described in Example 6 step (a)) and 4-bromo-2,5-difluorobenzoic acid (prepared as described in Example 58 step (a)) and a similar procedure to that described in Example 1 step (g)

$^1$H NMR (Method A) (DMSO-d$_6$): δ ppm 8.84 (s, 1H), 7.82 (d, J=7.9 Hz, 1H), 7.63-7.56 (m, 2H), 7.30 (d, J=8.0 Hz, 1H), 7.22 (dd, J=10.0, 5.8 Hz, 1H), 3.62-3.54 (m, 2H), 2.45 (s, 3H), 1.20-1.14 (m, 2H), 0.51-0.45 (m, 2H); LC-MS (Method E) 397.4 [M$^+$ H$^+$], RT 6.52 min

Example 48—7-[6-(benzylamino)pyridin-3-yl]-5-cyclopropyl-6-methyl-oxazolo[4,5-c]quinolin-4-one V1

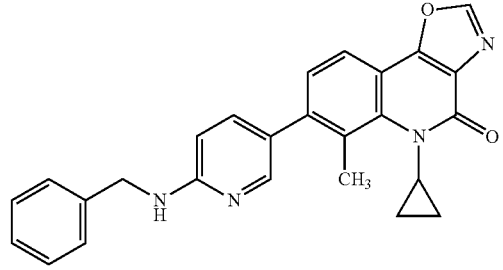 [SMILES: Cc1c(-c2ccc(NCc3ccccc3)nc2)ccc2c3ocnc3c(=O)n(C3CC3)c12]

Prepared using N-benzyl-5-(4,4,5,5-tetramethyl-1,3,2-dioxaborolan-2-yl)-2-pyridinamine and and 7-bromo-5-cyclopropyl-6-methyl-oxazolo[4,5-c]quinolin-4-one (prepared as described in Example 1 step (f)) and a similar procedure to that described in Example 1 step (g)

$^1$H NMR (Method A) (CDCl$_3$): δ ppm 8.18 (d, J=2.3 Hz, 1H), 8.05 (s, 1H), 7.75 (d, J=8.0 Hz, 1H), 7.49 (dd, J=8.6, 2.4 Hz, 1H), 7.43-7.27 (m, 5H), 7.23 (d, J=8.0 Hz, 1H), 6.52 (d, J=8.5 Hz, 1H), 5.18 (t, J=5.8 Hz, 1H), 4.59 (d, J=5.6 Hz, 2H), 3.66-3.59 (m, 1H), 2.57 (s, 3H), 1.29-1.258 (m, 2H), 0.68-0.64 (m, 2H); LC-MS (Method B) 423.4 [M+H]$^+$; RT 1.69 min

Example 49—7-(4-amino-1-piperidyl)-5-cyclopropyl-8-fluoro-2-methyl-oxazolo[4,5-c]quinolin-4-one W1

(a) 2,4,5-trifluorobenzoyl chloride

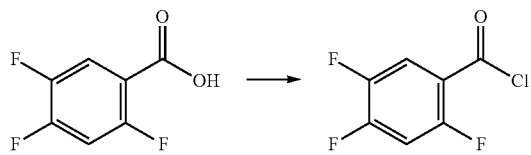 [SMILES: O=C(O)c1cc(F)c(F)cc1F ; O=C(Cl)c1cc(F)c(F)cc1F]

A suspension of 2,4,5-trifluorobenzoic acid (5 g, 28.4 mmol) in DCM (60 mL) was cooled to 0° C. Oxalyl chloride (3.72 mL, 42.59 mmol) was added followed by 3 drops of DMF and the reaction allowed to warm to room temperature. Effervescence commenced on warming.

The mixture was stirred at room temperature for 2 h then evaporated (co-evaporated from DCM×3) and used without further purification (b) ethyl 5-(2,4,5-trifluorophenyl)-oxazole-4-carboxylate

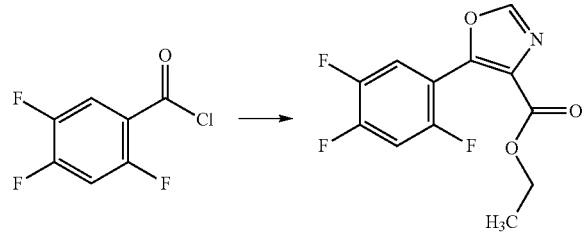 [SMILES: O=C(Cl)c1cc(F)c(F)cc1F ; CCOC(=O)c1ncoc1-c1cc(F)c(F)cc1F]

Ethyl isocyanoacetate (3.72 g, 31.23 mmol) in THF (30 mL) was cooled to 00° C. Et$_3$N (11.81 mL, 85.19 mmol) was added drop wise followed by the addition of 2,4,5-trifluorobenzoyl chloride (5.52 g, 28.4 mmol) in THF (30 mL) over 5 min. The reaction was allowed to warm to room temperature and stirred overnight. The mixture was diluted with DCM (100 mL) and washed with saturated aqueous NaHCO$_3$ (3×50 mL) and brine (50 mL). The organic phase was separated, dried over Na$_2$SO$_4$. filtered and solvent removed in vacuo to give a brown solid. Purification by flash chromatography eluting with 0-80% EtOAc in Petroleum ether (40-60) gave ethyl 5-(2,4,5-trifluorophenyl)-oxazole-4-carboxylate (3.7 g, 48% yield) as a cream solid.

LC-MS (Method C) 272.0 [M+H]$^+$; RT 1.97 min (c) ethyl (Z)-2-amino-3-hydroxy-3-(2,4,5-trifluorophenyl)prop-2-enoate

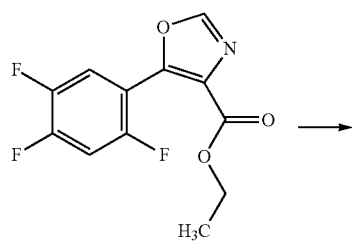

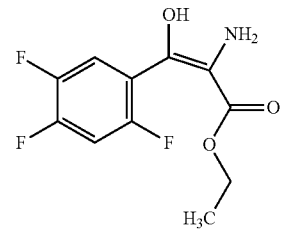

A solution of ethyl 5-(2,4,5-trifluorophenyl)-oxazole-4-carboxylate (2.70 g, 9.96 mmol) in 1,4-dioxane (50 mL) was treated with 1M aqueous HCl (50 mL). After stirring for 72 h at room temperature the solvent was removed in vacuo to give ethyl (Z)-2-amino-3-hydroxy-3-(2,4,5-trifluorophenyl) prop-2-enoate as a yellow oily solid (2.60 g) which was used without further purification.

LC-MS (Method C) 262.0 [M+H]$^+$; RT 0.72 min (d) ethyl 2-methyl-5-(2,4,5-trifluorophenyl)-oxazole-4-carboxylate

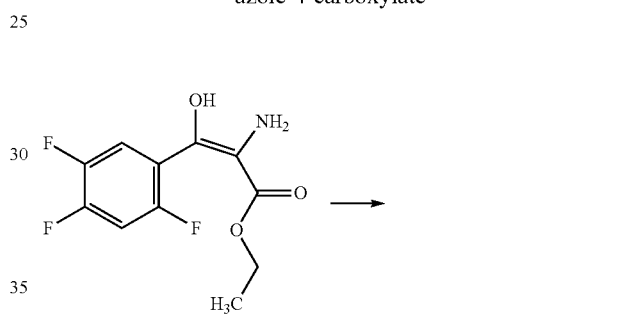

A mixture of ethyl (Z)-2-amino-3-hydroxy-3-(2,4,5-trifluorophenyl)prop-2-enoate (2.60 g, 9.95 mmol) and trimethyl orthoacetate (25. mL, 24.98 mmol) was heated under reflux at 110° C. for 2 h. After consumption of starting material (monitored by LCMS) the mixture was concentrated in vacuo to give ethyl 2-methyl-5-(2,4,5-trifluorophenyl)-oxazole-4-carboxylate (2.82 g) which was used without further purification; LC-MS (Method C) 286.1 [M+H]*; RT 1.70 min

(e) 2-methyl-5-(2,4,5-trifluorophenyl)-oxazole-4-carboxylic acid

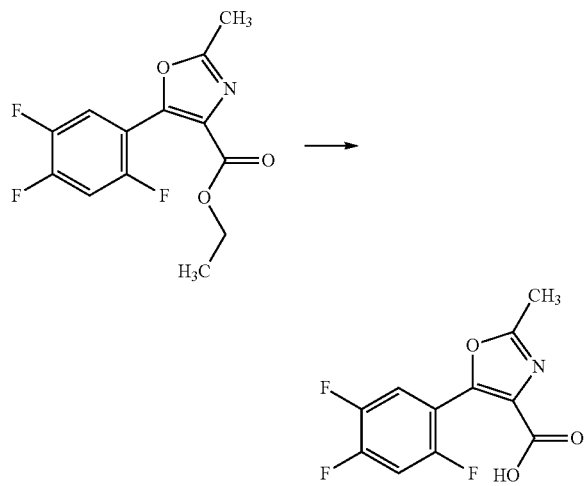

A solution of ethyl 2-methyl-5-(2,4,5-trifluorophenyl)-oxazole-4-carboxylate (2.82 g, 9.9 mmol) in 1,4-dioxane (60 mL) was treated with 1M aq. LiOH (59.4 mL) and stirred at room temperature overnight. The mixture was evaporated to a minimum, partitioned with EtOAc (50 mL) and H$_2$O (80 mL) and the aq. washed with EtOAc (2×50 mL). The aq. was acidified with 1M aqueous HCl (80 mL) and extracted with EtOAc (3×100 mL). The combined organic layers were washed with brine, dried over Na$_2$SO$_4$, filtered and concentrated in vacuo to give 2-methyl-5-(2,4,5-trifluorophenyl)-oxazole-4-carboxylic acid (2.50 g, 98% yield) as a cream solid.

LC-MS (Method C) 258.0 [M+H]$^+$; RT 1.41 min

(f) 2-methyl-5-(2,4,5-trifluorophenyl)-oxazole-4-carbonyl chloride

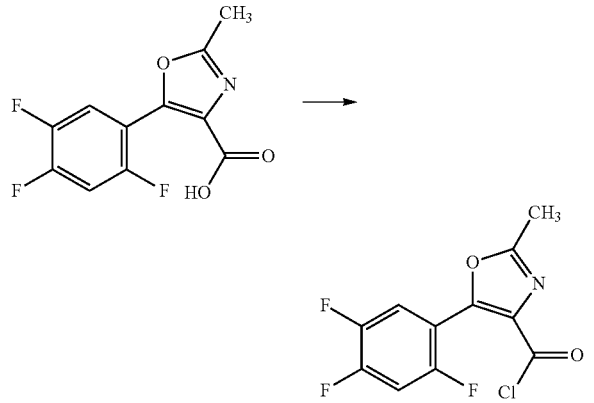

A suspension of 2-methyl-5-(2,4,5-trifluorophenyl)-oxazole-4-carboxylic acid (2.50 g, 9.72 mmol) in DCM (75 mL) was treated with oxalyl chloride (1.27 mL, 14.58 mmol) and cat. DMF (1 drop) and stirred at room temperature for 1 h under N$_2$. The mixture was then evaporated and co-evaporated from DCM (3×) to give a yellow powder, which was used immediately in step (g).

(g) N-cyclopropyl-2-methyl-5-(2,4,5-trifluorophenyl)-oxazole-4-carboxamide

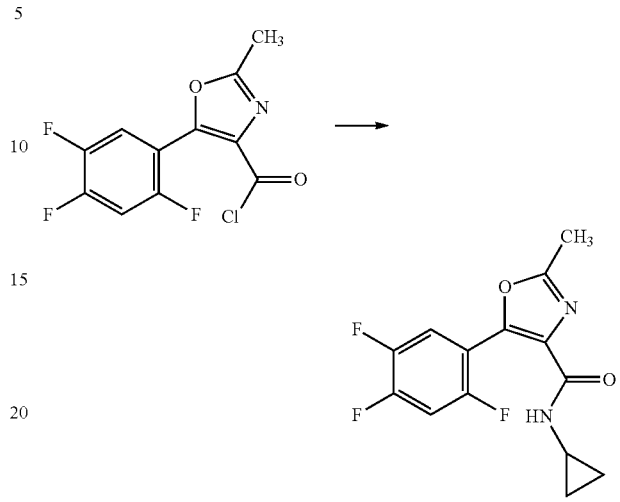

A solution of 2-methyl-5-(2,4,5-trifluorophenyl)-oxazole-4-carbonyl chloride (2.68 g, 9.72 mmol) in DCM (75 mL) was treated with cyclopropylamine (1.41 mL, 20.42 mmol) and stirred at room temperature overnight. The mixture was then diluted with DCM (50 mL) and washed with saturated aqueous NaHCO$_3$ (3×30 ml) and brine (30 ml). The organic phase was separated, dried over Na$_2$SO$_4$ filtered and solvent removed in vacuo to give N-cyclopropyl-2-methyl-5-(2,4,5-trifluorophenyl)-oxazole-4-carboxamide (2.30 g 79% yield) as a pale solid.

LC-MS (Method C) 297.1 [M+H]$^+$; RT 1.62 min

(h) 5-cyclopropyl-7,8-difluoro-2-methyl-oxazolo[4,5-c]quinolin-4-one

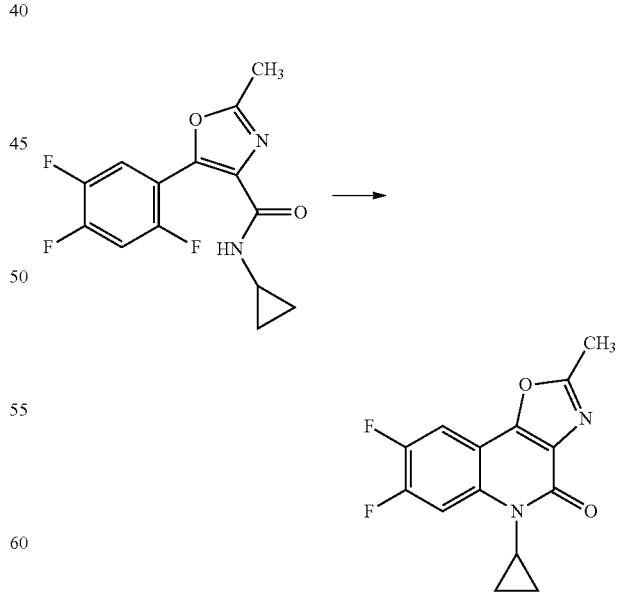

A solution of N-cyclopropyl-2-methyl-5-(2,4,5-trifluorophenyl)-oxazole-4-carboxamide (500 mg, 1.69 mmol) and 18-crown-6 (446 mg, 1.69 mmol) in DMSO (10 mL) was heated at 140° C. for 50 min. On cooling the reaction was diluted with EtOAc (100 ml) and washed 5× with H₂O followed by brine (30 ml). The organic phase was dried over Na₂SO₄, filtered and the solvent removed in vacuo. The resulting residue was purified by flash chromatography eluting with 0-100% EtOAc in heptane to give 5-cyclopropyl-7,8-difluoro-2-methyl-oxazolo[4,5-c]quinolin-4-one (300 mg, 64.% yield) as a pale brown powder.

LC-MS (Method C) 277.1 [M+H]⁺; RT 1.53 min (i) tert-butyl N-[1-(5-cyclopropyl-8-fluoro-2-methyl-4-oxo-oxazolo[4,5-c]quinolin-7-yl)-4-piperidyl]carbamate

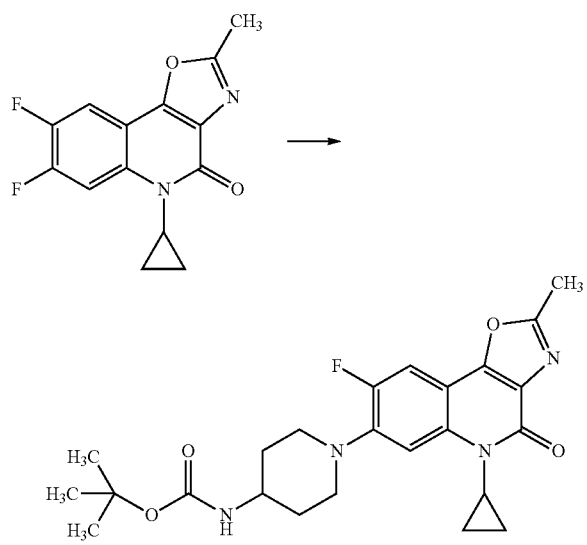

A mixture of 5-cyclopropyl-7,8-difluoro-2-methyl-oxazolo[4,5-c]quinolin-4-one (39.9 mg, 0.14 mmol), 4-Boc-aminopiperidine (37.6 mg, 0.19 mmol) and DIPEA (0.15 mL, 0.87 mmol) were heated in the microwave (Biotage Initiator) at 140° C. for 80 min. On cooling the reaction mixture was diluted with EtOAc (50 mL) and washed with water (5×15 mL), 0.5M aqueous HCl (2×30 mL), saturated aqueous NaHCO₃ (50 mL) and brine (50 mL). The organic phase was dried over Na₂SO₄, filtered and the solvent removed in vacuo to give tert-butyl N-[1-(5-cyclopropyl-8-fluoro-2-methyl-4-oxo-oxazolo[4,5-c]quinolin-7-yl)-4-piperidyl]carbamate (60 mg, 91% yield) as a brown solid.

LC-MS (Method C) 457.2 [M+H]⁺; RT 2.14 min (j) 7-(4-amino-1-piperidyl)-5-cyclopropyl-8-fluoro-2-methyl-oxazolo[4,5-c]quinolin-4-one W1

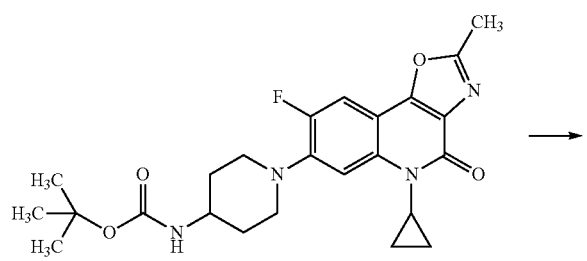

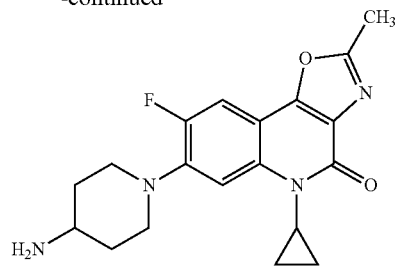

To a solution of tert-butyl N-[1-(5-cyclopropyl-8-fluoro-2-methyl-4-oxo-oxazolo[4,5-c]quinolin-7-yl)-4-piperidyl]carbamate (53.4 mg, 0.12 mmol) in DCM (3.5 mL) at room temperature was added TFA (0.11 mL, 1.4 mmol) and the mixture left stirring for 18 h. 0.5M aqueous HCl (20 mL) was added and the mixture washed with EtOAc (2×20 mL). The aqueous phase was basified with solid K₂CO₃ and extracted with DCM (3×30 mL). The combined organic phases were dried over Na₂SO₄, filtered, and concentrated in vacuo. The crude product was purified by flash chromatography eluting with 0-20% MeOH in DCM to give 7-(4-amino-1-piperidyl)-5-cyclopropyl-8-fluoro-2-methyl-oxazolo[4,5-c]quinolin-4-one W1 (11 mg, 26% yield) as an off-white solid.

¹H NMR (Method B) (MeOD): δ ppm 7.59 (d, J=7.4 Hz, 1H), 7.56 (d, J=7.83 Hz, 1H), 3.73-3.70 (m, 2H), 3.10-3.00 (m, 3H), 2.99-2.94 (m, 2H), 2.67 (s, 3H), 2.11-2.09 (m, 2H), 1.27-1.19 (m, 2H), 0.94-0.91 (m, 2H); LC-MS (Method C) 357.2 [M+H]⁺; RT 1.11 min Example 50—7-[(3R)-3-(2-aminopropan-2-yl)pyrrolidin-1-yl]-5-cyclopropyl-8-fluoro-2-methyl-oxazolo[4,5-c]quinolin-4-one X1

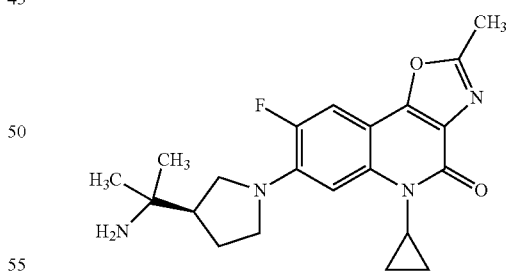

Prepared using tert-butyl N-(2-[(3R)-pyrrolidin-3-yl]propan-2-yl)carbamate and a similar procedure to that described in Example 49 steps (i) and (j)

¹H NMR (Method B) (MeOD): δ ppm 7.39 (d, J=13.04 Hz, 1H), 7.09 (d, J=12.02 Hz, 1H), 3.73-3.68 (m, 1H), 3.63-3.60 (m, 1H), 3.56-3.51 (m, 1H), 2.99-2.93 (m, 1H), 2.65 (s, 3H), 2.57-2.53 (m, 1H), 2.20-2.13 (m, 1H), 1.98-1.91 (m, 1H), 1.44-1.42 (m, 1H), 1.38 (s, 3H), 1.37 (s, 3H), 1.33-1.25 (m, 2H), 0.92-0.86 (m, 2H); LC-MS (Method C) 385.2 [M+H]⁺; RT 1.14 min

Example 51—7-(3-aminopiperidin-1-yl)-5-cyclopropyl-8-fluoro-2-methyl-oxazolo[4,5-c]quinolin-4-one Y1

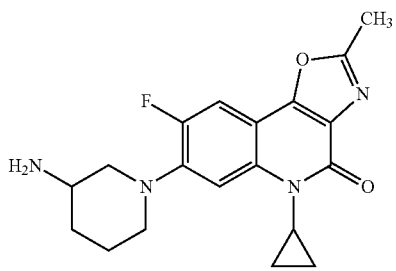 [SMILES: Cc1nc2c(=O)n(C3CC3)c3cc(N4CCCC(N)C4)c(F)cc3c2o1]

Prepared using tert-butyl N-(piperidin-3-yl)carbamate and a similar procedure to that described in Example 49 steps (i) and (j)

¹H NMR (Method B) (CD₃OD): δ ppm 7.56 (d, J=7.49 Hz, 1H), 7.09 (d, J=11.88 Hz, 1H), 3.59-3.56 (m, 1H), 3.46-3.41 (m, 1H), 3.19-3.14 (m, 1H), 3.06-2.97 (m, 2H), 2.87-2.82 (m, 1H), 2.67 (s, 3H), 2.57-2.53 (m, 1H), 2.08-2.04 (m, 1H), 2.00-1.96 (m, 1H), 1.86-1.82 (m, 1H), 1.45-1.41 (m, 2H), 1.32-1.28 (m, 1H), 0.92-0.88 (m, 2H); LC-MS (Method C) 357.2 [M+H]⁺; RT 1.03 min

Example 52—7-[(3R)-3-(aminomethyl)pyrrolidin-1-yl]-5-cyclopropyl-8-fluoro-2-methyl-oxazolo[4,5-c]quinolin-4-one Z1

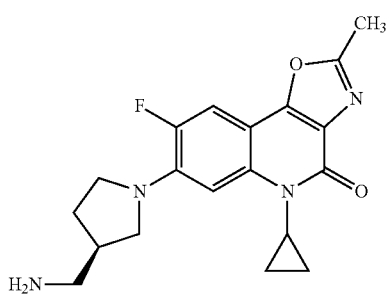 [SMILES: Cc1nc2c(=O)n(C3CC3)c3cc(N4CC[C@H](CN)C4)c(F)cc3c2o1]

Prepared using (3S) tert-butyl N-(pyrrolidin-3-ylmethyl)carbamate and a similar procedure to that described in Example 49 steps (i) and (j)

¹H NMR (Method B) (MeOD): δ ppm 7.36 (d, J=13.5 Hz, 1H), 7.06 (d, J=7.74 Hz, 1H), 3.59-3.56 (m, 1H), 3.46-3.41 (m, 1H), 3.19-3.14 (m, 1H), 2.96-2.92 (m, 2H), 2.90-2.88 (m, 1H), 2.64 (s, 3H), 2.53-2.47 (m, 1H), 2.28-2.21 (m, 1H), 1.86-1.79 (m, 1H), 1.86-1.82 (m, 1H), 1.45-1.41 (m, 2H), 0.89-0.85 (m, 2H); LC-MS (Method C) 357.2 [M+H]⁺; RT 1.11 min

Example 53—5-cyclopropyl-8-fluoro-7-(3-hydroxypyrrolidin-1-yl)-2-methyl-oxazolo[4,5-c]quinolin-4-one A2

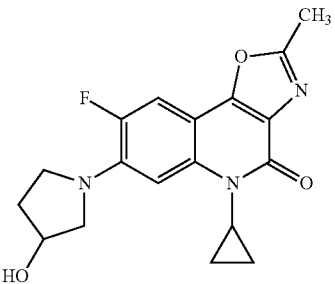 [SMILES: Cc1nc2c(=O)n(C3CC3)c3cc(N4CCC(O)C4)c(F)cc3c2o1]

Prepared using pyrrolidin-3-ol and a similar procedure to that described in Example 49 step (i)

¹H NMR (Method B) (CDCl₃): δ ppm 7.18 (d, J=13.0 Hz, 1H), 6.91 (d, J=7.99 Hz, 1H), 4.66 (m, 1H), 3.85-3.77 (m, 2H), 3.73-3.69 (m, 1H), 3.58-3.54 (m, 1H), 2.96-2.92 (m, 2H), 2.89-2.86 (m, 2H), 2.64 (s, 3H), 2.21-2.16 (m, 2H), 1.37-1.33 (m, 2H), 0.87-0.84 (m, 2H); LC-MS (Method C) 344.0 [M+H]⁺; RT 1.39 min

Example 54—7-[3-(1-aminoethyl)pyrrolidin-1-yl]-5-cyclopropyl-8-fluoro-2-methyl-oxazolo[4,5-c]quinolin-4-one B2

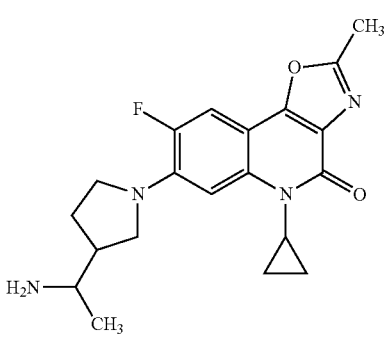 [SMILES: Cc1nc2c(=O)n(C3CC3)c3cc(N4CCC(C(C)N)C4)c(F)cc3c2o1]

Prepared using tert-butyl N-[1-(pyrrolidin-3-yl)ethyl]carbamate and a similar procedure to that described in Example 49 steps (i) and (j)

¹H NMR (Method B) (CD₃OD): δ ppm 7.34 (d, J=12.89 Hz, 1H), 7.03 (d, J=7.93 Hz, 1H), 3.69-3.60 (m, 3H), 3.39-3.37 (m, 1H), 3.18-3.14 (m, 1H), 2.95-2.91 (m, 1H), 2.64 (s, 3H), 2.40-2.29 (m, 2H), 1.92-1.82 (m, 1H), 1.43-1.40 (m, 2H), 1.32 (d, J=6.33 Hz, 3H), 0.88-0.85 (m, 2H); LC-MS (Method C) 371.4 [M+H]⁺; RT 1.12 min

Example 55—7-(4-amino-4-methylpiperidin-1-yl)-5-cyclopropyl-8-fluoro-2-methyl-oxazolo[4,5-c]quinolin-4-one C2

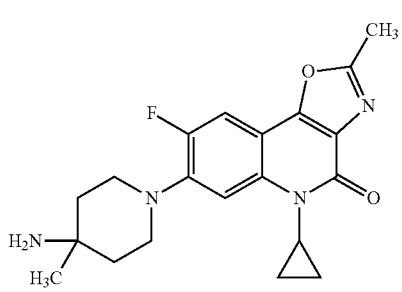 [SMILES: Cc1nc2c(=O)n(C3CC3)c3cc(N4CCC(C)(N)CC4)c(F)cc3c2o1]

Prepared using tert-butyl N-(4-methylpiperidin-4-yl)carbamate and a similar procedure to that described in Example 49 steps (i) and (j)

$^1$H NMR (Method B) (CD$_3$OD): δ ppm 7.58 (d, J=7.47 Hz, 1H), 7.51 (d, J=12.01 Hz, 1H), 3.46-3.40 (m, 2H), 3.27-3.21 (m, 2H), 3.06-3.01 (m, 1H), 2.66 (s, 3H), 1.89 (t, J=5.58 Hz, 4H), 1.46-1.41 (m, 2H), 1.37 (s, 3H), 0.93-0.88 (m, 2H); LC-MS (Method C) 357.2 [M+H]*; RT 1.05 min

Example 56—7-(3-aminopyrrolidin-1-yl)-5-cyclopropyl-8-fluoro-2-methyl-oxazolo[4,5-c]quinolin-4-one D2

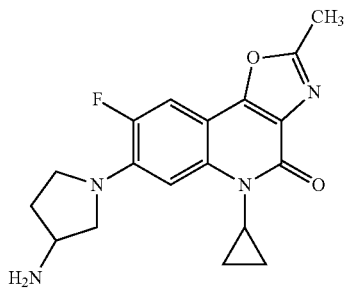 [SMILES: Cc1nc2c(=O)n(C3CC3)c3cc(N4CCC(N)C4)c(F)cc3c2o1]

Prepared using tert-butyl N-(pyrrolidin-3-yl)carbamate and a similar procedure to that described in Example 49 steps (i) and (j). Product isolated as a formate salt $^1$H NMR (Method B) (CD$_3$OD): δ ppm 8.20 (br s, 1H), 7.62 (d, J=13.4 Hz, 1H), 7.09 (d, J=8.03 Hz, 1H), 3.97 (m, 1H), 3.85 (m, 1H), 3.74 (m, 1H), 3.65 (m, 1H), 3.55 (m, 1H), 2.98 (m, 1H), 2.60 (s, 3H), 2.34 (m, 1H), 2.11 (m, 1H), 1.34 (m, 2H), 0.79 (m, 2H); LC-MS (Method C) 343.2 [M$^+$ H$^+$]; RT 1.81 min

Example 57—7-[3-(aminomethyl)pyrrolidin-1-yl]-5-cyclopropyl-8-fluoro-2-methyl-oxazolo[4,5-c]quinolin-4-one E2

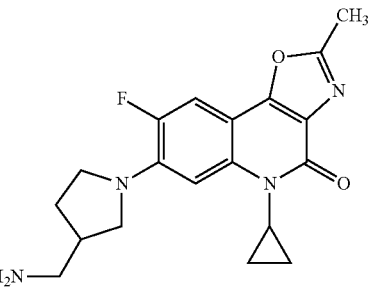

Prepared using tert-butyl N-(pyrrolidin-3-ylmethyl)carbamate and a similar procedure to that described in Example 49 steps (i) and (j). Product isolated as a HCl salt by stirring in 1M HCl in ether followed by removal of solvent.

$^1$H NMR (Method B) (DMSO-d$_6$): δ ppm 7.99 (br s, 2H), 7.58 (d, J=13.35 Hz, 1H), 7.07 (d, J=7.97 Hz, 1H), 3.72-3.51 (m, 4H), 2.97 (m, 4H), 2.59 (s, 3H), 2.19 (m, 1H), 1.82 (m, 1H), 1.36 (m, 2H) 0.78 (m, 2H); LC-MS (Method C) 357.3 [M$^+$ H$^+$]; RT 1.88 min

Example 58—4-(5-cyclopropyl-8-fluoro-4-oxo-oxazolo[4,5-c]quinolin-7-yl)benzamide F2

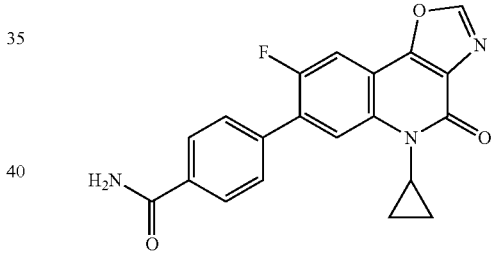

(a) 4-bromo-2,5-difluorobenzoic acid

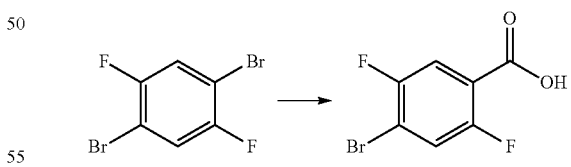

To a −78° C. solution of 1,4-dibromo-2,5-difluorobenzene (2.72 g, 9.99 mmol) in dry Et$_2$O (30 mL) under an inert atmosphere was added 2.5 M n-butyllithium solution in hexanes (4 mL, 9.99 mmol) drop-wise and the mixture left stirring for 2 h. Crushed CO$_2$ pellets were added slowly and the mixture was allowed to warm to ambient temperature and left stirring for 1 h.

After quenching with 1M aqueous HCl (10 mL) the mixture was basified with 1M aqueous NaOH (70 mL) and then washed with Et$_2$O (2×50 mL). The aqueous layer was acidified with 1M aqueous HCl (80 mL) and extracted with Et₂O (3×100 mL). The organic layer was washed with brine (50 mL), dried over Na₂SO₄, filtered and solvent was removed in vacuo to give 4-bromo-2,5-difluoro benzoic acid (2.3 g, 97%) as an off-white solid, which was used without further purification.

¹H NMR (Method B) (CDCl₃): δ ppm 9.50 (br s, 1H), 7.78 (dd, J=8.2, 6.1 Hz, 1H), 7.46 (dd, J=9.3, 5.4 Hz, 1H); LC-MS (Method C) 234.9/236.9 [M−H]⁺; RT 3.43 min (b) ethyl 5-(4-bromo-2,5-difluoro-phenyl)oxazole-4-carboxylate

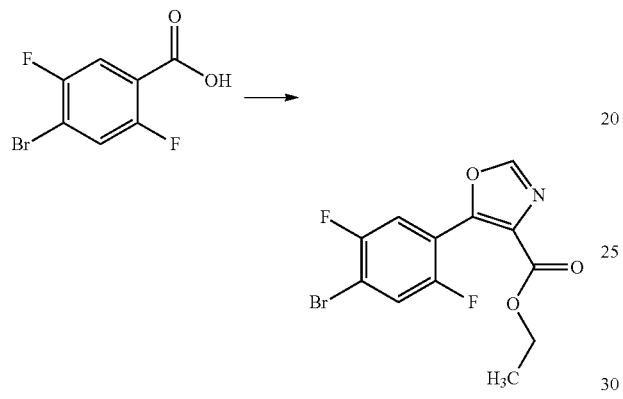

To an ice cooled solution of 4-bromo-2,5-difluorobenzoic acid (6.27 g, 26.46 mmol) in DCM (80 mL) was added oxalyl chloride (3.46 mL, 39.68 mmol), followed by several drops of DMF. The mixture was then removed from the ice bath and stirred for 2 h. The solvent was removed under reduced pressure to give 4-bromo-2,5-difluorobenzoyl chloride. To an ice cooled solution of ethyl isocyanoacetate (3.18 mL, 29.1 mmol) in THF (40 mL) was added Et₃N (11. mL, 79.37 mmol) followed by the slow addition of 4-bromo-2, 5-difluorobenzoyl chloride in THF (40 mL). The reaction mixture was then allowed to warm to room temperature and stirred for 18 h. The reaction mixture was then diluted with DCM and washed with sat aqueous NaHCO₃ followed by brine. The organic phase was dried over Na₂SO₄, filtered and concentrated in vacuo to give ethyl 5-(4-bromo-2,5-difluoro-phenyl)oxazole-4-carboxylate as a solid (7.78 g, 89% yield) LC-MS (Method C) 331.9/333.9 [M+H]⁺; RT 1.77 min.

(c) 5-(4-bromo-2,5-difluoro-phenyl)oxazole-4-carboxylic acid

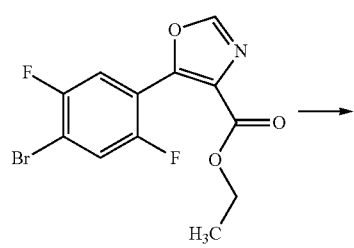

-continued

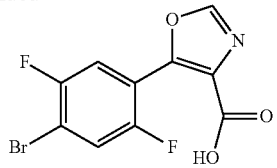

A solution of ethyl 5-(4-bromo-2,5-difluoro-phenyl)oxazole-4-carboxylate (7.78 g, 23.44 mmol) in 1,4-dioxane (50 mL) was treated with 2M aq. LiOH (50 mL) and stirred at room temperature overnight. The 1,4-dioxane was removed under reduced pressure and the remaining aqueous was acidified with 1M aqueous HCl, and then extracted with EtOAc.

The combined organic extracts were washed with brine, dried over Na₂SO₄, filtered and then concentrated in vacuo to give 5-(4-bromo-2,5-difluoro-phenyl)oxazole-4-carboxylic acid as an off white solid (6.05 g, 85% yield), which was used without further purification.

LC-MS (Method C) 303.9/305.8 [M+H]⁺; RT 1.46 min.

(d) 5-(4-bromo-2,5-difluoro-phenyl)-N-cyclopropyl-oxazole-4-carboxamide

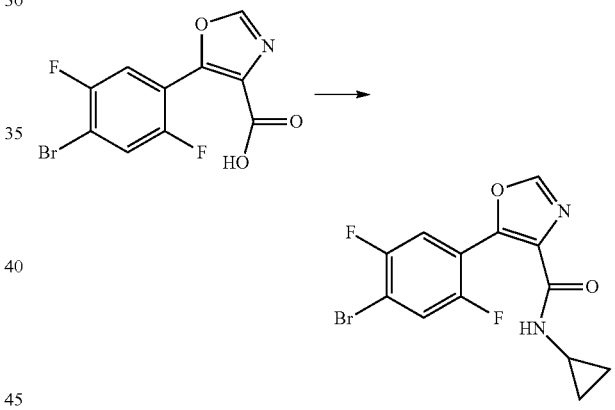

A suspension of 5-(4-bromo-2,5-difluoro-phenyl)oxazole-4-carboxylic acid (5.5 g, 18.09 mmol) in anhydrous DCM (80 mL) was cooled in an ice bath followed by the slow addition of oxalyl chloride (2.3 mL, 27.14 mmol). Several drops of DMF were added to catalyse the reaction. The reaction mixture was allowed to warm to room temperature and stirred for 2 h, before concentrating in vacuo to give a brown liquid, which was dissolved in DCM (80 mL) and treated with cyclopropylamine (2.75 mL, 39.69 mmol). After stirring at room temperature for 2 h the reaction mixture was diluted with DCM and washed with saturated aqueous NaHCO₃ The organic phase was separated, dried over Na₂SO₄, filtered and concentrated in vacuo to give 5-(4-bromo-2,5-difluoro-phenyl)-N-cyclopropyl-oxazole-4-carboxamide as a light brown solid (5.14 g, 83% yield), which was used without further purification.

LC-MS (Method C) 342.8/344.7 [M+H]⁺; RT 1.65 min (e) 7-bromo-5-cyclopropyl-8-fluoro-oxazolo[4,5-c]quinolin-4-one

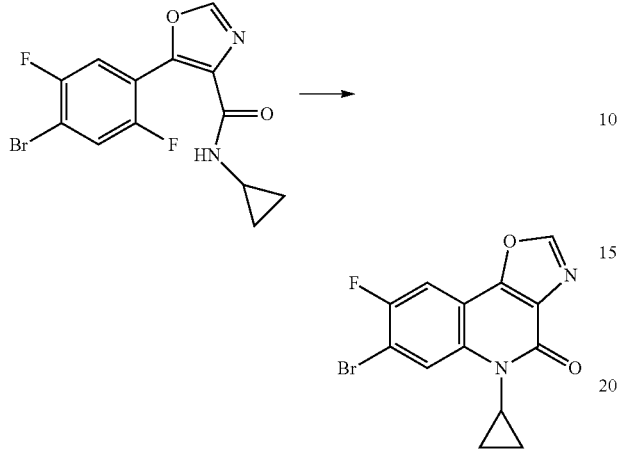

A mixture of 5-(4-bromo-2,5-difluoro-phenyl)-N-cyclopropyl-oxazole-4-carboxamide (1.5 g, 4.37 mmol), K$_2$CO$_3$ (1.81 g, 13.12 mmol) and 18-crown-6 (1.16 g, 4.37 mmol) in DMSO (20 mL) were heated in the microwave (Biotage Initiator) at 140° C. for 90 min.

The reaction mixture was then diluted with EtOAc, which was washed with H$_2$O several times followed by brine and then dried over Na$_2$SO$_4$, filtered and concentrated in vacuo to give a brown solid. The crude product was purified by flash chromatography eluting with 0-100% EtOAc in heptane to give 7-bromo-5-cyclopropyl-8-fluoro-oxazolo[4,5-c]quinolin-4-one (370 mg, 26% yield) as an off white solid.

$^1$H NMR (Method B) (CDCl$_3$): δ ppm 8.22 (d, J=5.7 Hz, 1H), 8.14 (s, 1H), 7.66 (d, J=7.5 Hz, 1H), 3.04 (tt, J=6.8, 4 Hz, 1H), 1.47 (m, 2H), 0.97 (m, 2H); LC-MS (Method C) 322.9/324.8 [M+H]$^+$; RT 1.55 min (f) 4-(5-cyclopropyl-8-fluoro-4-oxo-oxazolo[4,5-c]quinolin-7-yl)benzamide F2

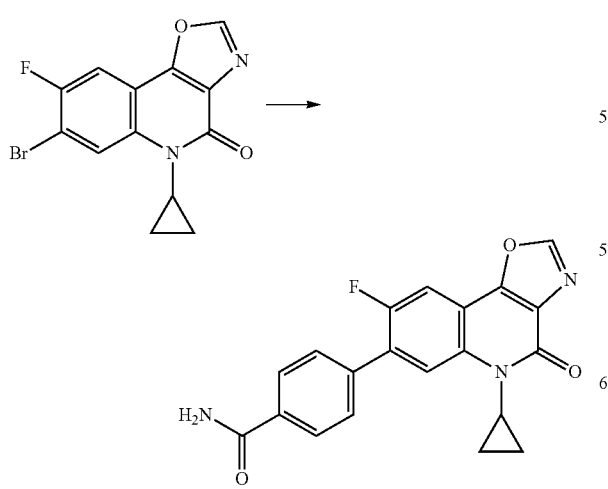

A mixture of 7-bromo-5-cyclopropyl-8-fluoro-oxazolo[4,5-c]quinolin-4-one (40. mg, 0.12 mmol), [1,1'-bis(diphenylphosphino)ferrocene]palladium(II) chloride dichloromethane complex (10.1 mg, 0.01 mmol), Cs$_2$CO$_3$ (121 mg, 0.37 mmol) and 4-(4,4,5,5-tetramethyl-1,3,2-dioxaborolan-2-yl)-benzamide (30.6 mg, 0.12 mmol) in dimethoxyethane (1 mL) and H$_2$O (0.25 mL) was heated in the microwave (Biotage Initiator) at 120° C. for 20 minute. The mixture was dry loaded onto silica and purified by flash chromatography eluting with 0-20% MeOH in DCM to give a solid, which was further purified by preparative HPLC (Method B) to give 4-(5-cyclopropyl-8-fluoro-4-oxo-oxazolo[4,5-c]quinolin-7-yl)benzamide F2 (10 mg, 22%) as a white solid $^1$H NMR (Method B) (CD$_3$OD): δ ppm 8.60 (s, 1H), 8.26 (d, J=6.5 Hz, 1H), 8.06 (m, 2H), 7.90 (d, J=9.8 Hz, 1H), 7.81 (dd, J=8.5 Hz, 2H), 3.20 (m, 1H), 1.47 (m, 2H), 1.01 (m, 2H); LC-MS (Method C) 364.1 [M+H]$^+$; RT 1.39 min Example 59—7-(3-chloro-4-pyridyl)-5-cyclopropyl-8-fluoro-oxazolo[4,5-c]quinolin-4-one G2

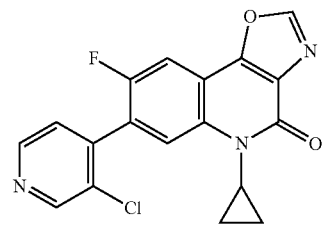 [SMILES: O=c1c2ncoc2c2cc(F)c(-c3ccncc3Cl)cc2n1C1CC1]

Prepared using 3-chloro-4-(4,4,5,5-tetramethyl-1,3,2-dioxaborolan-2-yl)pyridine and 7-bromo-5-cyclopropyl-8-fluoro-oxazolo[4,5-c]quinolin-4-one (prepared as described in Example 58 step (e)) and a similar procedure to that described in Example 58 step (f)

$^1$H NMR (Method B) (DMSO-d$_6$): δ ppm 8.92 (s, 1H), 8.86 (s, 1H), 8.71 (d, J=4.9 Hz, 1H), 8.07-8.03 (m, 2H), 7.66 (d, J=4.9 Hz, 1H), 3.07 (m, 1H), 1.35-1.30 (m, 2H), 0.87-0.83 (m, 2H); LC-MS (Method C) 356.2 [M+H]$^+$; RT 1.47 min Example 60—5-cyclopropyl-8-fluoro-7-[6-(trifluoromethyl)-3-pyridyl]oxazolo[4,5-c]quinolin-4-one H2

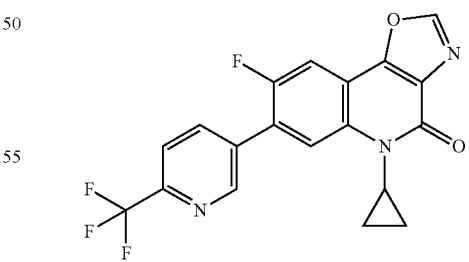

Prepared using [6-(trifluorormethyl)-3-pyridyl]boronic acid and 7-bromo-5-cyclopropyl-8-fluoro-oxazolo[4,5-c]quinolin-4-one (prepared as described in Example 58 step (e)) and a similar procedure to that described in Example 58 step (f)

$^1$H NMR (Method B) (DMSO-d$_6$): δ ppm 9.10 (s, 1H), 8.93 (s, 1H), 8.43 (d, J=8.3 Hz, 1H), 8.24 (d, J=6.5 Hz, 1H), 8.13 (d, J=7.8 Hz, 1H), 8.08 (d, J=9.9 Hz, 1H), 3.14 (m, 1H), 1.38 (m, 2H), 0.88 (m, 2H); LC-MS (Method C) 390.1 [M+H]⁺; RT 1.69 min Example 61—ethyl 4-(5-cyclopropyl-8-fluoro-4-oxo-oxazolo[4,5-c]quinolin-7-yl)benzoate 12

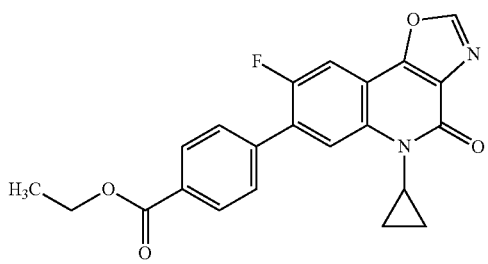 [SMILES: CCOC(=O)c1ccc(-c2cc3c(cc2F)c2ocnc2c(=O)n3C2CC2)cc1]

Prepared using ethyl 4-(4,4,5,5-tetramethyl-1,3,2-dioxaborolan-2-yl)benzoate and 7-bromo-5-cyclopropyl-8-fluoro-oxazolo[4,5-c]quinolin-4-one (prepared as described in Example 58 step (e)) and a similar procedure to that described in Example 58 step (f)

¹H NMR (Method B) (CDCl₃): b ppm 8.21-8.16 (m, 3H), 8.07 (d, J=6.4 Hz, 1H), 7.72 (m, 3H), 4.44 (q, J=7.1 Hz, 2H), 3.10 (br s, 1H), 1.48-1.42 (m, 5H), 1.02 (m, 2H); LC-MS (Method C) 393.2 [M+H]⁺; RT 1.80 min Example 62—7-(2-aminopyrimidin-5-yl)-5-cyclopropyl-8-fluoro-oxazolo[4,5-c]quinolin-4-one J2

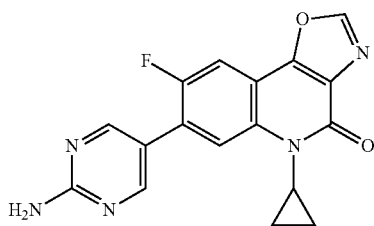 [SMILES: Nc1ncc(-c2cc3c(cc2F)c2ocnc2c(=O)n3C2CC2)cn1]

Prepared using 5-(4,4,5,5-tetramethyl-1,3,2-dioxaborolan-2-yl)-2-pyrimidinamine and 7-bromo-5-cyclopropyl-8-fluoro-oxazolo[4,5-c]quinolin-4-one (prepared as described in Example 58 step (e)) and a similar procedure to that described in Example 58 step (f)

¹H NMR (Method B) (DMSO-d₆): δ ppm 8.87 (s, 1H), 8.59 (d, J=1.3 Hz, 2H), 8.09 (d, J=6.7 Hz, 1H), 7.94 (d, J=9.9 Hz, 1H), 7.06 (s, 2H), 3.13 (m, 1H), 1.39 (m, 2H), 0.86 (m, 2H); LC-MS (Method C) 338.2 [M+H]⁺; RT 1.18 min Example 63—5-cyclopropyl-8-fluoro-7-(4-methoxyphenyl)oxazolo[4,5-c]quinolin-4-one

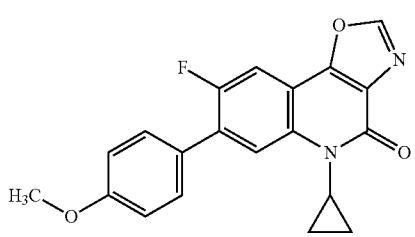 [SMILES: COc1ccc(-c2cc3c(cc2F)c2ocnc2c(=O)n3C2CC2)cc1]

Prepared using 4-methoxyphenylboronic acid and 7-bromo-5-cyclopropyl-8-fluoro-oxazolo[4,5-c]quinolin-4-one (prepared as described in Example 58 step (e)) and a similar procedure to that described in Example 58 step (f)

¹H NMR (Method B) (DMSO-d₆): δ ppm 8.88 (s, 1H), 8.06 (d, J=6.7 Hz, 1H), 7.92 (d, J=10 Hz, 1H), 7.64 (dd, J=6.7, 1.8 Hz, 2H), 7.14 (m, 2H), 3.85 (s, 3H), 3.15 (m, 1H), 1.36 (m, 2H), 0.87 (m, 2H); LC-MS (Method C) 351.1 [M+H]⁺; RT 1.72 min Example 64—5-cyclopropyl-8-fluoro-7-(4-hydroxyphenyl)oxazolo[4,5-c]quinolin-4-one L2

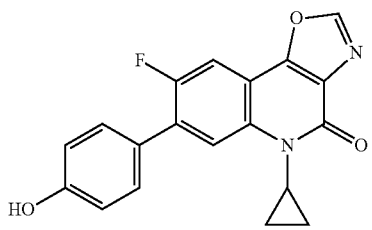 [SMILES: O=c1c2ncoc2c2cc(F)c(-c3ccc(O)cc3)cc2n1C1CC1]

Prepared using 4-hydroxphenylboronic acid and 7-bromo-5-cyclopropyl-8-fluoro-oxazolo[4,5-c]quinolin-4-one (prepared as described in Example 58 step (e)) and a similar procedure to that described in Example 58 step (f)

¹H NMR (Method B) (DMSO-d₆): δ ppm 9.83 (s, 1H), 8.86 (s, 1H), 8.03 (d, J=6.8 Hz, 1H), 7.89 (d, J=10.1 Hz, 1H), 7.53 (dd, J=8.5, 1.7 Hz, 2H), 6.95 (d, J=8.7 Hz, 2H), 3.14 (m, 1H), 1.36 (m, 2H), 0.86 (m, 2H); LC-MS (Method C) 337.1 [M+H]⁺; RT 1.44 min Example 65—4-(5-cyclopropyl-8-fluoro-4-oxo-oxazolo[4,5-c]quinolin-7-yl)-2,6-difluoro-benzonitrile M2

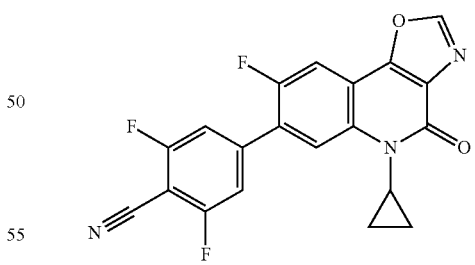

Prepared using 2,6-difluoro-4-(4,4,5,5-tetramethyl-1,3,2-dioxaborolan-2-yl)benzonitrile and 7-bromo-5-cyclopropyl-8-fluoro-oxazolo[4,5-c]quinolin-4-one (prepared as described in Example 58 step (e)) and a similar procedure to that described in Example 58 step (f)

¹H NMR (Method B) (CDCl₃) δ 8.18 (s, 1H), 8.02 (d, J=6.3 Hz, 1H), 7.76 (d, J=9.6 Hz, 1H), 7.35 (d, J=9.0 Hz, 2H), 3.10 (s, 1H), 1.53-1.43 (m, 2H), 1.10-0.93 (m, 2H); LC-MS (Method C) 382.0 [M+H]⁺; RT 1.71 min

Example 66—4-(5-cyclopropyl-8-fluoro-4-oxo-oxazolo[4,5-c]quinolin-7-yl)-N,N-dimethyl-benzamide N2

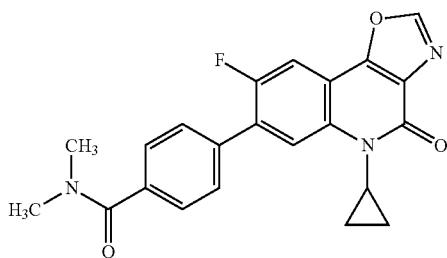 [SMILES: CN(C)C(=O)c1ccc(-c2cc3c(cc2F)c2ocnc2c(=O)n3C2CC2)cc1]

Prepared using 4-(dimethylcarbamoyl)phenylboronic acid and 7-bromo-5-cyclopropyl-8-fluoro-oxazolo[4,5-c]quinolin-4-one (prepared as described in Example 58 step (e)) and a similar procedure to that described in Example 58 step (f)

$^1$H NMR (Method B) (CDCl$_3$) δ 8.14 (s, 1H), 8.04 (d, J=6.3 Hz, 1H), 7.75-7.54 (m, 5H), 3.17-3.05 (m, 7H), 1.49-1.43 (m, 2H), 1.05-0.95 (m, 2H); LC-MS (Method C) 392.0 [M+H]$^+$; RT 1.39 min

Example 67—4-(5-cyclopropyl-8-fluoro-4-oxo-oxazolo[4,5-c]quinolin-7-yl)-2-fluoro-N-methyl-benzamide O2

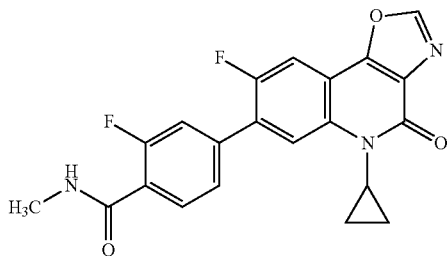 [SMILES: CNC(=O)c1ccc(-c2cc3c(cc2F)c2ocnc2c(=O)n3C2CC2)cc1F]

Prepared using [3-fluoro-4-(methylcarbamoyl)phenyl]boronic acid and 7-bromo-5-cyclopropyl-8-fluoro-oxazolo[4,5-c]quinolin-4-one (prepared as described in Example 58 step (e)) and a similar procedure to that described in Example 58 step (f)

$^1$H NMR (Method B, CDCl$_3$) δ 8.27 (t, 1H), 8.15 (s, 1H), 8.06 (d, J=6.3 Hz, 1H), 7.72 (d, J=9.5 Hz, 1H), 7.53 (d, J=8.0 Hz, 1H), 7.43 (d, J=12.9 Hz, 1H), 6.79 (s, 1H), 3.15-3.00 (m, 4H), 1.48 (d, J=6.6 Hz, 2H), 1.01 (s, 2H); LC-MS (Method C) 396.0 [M+H]$^+$; RT 1.37 min

Example 68—5-cyclopropyl-7-[2,5-difluoro-4-(hydroxymethyl)phenyl]-8-fluoro-oxazolo[4,5-c]quinolin-4-one P2

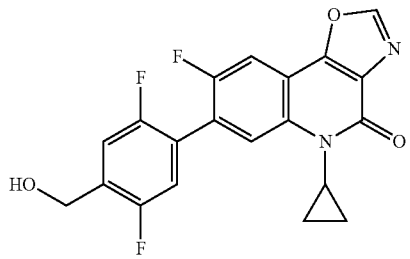 [SMILES: O=c1c2ncoc2c2cc(F)c(-c3cc(F)c(CO)cc3F)cc2n1C1CC1]

Prepared using [2,5-difluoro-4-(4,4,5,5-tetramethyl-1,3,2-dioxaborolan-2-yl)phenyl]methanol and 7-bromo-5-cyclopropyl-8-fluoro-oxazolo[4,5-c]quinolin-4-one (prepared as described in Example 58 step (e)) and a similar procedure to that described in Example 58 step (f)

$^1$H NMR (Method B) (CDCl$_3$) δ 8.08 (s, 1H), 7.96 (d, J=6.0 Hz, 1H), 7.65 (d, J=8.9 Hz, 1H), 7.31 (dd, J=9.8, 6.0 Hz, 1H), 7.13 (m, 1H), 4.79 (s, 2H), 2.99 (m, 1H), 1.37 (m, 2H), 0.93 (m, 2H); LC-MS (Method C) 387.1 [M+H]$^+$; RT 1.47 min

Example 69—7-(4-amino-2,5-difluoro-phenyl)-5-cyclopropyl-8-fluoro-oxazolo[4,5-c]quinolin-4-one Q2

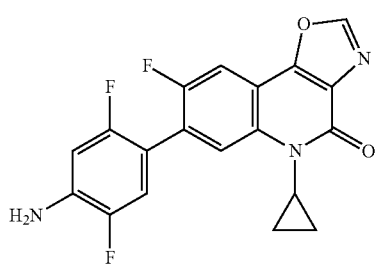 [SMILES: Nc1cc(F)c(-c2cc3c(cc2F)c2ocnc2c(=O)n3C2CC2)cc1F]

Prepared using 4-amino-2,5-difluorobenzeneboronic acid pinacol ester and 7-bromo-5-cyclopropyl-8-fluoro-oxazolo[4,5-c]quinolin-4-one (prepared as described in Example 58 step (e)) and a similar procedure to that described in Example 58 step (f)

$^1$H NMR (Method B) (DMSO-d$_6$): δ ppm 8.87 (s, 1H), 7.94 (dd, J=6.2, 7.8 Hz, 2H), 7.26 (dd, J=11.5, 6.8 Hz, 1H), 7.09 (s, 2H), 6.69 (dd, J=11.9, 7.4 Hz, 1H), 3.17-2.89 (m, 1H), 1.34 (t, J=6.8 Hz, 2H), 0.86 (d, J=3.7 Hz, 2H); LC-MS (Method C) 372.1 [M$^+$ H$^+$]; RT 1.90 min

Example 70—7-(6-amino-3-pyridyl)-5-cyclopropyl-8-fluoro-oxazolo[4,5-c]quinolin-4-one R2

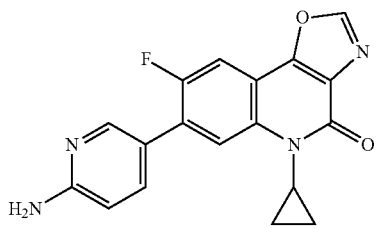 [SMILES: Nc1ccc(-c2cc3c(cc2F)c2ocnc2c(=O)n3C2CC2)cn1]

Prepared using 2-aminopyridine-5-boronic acid pinacol ester and 7-bromo-5-cyclopropyl-8-fluoro-oxazolo[4,5-c]quinolin-4-one (prepared as described in Example 57 step (e)) and a similar procedure to that described in Example 57, step (f)

$^1$H NMR (Method B) (DMSO-d$_6$): δ ppm 8.86 (s, 1H), 8.26 (t, J=2.0 Hz, 1H), 8.03 (d, J=6.7 Hz, 1H), 7.89 (d, J=10.1 Hz, 1H), 7.72 (dt, J=8.7, 2.2 Hz, 1H), 6.60 (d, J=8.7 Hz, 1H), 6.33 (s, 2H), 3.14 (qd, J=8.2, 7.2, 4.6 Hz, 1H), 1.43-1.29 (m, 2H), 0.92-0.78 (m, 2H); LC-MS (Method C) 337.1 [M+ H+]; RT 0.95 min.

Example 71—7-(4-amino-3-fluoro-phenyl)-5-cyclopropyl-8-fluoro-oxazolo[4,5-c]quinolin-4-one S2

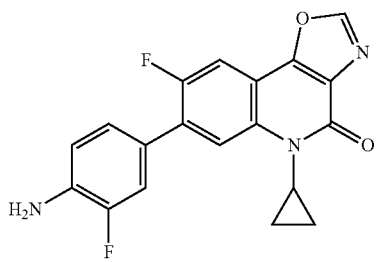 [SMILES: Nc1ccc(-c2cc3c(cc2F)c2ocnc2c(=O)n3C2CC2)cc1F]

Prepared using 2-fluoro-4-(4,4,5,5-tetramethyl-1,3,2-dioxaborolan-2-yl)aniline and 7-bromo-5-cyclopropyl-8-fluoro-oxazolo[4,5-c]quinolin-4-one (prepared as described in Example 58 step (e)) and a similar procedure to that described in Example 58 step (f)

$^1$H NMR (Method B) (CD$_3$OD): δ ppm 8.56 (s, 1H), 8.16 (d, J=6.76 Hz, 1H), 7.80 (d, J=9.88 Hz, 1H), 7.36-7.28 (m, 2H), 6.99-6.95 (m, 1H), 3.20-3.16 (m, 1H), 1.50-1.45 (m, 2H), 1.00-0.96 (m, 2H); LC-MS (Method C) 354.2 [M+H]+; RT 1.52 min

Example 72—4-(5-cyclopropyl-8-fluoro-2-methyl-4-oxo-oxazolo[4,5-c]quinolin-7-yl)benzaldehyde T2

(a) 7-bromo-5-cyclopropyl-8-fluoro-2-methyl-oxazolo[4,5-c]quinolin-4-one

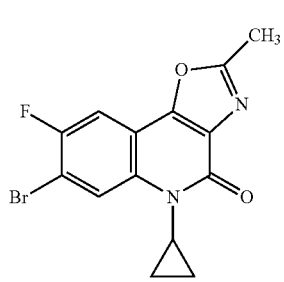 [SMILES: Cc1nc2c(=O)n(C3CC3)c3cc(Br)c(F)cc3c2o1]

Prepared using 4-bromo-2,5-difluorobenzoic acid (prepared as described in Example 58 step (a)) and a similar procedure to that described in Example 49 steps (a) to (h).

LC-MS (Method C) 336.8/338.8 [M+H]*; RT 1.61 min (b) 4-(5-cyclopropyl-8-fluoro-2-methyl-4-oxo-oxazolo[4,5-c]quinolin-7-yl)benzaldehyde T2

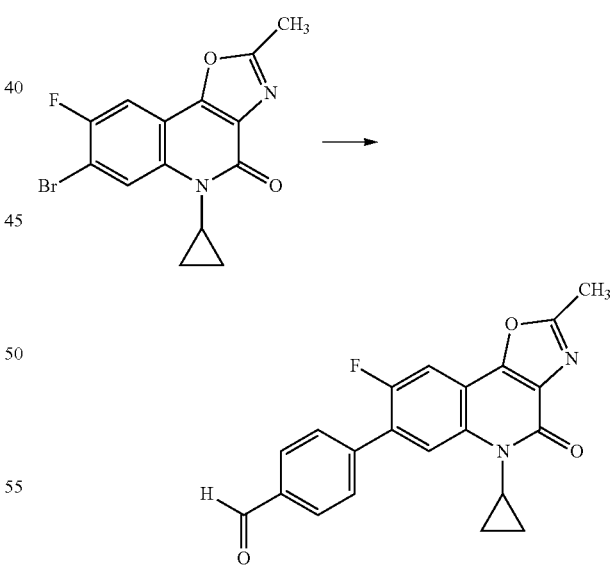

Prepared using 7-bromo-5-cyclopropyl-8-fluoro-2-methyl-oxazolo[4,5-c]quinolin-4-one and a similar procedure to that described in Example 58 step (f)

$^1$H NMR (Method B) (DMSO-d$_6$): δ ppm 10.12 (s, 1H), 8.14 (d, J=6.7 Hz, 1H), 8.10 (d, J=8.4 Hz, 2H), 7.93 (d, J=9.9 Hz, 3H), 3.15 (m, 1H), 2.68 (s, 3H), 1.36 (m, 2H), 0.87 (m, 2H); LC-MS (Method C) 363.1 [M+H]*; RT 3.63 min Example 73—5-cyclopropyl-8-fluoro-7-(1H-indazol-5-yl)-2-methyl-oxazolo[4,5-c]quinolin-4-one U2

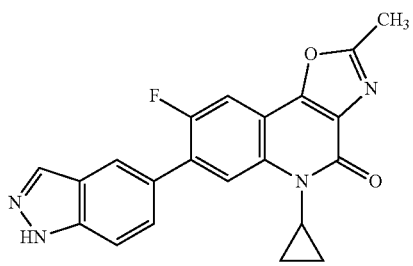 [SMILES: Cc1nc2c(=O)n(C3CC3)c3cc(-c4ccc5[nH]ncc5c4)c(F)cc3c2o1]

Prepared using 6-[4-(4,4,5,5-tetramethyl-1,3,2-dioxaborolan-2-yl)-1H-indazole and 7-bromo-5-cyclopropyl-8-fluoro-2-methyl-oxazolo[4,5-c]quinolin-4-one (prepared as described in Example 72 step (a)) and a similar procedure to that described in Example 58 step (f)

$^1$H NMR (Method B) (DMSO-d$_6$): b ppm 13.26 (s, 1H), 8.22 (s, 1H), 8.12 (d, J=6.8 Hz, 1H), 8.09 (s, 1H), 7.87 (d, J=10 Hz, 1H), 7.72 (d, J=8.7 Hz, 1H), 7.65 (dt, J=8.6, 1.4 Hz, 1H), 3.14 (m, 1H), 2.68 (s, 3H), 1.36 (m, 2H), 0.87 (m, 2H); LC-MS (Method C) 375.0 [M+H]$^+$; RT 1.44 min Example 74—5-cyclopropyl-8-fluoro-7-(3-fluoro-4-pyridyl)-2-methyl-oxazolo[4,5-c]quinolin-4-one V2

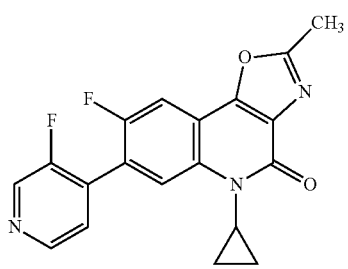 [SMILES: Cc1nc2c(=O)n(C3CC3)c3cc(-c4ccncc4F)c(F)cc3c2o1]

Prepared using 3-fluoro-4-pyridineboronic acid pinacol ester and 7-bromo-5-cyclopropyl-8-fluoro-2-methyl-oxazolo[4,5-c]quinolin-4-one (prepared as described in Example 72 step (a)) and a similar procedure to that described in Example 58 step (f)

$^1$H NMR (Method B) (DMSO-d$_6$): δ ppm 8.80 (d, J=1.7 Hz, 1H), 8.65 (dd, J=4.9, 1 Hz, 1H), 8.13 (d, J=6.1 Hz, 1H), 7.97 (d, J=9.3 Hz, 1H), 7.73 (t, J=5.6 Hz, 1H), 3.09 (m, 1H), 2.69 (s, 3H), 1.34 (m, 2H), 0.85 (m, 2H); LC-MS (Method C) 354.2 [M+H]$^+$; RT 1.46 min Example 75—5-cyclopropyl-8-fluoro-2-methyl-7-(4-pyridyl)oxazolo[4,5-c]quinolin-4-one W2

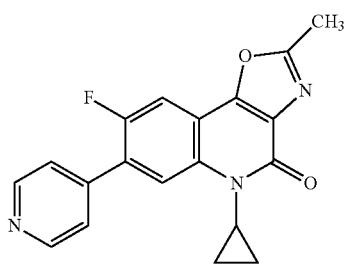 [SMILES: Cc1nc2c(=O)n(C3CC3)c3cc(-c4ccncc4)c(F)cc3c2o1]

Prepared using 4-pyridinylboronic acid pinacol ester and 7-bromo-5-cyclopropyl-8-fluoro-2-methyl-oxazolo[4,5-c]quinolin-4-one (prepared as described in Example 72 step (a)) and a similar procedure to that described in Example 58 step (f)

$^1$H NMR (Method B) (CDCl$_3$): δ ppm 8.80 (br s, 2H), 8.08 (d, J=4.3 Hz, 1H), 7.68 (d, J=9.7 Hz, 1H), 7.64 (br s, 2H), 3.10 (br s, 1H), 2.72 (s, 3H), 1.47 (br s, 2H), 1.00 (br s, 2H); LC-MS (Method C) 336.3 [M+H]$^+$; RT 1.16 min Example 76—7-[4-(aminomethyl)-3-fluoro-phenyl]-5-cyclopropyl-8-fluoro-2-methyl-oxazolo[4,5-c]quinolin-4-one X2

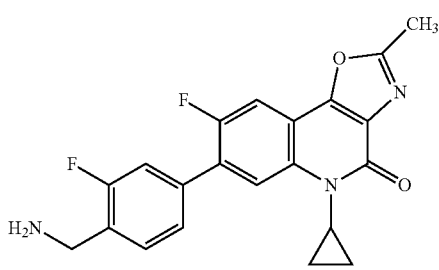 [SMILES: Cc1nc2c(=O)n(C3CC3)c3cc(-c4ccc(CN)c(F)c4)c(F)cc3c2o1]

Prepared using 4-(aminomethyl)-3-fluorophenylboronic acid and 7-bromo-5-cyclopropyl-8-fluoro-2-methyl-oxazolo[4,5-c]quinolin-4-one (prepared as described in Example 72 step (a)) and a similar procedure to that described in Example 58 step (f)

$^1$H NMR (Method B) (D$_2$O): δ ppm 8.44 (s, 1H), 7.74 (d, J=6.5 Hz, 1H), 7.51 (t, J=7.9 Hz, 1H), 7.24 (d, J=8.0 Hz, 1H), 7.15 (t, 2H), 4.29 (s, 2H), 2.87 (m, 1H), 2.49 (s, 3H), 1.51-1.28 (m, 2H), 0.82-0.55 (m, 2H); LC-MS (Method C) 382.3 [M+H]$^+$; RT 1.17 min Example 77—7-(4-acetyl-2,5-difluoro-phenyl)-5-cyclopropyl-8-fluoro-2-methyl-oxazolo[4,5-c]quinolin-4-one Y2

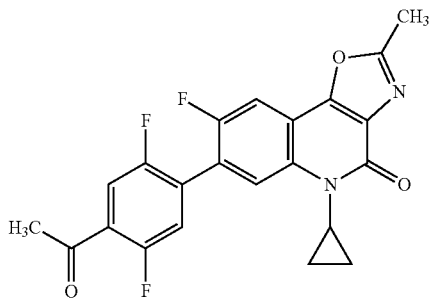 [SMILES: CC(=O)c1cc(F)c(-c2cc3c(cc2F)c2oc(C)nc2c(=O)n3C2CC2)cc1F]

Prepared using 1-[2,5-difluoro-4-(4,4,5,5-tetramethyl-1,3,2-dioxaborolan-2-yl)phenyl]ethanone and 7-bromo-5-cyclopropyl-8-fluoro-2-methyl-oxazolo[4,5-c]quinolin-4-one (prepared as described in Example 72 step (a)) and a similar procedure to that described in Example 58 step (f)

$^1$H NMR (Method B) (CD$_3$OD): δ ppm 8.20 (d, J=6.0 Hz, 1H), 7.85 (d, J=9.2 Hz, 1H), 7.74 (dd, J=10.0, 5.9 Hz, 1H), 7.54 (dd, J=10.6, 5.5 Hz, 1H), 3.18-3.08 (m, 1H), 2.74-2.59 (m, 6H), 1.51-1.37 (m, 2H), 1.02-0.91 (m, 2H); LC-MS (Method C) 413.1 [M+H]$^+$; RT 1.73 min Example 78—4-(5-cyclopropyl-8-fluoro-2-methyl-4-oxo-oxazolo[4,5-c]quinolin-7-yl)-2,5-difluorobenzamide Z2

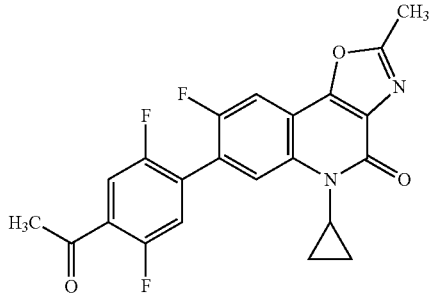 [SMILES: CC(=O)c1cc(F)c(-c2cc3c(cc2F)c2oc(C)nc2c(=O)n3C2CC2)cc1F]

Prepared using 2,5-difluoro-4-(4,4,5,5-tetramethyl-1,3,2-dioxaborolan-2-yl)benzamide and 7-bromo-5-cyclopropyl-8-fluoro-2-methyl-oxazolo[4,5-c]quinolin-4-one (prepared as described in Example 72 step (a)) and a similar procedure to that described in Example 58 step (f)

$^1$H NMR (Method B) (CDCl$_3$): b ppm 8.12-7.93 (m, 2H), 7.67 (d, J=9.1 Hz, 1H), 7.33 (m, 1H), 6.75 (d, J=11.6 Hz, 1H), 5.97 (s, 1H), 3.05 (m, 1H), 2.72 (s, 3H), 1.48-1.38 (m, 2H), 1.03-0.91 (m, 2H); LC-MS (Method C) 414.1 [M+H]$^+$; RT 1.41 min Example 79—7-(4-amino-2,5-difluoro-phenyl)-5-cyclopropyl-8-fluoro-2-methyl-oxazolo[4,5-c]quinolin-4-one A3

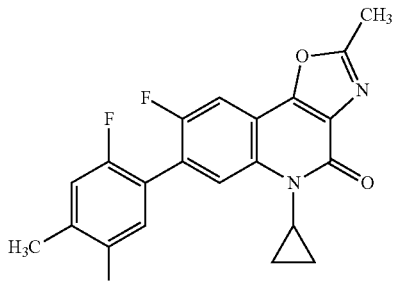

Prepared using 4-amino-2,5-difluorobenzeneboronic acid pinacol ester and 7-bromo-5-cyclopropyl-8-fluoro-2-methyl-oxazolo[4,5-c]quinolin-4-one (prepared as described in Example 72 step (a)) and a similar procedure to that described in Example 58 step (f)

$^1$H NMR (Method B) (DMSO-d$_6$): δ ppm 7.97 (d, J=6.2 Hz, 1H), 7.81 (d, J=9.4 Hz, 1H), 7.25 (dd, J=11.7, 6.7 Hz, 1H), 6.69 (dd, J=11.9, 7.6 Hz, 1H), 5.83 (s, 2H), 3.15-3.00 (m, 1H), 2.67 (s, 3H), 1.33 (d, J=6.8 Hz, 2H), 0.92-0.73 (m, 2H); LC-MS (Method C) 386.2 [M$^+$ H$^+$]; RT 1.59 min Example 80—7-(3-aminopyrrolidin-1-yl)-5-cyclopropyl-8-fluoro-oxazolo[4,5-c][1,8]naphthyridin-4-one B3

(a) 7-chloro-5-cyclopropyl-8-fluoro-oxazolo[4,5-c]1,8-naphthyridin-4-one

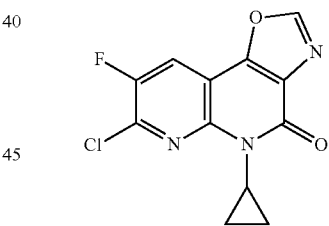

Prepared using 2,6-dichloro-5-fluoronicotinic acid and a similar procedure to that described in Example 49 steps (a) to (h)

(b) 7-(3-aminopyrrolidin-1-yl)-5-cyclopropyl-8-fluoro-oxazolo[4,5-c][1,8]napthyridin-4-one B3

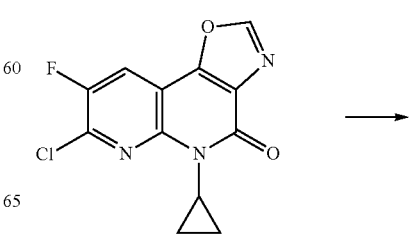

-continued

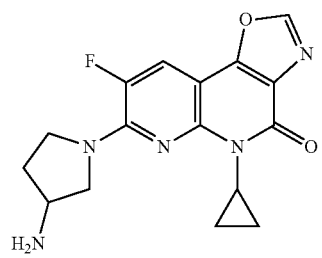

To a stirred solution of pyrrolidin-3-amine (25 mg, 0.30 mmol) in ACN (2 mL) was added 7-chloro-5-cyclopropyl-8-fluoro-oxazolo[4,5-c][1,8]naphthyridin-4-one (33 mg, 0.12 mmol) and the reaction mixture was heated to 80° C. for 15 min under microwave irradiation (Biotage Initiator). The solvent was then removed from the crude reaction mixture. The resulting residue was purified by flash silica chromatography using 0-2.5% MeOH/NH$_3$ in DCM to give 7-(3-aminopyrrolidin-1-yl)-5-cyclopropyl-8-fluoro-oxazolo[4,5-c][1,8]naphthyridin-4-one (6 mg, 15%) as a pale orange gum.

$^1$H NMR (Method A) (CDCl$_3$): b ppm 7.95 (s, 1H), 7.57 (d, J=11.9 Hz, 1H), 4.05-3.93 (m, 2H), 3.93-3.82 (m, 1H), 3.82-3.73 (m, 1H), 3.62-3.51 (m, 1H), 2.96 (s, 1H), 2.30-2.14 (m, 1H), 1.90-1.78 (m, 1H), 1.56 (s, 2H), 1.37-1.27 (m, 2H), 0.94-0.87 (m, 2H); LC-MS (Method B) 330.44 [M+H]$^+$; RT 1.11 min Example 81—7-[3-(aminomethyl)pyrrolidin-1-yl]-5-cyclopropyl-8-fluoro-oxazolo[4,5-c][1,8]naphthyridin-4-one C3

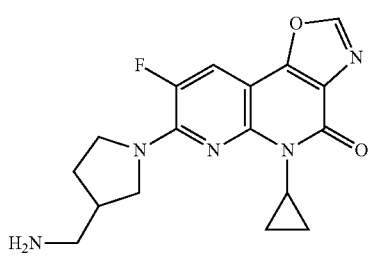 [SMILES: NCC1CCN(c2nc3c(cc2F)c2ocnc2c(=O)n3C2CC2)C1]

Prepared using tert-butyl N-(pyrrolidin-3-ylmethyl)carbamate and 7-chloro-5-cyclopropyl-8-fluoro-oxazolo[4,5-c][1,8]naphthyridin-4-one (prepared as described in Example 80 step (a)) and a similar procedure to that described in Example 80 step (b), followed by deprotection of the BOC group using the method described in Example 49 step (j).

$^1$H NMR (Method A) (CD$_3$OD): δ ppm 8.24 (s, 1H), 7.49 (d, J=12.2 Hz, 1H), 3.92-3.83 (m, 1H), 3.83-3.73 (m, 1H), 3.66-3.57 (m, 2H), 3.38-3.29 (m, 1H), 2.80-2.72 (m, 1H), 2.70-2.67 (m, 1H), 2.39-2.26 (m, 1H), 2.14-2.03 (m, 1H), 1.66 (m, 1H), 1.23-1.17 (m, 2H), 0.76-0.69 (m, 2H); LC-MS (Method B) 344.52 [M+H]$^+$; RT 1.14 min Example 82—7-(6-amino-3-azabicyclo[3.1.0]hexan-3-yl)-5-cyclopropyl-8-fluoro-oxazolo[4,5-c][1,8]naphthyridin-4-one D3

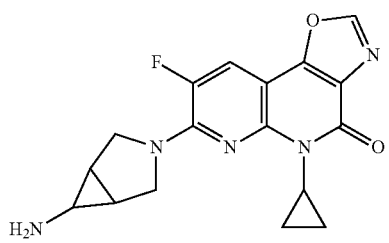 [SMILES: NC1C2CN(c3nc4c(cc3F)c3ocnc3c(=O)n4C3CC3)CC12]

Prepared using 3-azabicyclo[3.1.0]hexan-6-amine and 7-chloro-5-cyclopropyl-8-fluoro-oxazolo[4,5-c][1,8]naphthyridin-4-one (prepared as described in Example 80 step (a)) and a similar procedure to that described in Example 80 step (b), $^1$H NMR (Method A) (CDCl$_3$) δ ppm δ 7.95 (s, 1H), 7.57 (d, J=12.1 Hz, 1H), 4.06 (dd, J=11.5, 3.3 Hz, 2H), 3.83-3.75 (m, 2H), 2.95 (s, 1H), 2.25 (t, J=2.2 Hz, 1H), 1.76-1.69 (m, 1H), 1.62 (s, 2H), 1.37-1.28 (m, 2H), 1.27-1.25 (m, 1H), 0.93-0.86 (m, 2H); LC-MS (Method B) 342.47 [M+H]$^+$; RT 4.01 min Example 83—5-cyclopropyl-7-[3-(dimethylamino)pyrrolidin-1-yl]-8-fluoro-oxazolo[4,5-c][1,8]naphthyridin-4-one E3

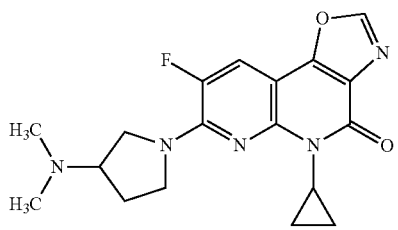 [SMILES: CN(C)C1CCN(c2nc3c(cc2F)c2ocnc2c(=O)n3C2CC2)C1]

Prepared using N,N-dimethylpyrrolidin-3-amine and 7-chloro-5-cyclopropyl-8-fluoro-oxazolo[4,5-c][1,8]naphthyridin-4-one (prepared as described in Example 80 step (a)) and a similar procedure to that described in Example 80 step (b), Example 84—7-(5-amino-2,4-difluorophenyl)-5-cyclopropyl-8-fluoro-oxazolo[4,5-c]1,8-naphthyridin-4-one F3

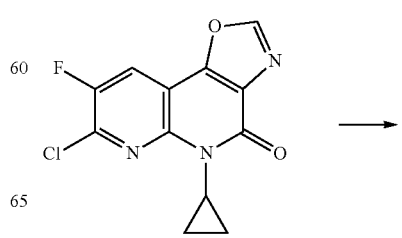

-continued

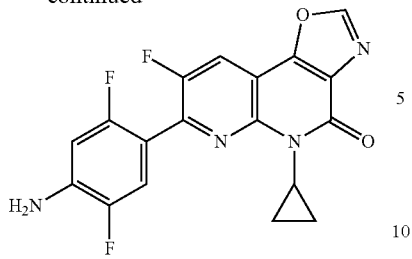

Prepared using 4-amino-2,5-difluorobenzeneboronic acid pinacol ester and 7-chloro-5-cyclopropyl-8-fluoro-oxazolo[4,5-c][1,8]naphthyridin-4-one (prepared as described in Example 80 step (a)) and a similar procedure to that described in Example 58 step (f)

$^1$H NMR (Method A) (DMSO-d$_6$): δ ppm 8.90 (s, 1H), 8.42 (d, J=9.2 Hz, 1H), 7.39 (dd, J=11.8, 6.4 Hz, 1H), 6.66 (dd, J=12.2, 7.3 Hz, 1H), 6.01 (s, 2H), 3.05-2.99 (m, 1H), 1.29-1.17 (m, 2H), 1.01-0.78 (m, 2H); LC-MS (Method B) 373.4 [M+H]$^+$; RT 2.10 min Example 85—7-(5-amino-2,4-difluorophenyl)-5-cyclopropyl-8-fluoro-oxazolo[4,5-c]1,8-naphthyridin-4-one G3

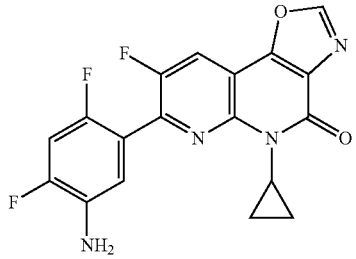 [SMILES: Nc1cc(-c2nc3c(cc2F)c2ocnc2c(=O)n3C2CC2)c(F)cc1F]

Prepared using 5-amino-2,4-difluorobenzeneboronic acid pinacol ester and 7-chloro-5-cyclopropyl-8-fluoro-oxazolo[4,5-c][1,8]naphthyridin-4-one (prepared as described in Example 80 step (a)) and a similar procedure to that described in Example 58 step (f)

$^1$H NMR (Method A) (DMSO-d$_6$) δ ppm 8.93 (s, 1H), 8.49 (d, J=9.0 Hz, 1H), 7.24 (dd, J=11.2, 10.0 Hz, 1H), 7.14 (dd, J=9.9, 7.2 Hz, 1H), 5.29 (s, 2H), 3.09-2.91 (m, 1H), 1.35-1.16 (m, 2H), 0.92-0.71 (m, 2H); LC-MS (Method D) 373.3 [M+H]$^+$; RT 2.11 min Example 86—7-(4-amino-2,5-difluorophenyl)-5-cyclopropyl-8-fluoro-2-methyl-oxazolo[4,5-c]1,8-naphthyridin-4-one H3

(a) 7-chloro-5-cyclopropyl-8-fluoro-2-methyl-oxazolo[4,5-c][1,8]naphthyridin-4-one

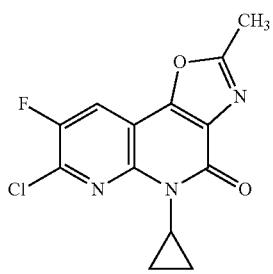 [SMILES: Cc1nc2c(=O)n(C3CC3)c3nc(Cl)c(F)cc3c2o1]

Prepared using 2,6-dichloro-5-fluoronicotinic acid and a similar procedure to that described in Example 49 steps (a) to (h)

LC-MS (Method B) 294.4/295.4 [M+H]$^+$; RT 2.08 min (b) 7-(4-amino 2,5-difluorophenyl)-5-cyclopropyl-8-fluoro-2-methyl-oxazolo[4,5c][1,8]naphthyridin-4-one H3

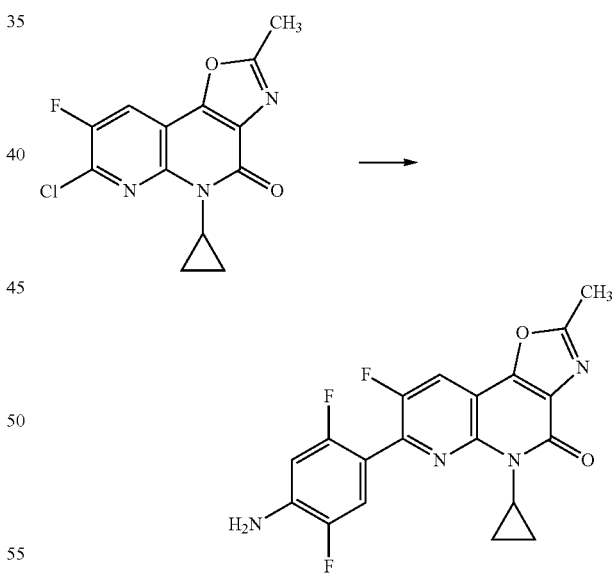

Prepared using 4-amino-2,5-difluorobenzeneboronic acid pinacol ester and 7-chloro-5-cyclopropyl-8-fluoro-2-methyl-oxazolo[4,5c][1,8]naphthyridin-4-one and a similar procedure to that described in Example 58 step (f)

$^1$H NMR (Method A) (DMSO-d$_6$) δ ppm 8.17 (d, J=9.2 Hz, 1H), 7.38 (dd, J=11.8, 6.4 Hz, 1H), 6.71 (dd, J=12.1, 7.3 Hz, 1H), 5.65 (s, 2H), 3.10-3.04 (m, 1H), 2.67 (s, 3H), 1.26-1.21 (m, 2H), 0.94-0.89 (m, 2H); LC-MS (Method B) 387.4/388.4 [M+H]$^+$; RT 2.17 min

Example 87—5-cyclopropyl-8-fluoro-7-(1H-indazol-5-yl)-oxazolo[4,5-c]1,8-naphthyridin-4-one I3

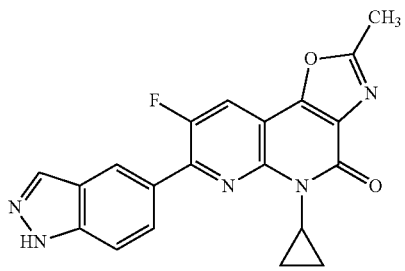 [SMILES: Cc1nc2c(=O)n(C3CC3)c3nc(-c4ccc5[nH]ncc5c4)c(F)cc3c2o1]

Prepared using 6-[4-(4,4,5,5-tetramethyl-1,3,2-dioxaborolan-2-yl)-1H-indazole and 7-chloro-5-cyclopropyl-8-fluoro-2-methyl-oxazolo[4,5c][1,8]naphthyridin-4-one (prepared as described in Example 86 step (a)) and a similar procedure to that described in Example 58 step (f)

LC-MS (Method B) 376.4 [M+H]⁺; RT 1.95 min

Example 88—(2S)-6-[3-(aminomethyl)pyrrolidin-1-yl]-7-fluoro-2,12-dimethyl-4,11-dioxa-1,13-diazatetracyclo[7.6.1.0⁵,¹⁶.0¹⁰,¹⁴]hexadeca-5(16),6,8,10(14),12-pentaen-15-one J3

(a) 2-methyl-5-(2,3,4,5-tetrafluorophenyl)oxazole-4-carbonyl chloride

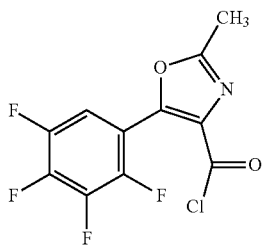 [SMILES: Cc1nc(C(=O)Cl)c(-c2cc(F)c(F)c(F)c2F)o1]

Prepared using 2,3,4,5-tetrafluorobenzoic acid and a similar procedure to that described in Example 49 steps (a) to (e)

(b) N-[(1S)-1-hydroxpropan-2-yl]-2-methyl-5-(2,3,4,5-tetrafluorophenyl)oxazole-4-carboxamide

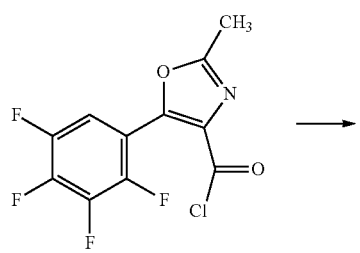

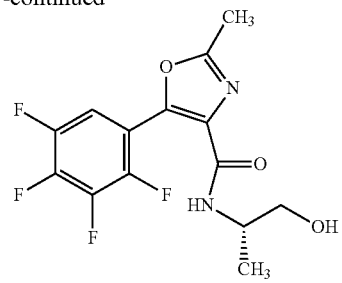

2-Methyl-5-(2,3,4,5-tetrafluorophenyl)oxazole-4-carbonyl chloride (1.54 g, 5.23 mmol) in DCM (75 mL) was treated with (2S)-(+)-2-aminopropan-1-ol (0.85 mL, 10.98 mmol) and stirred at room temperature overnight. The mixture was then diluted with DCM (50 mL) and washed with 0.5N aqueous HCl (2×50 ml) then saturated aqueous-NaHCO₃. (3×30 mL) and brine (30 mL). The organic phase was dried over Na₂SO₄, filtered and evaporated to in vacuo to give N-[(1S)-1-hydroxpropan-2-yl]-2-methyl-5-(2,3,4,5-tetrafluorophenyl)oxazole-4-carboxamide (1.34 g, 77% yield) as a yellow powder.

LC-MS (Method C) 333.0 [M⁺ H⁺], RT 3.42 min (c) (2S)-6,7-difluoro-2,12-dimethyl-4,11-dioxa-1,13-diazatetracyclo[7.6.1.0⁵,¹⁶.0¹⁰,¹⁴]hexadeca-5(16),6,8,10(14),12-pentaen-15-one

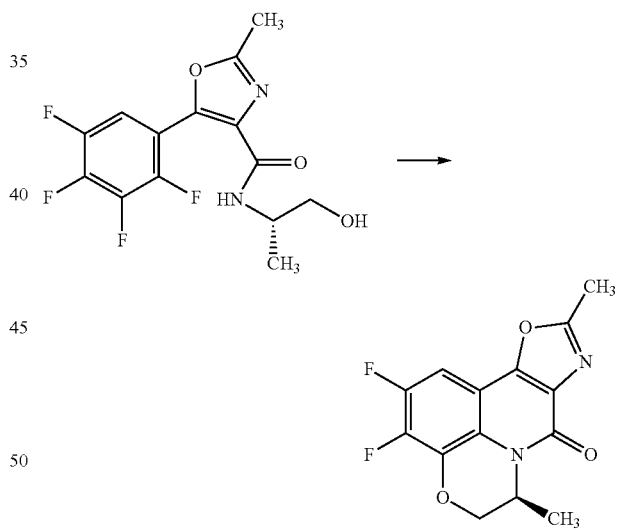

A mixture of N-[(1S)-1-hydroxypropan-2-yl]-2-methyl-5-(2,3,4,5-tetrafluorophenyl)oxazole-4-carboxamide (1.51 g, 4.54 mmol), 18-crown-6 (1.35 g, 5.09 mmol) and K₂CO₃ (3.14 g, 22.72 mmol) in DMSO (30 mL) was heated at 140° C. for 40 min The mixture was diluted with EtOAc (200 mL) and washed with H₂O (5×50 ml) then brine (100 ml). The organic extract was dried over Na₂SO₄ and solvent removed in vacuo to give a brown oil which was purified by flash chromatography eluting with 0-100% EtOAc in heptane to give (2S)-6,7-difluoro-2,12-dimethyl-4,11-dioxa-1,13-diazatetracyclo[7.6.1.0⁵,¹⁶.0¹⁰,¹⁴]hexadeca-5(16),6,8,10(14),12-pentaen-15-one (490 mg, 37% yield) as a yellow foam.

LC-MS (Method C) 293.1 [M+H⁺], RT 3.43 min

(d) (2S)-6-[3-(aminomethyl)pyrrolidin-1-yl]-7-fluoro-2,12-dimethyl-4,11-dioxa-1,13-diazatetracyclo[7.6.1.0$^{5,16}$.0$^{10,14}$]hexadeca-5(16),6,8,10(14),12-pentaen-15-one J3

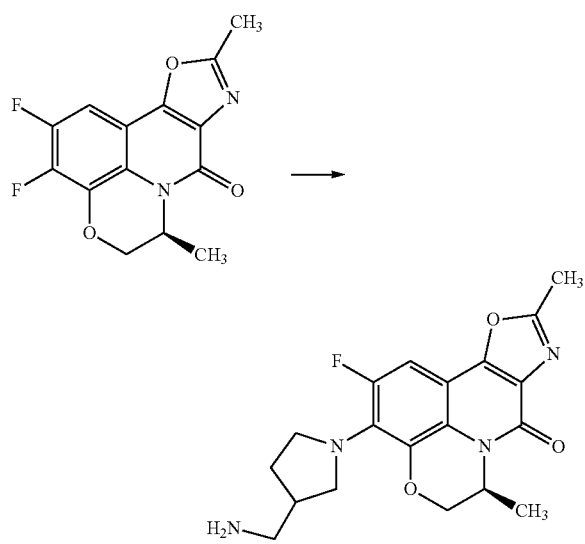

Prepared using tert-butyl N-(pyrrolidin-3-ylmethyl)carbamate and (2S)-6,7-difluoro-2,12-dimethyl-4,11-dioxa-1,13-diazatetracyclo[7.6.1.0$^{5,16}$.0$^{10,14}$]hexadeca-5(16),6,8,10(14),12-pentaen-15-one and a similar procedure to that described in Example 49 steps (i) and (j)

$^1$H NMR (Method B) (CD$_3$OD): δ ppm 8.35 (brs, 1H), 7.23 (m, 1H), 5.15 (m, 1H), 4.56 (d, J=11.14 Hz, 1H), 4.13 (m, 1H), 3.76-3.48 (m, 4H), 3.25-3.05 (m, 2H), 2.67 (s, 3H), 2.61 (m, 1H), 2.28 (m, 1H), 1.80 (m, 1H), 1.38 (m, 3H); LC-MS (Method C) 373.1 [M$^+$ H$^+$], RT 2.27 min

Example 89—(2S)-6-[(3R)-3-(aminomethyl)pyrrolidin-1-yl]-7-fluoro-2,12-dimethyl-4,11-dioxa-1,13-diazatetracyclo[7.6.1.0$^{5,16}$.0$^{10,14}$]hexadeca-5(16),6,8,10(14),12-pentaen-15-one K3

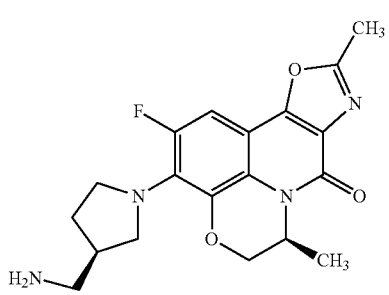 [SMILES: Cc1nc2c(=O)n3c4c(c(N5CC[C@H](CN)C5)c(F)cc4c2o1)OC[C@@H]3C]

Prepared using (S) tert-butyl N-(pyrrolidin-3-ylmethyl) carbamate and (2S)-6,7-difluoro-2,12-dimethyl-4,11-dioxa-1,13-diazatetracyclo[7.6.1.0$^{5,16}$.0$^{10,14}$]hexadeca-5(16),6,8,10(14),12-pentaen-15-one (prepared as described in Example 88 step (c)) and a similar procedure to that described in Example 88 step (d)

$^1$H NMR (Method B) (CDCl$_3$): δ ppm 7.16 (d, J=12.5 Hz, 1H), 5.25 (m, 1H), 4.45 (dd, J=11.1, 1.3 Hz, 1H), 4.14 (m, 1H), 3.73-3.57 (m, 3H), 3.38 (m, 1H), 2.82 (s, 2H), 2.66 (s, 3H), 2.33 (m, 1H), 2.10 (m, 1H), 1.68 (m, 1H), 1.40 (d, J=6.6 Hz, 3H); LC-MS (Method D) 373.4 [M$^+$ H$^+$], RT 1.70 min

Example 90—(2S)-6-[(3S)-3-(aminomethyl)pyrrolidin-1-yl]-7-fluoro-2,12-dimethyl-4,11-dioxa-1,13-diazatetracyclo[7.6.1.0$^{5,16}$.0$^{10,14}$]hexadeca-5(16),6,8,10(14),12-pentaen-15-one L3

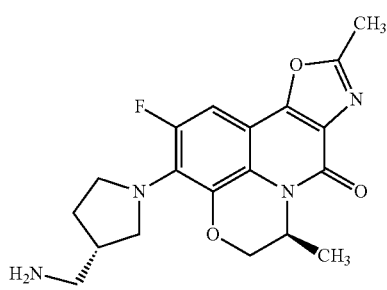 [SMILES: Cc1nc2c(=O)n3c4c(c(N5CC[C@@H](CN)C5)c(F)cc4c2o1)OC[C@@H]3C]

Prepared using (R) tert-butyl N-(pyrrolidin-3-ylmethyl) carbamate and (2S)-6,7-difluoro-2,12-dimethyl-4,11-dioxa-1,13-diazatetracyclo[7.6.1.0$^{5,16}$.0$^{10,14}$]hexadeca-5(16),6,8,10(14),12-pentaen-15-one (prepared as described in Example 88 step (c)) and a similar procedure to that described in Example 88 steps (d)

$^1$H NMR (Method B) (CDCl$_3$): δ ppm 7.15 (d, J=12.5 Hz, 1H), 5.26 (m, 1H), 4.45 (dd, J=11.1, 1.3 Hz, 1H), 4.06 (dd, J=11.2, 2.4 Hz, 1H), 3.75 (m, 1H), 3.63 (m, 1H), 3.53 (m, 1H), 3.48 (m, 1H), 2.85 (s, 2H), 2.66 (s, 3H), 2.45 (m, 1H), 2.11 (m, 1H), 1.65 (m, 1H), 1.40 (d, J=6.7 Hz, 3H); LC-MS (Method D) 373.4 [M$^+$ H$^+$], RT 1.70 min

Example 91—2R)-7-fluoro-2,12-dimethyl-6-(4-methylpiperazin-1-yl)-4,11-dioxa-1,13-diazatetracyclo[7.6.1.0$^{5,16}$.0$^{10,14}$]hexadeca-5(16),6,8,10(14),12-pentaen-15-one M3

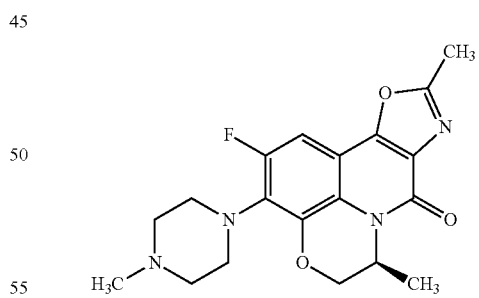

Prepared using 4-methylpiperazine and (2S)-6,7-difluoro-2,12-dimethyl-4,11-dioxa-1,13-diazatetracyclo[7.6.1.0$^{5,16}$.0$^{10,14}$]hexadeca-5(16),6,8,10(14),12-pentaen-15-one (prepared as described in Example 88 step (c)) and a similar procedure to that described in Example 88 step (d)

$^1$H NMR (Method B) (CD$_3$OD): δ ppm 8.47 (brs, 1H), 7.37 (d, J=11.0 Hz, 1H), 5.20 (m, 1H), 4.61 (dd, J=11.44, 0.92 Hz, 1H), 4.21 (dd, J=11.46, 2.30 Hz, 1H), 3.52 (m, 4H), 3.18 (m, 4H), 2.80 (s, 3H), 2.70 (s, 3H), 1.39 (d, J=6.61 Hz, 3H); LC-MS (Method C) 373.0 [M$^+$ H$^+$], RT 1.00 min Example 92—(2S)-6-(4-amino-4-methylpiperidin-1-yl)-7-fluoro-2,12-dimethyl-4,11-dioxa-1,13-diazatetracyclo[7.6.1.0⁵,¹⁶.0¹⁰,¹⁴]hexadeca-5(16),6,8,10(14),12-pentaen-15-one N3

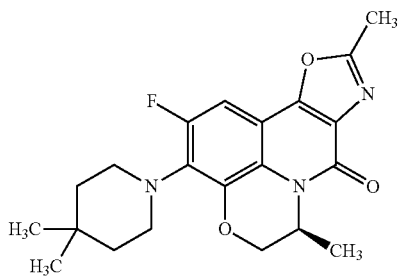 [SMILES: Cc1nc2c(=O)n3c4c(c(N5CCC(C)(C)CC5)c(F)cc4c2o1)OC[C@@H]3C]

Prepared using t-butyl N-(4-methylpiperidin-4-yl)carbamate and (2S)-6,7-difluoro-2,12-dimethyl-4,11-dioxa-1,13-diazatetracyclo[7.6.1.0⁵,¹⁶.0¹⁰,¹⁴]hexadeca-5(16),6,8,10(14),12-pentaen-15-one (prepared as described in Example 88 step (c)) and a similar procedure to that described in Example 88 step (d)

¹H NMR (Method B) (CD₃OD): δ ppm 8.15 (s, 2H), 7.32 (d, J=11.02 Hz, 1H), 5.21-5.16 (m, 1H), 4.61-4.58 (m, 1H), 4.21-4.18 (m, 1H), 3.44-3.37 (m, 4H), 2.69 (s, 3H), 2.06-1.99 (m, 2H), 1.92-1.87 (m, 2H), 1.51 (s, 3H), 1.39 (d, J=6.58 Hz, 3H); LC-MS (Method C) 387.1 [M+H]⁺; RT 1.08 min Example 93—(2S)-6-(4-amino-2,5-difluorophenyl)-2-methyl-4,11-dioxa-1,13-diazatetracyclo[7.6.1.0⁵,¹⁶.0¹⁰,¹⁴]hexadeca-5(16),6,8,10(14),12-pentaen-15-one O3

(a) 5-(4-bromo-2,3-difluorophenyl)-1,3-oxazole-4-carboxylic acid

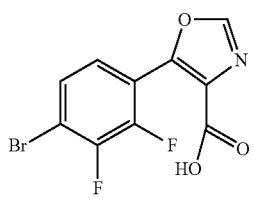

Prepared using 4-bromo-2,3-difluoro-benzoic acid and a similar procedure to that described in Example 58 steps (a) to (c)
LC-MS (Method A) 304.2/306.3 [M+H]⁺; RT 2.39 min (b) 5-(4-bromo-2,3-difluorophenyl)-N-[(2S)-1-hydroxypropan-2-yl)]oxazole-4-carboxamide

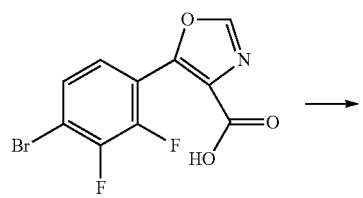

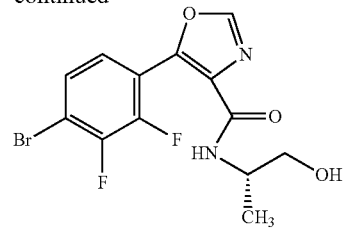

To a suspension of 5-(4-bromo-2,3-difluoro-phenyl)oxazole-4-carboxylic acid (1 g, 3.29 mmol) in dry DCM (15 mL) under N₂ was added oxalyl chloride (0.42 mL, 4.93 mmol) drop-wise at room temperature, followed by catalytic DMF (1 drop). This was allowed to stir for 1 h. The mixture was then evaporated to dryness to give 5-(4-bromo-2,3-difluoro-phenyl)oxazole-4-carbonyl chloride (1.06 g, 3.29 mmol) as a yellow powder. This was then diluted with dry DCM (75 mL) and treated with (2S)-(+)-2-aminopropan-1-ol (0.54 mL, 6.9 mmol) under N₂. This was allowed to stir at room temperature overnight. After which time the mixture was washed with saturated aqueous.NaHCO₃ (3×30 mL) followed by brine (30 ml). The organic layer was then dried through a hydrophobic frit and evaporated to dryness to give 5-(4-bromo-2,3-difluoro-phenyl)-N-[(1S)-2-hydroxy-1-methyl-ethyl]oxazole-4-carboxamide (1 g, 84% yield) as a pale yellow solid.

¹H NMR (Method A)) CDCl₃) δ 7.94 (s, 1H), 7.65 (ddd, J=8.7, 6.5, 2.1 Hz, 1H), 7.42 (ddd, J=8.6, 6.0, 2.0 Hz, 1H), 7.28-7.21 (m, 1H), 4.27-4.13 (m, 1H), 3.79-3.71 (m, 1H), 3.68-3.62 (m, 1H), 2.57 (bs, 1H), 1.29 (d, J=6.8 Hz, 3H); LC-MS (Method A) 361.2/363.2 [M+H]⁺; RT 2.38 min (c) (2S)-6-bromo-2-methyl-4,11-dioxa-1,13-diazatetracyclo[7.6.1.0⁵,¹⁶.0¹⁰,¹⁴]hexadeca-5(16),6,8,10(14),12-pentaen-15-one

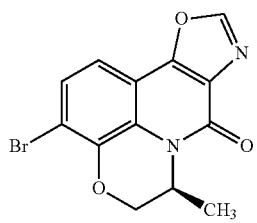

Prepared using 5-(4-bromo-2,3-difluoro-phenyl)-N-[(1S)-2-hydroxy-1-methyl-ethyl]oxazole-4-carboxamide and a similar procedure to that described in Example 88 step (c)

¹H NMR (Method A) (CDCl₃) δ 8.16 (s, 1H), 7.53-7.43 (m, 2H), 5.38-5.28 (m, 1H), 4.58 (dd, J=11.3, 1.3 Hz, 1H), 4.22 (dd, J=11.4, 2.4 Hz, 1H), 1.45 (d, J=6.7 Hz, 3H). LC-MS (Method A) 321.3/323.3 [M+H]⁺; RT 2.55 min.

(d) 2S)-6-(4-amino-2,5-difluorophenyl)-2-methyl-4,11-dioxa-1,13-diazatetracyclo[7.6.1.0$^{5,16}$.0$^{10,14}$]hexadeca-5(16),6,8,10(14),12-pentaen-15-one O3

Example 95—(-2S)-6-(6-aminopyridin-3-yl)-2-methyl-4,11-dioxa-1,13-diazatetracyclo[7.6.1.0$^{5,16}$.0$^{10,14}$]hexadeca-5(16),6,8,10(14),12-pentaen-15-one Q3

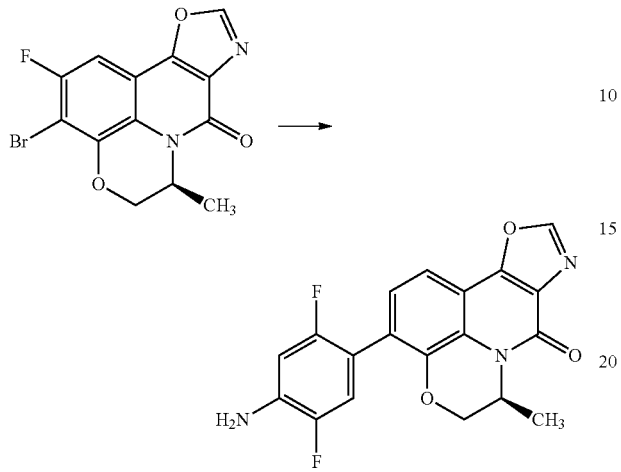

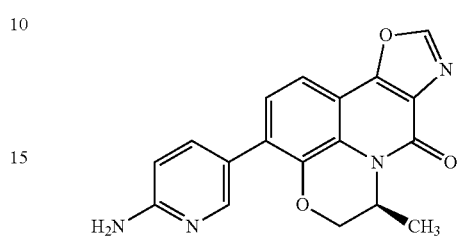

Prepared using 4-amino-2,5-difluorobenzeneboronic acid pinacol ester and (2S)-6-bromo-2-methyl-4,11-dioxa-1,13-diazatetracyclo[7.6.1.0$^{5,16}$.0$^{10,14}$]hexadeca-5(16),6,8,10(14),12 pentaen-15-one and a similar procedure to that described in Example 58 step (f)

$^1$H NMR (Method A) (CDCl$_3$): δ ppm 8.14 (s, 1H), 7.61 (d, J=8.2 Hz, 1H), 7.32-7.23 (m, 1H), 7.08 (dd, J=11.2, 6.4 Hz, 1H), 6.59 (dd, J=10.7, 7.5 Hz, 1H), 5.36-5.25 (m, 1H), 4.42 (dd, J=11.4, 1.3 Hz, 1H), 4.15 (dd, J=11.4, 2.4 Hz, 1H), 3.95 (s, 2H), 1.45 (d, J=6.6 Hz, 3H); LC-MS (Method A) 370.4 [M+H]$^+$; RT 2.54 min;

Prepared using 2-aminopyridine-5-boronic acid pinacol ester and (2S)-6-bromo-2methyl-4,11-dioxa-1,13-diazatetracyclo[7.6.1.0$^{5,16}$.0$^{10,14}$]hexadeca-5(16),6,8,10(14),12 pentaen-15-one (prepared as described in Example 93 step (c)) and a similar procedure to that described in Example 58 step (f)

$^1$H NMR (Method A) (CDCl$_3$): δ ppm 8.34 (dd, J=2.4, 0.8 Hz, 1H), 8.13 (s, 1H), 7.74 (dd, J=8.5, 2.4 Hz, 1H), 7.63 (d, J=8.2 Hz, 1H), 7.32 (d, J=8.2 Hz, 1H), 6.60 (d, J=8.5 Hz, 1H), 5.32 (qdd, J=6.7, 2.5, 1.3 Hz, 1H), 4.56 (s, 2H), 4.44 (dd, J=11.3, 1.3 Hz, 1H), 4.14 (dd, J=11.2, 2.4 Hz, 1H), 1.47 (d, J=6.7, 3H); LC-MS (Method E) 335.4 [M+H]$^+$; RT 4.59.

Example 94—(2S)-6-(2-aminopyrimidin-5-yl)-2-methyl-4,11-dioxa-1,13-diazatetracyclo[7.6.1.0$^{5,16}$.0$^{10,14}$]hexadeca-5(16),6,8,10(14),12-pentaen-15-one P3

Example 96—4-[(2S)-2-methyl-15-oxo-4,11-dioxa-1,13-diazatetracyclo[7.6.1.0$^{5,16}$.0$^{10,14}$]hexadeca-5(16),6,8,10(14),12-pentaen-6-yl]benzamide R3

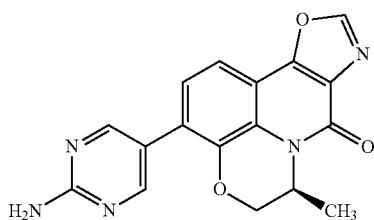

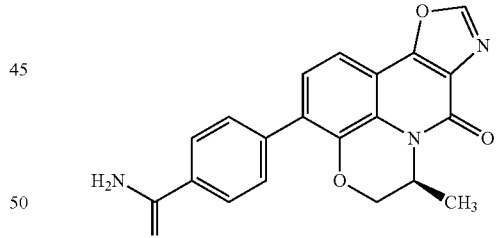

Prepared using 5-(4,4,5,5-tetramethyl-1,3,2-dioxaborolan-2-yl)-2-pyrimidinamine and (2S)-6-bromo-2methyl-4,11-dioxa-1,13-diazatetracyclo[7.6.1.0$^{5,16}$.0$^{10,14}$]hexadeca-5(16),6,8,10(14),12 pentaen-15-one (prepared as described in Example 93 step (c)) and a similar procedure to that described in Example 58 step (f)

$^1$H NMR (Method A) (CDCl$_3$): δ ppm 8.59 (s, 2H), 8.17 (s, 1H), 7.65 (d, J=8.2 Hz, 1H), 7.30 (d, J=8.2 Hz, 1H), 5.43 (s, 2H), 5.41-5.28 (m, 1H), 4.46 (dd, J=11.4, 1.3 Hz, 1H), 4.20-4.12 (m, 1H), 1.48 (d, J=6.6 Hz, 3H); LC-MS (Method E) 336.4 [M+H]$^+$; RT 4.94

Prepared using 4-(4,4,5,5-tetramethyl-1,3,2-dioxaborolan-2-yl)-benzamide and (2S)-6-bromo-2-methyl-4,11-dioxa-1,13-diazatetracyclo[7.6.1.0$^{5,16}$.0$^{10,14}$]hexadeca-5(16),6,8,10(14),12 pentaen-15-one (prepared as described in Example 93 step (c)) and a similar procedure to that described in Example 58 step (f)

$^1$H NMR (Method A) (CD$_3$OD): δ ppm 7.11 (s, 1H), 6.55-6.46 (m, 2H), 6.32-6.22 (m, 3H), 6.00 (d, J=8.2 Hz, 1H), 3.56 (m, 1H), 3.04 (dd, J=11.5, 1.3 Hz, 1H), 2.78-2.70 (m, 1H), 1.88 (s, 3H), 1.19 (s, 2H); LC-MS (Method D) 362.4 [M+H]$^+$; RT 5.58 min.

Example 97—7-(3-aminopyrrolidin-1-yl)-5-cyclopropyl-8-fluoro-6-methoxyoxazolo[4,5-c]quinolin-4-one S3

(a) 2,4,5-trifluoro-3-methoxybenzoate

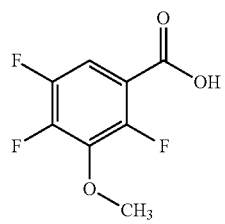

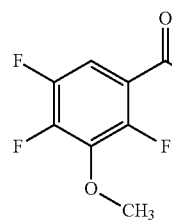

To 2,4,5-trifluoro-3-methoxy-benzoic acid (10 g, 48.52 mmol) in EtOH (60 mL) was added conc. sulphuric acid (2.4 mL) drop-wise. The reaction was then heated to 80° C. for 18 h. On cooling the reaction was concentrated to near dryness and DCM (200 ml) was added followed by 2M aqueous NaHCO₃ (200 mL). The aqueous layer was extracted with DCM (100 mL) and the combined organic extracts were dried through a hydrophobic frit and concentrated to dryness to give ethyl 2,4,5-trifluoro-3-methoxy-benzoate (11.3 g, 99% yield) as a colourless oil, which was used without further purification.

LC-MS (Method D) 235.4 [M+H]⁺; RT 2.87

(b) Ethyl 4-(3-{[tert-butoxy)carbonyl]amino}pyrrolidin-1-yl)-2,5-difluoro-3-methoxybenzoate

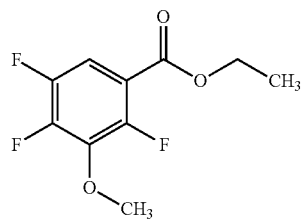

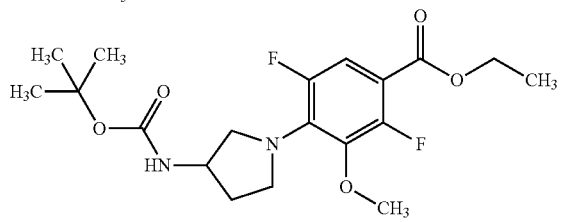

To a solution of ethyl 2,4,5-trifluoro-3-methoxy-benzoate (11.3 g, 49. mmol) in dry ACN (150 mL) under N₂ was added tert-butyl N-(pyrrolidin-3-yl)carbamate (2.35 mL, 134.23 mmol) at room temperature. The clear solution was heated at 80° C. for 4 h. On cooling the reaction mixture was partitioned between EtOAc (100 mL) and H₂O (50 mL). The organic layer was then washed with brine (100 mL) and dried over Na₂SO₄ The solvent was removed in vacuo to give the crude product as an amber gum, which was purified by flash chromatography using an eluent system of 0-10% EtOAc in Petroleum ether (40-60) to give ethyl 4-[3-(tert-butoxycarbonylamino)pyrrolidin-1-yl]-2,5-difluoro-3-methoxy-benzoate (11 g, 56% yield) as a colourless oil.

¹H NMR (Method A) C(DCl₃): δ ppm 7.31 (dd, J=14.4, 6.7 Hz, 1H), 4.73 (s, 1H), 4.37 (q, J=7.1 Hz, 2H), 4.26 (s, 1H), 3.88 (m, 1H), 3.83-3.72 (m, 4H), 3.63 (m, 1H), 3.46 (m, 1H), 2.17 (m, 1H), 1.86 (m, 1H), 1.46 (s, 9H), 1.37 (t, J=8.0 Hz, 3H); LC-MS (Method D) 401.5 [M+H]⁺; RT 3.23

(c) ethyl 4-(3-{[(tert-butoxy)carbonyl]amino}pyrrolidin-1-yl)-2-(cyclopropylamino)-5-fluoro-3-methoxybenzoate

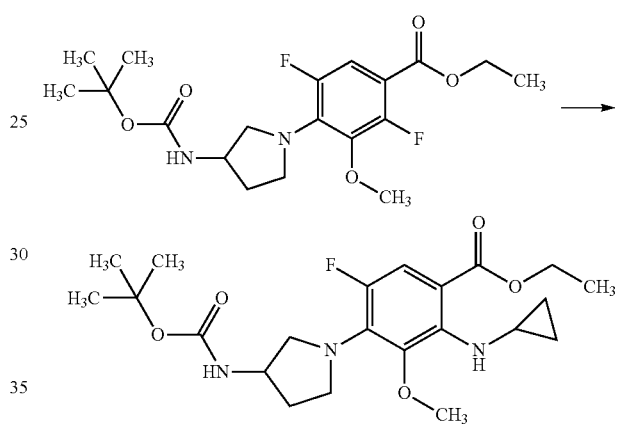

To a solution of ethyl 4-[3-(tert-butoxycarbonylamino)pyrrolidin-1-yl]-2,5-difluoro-3-methoxy-benzoate (2.2 g, 5.49 mmol) in dry DMSO (2 mL) under N₂ was added cyclopropylamine (2.28 mL, 32.97 mmol). The mixture was heated to 110° C. in a sealed vial (10 mL capacity) for 72 h. On cooling the reaction mixture was diluted with EtOAc (20 mL) and washed with H₂O (5×30 ml). The organic phase was dried over MgSO₄ and solvent removed in vacuo. The resulting residue was purified by flash chromatography using an eluent system of 0-50% EtOAc in Petroleum ether (40-60) to give ethyl 4-[3-(tert-butoxycarbonylamino)pyrrolidin-1-yl]-2-(cyclopropylamino)-5-fluoro-3-methoxy-benzoate (0.7 g, 29% yield) as a bright red oil.

LC-MS (Method D) 438.5 [M+H]⁺; RT 3.61

(d) 4-(3-{[(tert-butoxy)carbonyl]amino}pyrrolidin-1-yl)-2-(cyclopropylamino)-5-fluoro-3-methoxybenzoic acid

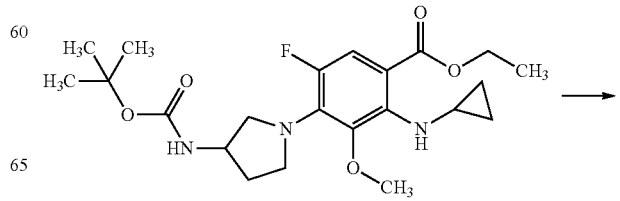

-continued

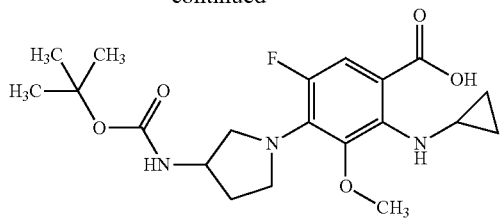

To a solution of ethyl 4-[3-(tert-butoxycarbonylamino)pyrrolidin-1-yl]-2-(cyclopropylamino)-5-fluoro-3-methoxy-benzoate (3.5 g, 8 mmol) in THF (90 mL) under $N_2$ was added 2M aq. lithium hydroxide (90 mL, 180 mmol). The reaction mixture was heated to 70° C. for 3 d. On cooling the THF was removed in vacuo and the reaction mixture was adjusted to pH 4 using 2M aqueous HCl and extracted with DCM (2×100 mL). The combined DCM layers were dried through a hydrophobic frit and concentrated to dryness. The resulting residue was purified by flash chromatography using an eluent system of 0-50% EtOAc in Petroleum ether (40-60) to give 4-[3-(tert-butoxycarbonylamino)pyrrolidin-1-yl]-2-(cyclopropylamino)-5-fluoro-3-methoxy-benzoic acid (0.86 g, 24%) as a beige solid.

$^1$H NMR (Method A, $CDCl_3$): δ ppm 7.42 (d, J=14.9 Hz, 1H), 4.80 (s, 1H), 4.28 (s, 1H), 3.89-3.37 (m, 7H), 2.93 (m, 1H), 2.19 (m, 1H), 1.94-1.78 (m, 1H), 1.47 (s, 9H), 0.68-0.43 (m, 4H); LC-MS (Method D) 410.4 [M+H]$^+$; RT 2.89

(e) tert-butyl N-[1-(1-cyclopropyl-6-fluoro-4-hydroxy-8-methoxy-3-nitro-2-oxo-7-quinolyl)pyrrolidin-3-yl]carbamate

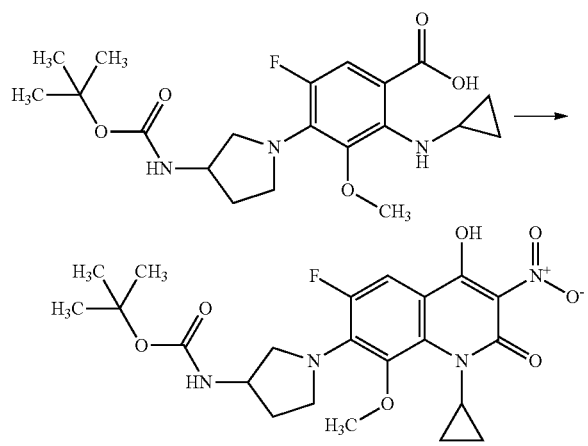

To a solution of 4-[3-(tert-butoxycarbonylamino)pyrrolidin-1-yl]-2-(cyclopropylamino)-5-fluoro-3-methoxy-benzoic acid (860 mg, 2.1 mmol) in THF (15 mL) at 00° C. was added a solution of phosgene, 20% in toluene (1.11 mL, 2.1 mmol) drop-wise over 2 min giving a yellow hazy suspension/solution. The reaction was allowed to warm to room temperature and stirred for 3 h. The solution was then re-cooled to 00° C. and ethyl nitroacetate (0.35 mL, 3.15 mmol) was added drop-wise followed by $NEt_3$ (0.44 mL, 3.15 mmol). The reaction was allowed to warm to room temperature and then heated to 70° C. for 18 h. On cooling the THF was removed in vacuo and the crude product was diluted with DCM (20 mL) followed by washing with 2 M aqueous HCl (20 mL), brine (20 ml) and $H_2O$ (20 mL). The organic extract was dried over $MgSO_4$ and concentrated to dryness in vacuo. The crude product was purified by flash chromatography using an eluent system of 0-10% MeOH in DCM to give tert-butyl N-[1-(1-cyclopropyl-6-fluoro-4-hydroxy-8-methoxy-3-nitro-2-oxo-7-quinolyl)pyrrolidin-3-yl]carbamate (146 mg, 15% yield) as an orange solid.

$^1$H NMR (Method A) ($CDCl_3$): δ ppm 7.34 (d, J=13.1 Hz, 1H), 5.08-5.01 (m, 1H), 4.36-4.22 (m, 1H), 3.96-3.66 (m, 3H), 3.57 (s, 3H), 3.54-3.43 (m, 1H), 3.31 (m, 1H), 2.24 (m, 1H), 1.97 (m, 1H), 1.46 (s, 9H), 1.16-1.04 (m, 2H), 0.78-0.63 (m, 2H); LC-MS (Method D) 479.4 [M+H]$^+$; RT 2.94

(f) tert-butyl N-[1-(3-amino-1-cyclopropyl-6-fluoro-4-hydroxy-8-methoxy-2-oxo-7-quinolyl)pyrrolidin-3-yl]carbamate

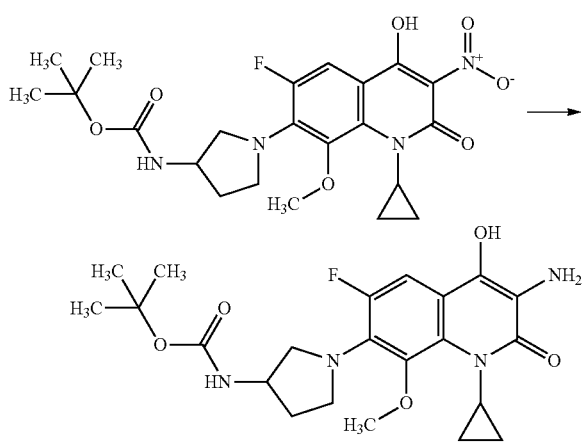

To a solution of tert-butyl N-[1-(1-cyclopropyl-6-fluoro-4-hydroxy-8-methoxy-3-nitro-2-oxo-7-quinolyl)pyrrolidin-3-yl]carbamate (146 mg, 0.31 mmol) in EtOH (10 mL) and $H_2O$ (1 mL) was added sodium hydrosulfite (212 mg, 1.22 mmol) in one portion The reaction was allowed to stir at 70° C. for 2 h. On cooling to room temperature a further addition of sodium hydrosulfite (212 mg, 1.22 mmol) was added and the reaction allowed to stir for 2 h. EtOH was then removed in vacuo and DCM (10 mL) and $H_2O$ (10 mL) was added. The aqueous was separated and further extracted with DCM (10 ml). The combined DCM extracts were then dried through a hydrophobic frit and concentrated to dryness to give tert-butyl N-[1-(3-amino-1-cyclopropyl-6-fluoro-4-hydroxy-8-methoxy-2-oxo-7-quinolyl)pyrrolidin-3-yl]carbamate (136 mg, 99% yield) as a brown oil, which was used without further purification LC-MS (Method D) 449.5 [M+H]$^+$; RT 2.47

(g) tert-butyl N-[1-(5-cyclopropyl-8-fluoro-6-methoxy-4-oxo-oxazolo[4,5-c]quinolin-7-yl)pyrrolidin-3-yl]carbamate

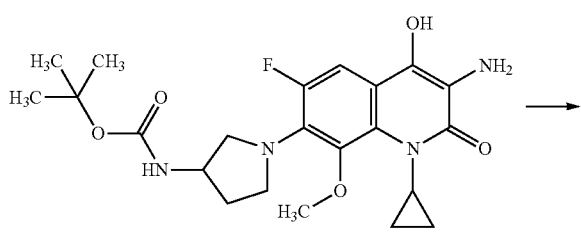

-continued

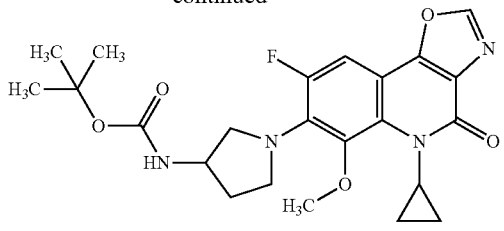

A solution of tert-butyl N-[1-(3-amino-1-cyclopropyl-6-fluoro-4-hydroxy-8-methoxy-2-oxo-7-quinolyl)pyrrolidin-3-yl]carbamate (100 mg, 0.22 mmol) in triethyl orthoformate (2.6 mL, 15.61 mmol) was heated to 105° C. overnight. On cooling the triethyl orthoformate was removed in vacuo to leave a dark brown solid, which was purified by flash chromatography using an eluent system of 0-100% EtOAc in Petroleum ether (40-60) to give brown solid. which on trituration with Et$_2$O gave tert-butyl N-[1-(5-cyclopropyl-8-fluoro-6-methoxy-4-oxo-oxazolo[4,5-c]quinolin-7-yl)pyrrolidin-3-yl]carbamate (63 mg, 62% yield) as a brown solid.

(h) 7-(3-aminopyrrolidin-1-yl)-5-cyclopropyl-8-fluoro-6-methoxy-oxazolo[4,5-c]quinolin-4-one S3

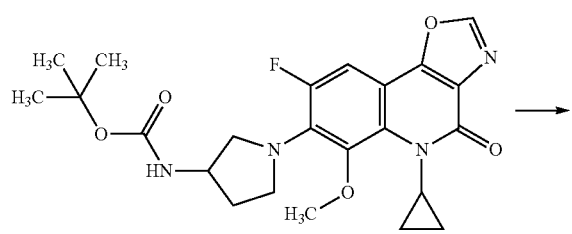

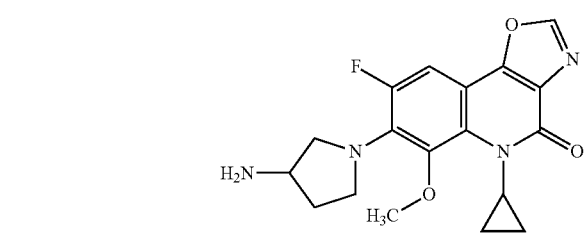

To a solution of tert-butyl N-[1-(5-cyclopropyl-8-fluoro-6-methoxy-4-oxo-oxazolo[4,5-c]quinolin-7-yl)pyrrolidin-3-yl]carbamate (63 mg, 0.14 mmol) in DCM (10 mL) was added trifluoroacetic acid (0.09 mL, 1.18 mmol). After stirring at room temperature for 4 h the solution was filtered through a NH$_2$ cartridge and the collected fractions evaporated to dryness. The resulting residue was purified by flash chromatography using an eluent system of 0-20% MeOH in DCM to give 7-(3-aminopyrrolidin-1-yl)-5-cyclopropyl-8-fluoro-6-methoxy-oxazolo[4,5-c]quinolin-4-one S3 (0.6 mg, 1.2% yield) as an off-white solid $^1$H NMR (Method A) (CDCl$_3$): δ ppm 7.97 (s, 1H), 7.26 (m, 1H), 3.86-3.78 (m, 2H), 3.75-3.52 (m, 2H), 3.52-3.44 (m, 4H), 3.32 (m, 1H), 2.19 (m, 1H), 1.78 (m, 1H), 1.26 (s, 2H), 1.22-1.13 (m, 2H), 0.63-0.54 (m, 2H); LC-MS (Method D) 359.4 [M+H]$^+$; RT 4.31.

Example 98—[7-(4-amino-2,5-difluorophenyl)-5-cyclopropyl-6-methyl-4-oxo-4H,5H-[1,3]oxazolo[4,5-c]quinolin-2-yl]methyl acetate T3

(a) 7-bromo-2-(chloromethyl)-5-cyclopropyl-6-methyl-oxazolo[4,5-c]quinolin-4-one

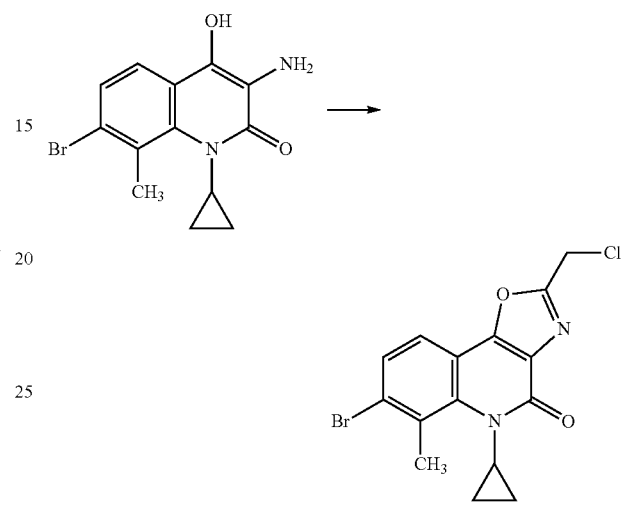

To a stirred suspension of 3-amino-7-bromo-1-cyclopropyl-4-hydroxy-8-methyl-quinolin-2-one (prepared as described in Example 4 step (a)) (5.46 g, 17.66 mmol) in DCM (60 mL) under N$_2$ at 0° C. was added 2-chloro-1,1,1-trimethoxyethane (3.33 mL, 24.73 mmol) followed by boron trifluoride diethyl etherate (2.4 mL, 19.43 mmol) drop-wise. After 35 min the reaction mixture was allowed to warm to room temperature, followed by the sequential addition of H$_2$O (30 mL) and DCM (60 mL). After separation of the layers the aqueous was extracted with DCM (2×60 mL). The organic phases were combined and solvent removed in vacuo to give a residue which was purified by flash chromatography using a slow gradient of 0-50% EtOAc in DCM as eluent to give 7-bromo-2-(chloromethyl)-5-cyclopropyl-6-methyl-oxazolo[4,5-c]quinolin-4-one (2.84 g, 44%) as a pale pink solid.

LC-MS (Method D) 367.2 [M+H]$^+$; RT 3.15 min.

(b) (7-bromo-5-cyclopropyl-6-methyl-4-oxo-oxazolo[4,5-c]quinolin-2-yl)methyl acetate

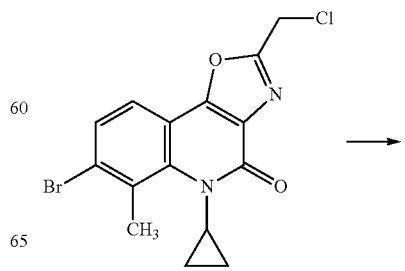

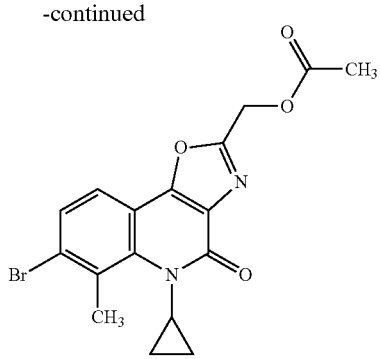

To a mixture of 7-bromo-2-(chloromethyl)-5-cyclopropyl-6-methyl-oxazolo[4,5-c]quinolin-4-one (325.0 mg, 0.88 mmol) and $Cs_2CO_3$ (432 mg, 1.33 mmol) in ACN (10 mL) was added acetic acid (0.13 mL, 2.21 mmol). The resulting mixture was stirred at 65° C. for 2.5 h. On cooling the solvent was removed under reduced pressure and the residue was partitioned between water (15 mL) and EtOAc (15 mL). The aqueous layer was extracted with EtOAc (3×10 mL). The combined organics were dried over $MgSO_4$, filtered and concentrated to give the crude product (7-bromo-5-cyclopropyl-6-methyl-4-oxo-oxazolo[4,5-c]quinolin-2-yl)methyl acetate (281 mg, 81% yield) as a burgundy solid.

LC-MS (Method D) 291.3/293.2 $[M+H]^+$; RT 2.86 min (c) [7-(4-amino-2,5-difluorophenyl)-5-cyclopropyl-6-methyl-4-oxooxazolo[4,5-c]quinolin-2-yl]methyl acetate T3

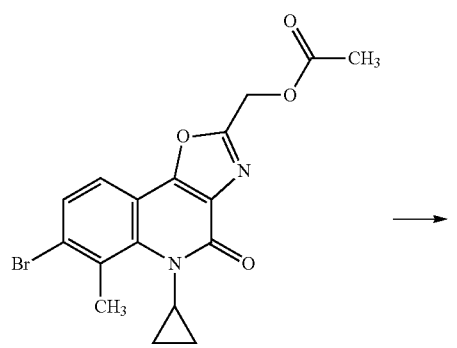

Prepared using 4-amino-2,5-difluorobenzeneboronic acid pinacol ester and (7-bromo-5-cyclopropyl-6-methyl-4-oxo-2,3-dihydrooxazolo[4,5-c]quinolin-2-yl)methyl acetate and a similar procedure to that described in Example 58 step (f)

$^1H$ NMR (Method A) ($CDCl_3$) δ ppm 7.75 (d, J=8.0 Hz, 1H), 7.21 (d, J=8.0 Hz, 1H), 6.95 (dd, J=11.0, 7.0 Hz, 1H), 6.61 (dd, J=10.6, 7.0 Hz, 1H), 5.35 (s, 2H), 4.01 (s, 2H), 3.66-3.59 (m, 1H), 2.53 (s, 3H), 2.20 (s, 3H), 1.33-1.28 (m, 2H), 0.69-0.61 (m, 2H); LC-MS (Method D) 440.4 $[M+H]^+$; RT 2.78 min Example 99—7-(4-amino-2,5-difluorophenyl)-5-cyclopropyl-2-(hydroxymethyl)-6-methyloxazolo[4,5-c]quinolin-4-one U3

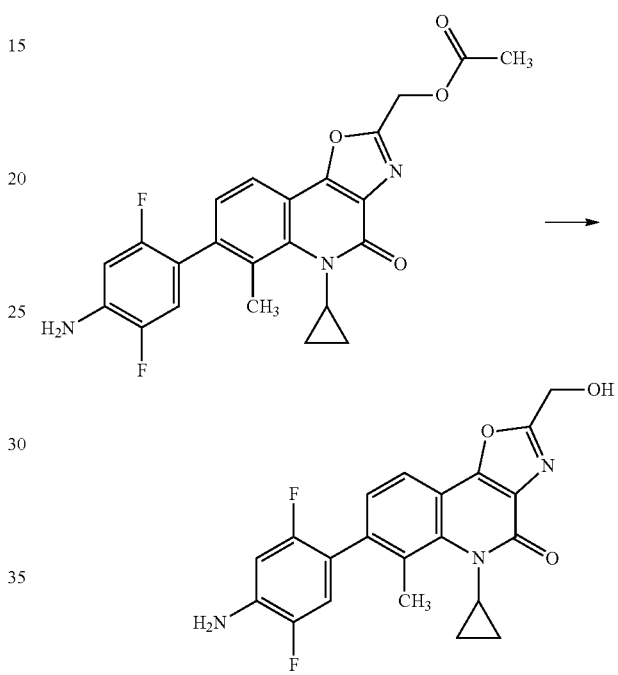

To a mixture of [7-(4-amino-2,5-difluoro-phenyl)-5-cyclopropyl-6-methyl-4-oxo-oxazolo[4,5-c]quinolin-2-yl] methyl acetate (prepared as described in Example 98 step (c)) (10 mg, 0.02 mmol) in $H_2O$ (2 mL) was added $EtN_3$ (0.03 mL, 0.23 mmol) and the resulting mixture was stirred at room temperature for 1.5 h. The reaction mixture was then diluted with aqueous $NH_4Cl$ (5 mL) and extracted with EtOAc (3×10 mL). The combined organic layers were washed with brine (10 mL), dried over $MgSO_4$, filtered and concentrated to give the crude product, which was purified by flash chromatography eluting with a gradient system 25 to 100% EtOAc in Petroleum ether (40-60) to give 7-(4-amino-2,5-difluorophenyl)-5-cyclopropyl-2-(hydroxymethyl)-6-methyl-4H,5H-[1,3]oxazolo[4,5-c]quinolin-4-one U3 (5.8 mg, 4% yield) as khaki brown solid.

$^1H$ NMR (Method A) (DMSO-$d_6$) δ ppm 7.74 (d, J=8.0 Hz, 1H), 7.25 (d, J=8.0 Hz, 1H), 7.07 (dd, J=11.5, 6.9 Hz, 1H), 6.67 (dd, J=11.6, 7.5 Hz, 1H), 5.99 (s, 1H), 5.70 (s, 2H), 4.71 (s, 2H), 3.60-3.56 (m, 1H), 2.47 (s, 3H), 1.20-1.16 (m, 3H), 0.52-0.48 (m, 2H); LC-MS (Method D) 398.4 $[M+H]^+$; RT 2.18 min

149

Example 100—7-(4-amino-2,5-difluoro-phenyl)-2-(aminomethyl)-5-cyclopropyl-6-methyl-oxazolo[4,5-c]quinolin-4-one V3

(a) 2-(azidomethyl)-7-bromo-5-cyclopropyl-6-methyl-oxazolo[4,5-c]quinolin-4-one

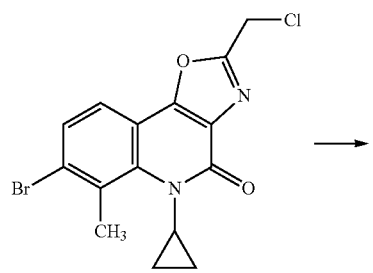

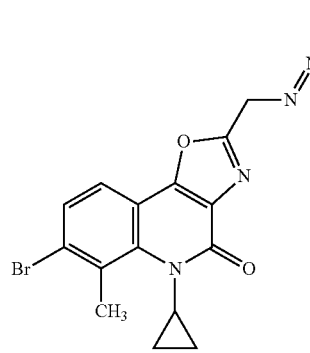

To a stirred solution of 7-bromo-2-(chloromethyl)-5-cyclopropyl-6-methyl-oxazolo[4,5-c]quinolin-4-one (prepared as described in Example 98 step (a)) (600 mg, 1.63 mmol) in DMSO (15 mL) was added sodium azide (106 mg, 1.63 mmol). The reaction mixture was allowed to stir at room temperature overnight. H$_2$O (15 mL) was added to the crude reaction mixture followed by EtOAc (50 mL) and the layers were separated. The organic layer was washed with H$_2$O (3×20 mL). The solvent was then removed in vacuo and the crude residue was purified by flash chromatography using 0-60% EtOAc in Petroleum ether (40-60) as eluent to give 2-(azidomethyl)-7-bromo-5-cyclopropyl-6-methyl-oxazolo[4,5-c]quinolin-4-one (531 mg, 86%) as a pale brown solid.
LC-MS (Method D) 374.3 [M+H]$^+$; RT 2.79 min.

(b) 7-(4-amino-2,5-difluoro-phenyl)-2-(azidomethyl)-5-cyclopropyl-6-methyl-oxazolo[4,5-c]quinolin-4-on

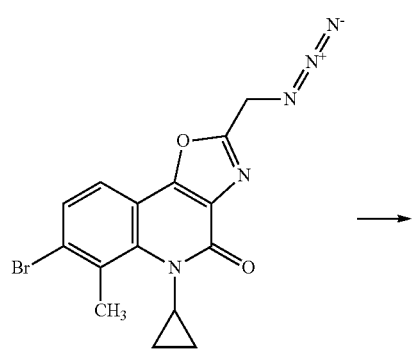

150

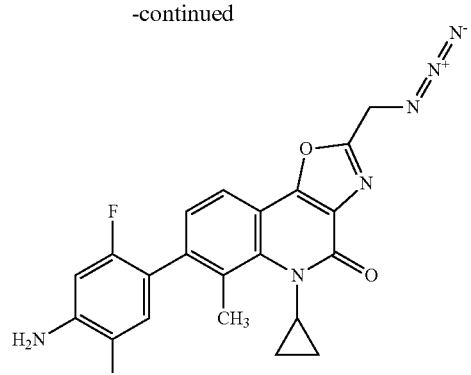

Prepared using 4-amino-2,5-difluorobenzeneboronic acid pinacol ester and 2-(azidomethyl)-7-bromo-5-cyclopropyl-6-methyl-oxazolo[4,5-c]quinolin-4-one and a similar procedure to that described in Example 58 step (f)
LC-MS (Method D) 423.4 [M+H]$^+$; RT 2.94 min.

(c) 7-(4-amino-2,5-difluoro-phenyl)-2-(aminomethyl)-5-cyclopropyl-6-methyl-oxazolo[4,5-c]quinolin-4-one V3

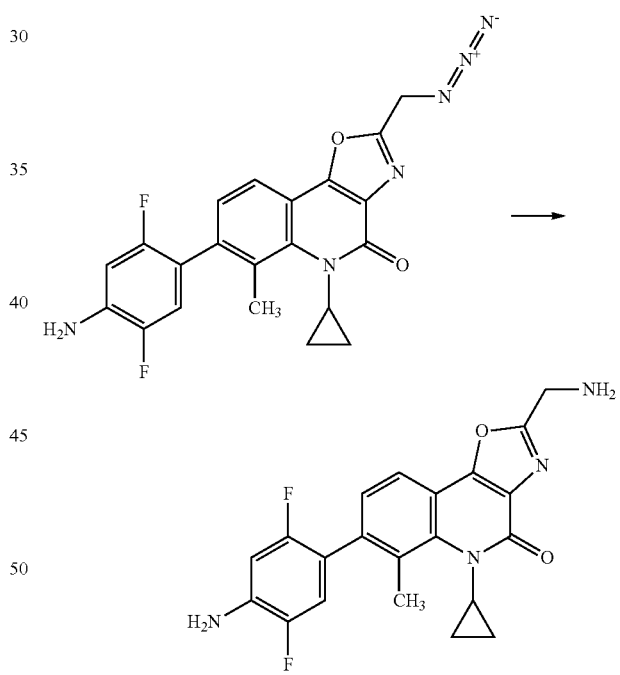

To a stirred solution of 7-(4-amino-2,5-difluoro-phenyl)-2-(azidomethyl)-5-cyclopropyl-6-methyl-oxazolo[4,5-c]quinolin-4-one (294 mg, 0.70 mmol) in a mixture of THF (20 mL) and H$_2$O (2 mL) was added PPh$_3$ (274 mg, 1.04 mmol) and the reaction mixture was heated to 75° C. for 2 h. On cooling the solvent was removed and the residual water was removed by azeotroping with toluene (2×5 mL). The resulting residue was then purified by flash chromatography using 0-10% MeOH/NH3 (2 M) in DCM as eluent. to give 7-(4-amino-2,5-difluoro-phenyl)-2-(aminomethyl)-5-cyclopropyl-6-methyl-oxazolo[4,5-c]quinolin-4-one V3 (236 mg, 86%) as a pale yellow solid.

¹H NMR (Method A) (CDCl₃): δ ppm 7.71 (d, J=8.0 Hz, 1H), 7.20 (d, J=8.0 Hz, 1H), 6.95 (dd, J=11.0, 6.6 Hz, 1H), 6.61 (dd, J=10.5, 7.5 Hz, 1H), 4.15 (s, 2H), 4.00 (s, 2H), 3.67-3.58 (m, 1H), 2.52 (d, J=1.5 Hz, 3H), 1.75 (s, 2H), 1.33-1.21 (m, 2H), 0.65 (s, 2H); LC-MS (Method B) 397.4 [M+H]⁺; RT 5.42 min Example 101—7-(4-amino-2,5-difluoro-phenyl)-5-cyclopropyl-2-[(dimethylamino)methyl]-6-methyl-oxazolo[4,5-c]quinolin-4-one W3

(a) 7-bromo-5-cyclopropyl-2-[(dimethylamino)methyl]-6-methyl-oxazolo[4,5-c]quinolin-4-one

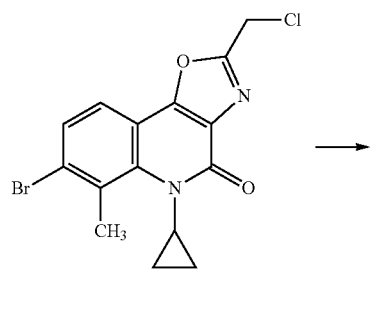

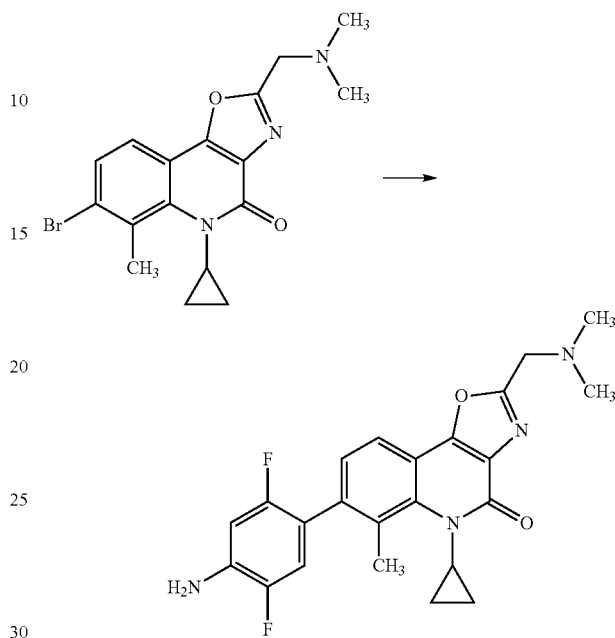

A solution of 7-bromo-2-(chloromethyl)-5-cyclopropyl-6-methyl-oxazolo[4,5-c]quinolin-4-one (40 mg, 0.11 mmol) (prepared as described in Example 98 step (a)) in dry dimethylamine (0.05 mL, 0.11 mmol) and DMF (5.5 mL). was treated with K₂CO₃ (23 mg, 0.16 mmol). The resulting reaction mixture was stirred at room temperature for 1 h. H₂O (10 mL) was added to the crude reaction mixture followed by EtOAc (30 mL) and the layers were separated. The organic layer was washed with H₂O (3×20 mL). The solvent was then removed in vacuo and the residue purified by flash chromatography using 0-5% MeOH/NH₃ (1M) in DCM as eluent to give 7-bromo-5-cyclopropyl-2-[(dimethylamino)methyl]-6-methyl-oxazolo[4,5-c]quinolin-4-one (30.6 mg, 75%).

LC-MS (Method B) 376.3 [M+H]⁺; RT 2.64 min (b) 7-(4-amino-2,5-difluoro-phenyl)-5-cyclopropyl-2-[(dimethylamino)methyl]-6-methyl-oxazolo[4,5-c]quinolin-4-one W3

Prepared using 4-amino-2,5-difluorobenzeneboronic acid pinacol ester and 7-bromo-5-cyclopropyl-2-[(dimethylamino)methyl]-6-methyl-oxazolo[4,5-c]quinolin-4-one and a similar procedure to that described in Example 58 step (f)

¹H NMR (Method A) (CDCl₃): δ ppm 7.79 (dd, J=8.0, 0.6 Hz, 1H), 7.20 (d, J=8.0 Hz, 1H), 6.95 (dd, J=11.0, 6.6 Hz, 1H), 6.61 (dd, J=10.5, 7.5 Hz, 1H), 3.99 (s, 2H), 3.85 (s, 2H), 3.62 (tt, J=6.8, 4.0 Hz, 1H), 2.52 (d, J=1.5 Hz, 3H), 2.42 (s, 6H), 1.26 (td, J=6.0, 4.9, 2.9 Hz, 2H), 0.72-0.60 (m, 2H); LC-MS (Method E) 425.4 [M+H]⁺; RT 7.00 min Example 102—4-[2-(aminomethyl)-5-cyclopropyl-6-methyl-4-oxo-oxazolo[4,5-c]quinolin-7-yl]benzoic acid X3

(a) 4-[2-(azidomethyl)-5-cyclopropyl-6-methyl-4-oxo-oxazolo[4,5-c]quinolin-7-yl]benzoic acid

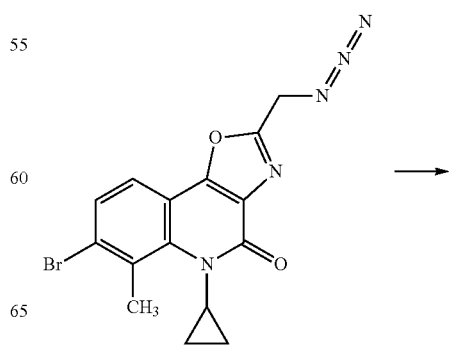

-continued

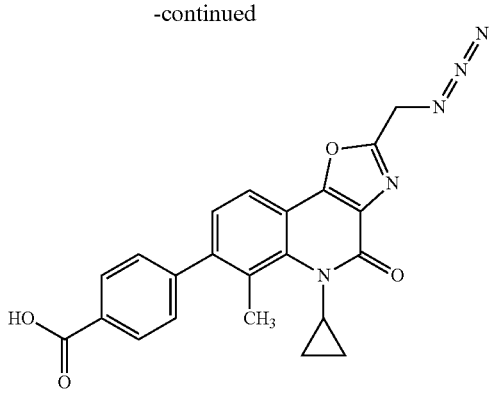

Prepared using 4-carboxybenzeneboronic acid pinacol ester and 2-(azidomethyl)-7-bromo-5-cyclopropyl-6-methyl-oxazolo[4,5-c]quinolin-4-one (prepared as described in Example 100 step (a)) and a similar procedure to that described in Example 58 step (f) LC-MS (Method B) 416.4 [M+H]⁺; RT 2.66 min (b) 4-[2-(aminomethyl)-5-cyclopropyl-6-methyl-4-oxo-oxazolo[4,5-c]quinolin-7-yl]benzoic acid X3

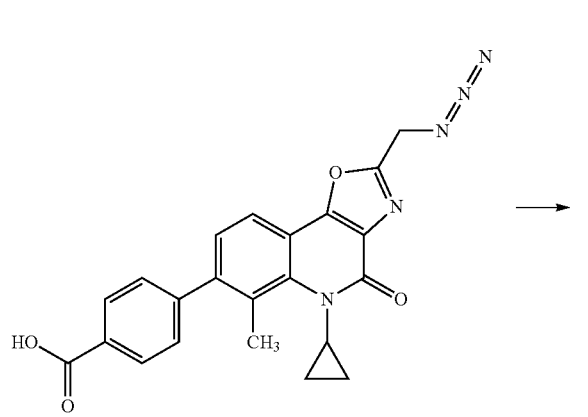

Prepared using a similar procedure to that described in Example 100 step (c)

LC-MS (Method B) 390.4 [M+H]⁺; RT 4.91 min

Example 103—2-(aminomethyl)-7-(2-aminopyrimidin-5-yl)-5-cyclopropyl-6-methyl-oxazolo[4,5-c]quinolin-4-one Y3

(a) 7-(2-aminopyrimidin-5-yl)-2-(azidomethyl)-5-cyclopropyl-6-methyl-oxazolo[4,5-c]quinolin-4-one

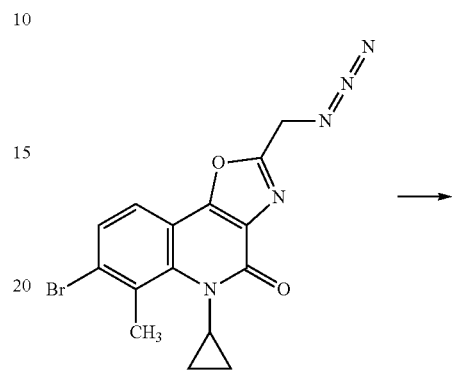

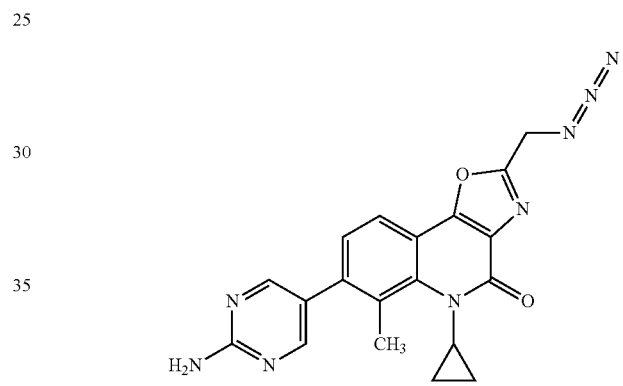

Prepared using 5-(4,4,5,5-tetramethyl-1,3,2-dioxaborolan-2-yl)-2-pyrimidinamine and 2-(azidomethyl)-7-bromo-5-cyclopropyl-6-methyl-oxazolo[4,5-c]quinolin-4-one (prepared as described in Example 100 step (a)) and a similar procedure to that described in Example 58 step (f)

(b) 2-(aminomethyl)-7-(2-aminopyrimidin-5-yl)-5-cyclopropyl-6-methyl-oxazolo[4,5-c]quinolin-4-one Y3

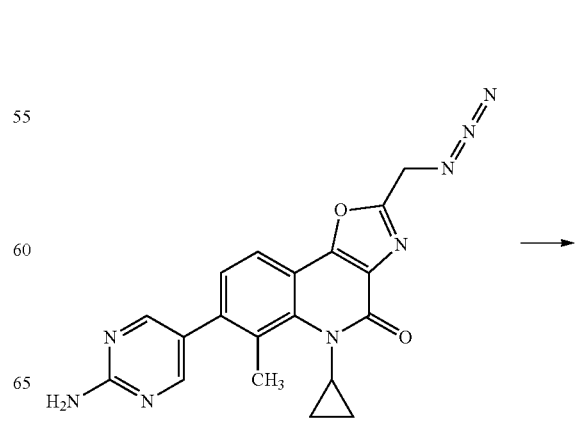

-continued

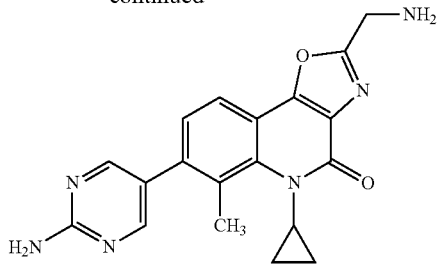

Prepared using a similar procedure to that described in Example 100 step (c)

¹H NMR (Method A) (CDCl₃): δ ppm 8.39 (s, 2H), 7.75 (d, J=7.9 Hz, 1H), 7.20 (d, J=7.9 Hz, 1H), 5.20 (s, 2H), 4.16 (s, 2H), 3.64 (tq, J=6.9, 4.0 Hz, 1H), 2.59 (s, 3H), 1.66 (s, 2H), 1.32-1.26 (m, 2H), 0.70-0.62 (m, 2H); LC-MS (Method B) 363.5 [M+H]⁺; RT 3.71 min Example 104—7-(4-amino-2,5-difluoro-phenyl)-5-ethyl-8-fluoro-6-methyl-oxazolo[4,5-c]quinolin-4-one Z3

(a) 5-fluoro-7-methyl-indoline-2,3-dione

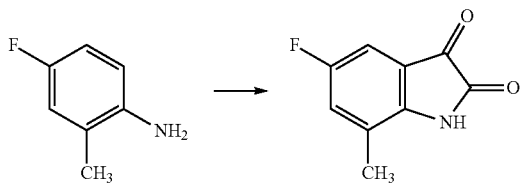

A mixture of 4-fluoro-2-methyl-aniline (8.88 mL, 79.91 mmol), chloral hydrate (19.62 g, 118.65 mmol), anhydrous Na₂SO₄ (124.86 g, 879.02 mmol) in hydrochloric acid (8.47 mL, 278.92 mmol) and H₂O (450 mL) was stirred vigorously at room temperature overnight. To the resulting mixture, hydroxylamine hydrochloride (7.73 g, 111.25 mmol) was added and the mixture was heated to reflux overnight. The reaction mixture was ice cooled, and the resulting precipitate was collected by vacuum filtration and washed copiously with H₂O and dried under suction. The precipitate was re-dissolved in EtOAc (~500 mL) and washed with H₂O (300 mL) and brine (300 mL) then dried over MgSO₄. The resulting filtrate was removed in vacuo to give 5-fluoro-7-methyl-indoline-2,3-dione as a dark brown solid which was used directly in the next step without further purification.

LC-MS 180.3 [M+H]⁺; RT 1.49 min (b) 4,6-dibromo-5-fluoro-7-methyl-indoline-2,3-dione

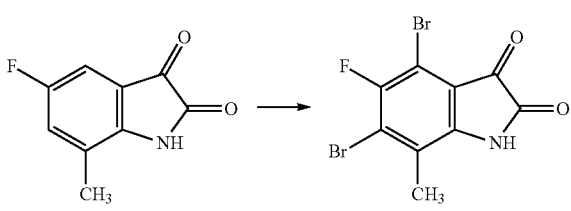

To an ice cold stirred solution of 5-fluoro-7-methyl-indoline-2,3-dione (9.9 g, 55.26 mmol) in H₂SO₄ (0.5 mL, 9.38 mmol) was added N-bromosuccinimide (19.67 g, 110.52 mmol) in portions over the course of 1 h. The reaction mixture was then allowed to warm to room temperature and stirred for 2 h, then re-cooled to 0-5° C. and a further portion of N-bromosuccinimide (4.92 g, 27.63 mmol) added. The reaction mixture was then allowed to warm to room temperature and stirred for a further 3 h, The reaction mixture was poured on to crushed ice with vigorous stirring forming a precipitate, which was filtered and washed with cold H₂O (20 ml). The filtrate was washed with DCM (200 mL) and H₂O (100 mL). The organic layer was dried over MgSO₄, filtered and concentrated to dryness in vacuo before being combined with the original precipitate to give 4,6-dibromo-5-fluoro-7-methyl-indoline-2,3-dione (17.29 g, 93% yield) which was used directly in the next step.

LC-MS 357.0 [M+Na]⁺; RT 2.27 min (c) 6-bromo-5-fluoro-7-methyl-indoline-2,3-dione

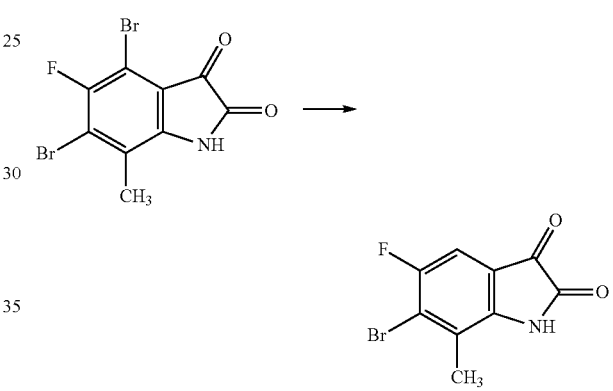

A round bottomed flask was charged with 4,6-dibromo-5-fluoro-7-methyl-indoline-2,3-dione (17.29 g, 51.31 mmol), copper (6.52 g, 102.63 mmol) and propionic acid (51.87 mL, 693.21 mmol). The resulting mixture was placed under a N₂ atmosphere and heated to 130° C. for 90 min. On cooling toluene (50 ml) was added and the mixture was filtered. The collected solids were washed with toluene (5×50 ml) and EtOAc (5×50 ml). The combined organics were washed with 2M aqueous HCl until the aqueous layer was yellow in colour. The organic layer was further washed with H₂O (50 mL), brine (50 mL) and dried over Na₂SO₄, filtered and evaporated in vacuo to give 6-bromo-5-fluoro-7-methyl-indoline-2,3-dione (11 g, 83% yield)

LC-MS 286.3/288.3 [M+H]⁺; RT 2.35 min (d) 6-bromo-5-fluoro-7-methyl-indoline-2,3-dione

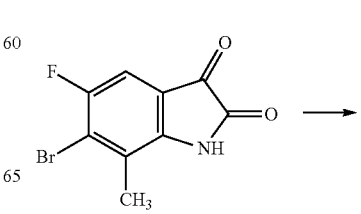

-continued

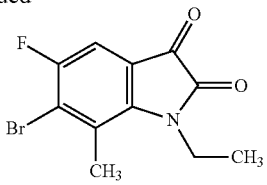

Iodoethane (1.25 mL, 15.5 mmol) was added drop-wise to a solution of 6-bromo-5-fluoro-7-methyl-indoline-2,3-dione (2. g, 7.75 mmol) and anhydrous $K_2CO_3$ (1.29 g, 9.3 mmol) in dry DMF (1 mL) and then heated to 100° C. for 1 h. On cooling the reaction mixture was diluted with EtOAc (100 mL) and $H_2O$ (100 mL) and the phases separated. The aqueous phase was extracted with EtOAc (2×70 mL) and the combined organic phases were washed with brine (200 mL), dried over $MgSO_4$ and solvent removed in vacuo to give 6-bromo-1-ethyl-5-fluoro-7-methyl-indoline-2,3-dione (2.2 g, 99% yield) which was used directly in the next step without further purification.

LC-MS (Method A) 268.3/270.3 $[M+H]^+$; RT 2.32 min (e) 4-bromo-2-(ethylamino)-5-fluoro-3-methyl-benzoic acid

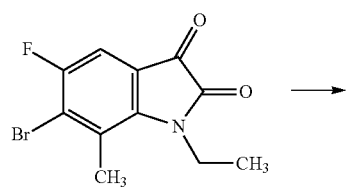

Drop-wise to a solution of 6-bromo-1-ethyl-5-fluoro-7-methyl-indoline-2,3-dione (2.2 g, 7.69 mmol) in 2M aq. NaOH (21 mL) was added $H_2O_2$(3.14 mL, 30.76 mmol. After 2 h stirring at room temperature the reaction mixture was diluted with DCM (150 mL) and the phases were separated. The aqueous phase was acidified to pH 3 with 2M aqueous HCl and the resulting precipitate was filtered, collected and dried overnight in a heated desiccator at 40° C. to give 4-bromo-2-(ethylamino)-5-fluoro-3-methyl-benzoic acid (1.85 g, 87% yield) as a pale yellow crystalline solid.

LC-MS (Method A) 276.3/278.3 $[M]^+$; RT 1.18 min (f) ethyl 5-[4-bromo-2-(ethylamino)-5-fluoro-3-methyl-phenyl]oxazole-4-carboxylate

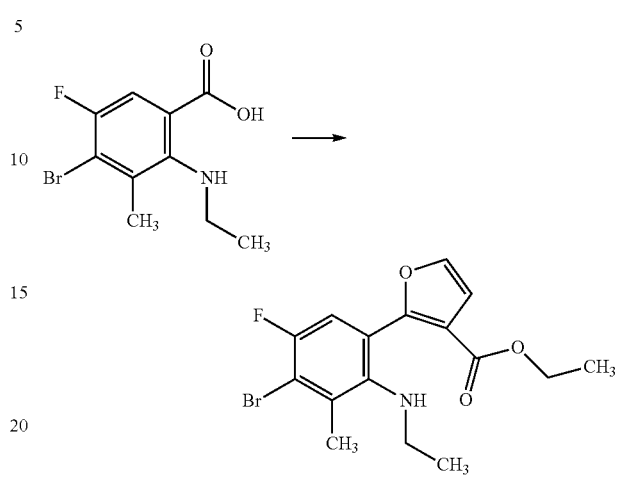

To a solution of 4-bromo-2-(ethylamino)-5-fluoro-3-methyl-benzoic acid (1.85 g, 6.7 mmol) in dry THF (50 mL) at room temperature under $N_2$ was added triphosgene (1.19 g, 4.02 mmol) in one portion. After stirring at room temperature for 3 h the solvent was carefully removed in vacuo. To the resulting residue under $N_2$ was added dry THF (40 mL), followed by $Et_3N$ (7.47 mL, 53.6 mmol) drop-wise. To the resulting mixture was added ethyl isocyanoacetate (1.1 mL, 10.05 mmol) in one portion and the reaction heated to 60° C. overnight. On cooling to room temperature the solvent was removed under reduced pressure. The residue was then partitioned between EtOAc (20 mL) and brine (20 mL). 2M aqueous HCl was then added to adjust the aqueous pH to around 3. The EtOAc layer was then separated, washed 4 times with $H_2O$, dried over $MgSO_4$, filtered and concentrated in vacuo to afford ethyl 5-[4-bromo-2-(ethylamino)-5-fluoro-3-methyl-phenyl]oxazole-4-carboxylate (2.1 g, 84.% yield) as a yellow solid.

LC-MS (Method A) 371.3/373.3 $[M+H]^+$; RT 2.79 min (g) 7-bromo-5-cyclopropyl-6-methyl-oxazolo[4,5-c]quinolin-4-one

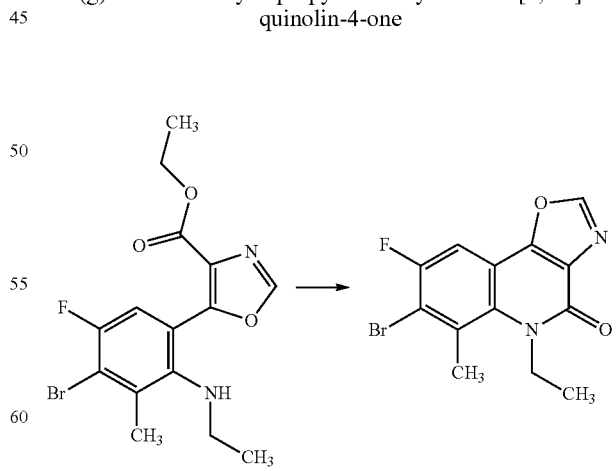

To a solution of ethyl 5-[4-bromo-2-(ethylamino)-5-fluoro-3-methyl-phenyl]oxazole-4-carboxylate (2.1 g, 5.66 mmol) in dry DMF (5 mL) was added NaH (60% dispersed in mineral oil) (61 mg, 1.52 mmol) in one portion. The reaction mixture was then heated to 100° C. for 1 h. On cooling to room temperature EtOAc (100 mL) and H₂O (30 mL) were added and the layers separated. The aqueous layer was washed with EtOAc (50 mL) and the combined organic extracts were washed with H₂O (4×30 mL). The organic extracts were dried over MgSO₄, filtered, and concentrated in vacuo. The resulting residue was purified by flash chromatography using 50% EtOAc/Petroleum ether (40-60) as the eluent to give 7-bromo-5-ethyl-8-fluoro-6-methyl-oxazolo[4,5-c]quinolin-4-one (380 mg, 21% yield).

LC-MS (Method A) 325.3/327.3 [M+H]⁺; RT 2.31 min (h) 7-(4-amino-2,5-difluoro-phenyl)-5-ethyl-8-fluoro-6-methyl-oxazolo[4,5-c]quinolin-4-one Z3

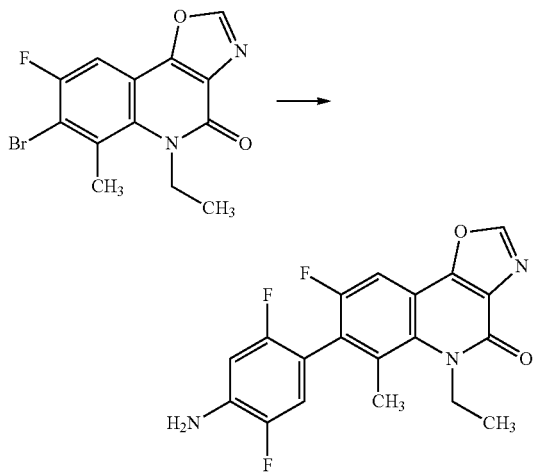

Prepared using 4-amino-2,5-difluorobenzeneboronic acid pinacol ester and 7-bromo-5-ethyl-8-fluoro-6-methyl-oxazolo[4,5-c]quinolin-4-one and a similar procedure to that described in Example 58 step (f)

¹H NMR (Method B) (CDCl₃): b 8.11 (s, 1H), 7.57 (d, J=7.7 Hz, 1H), 6.93 (ddd, J=1.07, 6.4, 10.95 Hz, 1H), 6.62 (dd, J=7.2, 10.4 Hz, 1H), 4.62-4.52 (m, 1H), 4.48-4.38 (m, 1H), 4.00 (br. s, 2H), 2.43 (s, 3H), 1.32 (t, J=6.99 Hz, 3H); LC-MS (Method A) 374.3 [M+H]⁺; RT 2.19 min Example 105—7-(5-amino-2,4-difluoro-phenyl)-5-ethyl-8-fluoro-6-methyl-oxazolo[4,5-c]quinolin-4-one A4

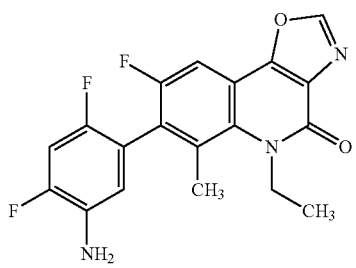

Prepared using 5-amino-2,4-difluorobenzeneboronic acid pinacol ester and 7-bromo-5-ethyl-8-fluoro-6-methyl-oxazolo[4,5-c]quinolin-4-one (prepared as described in Example 104 step (g)) and a similar procedure to that described in Example 58 step (f)

¹H NMR (Method A) (CDCl₃): δ ppm 8.04 (s, 1H), 7.51 (d, J=7.7 Hz, 1H), 6.88 (dd, 6.4, 10.95 Hz, 1H), 6.62 (dd, J=7.2, 10.4 Hz, 1H), 4.62-4.52 (m, 1H), 4.55-4.45 (m, 1H), 3.62 (br. s, 2H), 2.43 (s, 3H), 1.26 (t, J=6.99 Hz, 3H); LC-MS (Method A) 374.3 [M+H]⁺; RT 2.23 min Example 106—7-(6-amino-3-pyridyl)-5-ethyl-8-fluoro-6-methyl-oxazolo[4,5-c]quinolin-4-one B4

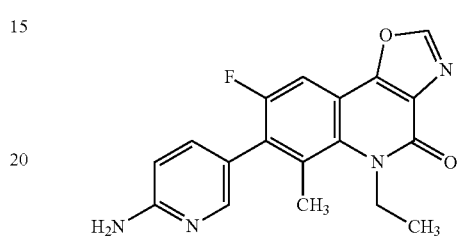

Prepared using 2-aminopyridine-5-boronic acid pinacol ester and 7-bromo-5-ethyl-8-fluoro-6-methyl-oxazolo[4,5-c]quinolin-4-one (prepared as described in Example 104 step (g)) and a similar procedure to that described in Example 58 step (f)

¹H NMR (Method A) (CDCl₃): δ ppm 8.12 (s, 1H), 8.07 (br. s, 1H), 7.58 (d, J=7.6 Hz, 1H), 7.47-7.42 (m, 1H), 6.66 (d, J=7.6 Hz, 1H), 4.70 (br. s, 2H), 4.50 (q, J=7.0 Hz 2H), 2.45 (s, 3H), 1.35 (t, J=7.0 Hz, 3H); LC-MS (Method A) 374.3 [M+H]⁺; RT 2.23 min Example 107—7-(4-amino-3-fluoro-phenyl)-5-ethyl-8-fluoro-6-methyl-oxazolo[4,5-c]quinolin-4-one C4

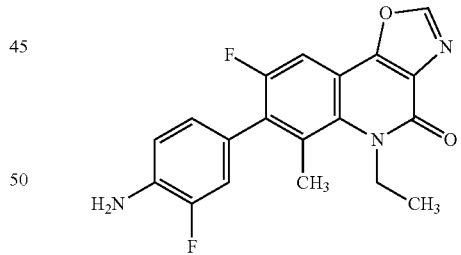

Prepared using 2-fluoro-4-(4,4,5,5-tetramethyl-1,3,2-dioxaborolan-2-yl)aniline and 7-bromo-5-ethyl-8-fluoro-6-methyl-oxazolo[4,5-c]quinolin-4-one (prepared as described in Example 104 step (g)) and a similar procedure to that described in Example 58 step (f)

¹H NMR (Method A) (CDCl₃) δ ppm 8.11 (s, 1H), 7.55 (d, J=8.0 Hz, 1H), 6.98 (d, 8.0 Hz, 1H), 6.93-6.84 (m, 1H), 4.49 (q, J=6.8 Hz, 2H), 3.90 (br. s, 2H), 2.40 (s, 3H), 1.33 (t, J=6.8 Hz, 3H); LC-MS (Method E) 356.4 [M+H]⁺; RT 6.17 min

Example 108—7-(4-amino-2,5-difluorophenyl)-5-cyclopropyl-6-methyl-thiazolo[4,5-c]quinolin-4-one D4

(a) 5-bromo-1,3-thiazole-4-carboxylic acid

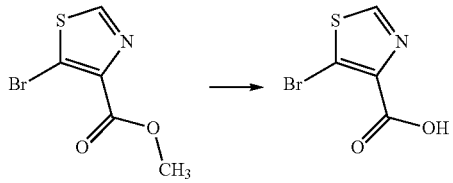

To a stirred solution of methyl 5-bromo-1,3-thiazole-4-carboxylate (5.00 g, 22.52 mmol) in THF (80 mL) was added an aq. solution of LiOH.H$_2$O (2.70 g, 112.58 mmol) in H$_2$O (20 mL). The reaction mixture was stirred at room temperature for 18 h. DCM (50 mL) and H$_2$O (20 mL) were then added and the reaction mixture acidified to pH-2 with 2M aqueous HCl, followed by extraction with DCM (3×20 mL). The combined organic extracts were washed with brine (20 mL), dried over MgSO$_4$, filtered and concentrated under reduced pressure to give 5-bromo-1,3-thiazole-4-carboxylic acid (3.09 g, 66% yield) as a yellow solid, which was used without further purification.

LC-MS (Method D) 208.3/210.3 [M+H]$^+$; RT 1.36 min (b) 5-bromo-N-cyclopropyl-1,3-thiazole-4-carboxamide

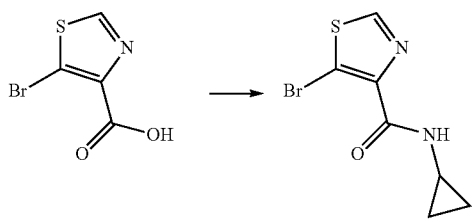 [SMILES: O=C(O)c1ncsc1Br ; O=C(NC1CC1)c1ncsc1Br]

To a solution of 5-bromo-1,3-thiazole-4-carboxylic acid (3.09 g, 14.85 mmol) in DCM (75 mL) was added DIPEA (5.17 mL, 29.71 mmol) followed by cyclopropylamine (1.18 mL, 17.08 mmol) and HATU (6.21 g, 16.34 mmol). The reaction mixture was allowed to stir at room temperature for 6 h. The mixture was then diluted with H$_2$O (50 mL) and the layers were separated. The aqueous layer was further extracted with DCM (3×25 mL) and the combined organics dried over MgSO$_4$, filtered and concentrated under reduced pressure. The crude reaction product was purified by flash chromatography eluting with a gradient system of 0-50% EtOAc in Petroleum ether (40-60) to give 5-bromo-N-cyclopropyl-1,3-thiazole-4-carboxamide (2.88 g, 78% yield) as a white solid.

LC-MS (Method D) 247.2/249.2 [M+H]$^+$; RT 1.82 min (c) 3-fluoro-2-methyl-4-(tetramethyl-1,3,2-dioxaborolan-2-yl)aniline

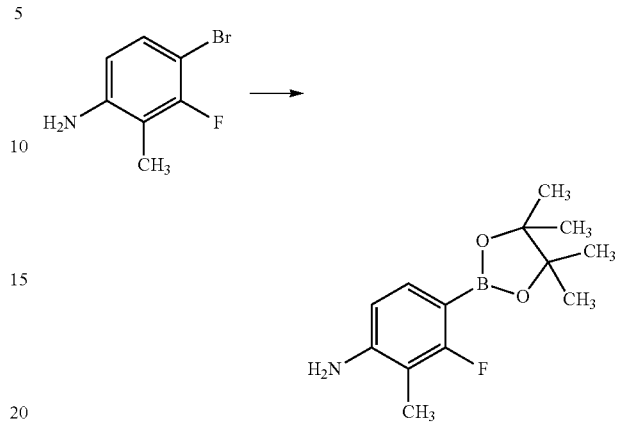

To a mixture of 4-bromo-3-fluoro-2-methylaniline (5.00 g, 24.51 mmol), potassium acetate (7.21 g, 73.52 mmol) and bis(pinacolato)diboron (7.47 g, 29.41 mmol) was added dry 1,2-dimethoxyethane (100 mL) and the mixture was flushed with N$_2$. To this [1,1'-bis(diphenylphosphino)ferrocene]palladium(II) chloride dichloromethane complex (2.14 g, 2.62 mmol) was added in one portion as a solid. The mixture was then heated to 90° C. for 18 h. On cooling all volatiles were removed under reduced and the crude product was purified by flash chromatography eluting with a gradient system of 0-50% EtOAc in Petroleum ether (40-60) to give 3-fluoro-2-methyl-4-(tetramethyl-1,3,2-dioxaborolan-2-yl)aniline (5.05 g, 82% yield) as an amber solid.

LC-MS (Method D) 252.6 [M+H]$^+$; RT 2.95 min (d) 5-(4-amino-2-fluoro-3-methylphenyl)-N-cyclopropyl-1,3-thiazole-4-carboxamide

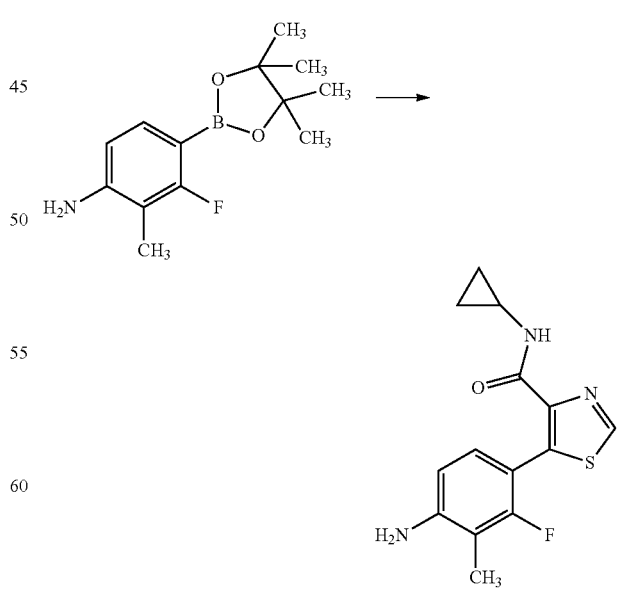

A mixture of 5-bromo-N-cyclopropyl-1,3-thiazole-4-carboxamide (2.88 g, 11.65 mmol), 3-fluoro-2-methyl-4-(tetramethyl-1,3,2-dioxaborolan-2-yl)aniline (3.66 g, 14.57 mmol) and Cs$_2$CO$_3$ (5.70 g, 17.48 mmol) in 1,4-dioxane (45 mL) and H$_2$O (5 mL) was heated to 70° C. for 10 min before addition of 1,1'-bis(diphenylphosphino)ferrocene-palladium (II) dichloride dichloromethane complex (1.43 g, 1.75 mmol) in one portion. The reaction was further stirred at 70° C. for 45 min. On cooling all volatiles were removed under reduced pressure and the crude product was purified by flash chromatography eluting with a gradient system of 20-100% EtOAc in Petroleum ether (40-60) to give 5-(4-amino-2-fluoro-3-methylphenyl)-N-cyclopropyl-1,3-thiazole-4-carboxamide (2.78 g, 82% yield) as a redwood brown solid.

LC-MS (Method D) 292.4 [M+H]$^+$; RT 2.13 min (e) 7-amino-5-cyclopropyl-6-methyl-thiazolo[4,5-c]quinolin-4-one

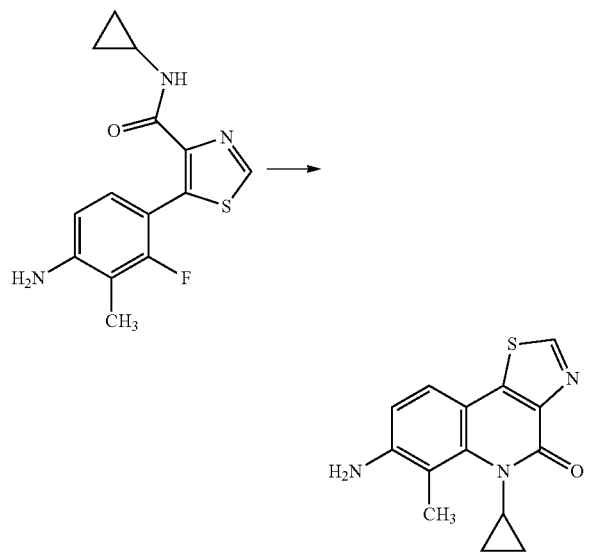

To a mixture of 5-(4-amino-2-fluoro-3-methylphenyl)-N-cyclopropyl-1,3-thiazole-4-carboxamide (2.00 g, 6.86 mmol), K$_2$CO$_3$ (4.74 g, 34.32 mmol) and 18-crown-6 (1.81 g, 6.86 mmol) was added DMSO (40 mL) and the reaction mixture was heated to 160° C. for 24 h. On cooling DMSO was removed under reduced pressure and the residue partitioned between H$_2$O (150 mL) and EtOAc (150 mL). The aq. layer was further extracted with EtOAc (2×100 mL). The combined organic extracts were washed with brine (50 mL), dried over MgSO$_4$, filtered and concentrated. The crude product was then triturated from DCM (20 mL) by dropwise addition of petroleum ether (40-60). The solid was collected by filtration, washed with cold Et$_2$O and air dried to give 7-amino-5-cyclopropyl-6-methyl-thiazolo[4,5-c]quinolin-4-one (1.29 g, 50% yield) as an amber solid.

LC-MS (Method D) 272.4 [M+H]$^+$; RT 1.84 min (f) 5-cyclopropyl-6-methyl-7-(tetramethyl-1,3,2-dioxaborolan-2-yl)-thiazolo[4,5-c]quinolin-4-one

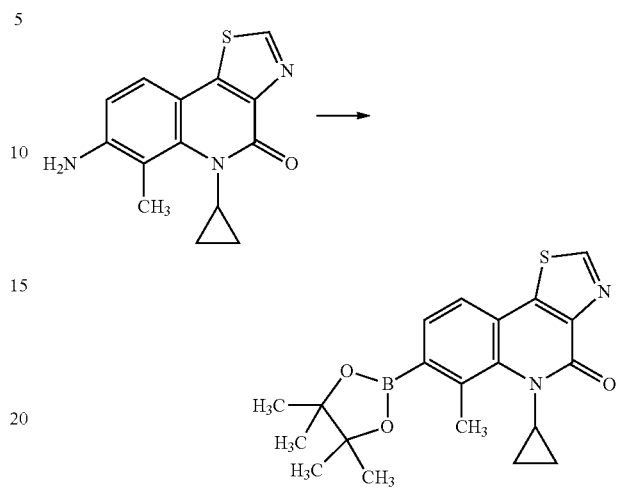

To a cooled to 0° C. solution of 7-amino-5-cyclopropyl-6-methyl-thiazolo[4,5-c]quinolin-4-one (146 mg, 0.54 mmol) in MeOH (1 mL) and H$_2$O (0.25 mL) was added 3M aq. HCl (0.54 mL, 1.61 mmol) and left to stir for 3 min. Sodium nitrite (37.1 mg, 0.54 mmol) was then added as a solution in H$_2$O (0.25 mL) in one portion and the mixture was left to stir at 0° C. for 30 min. Bis(pinacolato)diboron (410 mg, 1.61 mmol) in MeOH (2 mL) was then added in one portion and the resulting reaction mixture was stirred at room temperature for 1 h. The reaction mixture was then extracted with DCM (3×10 mL) and the combined organic layers dried over MgSO$_4$, filtered and concentrated to dryness to give 5-cyclopropyl-6-methyl-7-(tetramethyl-1,3,2-dioxaborolan-2-yl)-thiazolo[4,5-c]quinolin-4-one (120 mg, 58% yield) as a brown oil, which was used without further purification.

LC-MS (Method A) 383.4 [M+H]$^+$; RT 3.16 min (g) 7-(4-amino-2,5-difluorophenyl)-5-cyclopropyl-6-methyl-thiazolo[4,5-c]quinolin-4-one D4

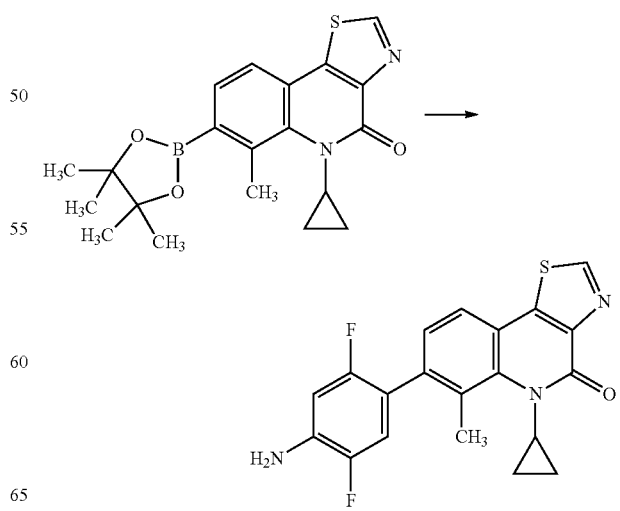

Prepared using 5-cyclopropyl-6-methyl-7-(tetramethyl-1,3,2-dioxaborolan-2-yl)-thiazolo[4,5-c]quinolin-4-one and 4-bromo-2,5-difluoroaniline and a similar procedure to that described in Example 1 step (g)

$^1$H NMR (Method A) (CDCl$_3$): δ ppm 8.88 (s, 1H), 7.54 (d, J=7.9 Hz, 1H), 7.16 (d, J=7.9 Hz, 1H), 6.95 (dd, J=11.0, 7.0 Hz, 1H), 6.61 (dd, J=10.5, 7.0 Hz, 1H), 3.98 (s, 2H), 3.68-3.63 (m, 1H), 2.53 (s, 3H), 1.34-1.17 (m, 2H), 0.77-0.59 (m, 2H); LC-MS (Method D) 384.3 [M+H]$^+$; RT 2.23 min Example 109—5-Cyclopropyl-7-(1H-indazol-5-yl)-6-methyl-thiazolo[4,5-c]quinolin-4-one E4

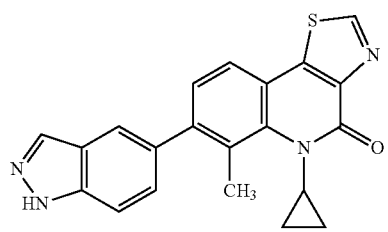

Prepared using 5-cyclopropyl-6-methyl-7-(tetramethyl-1,3,2-dioxaborolan-2-yl)-thiazolo[4,5-c]quinolin-4-one (prepared as described in Example 108 step (g)) and 5-bromoindazole and a similar procedure to that described in Example 1 step (g)

$^1$H NMR (Method A) (CDCl$_3$): δ ppm 8.89 (s, 1H), 8.89 (s, 1H), 8.17 (s, 1H), 7.78-7.76 (m, 1H), 7.62 (d, J=8.5 Hz, 1H), 7.58 (d, J=8.0 Hz, 1H), 7.45 (dd, J=8.5, 1.6 Hz, 1H), 7.28 (d, J=8.0 Hz, 1H), 3.72-3.67 (m, 1H), 2.56 (s, 3H), 1.40-1.28 (m, 2H), 0.78-0.73 (m, 2H); LC-MS (Method D) 373.4 [M+H]$^+$; RT 2.34 min Example 110—7-[3-(aminomethyl)pyrrolidin-1-yl]-6-chloro-5-cyclopropyl-8-fluoro-2-methyl-oxazolo[4,5-c]quinolin-4-one F4

(a) tert-butyl N-[[1-(5-cyclopropyl-8-fluoro-2-methyl-4-oxo-oxazolo[4,5-c]quinolin-7-yl)pyrrolidin-3-yl]methyl]carbamate

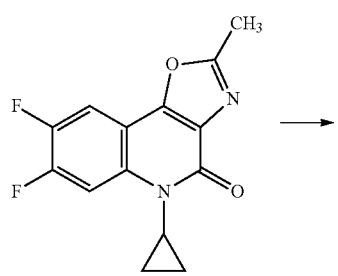

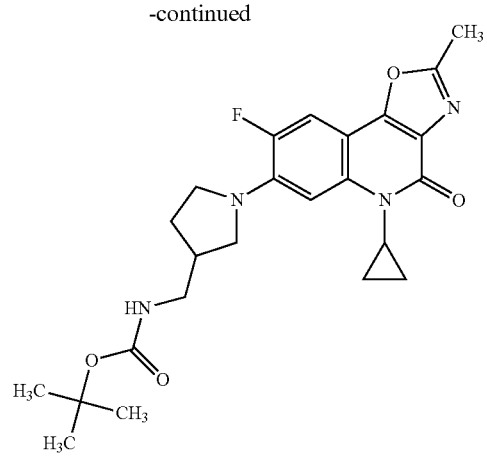

Prepared using tert-butyl N-(pyrrolidin-3-ylmethyl)carbamate and 5-cyclopropyl-7,8-difluoro-2-methyl-oxazolo[4,5-c]quinolin-4-one (prepared as described in Example 49 step (h)) and a similar procedure to that described in Example 49 step (i)

1H NMR (Method A) (CDCl$_3$): b 7.26 (d, J=13.1 Hz, 1H), 6.89 (d, J=7.8 Hz, 1H), 5.22 (s, 1H), 3.67-3.20 (m, 6H), 2.87 (m, J=6.8, 4.1, 2.8 Hz, 1H), 2.61 (s, 3H), 2.58-2.51 (m, 1H), 2.23-2.04 (m, 1H), 1.89-1.73 (m, 1H), 1.44 (s, 9H), 1.34 (m, J=8.6, 4.4, 2.9 Hz, 2H), 0.92-0.80 (m, 2H); LC-MS (Method D) 457.5 [M+H]$^+$; RT 2.91 min (b) tert-butyl N-[[1-(6-chloro-5-cyclopropyl-8-fluoro-2-methyl-4-oxo-oxazolo[4,5-c]quinolin-7-yl)pyrrolidin-3-yl]methyl]carbamate

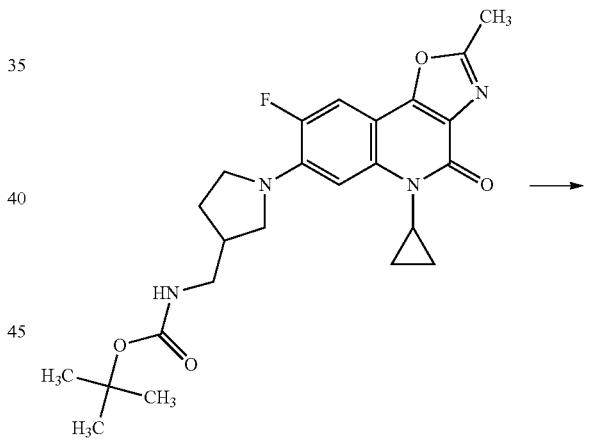

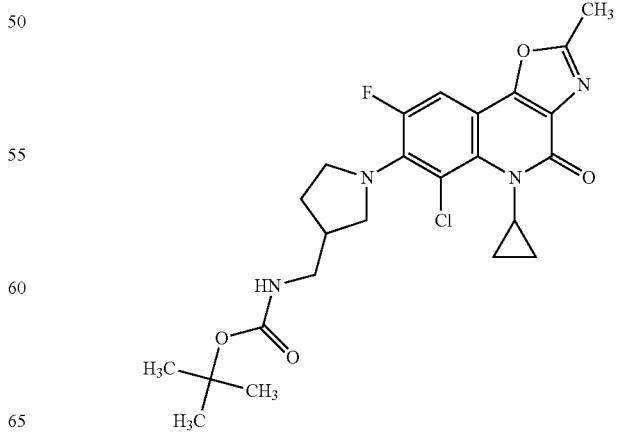

To a solution of tert-butyl N-[[1-(5-cyclopropyl-8-fluoro-2-methyl-4-oxo-oxazolo[4,5-c]quinolin-7-yl)pyrrolidin-3-yl]methyl]carbamate (71.6 mg, 0.16 mmol) in DCM (2 mL) was added 1,3-dichloro-5,5-dimethyl-imidazolidine-2,4-dione (46.4 mg, 0.24 mmol) in DCM (1.14 mL) and the reaction stirred at room temperature. After 1 h the reaction was quenched with aqueous sodium bisulfite (0.5 g in 5 mL) and diluted with DCM (5 mL). The layers were separated and the organic layer washed with saturated aqueous NaHCO$_3$ and then H$_2$O, dried over MgSO$_4$, filtered and the solvent removed in vacuo. The resulting residue was purified by flash chromatography using 0-10% MeOH in DCM to give tert-butyl N-[[1-(6-chloro-5-cyclopropyl-8-fluoro-2-methyl-4-oxo-oxazolo[4,5-c]quinolin-7-yl)pyrrolidin-3-yl]methyl]carbamate (37.9 mg, 49% yield).

LC-MS (Method D) 491.4/493.4 [M+H]$^+$; RT 3.13 min (c) 7-[3-(aminomethyl)pyrrolidin-1-yl]-6-chloro-5-cyclopropyl-8-fluoro-2-methyl-oxazolo[4,5-c]quinolin-4-one F4

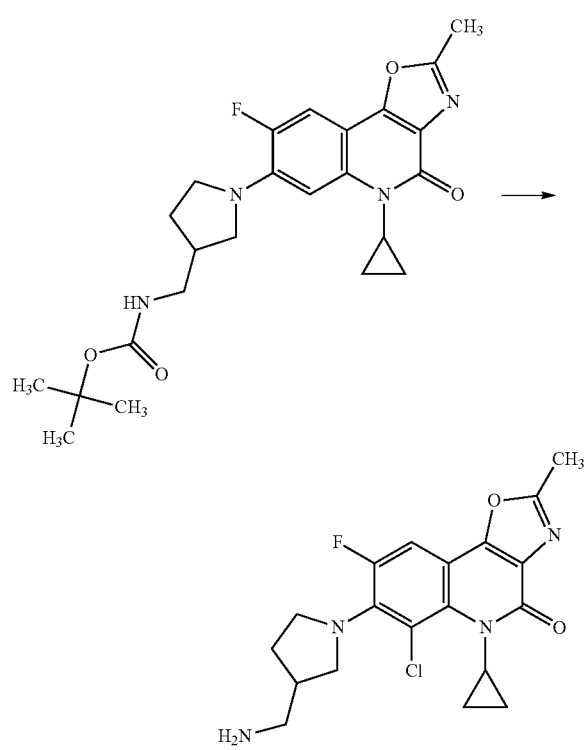

Prepared using a similar procedure to that described in Example 49 step (j). Product isolated as its TFA salt $^1$H NMR (Method A) (CDCl$_3$): b ppm 7.57 (d, J=11.6 Hz, 1H), 3.79-3.59 (m, 4H), 3.50-3.43 (m, 1H), 3.18-3.08 (m, 2H), 2.66 (s, 4H), 2.34-2.24 (m, 1H), 1.91-1.80 (m, 1H), 1.30-1.20 (m, 2H), 0.57-0.50 (m, 2H); LC-MS (Method D) 391.4/393.4 [M+H]$^+$; RT 1.65 min Example 111—Antibacterial susceptibility testing Minimum Inhibitory Concentrations (MICs) versus planktonic bacteria are determined by the broth microdilution procedure according to the guidelines of the Clinical and Laboratory Standards Institute (Clinical and Laboratory Standards Institute. Methods for Dilution Antimicrobial Susceptibility Tests for Bacteria That Grow Aerobically; Approved Standard-Ninth Edition. CLSI document M07-A9, 2012) and by the agar dilution procedure according to the guidelines of the Clinical and Laboratory Standards Institute (Clinical and Laboratory Standards Institute. Susceptibility testing of Mycobacteria, Nocardiae and other aerobic Actinomycetes, Approved Standard-Second Edition. CLSI document M24-A2, 2011). The broth dilution method involves a two-fold serial dilution of compounds in 96-well microtitre plates, giving a final concentration range of 0.001-128 µg/mL and a maximum final concentration of 1% DMSO. The agar dilution method involves a two-fold serial dilution of compounds in 24-well microtitre plates, giving a final concentration range of typically 0.03-32 µg/mL and a maximum final concentration of 1% DMSO. The bacterial strains tested include *Staphylococcus aureus* ATCC 29213 and *Escherichia coli* ATCC 25922 (Table 1), a panel of MRSA strains, *Enterococcus faecium* ATCC 19434 and *Streptococcus pneumoniae* ATCC BAA-255 (Table 2), *Haemophilus influenzae* ATCC 49247, *Moraxella catarrhalis* ATCC 25240, *Legionella pneumophila* ATCC 33152, *Neisseria gonorrhoeae* ATCC 49226, *Neisseria meningitidis* ATCC 13090 and *Mycobacterium smegmatis* ATCC 19420 (Table 4). Strains are grown in cation-adjusted Müller-Hinton broth (supplemented with 2% w/v NaCl in the case of methicillin-resistant *S. aureus* strains or supplemented with 5% blood in the case of *S. pneumoniae* and *N. meningitidis*), in haemophilus test medium broth, on Müller-Hinton agar at 37° C. (in the presence of 5% CO$_2$ in the case of *N. meningitidis*), or on supplemented GC agar at 37° C., 5% CO$_2$ (in the case of *N. gonorrhoeae*). The MIC is determined as the lowest concentration of compound that inhibits growth following a 16-20 h incubation period for all strains with the following exceptions: 24 h incubation for *Neisseria* spp., 48 h incubation for *L. pneumophila* and 72 h incubation for *M. smegmatis*. The data reported correspond to the modes of three independent experiments.

In Tables 1, 2 and 4 a MIC (in µg/mL) of less than 1 is assigned the letter A; a MIC of from 1 to 10 is assigned the letter B; a MIC of from 10 to 100 is assigned the letter C; and a MIC of over 100 is assigned the letter D.

TABLE 1

MIC values against wild type strains

| Compound | S. aureus ATCC 29213 | E. coli ATCC 25922 |
|---|---|---|
| 1 | A | D |
| 2 | B | D |
| 3 | B | D |
| 4 | A | B |
| 5 | A | B |
| 6 | C | D |
| 7 | B | D |
| 8 | C | D |
| 9 | A | B |
| 10 | A | D |
| 11 | B | D |
| 12 | B | C |
| 13 | A | D |
| 14 | A | C |
| 15 | A | C |
| 16 | A | C |
| 17 | B | B |
| 18 | A | D |
| 19 | A | D |
| 20 | A | B |
| 21 | A | C |
| 22 | A | B |

TABLE 1-continued

MIC values against wild type strains

| Compound | S. aureus ATCC 29213 | E. coli ATCC 25922 |
|---|---|---|
| 23 | A | B |
| 24 | A | C |
| 25 | A | B |
| 26 | A | D |
| 27 | A | B |
| 28 | C | C |
| 29 | B | C |
| 30 | B | D |
| 31 | D | D |
| 32 | A | B |
| 33 | A | D |
| 34 | A | B |
| 35 | A | B |
| 36 | A | B |
| 37 | C | D |
| 38 | A | B |
| 39 | A | B |
| 40 | A | B |
| 41 | B | D |
| 42 | C | D |
| 43 | B | C |
| 44 | D | D |
| 45 | C | D |
| 46 | A | B |
| 47 | C | D |
| 48 | B | C |
| 49 | B | B |
| 50 | B | B |
| 51 | B | B |
| 52 | B | B |
| 53 | C | C |
| 54 | B | B |
| 55 | B | C |
| 56 | B | B |
| 57 | A | B |
| 58 | B | C |
| 59 | B | C |
| 60 | C | D |
| 61 | D | D |
| 62 | B | C |
| 63 | D | D |
| 64 | A | C |
| 65 | B | D |
| 66 | B | D |
| 67 | B | D |
| 68 | A | B |
| 69 | A | B |
| 70 | C | D |
| 71 | B | B |
| 72 | C | D |
| 73 | A | D |
| 74 | C | C |
| 75 | B | C |
| 76 | A | B |
| 77 | C | D |
| 78 | D | D |
| 79 | A | C |
| 80 | B | B |
| 81 | B | B |
| 82 | C | B |
| 83 | C | B |
| 84 | D | D |
| 85 | C | C |
| 86 | D | D |
| 87 | D | D |
| 88 | A | B |
| 89 | B | B |
| 90 | A | B |
| 91 | C | C |
| 92 | B | B |
| 93 | B | B |
| 94 | B | C |
| 95 | B | B |
| 96 | B | C |
| 97 | A | B |
| 98 | A | B |
| 99 | A | B |
| 100 | A | A |
| 101 | A | C |
| 102 | B | D |
| 103 | B | B |
| 104 | B | D |
| 105 | C | C |
| 106 | C | D |
| 107 | C | D |
| 108 | A | B |
| 109 | A | A |
| 110 | A | A |

TABLE 2

Potency of reference compounds and test compounds against fluoroquinolone (FQ) susceptible and resistant *Staphylococcus* spp. and other Gram-positive bacteria

| Compound | S. aureus (MSSA) ATCC 29213 CLSI control strain | S. aureus NRS482 MRSA FQ resistant | S. aureus (MRSA) ATCC 43300 Heterogeneous MRSA strain | S. aureus NRS1 MRSA AMG & TET resistant | S. aureus NRS70 MRSA | S. aureus NRS100 MRSA | S. aureus SACPX1-SP25 MSSA - FQ resistant (isogenic mutant of ATCC 29213) | S. aureus NRS127 MRSA LZD resistant | S. aureus VRS1 MRSA VAN resistant | S. aureus NRS107 MUP resistant | S. epidermidis NRS101 MRSE AMG, ERY resistant | E. faecium ATCC 19434 | S. pneumoniae ATCC BAA-255 |
|---|---|---|---|---|---|---|---|---|---|---|---|---|---|
| Ciprofloxacin | A | C | A | C | A | A | C | D | C | A | A | B | A |
| Levofloxacin | A | B | A | C | A | A | B | D | C | A | A | B | A |
| Oxacillin | A | | A | D | C | D | B | A | A | B | B | C | A |
| Vancomycin | A | B | B | B | A | B | A | B | A | A | A | A | B |
| 1 | A | A | | | | | | | | | | D | |
| 2 | B | B | | | | | | | | | | D | |
| 3 | B | | | | | | | | | | | D | |
| 4 | A | A | A | B | | | A | A | A | | | C | |
| 5 | A | | | | | | | | | | | D | |
| 6 | C | | | | | | | | | | | C | |
| 7 | B | | | | | | | | | | | D | |
| 8 | D | | | | | | | | | | | D | |
| 9 | A | | | | | | | | | | | D | |
| 10 | A | | | | | | | | | | | D | |
| 11 | B | | | | | | | | | | | D | |
| 12 | D | | | | | | | | | | | D | |
| 13 | D | | | | | | | | | | | D | |
| 14 | A | B | B | B | | | B | | | | | C | |
| 15 | A | A | | | | | | A | | | | D | |
| 16 | B | | | | | | | | | | | C | |
| 17 | B | | | | | | | | | | | D | |
| 18 | B | | | | | | | | | | | D | |
| 19 | A | | | | | | | | | | | B | |
| 20 | A | A | A | A | | | A | A | A | A | A | B | |
| 21 | A | A | A | A | | | | A | A | A | A | C | |
| 22 | A | | | | | | | | | | | D | |
| 23 | A | B | A | B | | | B | B | C | B | B | D | |
| 24 | A | | | | | | | | | | | C | |
| 25 | A | A | A | A | | | | A | A | A | A | D | |
| 26 | A | B | B | B | | | | B | B | A | A | D | |
| 27 | A | A | A | B | | | | C | C | B | A | C | |
| 28 | B | | | | | | | | | | | D | |
| 29 | B | | | | | | | | | | | D | |
| 30 | B | B | B | B | | | | B | B | | | D | |
| 31 | D | D | | | | | | | | | | | |
| 32 | A | | | | | | | | | | | C | |
| 33 | A | | | | | | | | | | | D | |
| 34 | A | B | A | B | A | B | B | B | C | B | | C | |
| 35 | A | B | A | D | | | | | | | | C | |
| 36 | A | B | A | | | | B | B | C | B | C | | B |

TABLE 2-continued

Potency of reference compounds and test compounds against fluoroquinolone (FQ) susceptible and resistant Staphylococcus spp. and other Gram-positive bacteria

| Compound | S. aureus (MSSA) ATCC 29213 CLSI control strain | S. aureus NRS482 MRSA FQ resistant | S. aureus (MRSA) ATCC 43300 Heterogeneous MRSA strain | S. aureus NRS1 MRSA AMG & TET resistant | S. aureus NRS70 MRSA | S. aureus NRS100 MRSA | S. aureus SACPX1-SP25 MSSA - FQ resistant (isogenic mutant of ATCC 29213) | S. aureus NRS127 MRSA LZD resistant | S. aureus VRS1 MRSA VAN resistant | S. aureus NRS107 MUP resistant | S. epidermidis NRS101 MRSE AMG, ERY resistant | E. faecium ATCC 19434 | S. pneumoniae ATCC BAA-255 |
|---|---|---|---|---|---|---|---|---|---|---|---|---|---|
| 37 | C | | | | | | | | | | | | |
| 38 | A | B | | | | | | | | | | D | |
| 39 | A | A | A | A | A | A | A | A | A | A | A | D | A |
| 40 | A | | | | | | A | | | | | C | |
| 41 | B | | | | | | | | | | | D | |
| 42 | C | | | | | | | | | | | D | |
| 43 | B | | | | | | | | | | | D | |
| 44 | D | | | | | | | | | | | D | |
| 45 | C | | | | | | | | | | | D | |
| 46 | A | | | | | | | | | | | D | |
| 47 | C | | | | | | | | | | | D | |
| 48 | B | | | | | | | | | | | D | |
| 49 | B | C | B | C | | | | C | D | | | C | |
| 50 | B | | | | | | | | | | | D | |
| 51 | B | | | | | | | | | | | C | |
| 52 | B | B | A | B | | | B | B | B | | | C | |
| 53 | C | | | | | | | | | | | C | |
| 54 | B | | | | | B | | | | | | D | |
| 55 | B | | | | | | | | | | | D | |
| 56 | B | | | | | | | | | | | D | |
| 57 | A | B | A | B | | | B | | | | | C | |
| 58 | B | | | | | | | | | | | C | |
| 59 | B | | | | | | | | | | | D | |
| 60 | C | | | | | | | | | | | D | |
| 61 | D | | | | | | | | | | | D | |
| 62 | B | | | | | | | | | | | D | |
| 63 | D | | | | | | | | | | | D | |
| 64 | A | | | | | | | | | | | D | |
| 65 | B | | | | | | | | | | | D | |
| 66 | B | | | | | | | | | | | D | |
| 67 | B | | | | | | | | | | | D | |
| 68 | A | | | | | | | | | | | D | |
| 69 | A | B | A | | | | | A | A | A | B | D | |
| 70 | C | | | | | | | | | | | D | |
| 71 | B | | | | | | | | | | | D | |
| 72 | C | | | | | | | | | | | C | |
| 73 | A | | | | | | | | | | | D | |
| 74 | C | | | | | | | | | | | D | |
| 75 | B | | | | | | | | | | | D | |
| 76 | A | B | A | B | | | | B | C | | | C | |
| 77 | C | | | | | | | | | | | D | |
| 78 | D | | | | | | | | | | | D | |

TABLE 2-continued

Potency of reference compounds and test compounds against fluoroquinolone (FQ) susceptible and resistant Staphylococcus spp. and other Gram-positive bacteria

| Compound | S. aureus (MSSA) ATCC 29213 CLSI control strain | S. aureus NRS482 MRSA FQ resistant | S. aureus (MRSA) ATCC 43300 Heterogeneous MRSA strain | S. aureus NRS1 MRSA AMG & TET resistant | S. aureus NRS70 MRSA | S. aureus NRS100 MRSA | S. aureus SACPX1-SP25 MSSA - FQ resistant (isogenic mutant of ATCC 29213) | S. aureus NRS127 MRSA LZD resistant | S. aureus VRS1 MRSA VAN resistant | S. aureus NRS107 MUP resistant | S. epidermidis NRS101 MRSE AMG, ERY resistant | E. faecium ATCC 19434 | S. pneumoniae ATCC BAA-255 |
|---|---|---|---|---|---|---|---|---|---|---|---|---|---|
| 79  | A |   |   |   |   |   |   |   |   |   |   | D |   |
| 80  | B |   |   |   |   |   |   |   |   |   |   | C |   |
| 81  | B |   |   |   |   |   |   |   |   |   |   | D |   |
| 82  | C |   |   |   |   |   |   |   |   |   |   | D |   |
| 83  | C |   |   |   |   |   |   |   |   |   |   | D |   |
| 84  | D |   |   |   |   |   |   |   |   |   |   | D |   |
| 85  | C |   |   |   |   |   |   |   |   |   |   | D |   |
| 86  | C |   |   |   |   |   |   |   |   |   |   | D |   |
| 87  | C |   |   |   |   |   |   |   |   |   |   | C |   |
| 88  | A | B | B | B |   |   | B | B | B |   |   | C |   |
| 89  | B | B | B | B |   |   | B | C | B |   |   | C |   |
| 90  | A | B | A | B |   |   | B | B | C |   |   |   |   |
| 91  | C |   |   |   |   |   |   |   |   |   |   |   |   |
| 92  | B | C | B | C |   |   | B | C | D |   | B | D |   |
| 93  | B | B | A |   |   |   |   |   | B |   |   | D |   |
| 94  | B |   |   |   |   |   |   |   |   |   |   |   |   |
| 95  | B | B | B | B |   |   |   | B | B |   | B | C |   |
| 96  | B | B | B | B |   |   |   | B | B |   |   | C |   |
| 97  | A |   |   |   |   |   |   |   |   |   |   | C |   |
| 98  | A | A |   |   |   |   |   |   |   |   |   |   |   |
| 99  | A | A | A | B |   |   |   |   |   |   |   |   |   |
| 100 | A | A | A | A |   |   | A | B | B |   | A | B |   |
| 101 | B | B |   |   |   |   |   |   |   |   |   |   |   |
| 102 | B |   |   |   |   |   |   |   |   |   |   | D |   |
| 103 | B |   |   |   |   |   |   |   |   |   |   | C |   |
| 104 | B |   |   |   |   |   |   |   |   |   |   | C |   |
| 105 | C |   |   |   |   |   |   |   |   |   |   | C |   |
| 106 | C |   |   |   |   |   |   |   |   |   |   | D |   |
| 107 | C |   |   |   |   |   |   |   |   |   |   | D |   |
| 108 | A | A | A | A |   |   | A | A | A |   | A | C |   |
| 109 | A | A | A | A |   |   |   | A | A |   | B | D |   |

In addition to methicillin and, where present, fluoroquinolone resistance, the strains mentioned in Table 2 are also resistant to other antibiotics as indicated in Table 3

TABLE 3

Additional resistance of tested *Staphylococcus* spp.

| Strain | Also resistant to: |
|---|---|
| S. aureus NRS482 (USA300 FPR3757) | erythromycin |
| S. aureus NRS1 (Mu50) | aminoglycosides (AMG), vancomycin (intermediate), tetracycline (TET) |
| S. aureus NRS70 (N315) | clindamycin, erythromycin |
| S. aureus NRS100 | tetracycline |
| S. aureus NRS127 | linezolid (LZD) |
| S. aureus VRS1 | vancomycin (VAN) |
| S. aureus NRS107 | mupirocin (MUP) |

TABLE 3-continued

Additional resistance of tested *Staphylococcus* spp.

| Strain | Also resistant to: |
|---|---|
| S. epidermidis NRS101 | MRSE = methicillin-resistant S. epidermidis, aminoglycosides (AMG), erythromycin (ERY), |

Compound 1 has also been tested and has shown activity (MIC less than 1 μg/mL) against all of the following bacterial strains:
S. aureus NRS106 (fluoroquinolone susceptible MSSA);
S. aureus NRS384 (MRSA - fluoroquinolone susceptible);
S. aureus NRS74, S. aureus NRS108, S. aureus NRS271, S. aureus VRS8 (all strains are fluoroquinolone resistant MRSA);
S. aureus SACPX1-SP28 (MSSA - fluoroquinolone resistant);

Thus, certain compounds of the invention, including compound 1, exhibit excellent activity against all strains of *S. aureus* tested, including those which are resistant to fluoroquinolone antibiotics and other antibiotics.

TABLE 4

Potency of reference compounds and test compounds against a panel of Gram-negative and *mycobacterium* strains

| Compound | Haemophilus influenzae ATCC 49247 | Moraxella catarrhalis ATCC 25240 | Legionella pneumophila ATCC 33152 | Neisseria gonorrhoeae ATCC 49226 | Neisseria meningitidis ATCC 13090 | Mycobacterium smegmatis ATCC 19420 |
|---|---|---|---|---|---|---|
| Ciprofloxacin | A | A | A | A | A | A |
| Levofloxacin | A | A | A | A | A | |
| Oxacillin | D | | | | | |
| Vancomycin | C | | | | | |
| 1 | A | A | A | A | A | A |
| 2 | C | | | | | |
| 3 | B | | | | | |
| 4 | A | | | | | |
| 5 | A | | | | | |
| 6 | D | | | | | |
| 7 | C | | | | | |
| 8 | B | | | | | |
| 9 | B | | | | | |
| 10 | C | | | | | |
| 11 | C | | | | | |
| 12 | B | | | | | |
| 13 | D | | | | | |
| 14 | B | | | | | |
| 15 | B | | | | | |
| 16 | C | | | | | |
| 17 | A | | | | | |
| 18 | B | | | | | |
| 19 | B | | | | | |
| 20 | A | | | | | |
| 21 | B | | | | | |
| 22 | B | | | | | |
| 23 | B | | | B | | |
| 24 | B | | | | | |
| 25 | A | | | | | |
| 26 | B | | | | | |
| 27 | B | | | | | |
| 28 | B | | | | | |
| 29 | B | | | | | |
| 30 | B | | | | | |
| 31 | D | | | | | |
| 32 | B | | | | | |
| 33 | C | | | | | |
| 34 | B | | | | | |
| 35 | B | | | | | |
| 36 | B | B | A | C | A | |
| 37 | C | | | | | |
| 38 | A | | | | | |
| 39 | A | | | A | A | B |
| 40 | B | | | | | |
| 41 | C | | | | | |
| 42 | D | | | | | |
| 43 | C | | | | | |
| 44 | D | | | | | |
| 45 | C | | | | | |
| 46 | D | | | | | |
| 47 | D | | | | | |

TABLE 4-continued

Potency of reference compounds and test compounds against a panel of Gram-negative and *mycobacterium* strains

| Compound | Haemophilus influenzae ATCC 49247 | Moraxella catarrhalis ATCC 25240 | Legionella pneumophila ATCC 33152 | Neisseria gonorrhoeae ATCC 49226 | Neisseria meningitidis ATCC 13090 | Mycobacterium smegmatis ATCC 19420 |
|---|---|---|---|---|---|---|
| 48 | B | | | | | |
| 49 | B | | | | | |
| 50 | C | | | | | |
| 51 | B | | | | | |
| 52 | B | | | | | |
| 53 | B | | | | | |
| 54 | B | | | | | |
| 55 | B | | | | | |
| 56 | B | | | | | |
| 57 | B | | | | B | |
| 58 | B | | | | | |
| 59 | B | | | | | |
| 60 | B | | | | | |
| 61 | D | | | | | |
| 62 | B | | | | | |
| 63 | D | | | | | |
| 64 | A | | | | | |
| 65 | C | | | | | |
| 66 | C | | | | | |
| 67 | C | | | | | |
| 68 | A | | | | | |
| 69 | A | | | | | |
| 70 | D | | | | | |
| 71 | A | | | | | |
| 72 | B | | | | | |
| 73 | B | | | | | |
| 74 | B | | | | | |
| 75 | B | | | | | |
| 76 | B | | | | | |
| 77 | D | | | | | |
| 78 | C | | | | | |
| 79 | A | | | | | |
| 80 | C | | | | | |
| 81 | B | | | | | |
| 82 | C | | | | | |
| 83 | C | | | | | |
| 84 | D | | | | | |
| 85 | B | | | | | |
| 86 | C | | | | | |
| 87 | C | | | | | |
| 88 | B | B | B | B | B | |
| 89 | B | | B | | | |
| 90 | B | B | B | | | |
| 91 | B | | | | | |
| 92 | C | | | | | |
| 93 | A | B | A | A | | |
| 94 | B | | | | | |
| 95 | A | | | | | |
| 96 | B | | | | | |
| 97 | B | | | | | |
| 98 | B | | | | | |
| 99 | A | | | | | |
| 100 | A | A | A | A | A | |
| 101 | B | | | | | |
| 102 | C | | | | | |
| 103 | A | | | | | |
| 104 | C | | | | | |
| 105 | C | | | | | |
| 106 | C | | | | | |
| 107 | D | | | | | |
| 108 | A | | | | | |
| 109 | B | | | | | |

Thus, certain compounds of the invention have shown good activity against Gram negative bacterial strains. In particular, some compounds of the invention have shown good activity against fastidious Gram negative bacterial strains as exemplified by *Neisseria* spp.

Certain compounds of the invention have also shown activity against *M. smegmatis*, a recognised fast-growing and non-pathogenic surrogate for *M. tuberculosis* (Tuberculosis, 2010, 90, 333). Compound 1 has also been tested and shown activity (MIC less than 8 µg/mL) against the virulent tuberculosis-causative bacterial strain *Mycobacterium tuberculosis* H37Rv.

Example 112—Human Cell Viability Assay

Compounds are assessed for potential non-specific cytotoxic effects against a human hepatic cell line (HepG2 ATCC HB-8065). HepG2 cells are seeded at 20,000 cells/well in 96-well microtitre plates in minimal essential medium (MEM) supplemented with a final concentration of 10% FBS and 1 mM sodium pyruvate. After 24 h compound dilutions are prepared in Dulbecco's minimum essential media (DMEM) supplemented with final concentrations of 0.001% FBS, 0.3% bovine albumin and 0.02% HEPES and added to cells. Compounds are tested in two-fold serial dilutions over a final concentration range of 1-128 μg/mL in a final DMSO concentration of 1% vol/vol. Chlorpromazine is used as a positive control. Cells are incubated with compound at 37° C. and 5% $CO_2$ for a further 24 h, after which time the CellTiter-Glo reagent (Promega) is added. Luminescence is measured on a BMG Omega plate reader. Data are analysed using GraphPad Prism software to determine the concentration of compound that inhibits cell viability by fifty percent ($IC_{50}$). The results are provided in Table 5.

In Table 5, an $IC_{50}$ of less than 10 is assigned the letter C; an $IC_{50}$ of from 10 to 100 is assigned the letter B; and an $IC_{50}$ of over 100 is assigned the letter A.

TABLE 5

$IC_{50}$ values against HepG2

| Compound | HepG2 |
|---|---|
| Ciprofloxacin | A |
| Levofloxacin | A |
| Oxacillin | B |
| Vancomycin | B |
| 1 | A |
| 2 | B |
| 4 | B |
| 5 | B |
| 8 | A |
| 9 | B |
| 10 | B |
| 11 | A |
| 14 | B |
| 18 | B |
| 19 | B |
| 20 | A |
| 21 | B |
| 22 | B |
| 24 | A |
| 25 | B |
| 26 | A |
| 27 | B |
| 28 | B |
| 29 | A |
| 30 | B |
| 33 | B |
| 34 | A |
| 35 | B |
| 36 | A |
| 38 | A |
| 39 | B |
| 40 | A |
| 41 | B |
| 46 | B |
| 48 | B |
| 49 | B |
| 50 | B |
| 52 | B |
| 54 | B |
| 55 | A |
| 56 | B |
| 57 | B |
| 58 | B |
| 64 | B |
| 71 | A |
| 79 | B |
| 81 | A |
| 88 | B |

TABLE 5-continued $IC_{50}$ values against HepG2

| Compound | HepG2 |
|---|---|
| 89 | B |
| 90 | B |
| 92 | A |
| 93 | A |
| 95 | A |
| 96 | B |
| 98 | A |
| 100 | A |
| 101 | B |
| 108 | B |

Thus, the tested compounds show low toxicities against human hepatic cell lines. In particular, certain compounds of the invention showed no detectable toxicity against human hepatic cell lines.

These compounds therefore show an excellent therapeutic benefit relative to their hepatic toxicity as expressed by the ratio of hepatic toxicity. All other compounds tested also demonstrate an acceptable level of hepatic toxicity relative to therapeutic activity.

The invention claimed is:

1. A compound of formula (VII), or a pharmaceutically acceptable salt or N-oxide thereof:

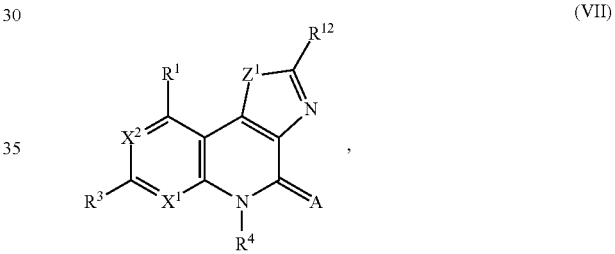

(VII)

wherein $X^1$ is independently selected from N and $CR^5$;
$X^2$ is independently selected from N and $CR^2$;
=A is independently selected from =O, =S, =$NR^6$ and =$NOR^6$;
$Z^1$ is selected from O and S;
$R^1$ is independently selected from H, F, $NR^6R^7$, $NR^6NR^6R^7$ and $C_1$-$C_4$-alkyl;
$R^2$ is independently selected from H, $C_1$-$C_4$-alkyl and halo;
$R^3$ is independently selected from —$(CR^8R^8)_n$—$C_3$-$C_{10}$ heterocycloalkyl, —$(CR^8R^8)_n$-aryl, —$(CR^8R^8)_n$-heteroaryl, and —$(CR^8R^8)_n$—$C_3$-$C_{10}$ cycloalkyl; wherein the aryl, heteroaryl, heterocycloalkyl or cycloalkyl group is optionally substituted with 1, 2 or 3 $R^{15}$ groups; wherein $R^{15}$ is independently at each occurrence selected from oxo, =$NR^6$, =$NOR^6$, $C_3$-$C_5$-heterocycloalkyl, halo, nitro, cyano, $NR^6R^7$, $NR^6S(O)_2R^6$, $NR^6CONR^6R^6$, $NR^6CO_2R^6$, $OR^6$; $SR^6$, $SOR^6$, $SO_3R^6$, $SO_2R^6$, $SO_2NR^6R^6$, $CO_2R^6C(O)R^6$, $CONR^6R^6$, $C(O)NR^6CR^6R^6C(O)OR^6$, $C_1$-$C_4$-alkyl, $C_2$-$C_4$-alkenyl, $C_2$-$C_4$-alkynyl, $C_1$-$C_4$ haloalkyl, $CR^6R^6OR^6$, $CR^6R^6NR^7R^6$, and =$CR^6CR^6R^6NR^7R^6$;
$R^4$ is independently selected from $C_1$-$C_8$ alkyl, $C_2$-$C_8$ alkenyl, $C_2$-$C_8$ alkynyl, $C_1$-$C_8$ haloalkyl, —$(CR^8R^8)_n$—$C_3$-$C_6$ cycloalkyl, —$(CR^8R^8)_n$—$C_3$-$C_6$ heterocycloalkyl, —$(CR^8R^8)_n$—$C_3$-$C_6$ halocycloalkyl, —$(CR^8R^8)_n$-phenyl, and —$(CR^8R^8)_n$-heteroaryl;

$R^5$ is independently selected from H, O—$C_1$-$C_8$ alkyl, halo, $C_1$-$C_8$ alkyl, $C_2$-$C_8$ alkenyl, $C_2$-$C_8$ alkynyl, $C_1$-$C_8$ haloalkyl, O—$C_1$-$C_8$ haloalkyl, $C_3$-$C_6$ cycloalkyl, $C_3$-$C_6$ heterocycloalkyl, and $C_3$-$C_6$ halocycloalkyl; or $R^4$ and $R^5$ together form an alkylene or heteroalkylene chain of the form —$(CR^8R^8)_r$—$W^1$—$(CR^8R^8)_s$—$W^2$—$(CR^8R^8)_t$— and which is attached at its respective ends to the substitution point for $R^4$ and $R^5$ respectively; wherein $W^1$ and $W^2$ are each independently selected from a bond, O, S and $NR^9$; wherein r, s, and t are each independently an integer selected from 0, 1 and 2 and wherein definitions of r, s, t, $W^1$ and $W^2$ are chosen such that the total length of the alkylene or heteroalkylene chain is 2, 3 or 4 atoms;

$R^6$, $R^9$ and $R^{13}$ are independently at each occurrence selected from H, $C_1$-$C_4$ alkyl, and $C_1$-$C_4$ haloalkyl;

$R^7$ and $R^{14}$ are each independently at each occurrence selected from H, $C_1$-$C_4$ alkyl, $C_1$-$C_4$ haloalkyl, $S(O)_2$—$C_1$-$C_4$alkyl, $C(O)$—$C_1$-$C_4$ alkyl, $C(O)$—O—$C_1$-$C_4$ alkyl and $CH_2$-phenyl;

$R^8$ is independently at each occurrence selected from H, Me, $CF_3$ and F;

$R^{12}$ is independently at each occurrence selected from H, halo, nitro, cyano, $NR^{13}R^{14}$, $NR^{13}S(O)_2R^{13}$, $NR^{13}CONR^{13}R^{13}$, $NR^{13}CO_2R^{13}$, $OR^{13}$, $SR^{13}$, $SOR^{13}$, $SO_3R^{13}$, $SO_2R^{13}$, $SO_2NR^{13}R^{13}$, $CO_2R^{13}C(O)R^{13}$, $CONR^{13}R^{13}$, $C_1$-$C_4$-alkyl, $C_2$-$C_4$-alkenyl, $C_2$-$C_4$-alkynyl, $C_1$-$C_4$ haloalkyl, $CR^{13}R^{13}OR^{13}$, $CR^{13}R^{13}OC(O)R^{13}$; and $CR^{13}R^{13}NR^{13}R^{14}$; and n is an integer independently selected at each occurrence from 0, 1, 2 and 3; and wherein each of said aryl, heteroaryl, $C_3$-$C_{10}$ heterocycloalkyl or $C_3$-$C_{10}$ cycloalkyl groups is monocyclic or bicyclic; and wherein when the $R^1$, $R^2$, $R^4$, $R^6$, $R^7$, $R^9$, and $R^{15}$ groups are an alkyl, alkenyl, alkynyl, haloalkyl, cycloalkyl, halocycloalkyl, heterocycloalkyl, aryl or heteroaryl group, said alkyl, alkenyl, alkynyl, haloalkyl, cycloalkyl, halocycloalkyl, heterocycloalkyl, aryl or heteroaryl group is optionally substituted, where chemically possible, by 1 to 5 substituents which are each independently at each occurrence selected from oxo, $=NR^a$, $=NOR^a$, halo, nitro, cyano, $NR^aR^a$, $NR^aS(O)_2R^a$, $NR^aCONR^aR^a$, $NR^aCO_2R^a$, $OR^a$; $SR^a$, $S(O)R^a$, $S(O)_2OR^a$, $S(O)_2R^a$, $S(O)_2NR^aR^a$, $CO_2R^a$ $C(O)R^a$, $CONR^aR^a$, $C_1$-$C_4$-alkyl, $C_2$-$C_4$-alkenyl, $C_2$-$C_4$-alkynyl, $C_1$-$C_4$ haloalkyl, $CR^bR^bOR^a$, $CR^bR^bNR^aR^a$, and $=CR^bCR^bR^bNR^aR^a$; wherein $R^a$ is independently at each occurrence selected from H, $C_1$-$C_4$ alkyl and $C_1$-$C_4$ haloalkyl; and $R^b$ is independently at each occurrence selected from H, halogen, $C_1$-$C_4$ alkyl and $C_1$-$C_4$ haloalkyl.

2. The compound of claim 1, wherein $Z^1$ is O.

3. The compound of claim 1, wherein $R^{12}$ is independently at each occurrence selected from H, $C_1$-$C_4$-alkyl, $CR^{13}R^{13}OR^{13}$, $CR^{13}R^{13}OC(O)R^{13}$ and $CR^{13}R^{13}NR^{13}R^{14}$.

4. The compound of claim 1, wherein $=A$ is $=O$.

5. The compound of claim 1, wherein $R^1$ is H.

6. The compound of claim 1, wherein $X^2$ is $CR^2$.

7. The compound of claim 1, wherein $X^1$ is $CR^5$.

8. The compound of claim 7, wherein $R^5$ is independently selected from Cl, O—$C_1$-$C_4$ alkyl, and $C_1$-$C_4$ alkyl.

9. The compound of claim 7, wherein $R^4$ and $R^5$ together form an alkylene or heteroalkylene chain of the form —O—$(CR^8R^8)_2$— and which is attached at its respective ends to the substitution point for $R^4$ and $R^5$ respectively.

10. The compound of claim 1, wherein $R^4$ is independently selected from $C_1$-$C_4$ alkyl, $C_1$-$C_4$ haloalkyl, cyclopropyl and halocyclopropyl.

11. The compound of claim 1, wherein $R^3$ is selected from phenyl and 6- or 9-membered heteroaryl comprising at least one nitrogen.

12. The compound of claim 1, wherein $R^3$ is

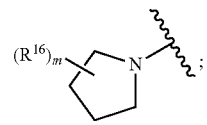

wherein $R^{16}$ is $R^{15}$; or wherein two $R^{16}$ groups together with the carbon or carbons to which they are attached form a 3-6 membered cycloalkyl, a 3-6 membered heterocycloalkyl ring or a 6-membered aryl or heteroaryl ring; wherein where two $R^{16}$ groups form a heterocycloalkyl ring, said heterocycloalkyl ring will comprise 1 or 2 heteroatoms selected from N, O and S in the ring system; wherein where two $R^{16}$ groups form a cycloalkyl or heterocycloalkyl ring, said cycloalkyl or heterocycloalkyl ring is optionally substituted with one or two $R^{15}$ groups; wherein $R^{15}$ is independently selected from oxo, $=NOR^6$, $NR^6R^7$, $OR^6$, $C_1$-$C_4$-alkyl, $C_2$-$C_4$-alkenyl, $C_2$-$C_4$-alkynyl, $CR^6R^6NR^6R^7$ and $=CR^6CR^6R^6NR^6R^7$; and m is an integer independently selected from 0, 1, 2 and 3.

13. The pharmaceutical formulation, comprising a compound of claim 1; and a pharmaceutically acceptable excipient.

14. The pharmaceutical formulation of claim 13, further comprising at least one other antibiotic.

15. The pharmaceutical formulation of claim 14, wherein the at least one other antibiotic is a fluoroquinolone antibiotic.

16. A method of treating a bacterial or mycobacterial infection, comprising administering to a subject in need thereof a therapeutically effective amount of a compound of formula (VII), or a pharmaceutically acceptable salt or N-oxide thereof:

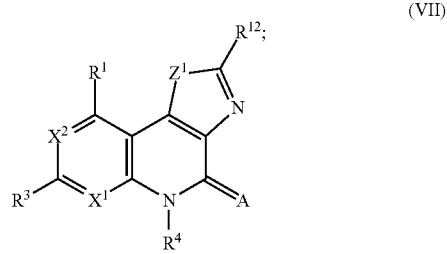

(VII)

wherein $X^1$ is independently selected from N and $CR^5$;
$X^2$ is independently selected from N and $CR^2$;
$=A$ is independently selected from $=O$, $=S$, $=NR^6$ and $=NOR^6$;
$Z^1$ is selected from O and S;
$R^1$ is independently selected from H, F, $NR^6R^7$, $NR^6NR^6R^7$ and $C_1$-$C_4$-alkyl;
$R^2$ is independently selected from H, $C_1$-$C_4$-alkyl and halo;
$R^3$ is independently selected from —$(CR^8R^8)_n$—$C_3$-$C_{10}$ heterocycloalkyl, —$(CR^8R^8)_n$-aryl, —$(CR^8R^8)_n$-heteroaryl, and —(CR$^8$R$^8$)$_n$—C$_3$-C$_{10}$ cycloalkyl; wherein the aryl, heteroaryl, heterocycloalkyl or cycloalkyl group is optionally substituted with 1, 2 or 3 R$^{15}$ groups; wherein R$^{15}$ is independently at each occurrence selected from oxo, =NR$^6$, =NOR$^6$, C$_3$-C$_5$-heterocycloalkyl, halo, nitro, cyano, NR$^6$R$^7$, NR$^6$S(O)$_2$R$^6$, NR$^6$CONR$^6$R$^6$, NR$^6$CO$_2$R$^6$, OR$^6$; SR$^6$, SOR$^6$, SO$_3$R$^6$, SO$_2$R$^6$, SO$_2$NR$^6$R$^6$, CO$_2$R$^6$C(O)R$^6$, CONR$^6$R$^6$, C(O)NR$^6$CR$^6$R$^6$C(O)OR$^6$, C$_1$-C$_4$-alkyl, C$_2$-C$_4$-alkenyl, C$_2$-C$_4$-alkynyl, C$_1$-C$_4$ haloalkyl, CR$^6$R$^6$OR$^6$, CR$^6$R$^6$NR$^7$R$^6$, and =CR$^6$CR$^6$R$^6$NR'R$^6$;

R$^4$ is independently selected from C$_1$-C$_8$ alkyl, C$_2$-C$_8$ alkenyl, C$_2$-C$_8$ alkynyl, C$_1$-C$_8$ haloalkyl, —(CR$^8$R$^8$)$_n$—C$_3$-C$_6$ cycloalkyl, —(CR$^8$R$^8$)$_n$—C$_3$-C$_6$ heterocycloalkyl, —(CR$^8$R$^8$)$_n$—C$_3$-C$_6$ haloalkyl, —(CR$^8$R$^8$)$_n$-phenyl, and —(CR$^8$R$^8$)$_n$-heteroaryl;

R$^5$ is independently selected from H, O—C$_1$-C$_8$ alkyl, halo, C$_1$-C$_8$ alkyl, C$_2$-C$_8$ alkenyl, C$_2$-C$_8$ alkynyl, C$_1$-C$_8$ haloalkyl, O—C$_1$-C$_8$ haloalkyl, C$_3$-C$_6$ cycloalkyl, C$_3$-C$_6$ heterocycloalkyl, and C$_3$-C$_6$ halocycloalkyl; or R$^4$ and R$^5$ together form an alkylene or heteroalkylene chain of the form —(CR$^8$R$^8$)$_r$—W$^1$—(CR$^8$R$^8$)$_s$—W$^2$—(CR$^8$R$^8$)$_t$— and which is attached at its respective ends to the substitution point for R$^4$ and R$^5$ respectively; wherein W$^1$ and W$^2$ are each independently selected from a bond, O, S and NR$^9$; wherein r, s, and t are each independently an integer selected from 0, 1 and 2 and wherein definitions of r, s, t, W$^1$ and W$^2$ are chosen such that the total length of the alkylene or heteroalkylene chain is 2, 3 or 4 atoms;

R$^6$, R$^9$ and R$^{13}$ are independently at each occurrence selected from H, C$_1$-C$_4$ alkyl, and C$_1$-C$_4$ haloalkyl;

R$^7$ and R$^{14}$ are each independently at each occurrence selected from H, C$_1$-C$_4$ alkyl, C$_1$-C$_4$ haloalkyl, S(O)$_2$—C$_1$-C$_4$alkyl, C(O)—C$_1$-C$_4$ alkyl, C(O)—O—C$_1$-C$_4$ alkyl and CH$_2$-phenyl;

R$^8$ is independently at each occurrence selected from H, Me, CF$_3$ and F;

R$^{12}$ is independently at each occurrence selected from H, halo, nitro, cyano, NR$^{13}$R$^{14}$, NR$^{13}$S(O)$_2$R$^{13}$, NR$^{13}$CONR$^{13}$R$^{13}$, NR$^{13}$CO$_2$R$^{13}$, OR$^{13}$; SR$^{13}$, SOR$^{13}$, SO$_3$R$^{13}$, SO$_2$R$^{13}$, SO$_2$NR$^{13}$R$^{13}$, CO$_2$R$^{13}$C(O)R$^{13}$, CONR$^{13}$R$^{13}$, C$_1$-C$_4$-alkyl, C$_2$-C$_4$-alkenyl, C$_2$-C$_4$-alkynyl, C$_1$-C$_4$ haloalkyl, CR$^{13}$R$^{13}$OR$^{13}$, CR$^{13}$R$^{13}$OC(O)R$^{13}$; and CR$^{13}$R$^{13}$NR$^{13}$R$^{14}$; and n is an integer independently selected at each occurrence from 0, 1, 2 and 3; and wherein each of said aryl, heteroaryl, C$_3$-C$_{10}$ heterocycloalkyl or C$_3$-C$_{10}$ cycloalkyl groups is monocyclic or bicyclic; and wherein when the R$^1$, R$^2$, R$^4$, R$^6$, R$^7$, R$^9$, and R$^{15}$ groups are an alkyl, alkenyl, alkynyl, haloalkyl, cycloalkyl, halocycloalkyl, heterocycloalkyl, aryl or heteroaryl group, said alkyl, alkenyl, alkynyl, haloalkyl, cycloalkyl, halocycloalkyl, heterocycloalkyl, aryl or heteroaryl group is optionally substituted, where chemically possible, by 1 to 5 substituents which are each independently at each occurrence selected from oxo, =NR$^a$, =NOR$^a$, halo, nitro, cyano, NR$^a$R$^a$, NR$^a$S(O)$_2$R$^a$, NR$^a$CONR$^a$R$^a$, NR$^a$CO$_2$R$^a$, OR$^a$; SR$^a$, S(O)R$^a$, S(O)$_2$OR$^a$, S(O)$_2$R$^a$, S(O)$_2$NR$^a$R$^a$, CO$_2$R$^a$C(O)R$^a$, CONR$^a$R$^a$, C$_1$-C$_4$-alkyl, C$_2$-C$_4$-alkenyl, C$_2$-C$_4$-alkynyl, C$_1$-C$_4$ haloalkyl, CR$^b$R$^b$OR$^a$, CR$^b$R$^b$NR$^a$R$^a$, and =CR$^b$CR$^b$R$^b$NR$^a$R$^a$; wherein R$^a$ is independently at each occurrence selected from H, C$_1$-C$_4$ alkyl and C$_1$-C$_4$ haloalkyl; and R$^b$ is independently at each occurrence selected from H, halogen, C$_1$-C$_4$ alkyl and C$_1$-C$_4$ haloalkyl.

17. The method of claim 16, wherein the bacterial infection is caused by Gram negative bacteria.

18. The method of claim 16, wherein the bacterial infection is caused by a bacterial strain selected from *Haemophilus* spp., *Moraxella* spp., *Legionella* spp. and *Neisseria* spp.

19. The method of claim 18, wherein the bacterial infection is gonorrhoea.

20. The method of claim 16, wherein the bacterial infection is caused by Gram positive bacteria.

21. The method of claim 20, wherein the bacterial infection is caused by methicillin-resistant *Staphylococcus aureus* or methicillin-resistant *Staphylococcus epidermidis*.

22. The method of claim 16, wherein the bacterial infection is caused by mycobacteria.

23. The method of claim 22, wherein the mycobacterial infection is tuberculosis (TB).

24. The method of claim 16, wherein the bacterial infection is caused by a bacterial strain which is resistant to one or more fluoroquinolone antibiotics.

* * * * *